US012600698B2

(12) United States Patent
Coburn et al.

(10) Patent No.: US 12,600,698 B2
(45) Date of Patent: Apr. 14, 2026

(54) KINASE INHIBITORS

(71) Applicant: Vidya Therapeutics, Inc., Encinitas, CA (US)

(72) Inventors: Craig A. Coburn, San Diego, CA (US); Daniel J. Buzard, San Diego, CA (US); Dange Vijay Kumar, San Diego, CA (US)

(73) Assignee: VIDYA THERAPEUTICS, INC., Encinitas, CA (US)

(*) Notice: Subject to any disclaimer, the term of this patent is extended or adjusted under 35 U.S.C. 154(b) by 730 days.

(21) Appl. No.: 17/898,274

(22) Filed: Aug. 29, 2022

(65) Prior Publication Data

US 2023/0174481 A1 Jun. 8, 2023

Related U.S. Application Data

(63) Continuation of application No. 17/573,386, filed on Jan. 11, 2022, now abandoned.

(60) Provisional application No. 63/136,594, filed on Jan. 12, 2021.

(51) Int. Cl.
*C07D 209/30* (2006.01)
*C07D 209/08* (2006.01)

(52) U.S. Cl.
CPC ......... *C07D 209/30* (2013.01); *C07D 209/08* (2013.01); *C07B 2200/07* (2013.01)

(58) Field of Classification Search
CPC .................................................... C07D 209/30
See application file for complete search history.

(56) References Cited

U.S. PATENT DOCUMENTS

2015/0005279 A1 1/2015 Bonafoux et al.

FOREIGN PATENT DOCUMENTS

WO WO-2014210255 A1 12/2014
WO 2016/065226 A1 4/2016
WO 2018/045157 A2 3/2018
WO WO-2022155111 A1 7/2022

OTHER PUBLICATIONS

Watterson "Discovery of Branebrutinib (BMS-986195): A Strategy for Identifying a Highly Potent and Selective Covalent Inhibitor Providing Rapid in Vivo Inactivation of Bruton's Tyrosine Kinase (BTK)." Journal of Medicinal Chemistry, 2019, 62(7), 3228-3250.*

Liu "Conversion of carbazole carboxamide based reversible inhibitors of Bruton's tyrosine kinase (BTK) into potent, selective irreversible inhibitors in the carbazole, tetrahydrocarbazole, and a new 2,3-dimethylindole series" Bioorganic & Medicinal Chemistry Letters 28 (2018) 3080-3084.*

Gruber et al., BTK regulates microglial function and neuroinflammation in human stem cell models and mouse models of multiple sclerosis. Nature Communications 15:10116, 17 pages. https://doi.org/10.1038/s41467-024-54430-8 (2004).

Kramer et al., Bruton tyrosine kinase inhibitors for multiple sclerosis. Nature Reviews Neurology 19:289-304 (2023).

Magliozzi et al., Meningeal B-cell follicles in secondary progressive multiple sclerosis associate with early onset of disease and severe cortical pathology. Brain 130:1089-1104 (2007).

PCT/US2022/011919 International Search Report and Written Opinion dated Apr. 11, 2022.

Shi et al., Brain penetrant kinase inhibitors: Learning from kinase neuroscience discovery. Bioorganic & Medicinal Chem. Letters 28:1981-1991, https://doi.org/10.1016/j.bmcl.2018.05.007 (2018).

* cited by examiner

*Primary Examiner* — David K O'Dell
(74) *Attorney, Agent, or Firm* — WILSON SONSINI GOODRICH & ROSATI

(57) ABSTRACT

Disclosed herein, are protein kinase inhibitors, in particular Bruton tyrosine kinase (BTK) inhibitors, pharmaceutical compositions comprising them, processes for preparing them and uses of the inhibitors to treat or prevent diseases, disorders and conditions associated with kinase function. In particular, the present invention relates to CNS penetrable BTK inhibitors.

21 Claims, No Drawings

KINASE INHIBITORS

FIELD OF THE INVENTION

The present invention relates generally to protein kinase inhibitors, in particular Bruton tyrosine kinase (BTK) inhibitors, pharmaceutical compositions comprising them, processes for preparing them and uses of such inhibitors to treat or prevent diseases, disorders and conditions associated with kinase function.

BACKGROUND

Protein kinases are a large group of intracellular and transmembrane signaling proteins in eukaryotic cells. These enzymes are responsible for transfer of the terminal (gamma) phosphate from ATP to specific amino acid residues of target proteins. Phosphorylation of specific amino acid residues in target proteins can modulate their activity leading to profound changes in cellular signaling and metabolism. Protein kinases can be found in the cell membrane, cytosol and organelles such as the nucleus and are responsible for mediating multiple cellular functions including metabolism, cellular growth and differentiation, cellular signaling, modulation of immune responses, and cell death. Serine kinases specifically phosphorylate serine or threonine residues in target proteins. Similarly, tyrosine kinases, including tyrosine receptor kinases, phosphorylate tyrosine residues in target proteins. Tyrosine kinase families include: TEC, SRC, ABL, JAK, CSK, FAK, SYK, FER, ACK and the receptor tyrosine kinase subfamilies including ERBB, FGFR, VEGFR, RET and EPH. Subclass I of the receptor tyrosine kinase superfamily includes the ERBB receptors and comprises four members: ErbB1 (also called epidermal growth factor receptor (EGFR)), ErbB2, ErbB3 and ErbB4.

Kinases exert control on key biological processes related to health and disease. Furthermore, aberrant activation or excessive expression of various protein kinases are implicated in the mechanism of multiple diseases and disorders characterized by benign and malignant proliferation, as well as diseases resulting from inappropriate activation of the immune system. Thus, inhibitors of select kinases or kinase families are considered useful in the treatment of cancer, vascular disease, autoimmune diseases, and inflammatory conditions including, but not limited to: solid tumors, hematological malignancies, thrombus, arthritis, graft versus host disease, lupus erythematosus, psoriasis, colitis, illeitis, multiple sclerosis, uveitis, coronary artery vasculopathy, systemic sclerosis, atherosclerosis, asthma, transplant rejection, allergy, ischemia, dermatomyositis, pemphigus, and the like.

Tec kinases are a family of non-receptor tyrosine kinases predominantly, but not exclusively, expressed in cells of hematopoietic origin. The Tec family includes TEC, Bruton's tyrosine kinase (BTK), inducible T-cell kinase (ITK), resting lymphocyte kinase (RLK/TXK for Tyrosine Protein Kinase), and bone marrow-expressed kinase (BMX/ETK).

BTK is important in B-cell receptor signaling and regulation of B-cell development and activation. Mutation of the gene encoding BTK in humans leads to X-linked agammaglobulinemia which is characterized by reduced immune function, including impaired maturation of B-cells, decreased levels of immunoglobulin and peripheral B cells, and diminished T-cell independent immune response. BTK is activated by Src-family kinases and phosphorylates PLC gamma leading to effects on B-cell function and survival. Additionally, BTK is important for cellular function of mast cells, macrophage and neutrophils indicating that BTK inhibition is effective in treatment of diseases mediated by these and related cells including inflammation, bone disorders, and allergic disease. BTK inhibition is also important in survival of lymphoma cells indicating that inhibition of BTK is useful in the treatment of lymphomas and other cancers. As such, inhibitors of BTK and related kinases are of great interest as anti-inflammatory, as well as anti-cancer, agents. BTK is also important for platelet function and thrombus formation indicating that BTK-selective inhibitors are also useful as antithrombotic agents. Furthermore, BTK is required for inflammasome activation, and inhibition of BTK may be used in treatment of inflammasome-related disorders, including; stroke, gout, type 2 diabetes, obesity-induced insulin resistance, atherosclerosis and Muckle-Wells syndrome. In addition, BTK is expressed in HIV infected T-cells and treatment with BTK inhibitors sensitizes infected cells to apoptotic death and results in decreased virus production. Accordingly, BTK inhibitors are considered useful in the treatment of HIV-AIDS and other viral infections.

Accordingly, there remains a need for compounds that modulateprotein kinases generally, as well as compounds that modulate specific protein kinases, such as BTK, as well as for related compositions and methods for treating diseases, disorders and conditions that would benefit from such modulation.

BRIEF SUMMARY

In one aspect, compounds are provided having the structure of Formula (I):

Formula (I)

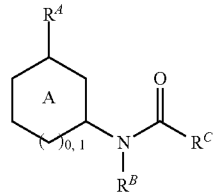

or a pharmaceutically acceptable salt, solvate, hydrate, isomer, tautomer, racemate or isotope thereof, wherein:

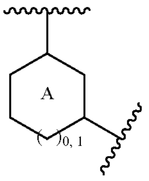

is

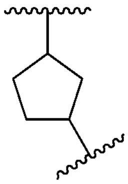

,

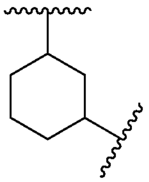

,

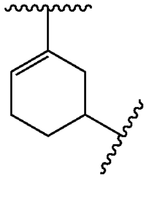

or

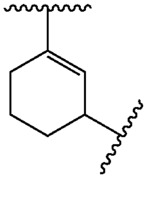

$R^B$ is —H or -Me;

$R^C$ is —CH═CH$_2$, —C≡CH or —C≡C—CH$_3$;

$R^A$ is

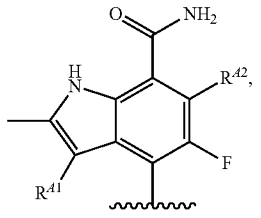

wherein $R^{A1}$ is —H, —F, —Cl, —CH$_3$, or —CN; and $R^{A2}$ is —H or —F.

In one embodiment, a pharmaceutical composition is provided comprising a compound having the structure of Formula (I), or a pharmaceutically acceptable salt, solvate, hydrate, isomer, tautomer, racemate, or isotope thereof, and at least one pharmaceutically acceptable excipient.

In one embodiment, a method of modulating a protein kinase is provided comprising contacting the protein kinase with an effective amount of a compound having the structure of Formula (I), or a pharmaceutically acceptable salt, solvate, hydrate, isomer, tautomer, racemate, isotope, or pharmaceutical composition thereof. In one embodiment, the protein kinase is BTK.

In one embodiment, a method for treating a BTK dependent condition is provided, comprising administering to a subject in need thereof an effective amount of a compound having the structure of Formula (I), or a pharmaceutically acceptable salt, solvate, hydrate, isomer, tautomer, racemate, isotope, or pharmaceutical composition thereof.

In one embodiment, the use of a compound having the structure of Formula (I), or a pharmaceutically acceptable salt, solvate, hydrate, isomer, tautomer, racemate, isotope, or pharmaceutical composition thereof is provided, in the manufacture of a medicament.

DETAILED DESCRIPTION

Unless defined otherwise, all technical and scientific terms used herein have the same meaning as is commonly understood by one of skill in the art to which the claimed subject matter belongs. It is to be understood that the detailed description is exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 100 μL" means "about 100 μL" and also "100 μL." In some embodiments, about means within 5% of the value. Hence, "about 100 μL" means 95-105 μL. Generally, the term "about" includes an amount that would be expected to be within experimental error.

As used herein, "alkyl" means a straight chain or branched saturated hydrocarbon group. "Lower alkyl" means a straight chain or branched alkyl group having from 1 to 8 carbon atoms, in some embodiments from 1 to 6 carbon atoms, in some embodiments from 1 to 4 carbon atoms, and in some embodiments from 1 to 2 carbon atoms. Examples of straight chain lower alkyl groups include, but are not limited to, methyl, ethyl, n-propyl, n-butyl, n-pentyl, n-hexyl, n-heptyl, and n-octyl groups. Examples of branched lower alkyl groups include, but are not limited to, isopropyl, iso-butyl, sec-butyl, t-butyl, neopentyl, isopentyl, and 2,2-dimethylpropyl groups.

"Alkenyl" groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH═CH$_2$, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, —CH═CHCH$_2$CH$_3$, —CH═CH(CH$_2$)$_2$CH$_3$, —CH═CH(CH$_2$)$_3$CH$_3$, —CH═CH(CH$_2$)$_4$CH$_3$, vinyl, cyclohexenyl, cyclopentenyl, cyclohexadienyl, butadienyl, pentadienyl, and hexadienyl among others.

"Alkynyl" groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

As used herein, "alkylene" means a divalent alkyl group. Examples of straight chain lower alkylene groups include, but are not limited to, methylene (i.e., —CH$_2$—), ethylene (i.e., —CH$_2$CH$_2$—), propylene (i.e., —CH$_2$CH$_2$CH$_2$—), and butylene (i.e., —CH$_2$CH$_2$CH$_2$CH$_2$—). As used herein, "heteroalkylene" is an alkylene group of which one or more carbon atoms is replaced with a heteroatom such as, but not limited to, N, O, S, or P.

"Alkoxy" refers to an alkyl as defined above joined by way of an oxygen atom (i.e., —O-alkyl). Examples of lower alkoxy groups include, but are not limited to, methoxy, ethoxy, n-propoxy, n-butoxy, isopropoxy, sec-butoxy, tert-butoxy, and the like.

The terms "carbocyclic" and "carbocycle" denote a ring structure wherein the atoms of the ring are carbon. Carbocycles may be monocyclic or polycyclic. Carbocycle encompasses both saturated and unsaturated rings. Carbocycle encompasses both cycloalkyl and aryl groups. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, alkyl, amino, hydroxy, cyano, carboxy, nitro, thio, alkoxy, and halogen groups.

"Cycloalkyl" groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

"Aryl" groups are cyclic aromatic hydrocarbons that do not contain heteroatoms. Thus, aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The terms "aryl" and "aryl groups" include fused rings wherein at least one ring, but not necessarily all rings, are aromatic, such as fused aromatic-aliphatic ring systems (e.g., indanyl, tetrahydronaphthyl, and the like).

"Carbocyclealkyl" refers to an alkyl as defined above with one or more hydrogen atoms replaced with carbocycle. Examples of carbocyclealkyl groups include, but are not limited to, benzyl and the like.

As used herein, "heterocycle" or "heterocyclyl" groups include aromatic and non-aromatic ring compounds (heterocyclic rings) containing 3 or more ring members, of which one or more is a heteroatom such as, but not limited to, N, O, S, or P. A heterocycle group as defined herein can be a heteroaryl group or a partially or completely saturated cyclic group including at least one ring heteroatom. In some embodiments, heterocycle groups include 3 to 20 ring members, whereas other such groups have 3 to 15 ring members. At least one ring contains a heteroatom, but every ring in a polycyclic system need not contain a heteroatom. For example, a dioxolanyl ring and a benzodioxolanyl ring system (methylenedioxyphenyl ring system) are both heterocycle groups within the meaning herein. A heterocycle group designated as a $C_2$-heterocycle can be a 5-membered ring with two carbon atoms and three heteroatoms, a 6-membered ring with two carbon atoms and four heteroatoms and so forth. Likewise, a $C_4$-heterocycle can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

"Heteroaryl" groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise, a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl.

"Heterocyclealkyl" refers to an alkyl as defined above with one or more hydrogen atoms replaced with heterocycle. Examples of heterocyclealkyl groups include, but are not limited to, morpholinoethyl and the like.

"Halo" or "halogen" refers to fluorine, chlorine, bromine and iodine.

"Haloalkyl" refers to an alkyl as defined above with one or more hydrogen atoms replaced with halogen. Examples of lower haloalkyl groups include, but are not limited to, $-CF_3$, $-CH_2CF_3$, and the like.

"Haloalkoxy" refers to an alkoxy as defined above with one or more hydrogen atoms replaced with halogen. Examples of lower haloalkoxy groups include, but are not limited to $-OCF_3$, $-OCH_2CF_3$, and the like.

"Hydroxyalkyl" refers to an alkyl as defined above with one or more hydrogen atoms replaced with $-OH$. Examples of lower hydroxyalkyl groups include, but are not limited to $-CH_2OH$, $-CH_2CH_2OH$, and the like.

As used herein, the term "optionally substituted" refers to a group (e.g., an alkyl, carbocycle, or heterocycle) having 0, 1, or more substituents, such as 0-25, 0-20, 0-10 or 0-5 substituents. Substituents include, but are not limited to $-OR^a$, $-NR^aR^b$, $-S(O)_2R^a$ or $-S(O)_2OR^a$, halogen, cyano, alkyl, haloalkyl, alkoxy, carbocycle, heterocycle, carbocyclalkyl, or heterocyclealkyl, wherein each $R^a$ and $R^b$ is, independently, H, alkyl, haloalkyl, carbocycle, or heterocycle, or $R^a$ and $R^b$, together with the atom to which they are attached, form a 3-8 membered carbocycle or heterocycle.

"Isomer" is used herein to encompass all chiral, diastereomeric or racemic forms of a structure, unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized to be substantially free of their enantiomeric or diastereomeric partners, and these are all within the scope of certain embodiments of the disclosure. The isomers resulting from the presence of a chiral center comprise a pair of non-superimposable isomers that are called "enantiomers." Single enantiomers of a pure compound are optically active (i.e., they can rotate the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out).

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrans, and an isotope of a compound of Formula (I) includes any such compound wherein one or more atoms are replaced by an isotope of that atom. For example, carbon 12, the most common form of carbon, has six protons and six neutrans, whereas carbon 13 has six protons and seven neutrans, and carbon 14 has six protons and eight neutrans. Hydrogen has two stable isotopes, deuterium (one proton and one neutron) and tritium (one proton and two neutrans). While fluorine has several isotopes, fluorine 19 is longest-lived. Thus, an isotope of a compound having the structure of Formula (I) includes, but not limited to, compounds of Formula (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, Int. J. Pharm., 33, 201-217, 1986) (incorporated by reference herein).

Pharmaceutically acceptable base addition salts of compounds of the disclosure include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, -galactaric, and galacturonic acid.

Although pharmaceutically unacceptable salts are not generally useful as medicaments, such salts may be useful, for example as intermediates in the synthesis of the compounds described herein, for example in their purification by recrystallization.

In certain embodiments, the disclosure provides a pharmaceutical composition comprising a compound as described herein, or a pharmaceutically acceptable isomer, racemate, hydrate, solvate, isotope, or salt thereof, together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, homolog or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

In other embodiments, there are provided methods of making a composition of a compound described herein including formulating a compound of the disclosure with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

As used herein, the term "pharmaceutically acceptable carrier" refers to any ingredient other than the disclosed compounds, or a pharmaceutically acceptable isomer, racemate, hydrate, solvate, homolog or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the disclosure to the appropriate or desired site of action, such as oral, nasal, pulmonary, buccal, subdermal, intradermal, transdermal, or parenteral, e.g., rectal, depot, subcutaneous, intravenous, intraurethral, intramuscular, intranasal, ophthalmic solution, or an ointment, the oral route being preferred.

Dosage forms can be administered once a day, or more than once a day, such as twice or thrice daily. Alternatively, dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the Physicians' Desk Reference, incorporated herein by reference.

As used herein, the term "administering" or "administration" refers to providing a compound, a pharmaceutical composition comprising the same, to a subject by any acceptable means or route, including (for example) by oral, parenteral (e.g., intravenous), or topical administration.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a neurodegenerative disease involving demyelination, insufficient myelination, or underdevelopment of a myelin sheath, e.g., a subject diagnosed with multiple sclerosis or cerebral palsy, or one at risk of developing the condition. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the term "effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

As used herein, the terms "modulate" or "modulating" refer to the ability to increase or decrease the activity of one or more protein kinases. Accordingly, compounds of the invention can be used in methods of modulating a protein kinase by contacting the protein kinase with any one or more of the compounds or compositions described herein. In some embodiments, the compounds can act as inhibitors of one or more protein kinases. In some embodiments, the compounds can act to stimulate the activity of one or more protein kinases. In further embodiments, the compounds of the invention can be used to modulate activity of a protein kinase in an individual in need of modulation of the receptor by administering a modulating amount of a compound as described herein.

As used herein, the term "BTK-mediated" or BTK-modulated or "BTK-dependent" diseases or disorders means any disease or other deleterious condition in which BTK, or a mutant thereof, is known to play a role. Accordingly, another embodiment of the present application relates to treating or lessening the severity of one or more diseases in which BTK, or a mutant thereof, is known to play a role. Specifically, the present application relates to a method of treating or lessening the severity of a disease or condition selected from a proliferative disorder or an autoimmune disorder, wherein said method comprises administering to a patient in need thereof a compounds of Formula (I) or a composition according to the present application.

Compounds

Disclosed herein are compounds having the structure of formula (I):

Formula (I)

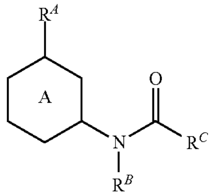

or a pharmaceutically acceptable salt, solvate, hydrate, isomer, tautomer, racemate or isotope thereof, wherein:

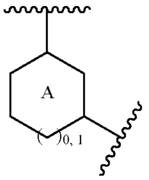

is

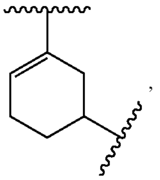

,

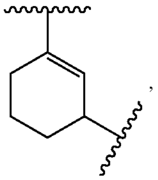

,

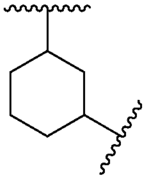

or

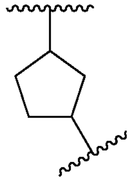

$R^B$ is —H or -Me;

$R^C$ is —CH═CH$_2$, —C≡CH or —C≡C—CH$_3$;

$R^A$ is

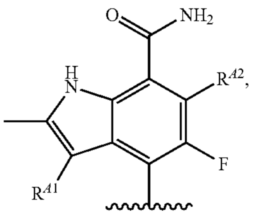

wherein $R^{A1}$ is —H, —F, —Cl, —CH$_3$, or —CN; and $R^{A2}$ is —H or —F.

In some embodiments, the compounds have the structure of Formula (IA):

Formula (IA)

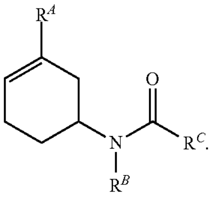

In other embodiments, the compounds have the structure of Formula I-A-(S) or I-A-(R):

Formula I-A-(S)

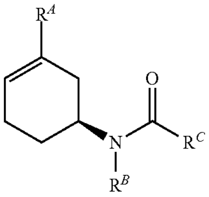

Formula I-A-(R)

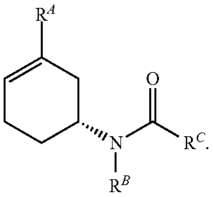

In some embodiments, the compounds have the structure of Formula (IB):

Formula (IB)

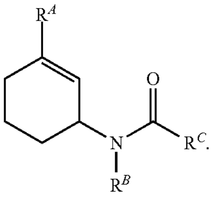

In other embodiments, the compounds have the structure of Formula I-B-(S) or I-B-(R):

Formula I-B-(S)

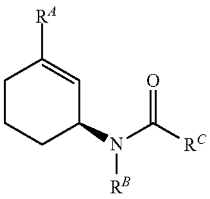

-continued

Formula I-B-(R)

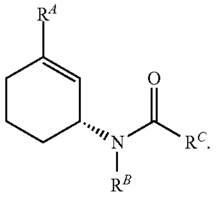

In some embodiments, the compounds have the structure of Formula (IC):

Formula (IC)

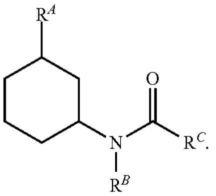

In other embodiments, the compounds have the structure of Formula I-C-(S) or I-C-(R):

Formula I-C-(S)

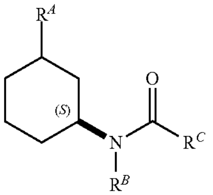

Formula I-C-(R)

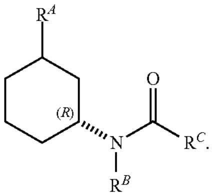

In yet other embodiments, the compounds have the structure of Formula I-C-(1R,3S), 1-C-(1S,3R), 1-C-(1R,3R) or 1-C-(1S,3S):

1-C-(1R,3S)

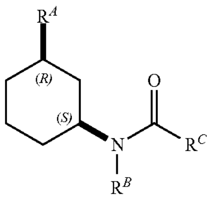

-continued

1-C-(1S,3R)

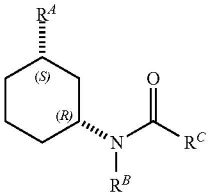

1-C-(1R,3R)

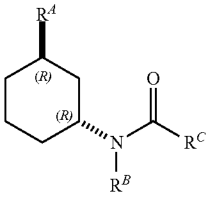

1-C-(1S,3S)

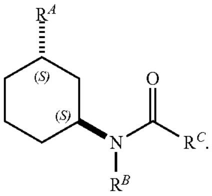

In some embodiments, the compounds have the structure of Formula (ID):

Formula (ID)

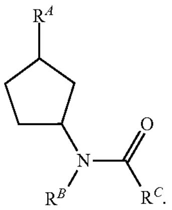

In other embodiments, the compounds have the structure of Formula 1-D-(1R,3S), 1-D-(1S,3R), 1-D-(1R,3R) or 1-D-(1S,3S):

1-D-(1R,3R)

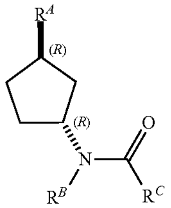

1-D-(1R,3S)

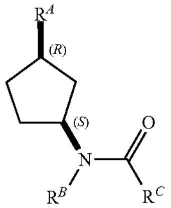

-continued

1-D-(1S,3R)

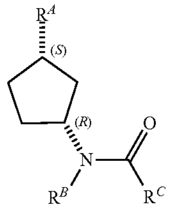

1-D-(1S,3S)

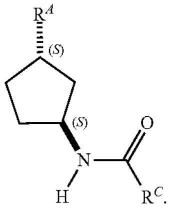

In some embodiments, $R^B$ is H. In other embodiments $R^B$ is Me.

In some embodiments, $R^C$ is —CH═$CH_2$. In other embodiments $R^C$ is —C≡C—$CH_3$. In other embodiments $R^C$ is —C≡CH. In other embodiments $R^C$ is —CH═$CH_2$ or —C≡C—$CH_3$.

In some embodiments, $R^{A1}$ is —F. In other embodiments, $R^{A1}$ is —Cl. In other embodiments, $R^{A1}$ is —$CH_3$. In other embodiments, $R^{A1}$ is —CN. In other embodiments, $R^{A1}$ is —F or —Cl. In other embodiments, $R^{A1}$ is —F, —Cl or —CN. In other embodiments, $R^{A1}$ is H.

In some embodiments, $R^{A2}$ is —H. In other embodiments $R^{A2}$ is —F.

In some embodiments, $R^{A1}$ is —Cl or —CN; and $R^C$ is —C≡C—$CH_3$. In some embodiments, $R^{A1}$ is —Cl; $R^{A2}$ is —H and $R^C$ is —C≡C—$CH_3$. In some embodiments, $R^{A1}$ is —CN, $R^{A2}$ is —F and $R^C$ is —C≡C—$CH_3$.

In some embodiments, the compound is a salt of a compound having the structure of Formula (I). In other embodiments, the salt is a pharmaceutically acceptable salt. In some embodiments, the compound is a solvate of a compound having the structure of Formula (I). In some embodiments, the compound is a hydrate of a compound having the structure of Formula (I). In some embodiments, the compound is an isomer of a compound having the structure of Formula (I). In some embodiments, the compound is a tautomer of a compound having the structure of Formula (I). In some embodiments, the compound is an isotope of a compound having the structure of Formula (I).

In some embodiments, the compound having the structure of Formula (I) exists as a mixture of isomers. In some embodiments, the compound having the structure of Formula (I) exists as a 50/50 mixture of isomers. In some embodiments, the compound having the structure of Formula (I) exists as a mixture of isomers, wherein one isomer is present in greater amounts than the other isomer. In some embodiments, the compound having the structure of Formula (I) exists as a racemic mixture.

In some embodiments, the compound having the structure of Formula (I) exists as a single isomer. In some embodiments, the isomers are cis-isomers. In some embodiments, the isomers are trans-isomers.

In some embodiments, the compound having the structure of Formula (I) exists as a single enantiomer. In some embodiments, the isomers are enantiomers. In some embodiments, the isomer is the (1R, 3S) isomer. In some embodiments, the isomer is the (1R, 3R) isomer. In some embodiments, the isomer is the (1S, 3S) isomer. In some embodiments, the isomer is the (1S, 3R) isomer.

Also provided herein are pharmaceutical compositions comprising a compound of formula (I), or a pharmaceutically acceptable salt, solvate, hydrate, isomer, tautomer, racemate, or isotope thereof, and at least one pharmaceutically acceptable excipient.

Further provided herein are methods of inhibiting a protein kinase comprising contacting the protein kinase with an effective amount of a compound of formula (I), or a pharmaceutically acceptable salt, solvate, hydrate, isomer, tautomer, racemate, isotope, or pharmaceutical composition thereof. In some embodiments, the protein kinase is BTK.

Also provided herein are methods for treating a BTK dependent condition, comprising administering to a subject in need thereof, an effective amount of a compound of formula (I), or a pharmaceutically acceptable salt, solvate, hydrate, isomer, tautomer, racemate, isotope, or pharmaceutical composition thereof. In some embodiments, the BTK dependent condition is cancer, an autoimmune disease, an inflammatory disease, or a theromboembolic disease.

In some embodiments, the autoimmune disease is multiple sclerosis, rheumatoid arthritis, psoriasis, Sjogren's syndrome, or systemic lupus erythematosus. In some embodiments, the inflammatory disease is urticaria.

Also provided herein are uses of a compound of formula (I), or a pharmaceutically acceptable salt, solvate, hydrate, isomer, tautomer, racemate, isotope, or pharmaceutical composition thereof, in the manufacture of a medicament. In some embodiments, the medicament is for the treatment of cancer, an autoimmune disease, an inflammatory disease, or a theromboembolic disease. In some embodiments, the autoimmune disease is multiple sclerosis, rheumatoid arthritis, psoriasis, Sjogren's syndrome, or systemic lupus erythematosus. In some embodiments, the inflammatory disease is urticaria.

In one embodiment, a compound of Formula (IA) is provided, or a pharmaceutically acceptable salt, solvate, hydrate, isomer, tautomer, racemate, or isotope thereof, having the structure of a compound of Table 1.

Formula (IA)

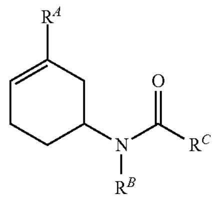

TABLE 1
| Compounds of Formula (IA) | |
|---|---|
| Structure | Name |
| 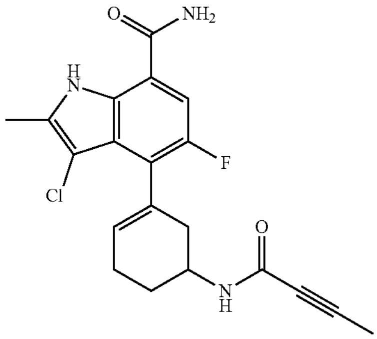 [SMILES: CC#CC(=O)NC1CCC=C(c2c(F)cc(C(N)=O)c3[nH]c(C)c(Cl)c23)C1] | 4-(5-(but-2-ynamido)cyclohex-1-en-1-yl)-3-chloro-5-fluoro-2-methyl-1H-indole-7-carboxamide |
| 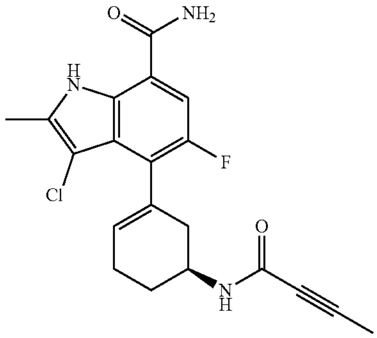 [SMILES: CC#CC(=O)N[C@H]1CCC=C(c2c(F)cc(C(N)=O)c3[nH]c(C)c(Cl)c23)C1] | (S)-4-(5-(but-2-ynamido)cyclohex-1-en-1-yl)-3-chloro-5-fluoro-2-methyl-1H-indole-7-carboxamide |
| 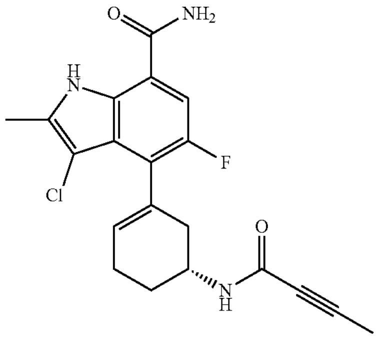 [SMILES: CC#CC(=O)N[C@@H]1CCC=C(c2c(F)cc(C(N)=O)c3[nH]c(C)c(Cl)c23)C1] | (R)-4-(5-(but-2-ynamido)cyclohex-1-en-1-yl)-3-chloro-5-fluoro-2-methyl-1H-indole-7-carboxamide |
| 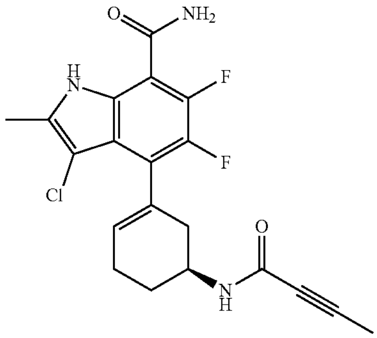 [SMILES: CC#CC(=O)N[C@H]1CCC=C(c2c(F)c(F)c(C(N)=O)c3[nH]c(C)c(Cl)c23)C1] | (S)-4-(5-(but-2-ynamido)cyclohex-1-en-1-yl)-3-chloro-5,6-difluoro-2-methyl-1H-indole-7-carboxamide |

TABLE 1-continued
| Compounds of Formula (IA) | |
|---|---|
| Structure | Name |
| 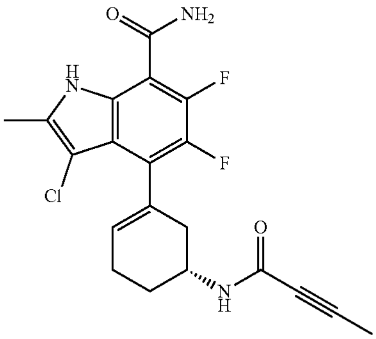 [SMILES: CC#CC(=O)N[C@@H]1CCC=C(c2c(F)c(F)c(C(N)=O)c3[nH]c(C)c(Cl)c23)C1] | (R)-4-(5-(but-2-ynamido)cyclohex-1-en-1-yl)-3-chloro-5,6-difluoro-2-methyl-1H-indole-7-carboxamide |
| 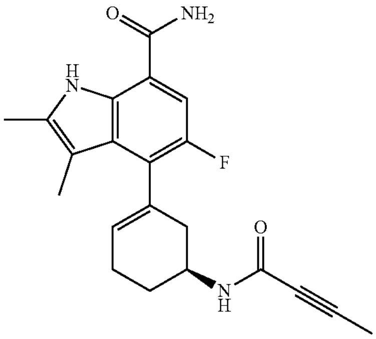 [SMILES: CC#CC(=O)N[C@H]1CCC=C(c2c(F)cc(C(N)=O)c3[nH]c(C)c(C)c23)C1] | (S)-4-(5-(but-2-ynamido)cyclohex-1-en-1-yl)-5-fluoro-2,3-dimethyl-1H-indole-7-carboxamide |
| 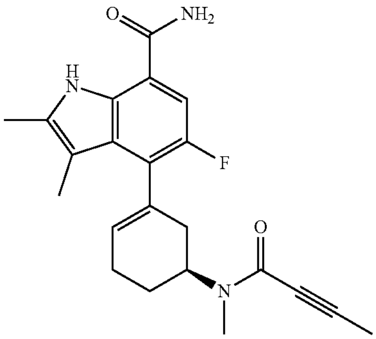 [SMILES: CC#CC(=O)N(C)[C@H]1CCC=C(c2c(F)cc(C(N)=O)c3[nH]c(C)c(C)c23)C1] | (S)-5-fluoro-2,3-dimethyl-4-(5-(N-methylbut-2-ynamido)cyclohex-1-en-1-yl)-1H-indole-7-carboxamide |
| 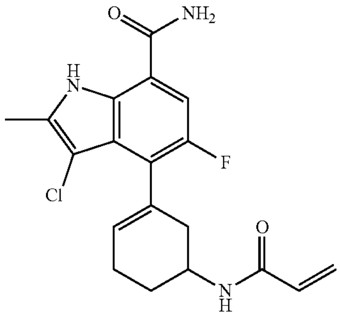 [SMILES: C=CC(=O)NC1CCC=C(c2c(F)cc(C(N)=O)c3[nH]c(C)c(Cl)c23)C1] | 4-(5-acrylamidocyclohex-1-en-1-yl)-3-chloro-5-fluoro-2-methyl-1H-indole-7-carboxamide |

TABLE 1-continued
| Compounds of Formula (IA) | |
|---|---|
| Structure | Name |
| 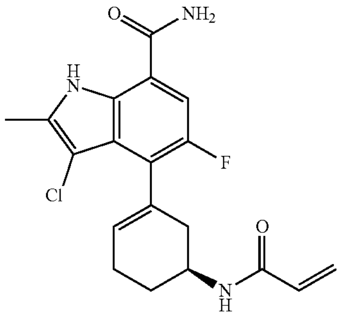 [SMILES: C=CC(=O)N[C@H]1CCC=C(c2c(F)cc(C(N)=O)c3[nH]c(C)c(Cl)c23)C1] | (S)-4-(5-acrylamidocyclohex-1-en-1-yl)-3-chloro-5-fluoro-2-methyl-1H-indole-7-carboxamide |
| 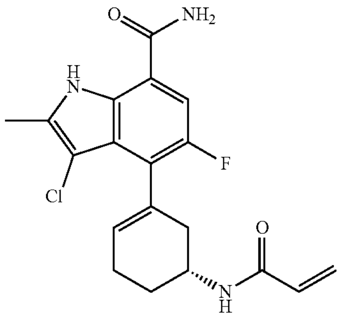 [SMILES: C=CC(=O)N[C@@H]1CCC=C(c2c(F)cc(C(N)=O)c3[nH]c(C)c(Cl)c23)C1] | (R)-4-(5-acrylamidocyclohex-1-en-1-yl)-3-chloro-5-fluoro-2-methyl-1H-indole-7-carboxamide |
| 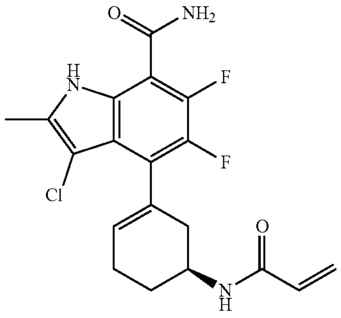 [SMILES: C=CC(=O)N[C@H]1CCC=C(c2c(F)c(F)c(C(N)=O)c3[nH]c(C)c(Cl)c23)C1] | (S)-4-(5-acrylamidocyclohex-1-en-1-yl)-3-chloro-5,6-difluoro-2-methyl-1H-indole-7-carboxamide |
| 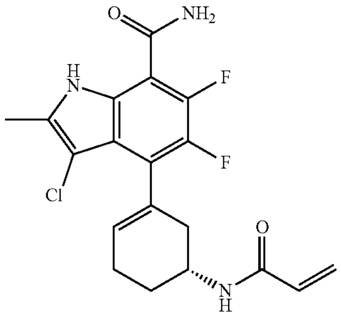 [SMILES: C=CC(=O)N[C@@H]1CCC=C(c2c(F)c(F)c(C(N)=O)c3[nH]c(C)c(Cl)c23)C1] | (R)-4-(5-acrylamidocyclohex-1-en-1-yl)-3-chloro-5,6-difluoro-2-methyl-1H-indole-7-carboxamide |

TABLE 1-continued

| Compounds of Formula (IA) | |
|---|---|
| Structure | Name |
| 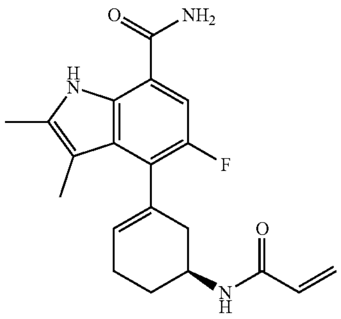 [SMILES: C=CC(=O)N[C@H]1CCC=C(c2c(F)cc(C(N)=O)c3[nH]c(C)c(C)c23)C1] | (S)-4-(5-acrylamidocyclohex-1-en-1-yl)-5-fluoro-2,3-dimethyl-1H-indole-7-carboxamide |
| 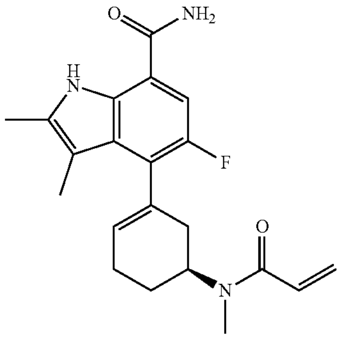 [SMILES: C=CC(=O)N(C)[C@H]1CCC=C(c2c(F)cc(C(N)=O)c3[nH]c(C)c(C)c23)C1] | (S)-5-fluoro-2,3-dimethyl-4-(5-(N-methylacrylamido)cyclohex-1-en-1-yl)-1H-indole-7-carboxamide |

In another embodiment, a compound of Formula (IB) is provided, or a pharmaceutically acceptable salt, solvate, hydrate, isomer, tautomer, racemate, or isotope thereof, having the structure of a compound of Table 2.

Formula (IB)

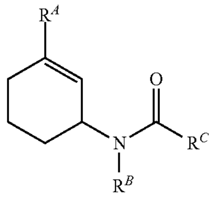

TABLE 2

| Compounds of Formula (IB) | |
|---|---|
| Structure | Name |
| 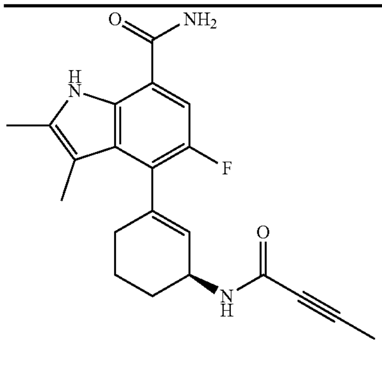 | (S)-4-(3-(but-2-ynamido)cyclohex-1-en-1-yl)-5-fluoro-2,3-dimethyl-1H-indole-7-carboxamide |

TABLE 2-continued
| Compounds of Formula (IB) | |
|---|---|
| Structure | Name |
| 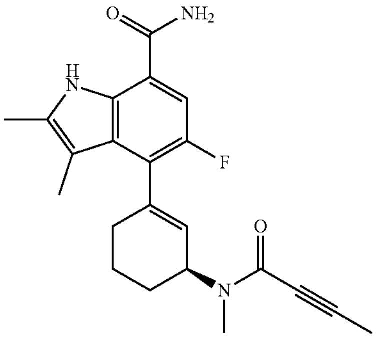 [SMILES: CC#CC(=O)N(C)[C@@H]1C=C(c2c(F)cc(C(N)=O)c3[nH]c(C)c(C)c23)CCC1] | (S)-5-fluoro-2,3-dimethyl-4-(3-(N-methylbut-2-ynamido)cyclohex-1-en-1-yl)-1H-indole-7-carboxamide |
| 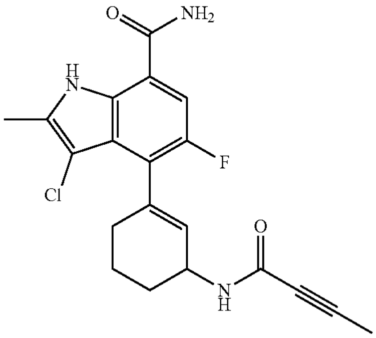 [SMILES: CC#CC(=O)NC1C=C(c2c(F)cc(C(N)=O)c3[nH]c(C)c(Cl)c23)CCC1] | 4-(3-(but-2-ynamido)cyclohex-1-en-1-yl)-3-chloro-5-fluoro-2-methyl-1H-indole-7-carboxamide |
| 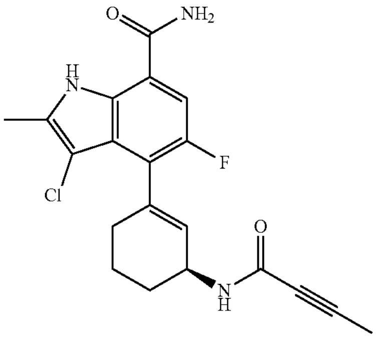 [SMILES: CC#CC(=O)N[C@@H]1C=C(c2c(F)cc(C(N)=O)c3[nH]c(C)c(Cl)c23)CCC1] | 4-(3-(but-2-ynamido)cyclohex-1-en-1-yl)-3-chloro-5-fluoro-2-methyl-1H-indole-7-carboxamide |
| 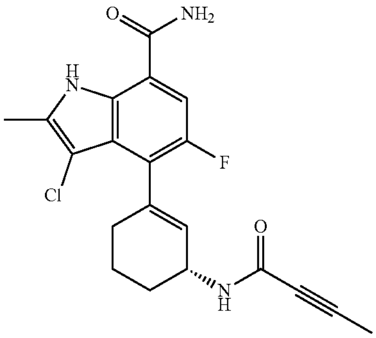 [SMILES: CC#CC(=O)N[C@H]1C=C(c2c(F)cc(C(N)=O)c3[nH]c(C)c(Cl)c23)CCC1] | (R)-4-(3-(but-2-ynamido)cyclohex-1-en-1-yl)-3-chloro-5-fluoro-2-methyl-1H-indole-7-carboxamide |

TABLE 2-continued
| Compounds of Formula (IB) | |
|---|---|
| Structure | Name |
| 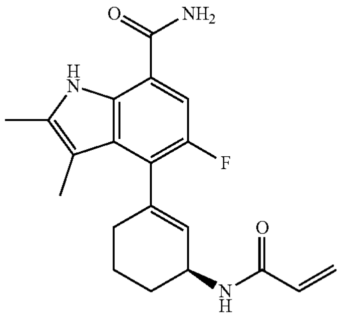 [SMILES: C=CC(=O)N[C@@H]1C=C(c2c(F)cc(C(N)=O)c3[nH]c(C)c(C)c23)CCC1] | (S)-4-(3-acrylamidocyclohex-1-en-1-yl)-5-fluoro-2,3-dimethyl-1H-indole-7-carboxamide |
| 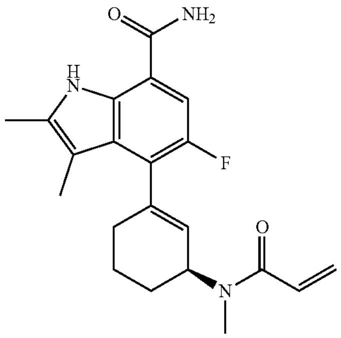 [SMILES: C=CC(=O)N(C)[C@@H]1C=C(c2c(F)cc(C(N)=O)c3[nH]c(C)c(C)c23)CCC1] | (S)-5-fluoro-2,3-dimethyl-4-(3-(N-methylacrylamido)cyclohex-1-en-1-yl)-1H-indole-7-carboxamide |
| 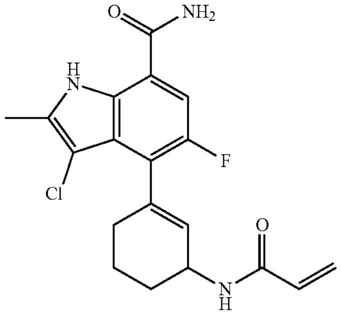 [SMILES: C=CC(=O)NC1C=C(c2c(F)cc(C(N)=O)c3[nH]c(C)c(Cl)c23)CCC1] | 4-(3-acrylamidocyclohex-1-en-1-yl)-3-chloro-5-fluoro-2-methyl-1H-indole-7-carboxamide |
| 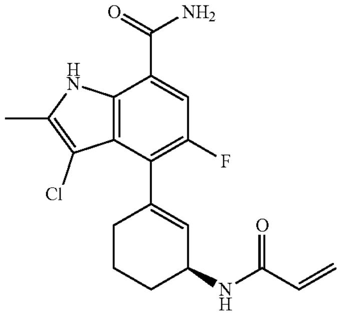 [SMILES: C=CC(=O)N[C@@H]1C=C(c2c(F)cc(C(N)=O)c3[nH]c(C)c(Cl)c23)CCC1] | (S)-4-(3-acrylamidocyclohex-1-en-1-yl)-3-chloro-5-fluoro-2-methyl-1H-indole-7-carboxamide |

TABLE 2-continued

| Compounds of Formula (IB) | |
|---|---|
| Structure | Name |
| 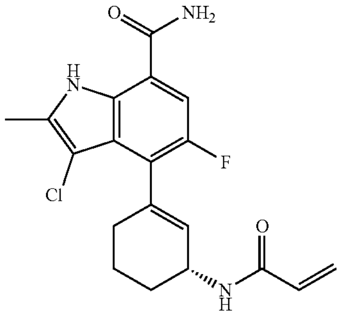 [SMILES: C=CC(=O)N[C@H]1C=C(c2c(F)cc(C(N)=O)c3[nH]c(C)c(Cl)c23)CCC1] | (R)-4-(3-acrylamidocyclohex-1-en-1-yl)-3-chloro-5-fluoro-2-methyl-1H-indole-7-carboxamide |

In yet another embodiment, a compound of Formula (IC) is provided, or a pharmaceutically acceptable salt, solvate, hydrate, isomer, tautomer, racemate, or isotope thereof, having the structure of a compound of Table 3.

Formula (IC)

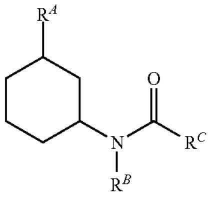

TABLE 3

| Compounds of Formula (IC) | |
|---|---|
| Structure | Name |
| 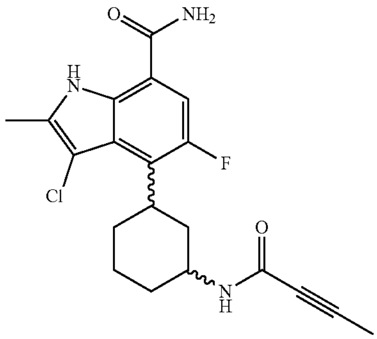 [SMILES: CC#CC(=O)NC1CCCC(c2c(F)cc(C(N)=O)c3[nH]c(C)c(Cl)c23)C1] | 4-(3-(but-2-ynamido)cyclohexyl)-3-chloro-5-fluoro-2-methyl-1H-indole-7-carboxamide |

TABLE 3-continued
| Compounds of Formula (IC) | |
|---|---|
| Structure | Name |
| 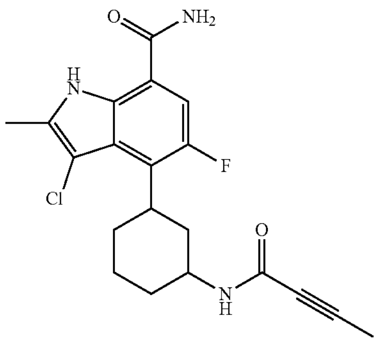 [SMILES: CC#CC(=O)NC1CCCC(c2c(F)cc(C(N)=O)c3[nH]c(C)c(Cl)c23)C1] | cis-4-(3-(but-2-ynamido)cyclohexyl)-3-chloro-5-fluoro-2-methyl-1H-indole-7-carboxamide |
| 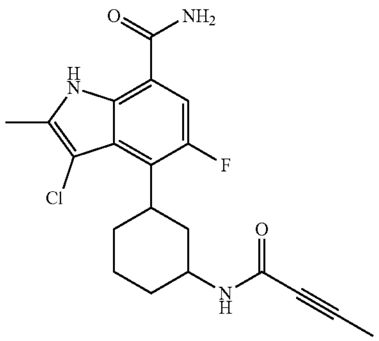 [SMILES: CC#CC(=O)NC1CCCC(c2c(F)cc(C(N)=O)c3[nH]c(C)c(Cl)c23)C1] | trans-4-(3-(but-2-ynamido)cyclohexyl)-3-chloro-5-fluoro-2-methyl-1H-indole-7-carboxamide |
| 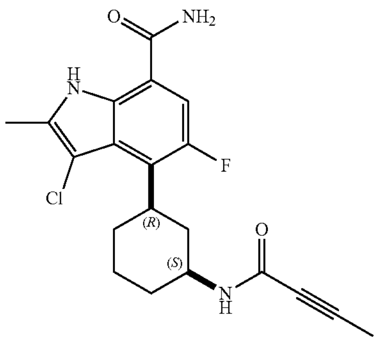 | 4-((1R,3S)-3-(but-2-ynamido)cyclohexyl)-3-chloro-5-fluoro-2-methyl-1H-indole-7-carboxamide |
| 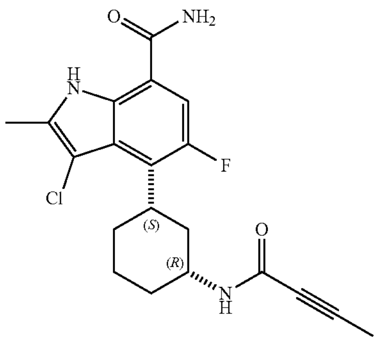 | 4-((1S,3R)-3-(but-2-ynamido)cyclohexyl)-3-chloro-5-fluoro-2-methyl-1H-indole-7-carboxamide |

TABLE 3-continued
Compounds of Formula (IC)
| Structure | Name |
| --- | --- |
| 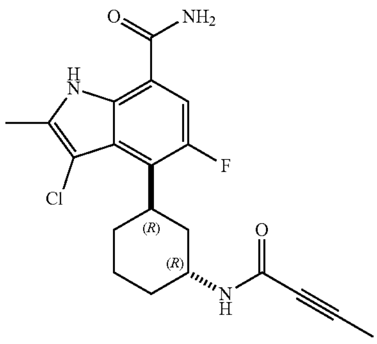 | 4-((1R,3R)-3-(but-2-ynamido)cyclohexyl)-3-chloro-5-fluoro-2-methyl-1H-indole-7-carboxamide |
| 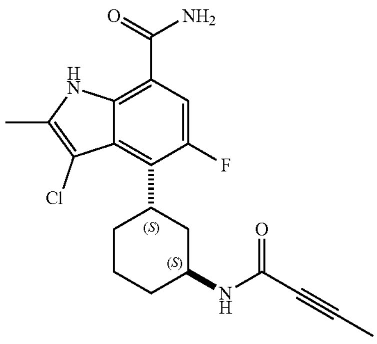 | 4-((1S,3S)-3-(but-2-ynamido)cyclohexyl)-3-chloro-5-fluoro-2-methyl-1H-indole-7-carboxamide |
| 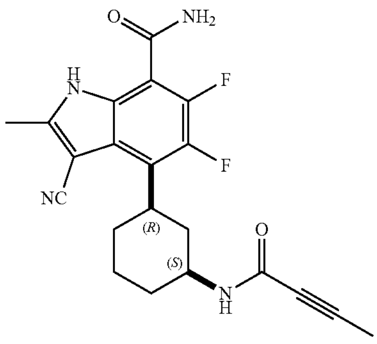 | 4-((1R,3S)-3-(but-2-ynamido)cyclohexyl)-3-cyano-5,6-difluoro-2-methyl-1H-indole-7-carboxamide |
| 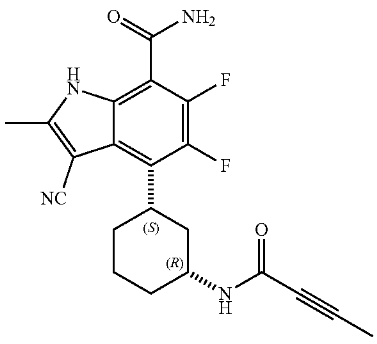 | 4-((1S,3R)-3-(but-2-ynamido)cyclohexyl)-3-cyano-5,6-difluoro-2-methyl-1H-indole-7-carboxamide |

TABLE 3-continued
| Compounds of Formula (IC) | |
|---|---|
| Structure | Name |
| 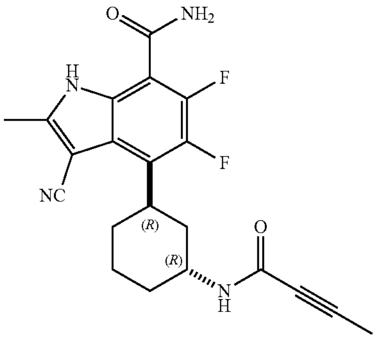 | 4-((1R,3R)-3-(but-2-ynamido)cyclohexyl)-3-cyano-5,6-difluoro-2-methyl-1H-indole-7-carboxamide |
| 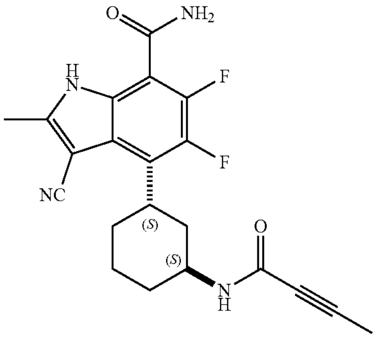 | 4-((1S,3S)-3-(but-2-ynamido)cyclohexyl)-3-cyano-5,6-difluoro-2-methyl-1H-indole-7-carboxamide |
| 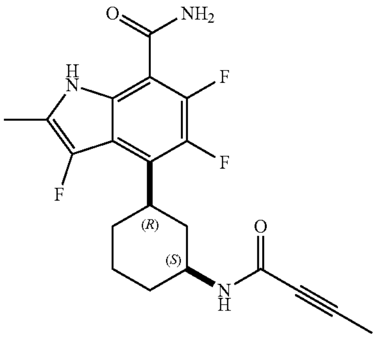 | 4-((1R,3S)-3-(but-2-ynamido)cyclohexyl)-3,5,6-trifluoro-2-methyl-1H-indole-7-carboxamide |
| 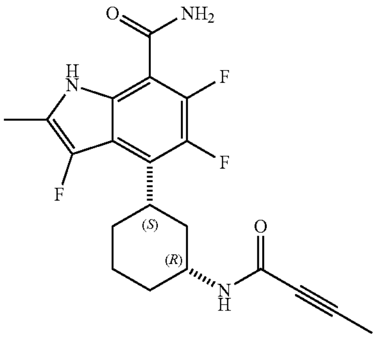 | 4-((1S,3R)-3-(but-2-ynamido)cyclohexyl)-3,5,6-trifluoro-2-methyl-1H-indole-7-carboxamide |

TABLE 3-continued
| Compounds of Formula (IC) | |
|---|---|
| Structure | Name |
| 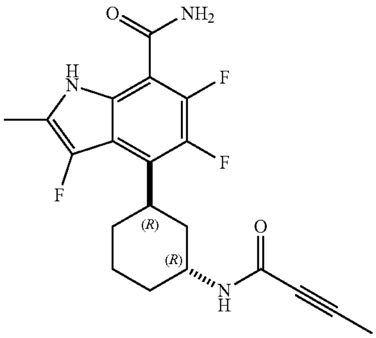 | 4-((1R,3R)-3-(but-2-ynamido)cyclohexyl)-3,5,6-trifluoro-2-methyl-1H-indole-7-carboxamide |
| 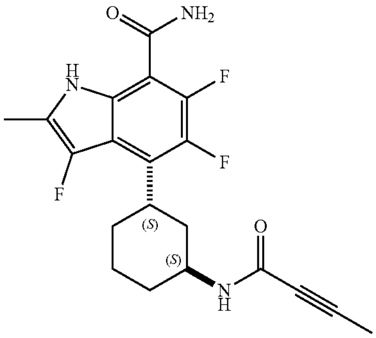 | 4-((1S,3S)-3-(but-2-ynamido)cyclohexyl)-3,5,6-trifluoro-2-methyl-1H-indole-7-carboxamide |
| 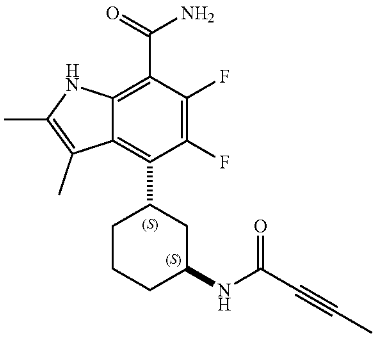 | 4-((1S,3S)-3-(but-2-ynamido)cyclohexyl)-5,6-difluoro-2,3-dimethyl-1H-indole-7-carboxamide |
| 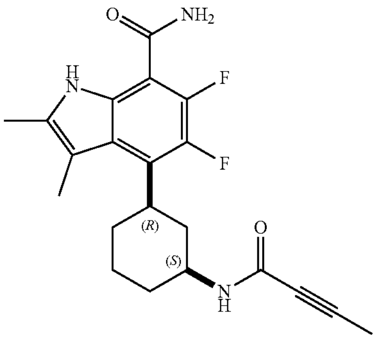 | 4-((1R,3S)-3-(but-2-ynamido)cyclohexyl)-5,6-difluoro-2,3-dimethyl-1H-indole-7-carboxamide |

TABLE 3-continued
| Compounds of Formula (IC) | |
|---|---|
| Structure | Name |
| 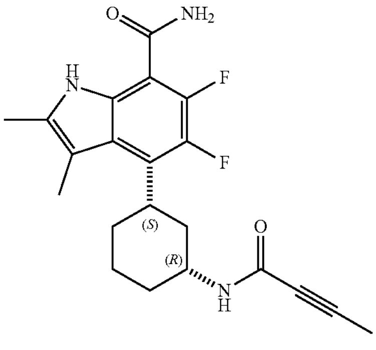 | 4-((1S,3R)-3-(but-2-ynamido)cyclohexyl)-5,6-difluoro-2,3-dimethyl-1H-indole-7-carboxamide |
| 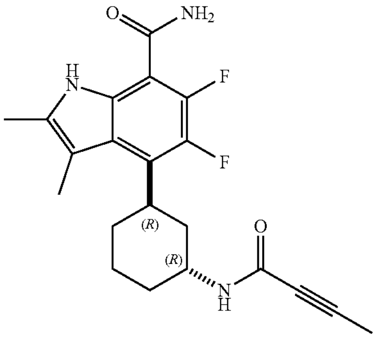 | 4-((1R,3R)-3-(but-2-ynamido)cyclohexyl)-5,6-difluoro-2,3-dimethyl-1H-indole-7-carboxamide |
| 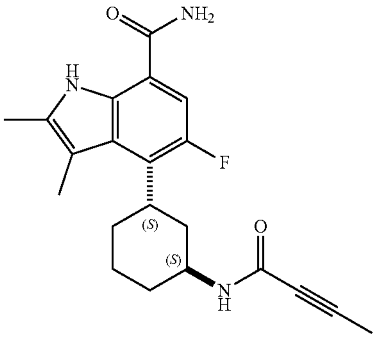 | 4-((1S,3S)-3-(but-2-ynamido)cyclohexyl)-5-fluoro-2,3-dimethyl-1H-indole-7-carboxamide |
| 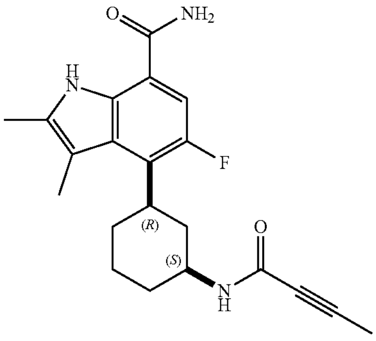 | 4-((1R,3S)-3-(but-2-ynamido)cyclohexyl)-5-fluoro-2,3-dimethyl-1H-indole-7-carboxamide |

TABLE 3-continued
| Compounds of Formula (IC) | |
|---|---|
| Structure | Name |
| 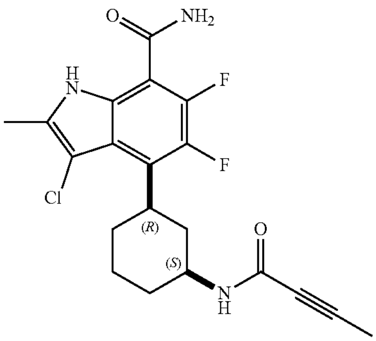 | 4-((1R,3S)-3-(but-2-ynamido)cyclohexyl)-3-chloro-5,6-difluoro-2-methyl-1H-indole-7-carboxamide |
| 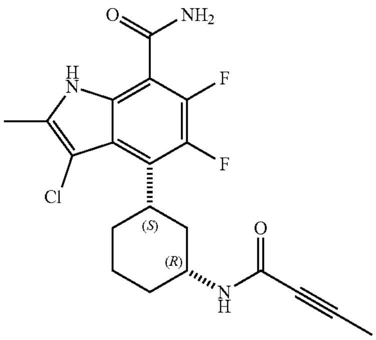 | 4-((1S,3R)-3-(but-2-ynamido)cyclohexyl)-3-chloro-5,6-difluoro-2-methyl-1H-indole-7-carboxamide |
| 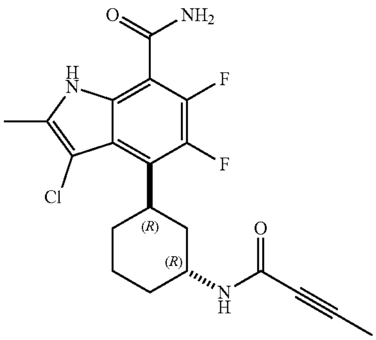 | 4-((1R,3R)-3-(but-2-ynamido)cyclohexyl)-3-chloro-5,6-difluoro-2-methyl-1H-indole-7-carboxamide |
| 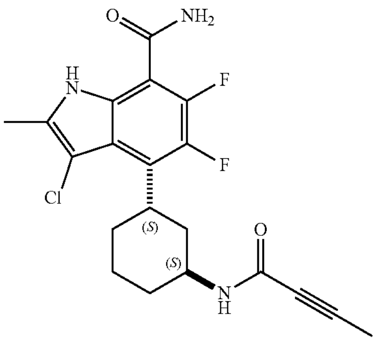 | 4-((1S,3S)-3-(but-2-ynamido)cyclohexyl)-3-chloro-5,6-difluoro-2-methyl-1H-indole-7-carboxamide |

In yet another embodiment, a compound of Formula (ID) is provided, or a pharmaceutically acceptable salt, solvate, hydrate, isomer, tautomer, racemate, or isotope thereof, having the structure of a compound of Table 4.

Formula (ID)

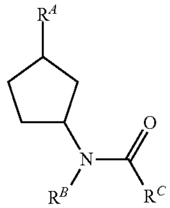

TABLE 4

| Compounds of Formula (ID) | |
|---|---|
| Structure | Name |
| 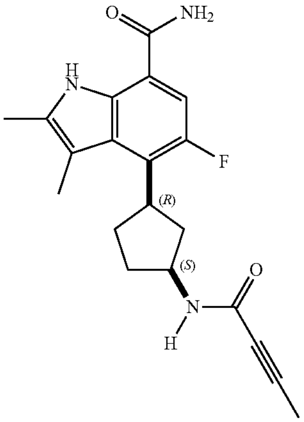 | 4-((1R,3S)-3-(but-2-ynamido)cyclopentyl)-5-fluoro-2,3-dimethyl-1H-indole-7-carboxamide |
| 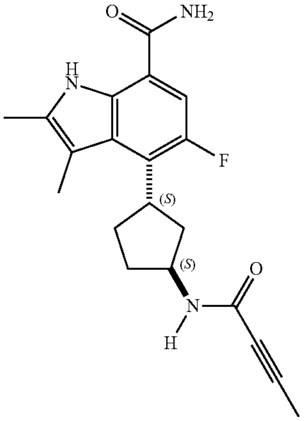 | 4-((1S,3S)-3-(but-2-ynamido)cyclopentyl)-5-fluoro-2,3-dimethyl-1H-indole-7-carboxamide |

TABLE 4-continued

| Compounds of Formula (ID) | |
|---|---|
| Structure | Name |
| 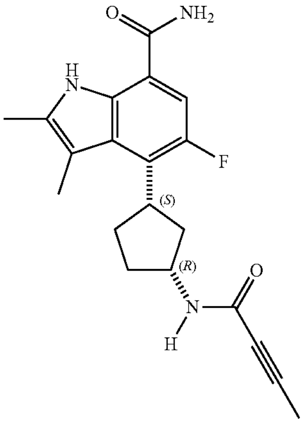 | 4-((1S,3R)-3-(but-2-ynamido)cyclopentyl)-5-fluoro-2,3-dimethyl-1H-indole-7-carboxamide |
| 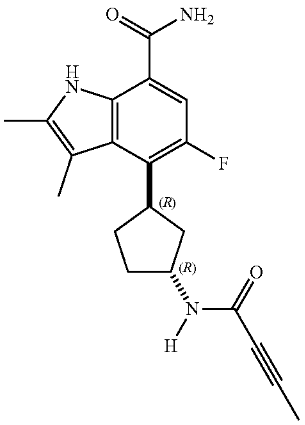 | 4-((1R,3R)-3-(but-2-ynamido)cyclopentyl)-5-fluoro-2,3-dimethyl-1H-indole-7-carboxamide |

In further embodiments are pharmaceutically acceptable salts of compounds of formula (I). In other embodiments are solvates of compounds of formula (I). In other embodiments are hydrates of compounds of formula (I). In other embodiments are isomers of compounds of formula (I). In other embodiments are tautomers of compounds of formula (I). In other embodiments are racemates of compounds of formula (I). In other embodiments are isotopic forms of compounds of formula (I).

In further embodiments, are pharmaceutical compositions comprising a compound of Formula (I), and at least one pharmaceutically acceptable excipient.

Diseases

Described herein is a method of inhibiting a protein kinase comprising contacting the protein kinase with an effective amount of a compound of Formula (I), or a pharmaceutically acceptable salt, solvate, hydrate, isomer, tautomer, racemate, isotope, or pharmaceutical composition thereof. In some embodiments, the protein kinase is BTK.

Also described herein are methods for treating a BTK dependent condition, comprising administering to a subject in need thereof, an effective amount of a compound of Formula (I), or a pharmaceutically acceptable salt, solvate, hydrate, isomer, tautomer, racemate, isotope, or pharmaceutical composition thereof.

In some embodiments the BTK dependent condition is cancer, an autoimmune disease, an inflammatory disease, or a theromboembolic disease. In some embodiments the autoimmune disease is multiple sclerosis, rheumatoid arthritis, psoriasis, Sjogren's syndrome, or systemic lupus erythematosus. In some embodiments the inflammatory disease is urticaria. In some embodiments the BTK dependent condition is cancer. In some embodiments the BTK dependent condition is an autoimmune disease. In some embodiments the BTK dependent condition is an inflammatory disease. In some embodiments the BTK dependent condition is a theromboembolic disease. In some embodiments the BTK dependent condition is multiple sclerosis. In some embodiments the BTK dependent condition is rheumatoid arthritis. In some embodiments the BTK dependent condition is psoriasis. In some embodiments the BTK dependent condition is Sjogren's syndrome. In some embodiments the BTK dependent condition is systemic lupus erythematosus. In some embodiments the BTK dependent condition is urticaria.

In some embodiments are uses of a compound of Formula (I), or a pharmaceutically acceptable salt, solvate, hydrate, isomer, tautomer, racemate, isotope, or pharmaceutical composition thereof in the manufacture of a medicament. In some embodiments the medicament is for the treatment of cancer. In some embodiments the medicament is for the treatment of an autoimmune disease. In some embodiments the medicament is for the treatment of an inflammatory disease. In some embodiments the medicament is for the treatment of a theromboembolic disease. In some embodiments the medicament is for the treatment of multiple sclerosis. In some embodiments the medicament is for the treatment of rheumatoid arthritis. In some embodiments the medicament is for the treatment of psoriasis. In some embodiments the medicament is for the treatment of Sjogren's syndrome. In some embodiments the medicament is for the treatment of systemic lupus erythematosus. In some embodiments the medicament is for the treatment of urticaria.

Thus, inhibition of BTK activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, alleigic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evans syndrome, hemolytic uremic syndrome/thrombotic thrombocytopenic purpura, sarcoidosis, Sjogren's syndrome, peripheral neuropathies (e.g., Guillain-Barre syndrome), pemphigus vulgaris, and asthma.

In addition, BTK has been reported to play a role in controlling B-cell survival in certain B-cell cancers. For example, BTK has been shown to be important for the survival of BCR-Abl-positive B-cell acute lymphoblastic leukemia cells. Thus, inhibition of BTK activity can be useful for the treatment of B-cell lymphoma and leukemia.

The compounds described herein or pharmaceutically acceptable salts, solvates, hydrates or tautomers thereof may be useful for the treatment of the above listed diseases optionally in combination with a corticosteroid, noncorticosteroidal, immunosupressive, and/or antiinflammatory agents. In one embodiment, the immunosuppressive agent is selected from interferon alpha, interferon gamma, cyclophosphamide, tacrolimus, mycophenolate mofetil, methotrexate, dapsone, sulfasalazine, azathioprine, an anti-CD20 agent (such as rituximab, ofatumumab, obinutuzumab, or veltuzumab, or a biosimilar version thereof), anti-TNFalpha agent (such as entanercept, infliximab, golilumab, adalimumab, or certolizumab pegol or a biosimilar version thereof), anti-IL6 agent toward ligand or its receptors (such as tocilizumab, sarilumab, olokizumab, elsililumab, or siltuximab), anti-IL17 agent to ligand or its receptors (such as secukinumab, ustekinumab, brodalumab, or ixekizumab), anti-IL1 agent to ligand or its receptors (such as with rilonacept, canakinumab, or anakinra), anti-IL2 agent to ligand or its receptors (such as basiliximab or daclizumab), anti-CD2 agent such as alefacept, anti-CD3 agent such as muromonab-cd3, anti-CD80/86 agent such as abatacept or belatacept, anti-sphingosine-1-phosphate receptor agent such as fingolimod, anti-C5 agent such as eculizumab, anti-integrin alpha4 agent such as natalizumab, anti-$\alpha_4\beta_7$ agent such as vedolizumab, anti-mTOR agent such as sirolimus or everolimus, anti-calcineurin agent such as tacrolimus, and anti-BAFF/BlyS agent (such as belimumab, VAY736, or blisibimod), leflunomide and teriflunomide. Preferably, the immunosuppressive agent is rituximab, ofatumumab, obinutuzumab, or veltuzumab, or a biosimilar version thereof.

Compound Synthesis

Compounds having the structure of Formula (I) can be synthesized using standard synthetic techniques known to those of skill in the art. For example, compounds of the present disclosure can be synthesized using the general synthetic procedures set forth in Schemes 1-17.

Compounds having the structure of Formula (IA) and (1B) can be synthesized according to general scheme 1, starting from 3-amino-protected cyclohexan-1-one (i) by first converting the ketone to the enol triflate (ii) using a strong base such as LDA in THF and N-phenyl-bis(trifluoromethanesulfonimide). Conversion to the isomeric vinyl boronate esters (iii) can be achieved by reacting compound (ii) with bis(pinacolato)diboron and a palladium catalyst such as (1,1'-bis(diphenylphosphino) ferrocene)-palladium (II) dichloride. Intermediates (iv) can be formed using palladium-catalyzed cross coupling between aryl halides and vinylboronates (iii). Products (iv) can be deprotected to provide amine salts (v) which can be acylated using standard procedures for amide bond formation such as HATU and a tertiary amine base. Alternatively, the aromatic ring of intermediates (iv) can be further functionalized to provide intermediates (vii) which can be elaborated to final targets (ix) using protocols described above. In some instances, the final targets are purified using chiral chromatography to provide single isomers of the desired compounds.

Scheme 1: General synthesis for preparation of compounds of formula (I)
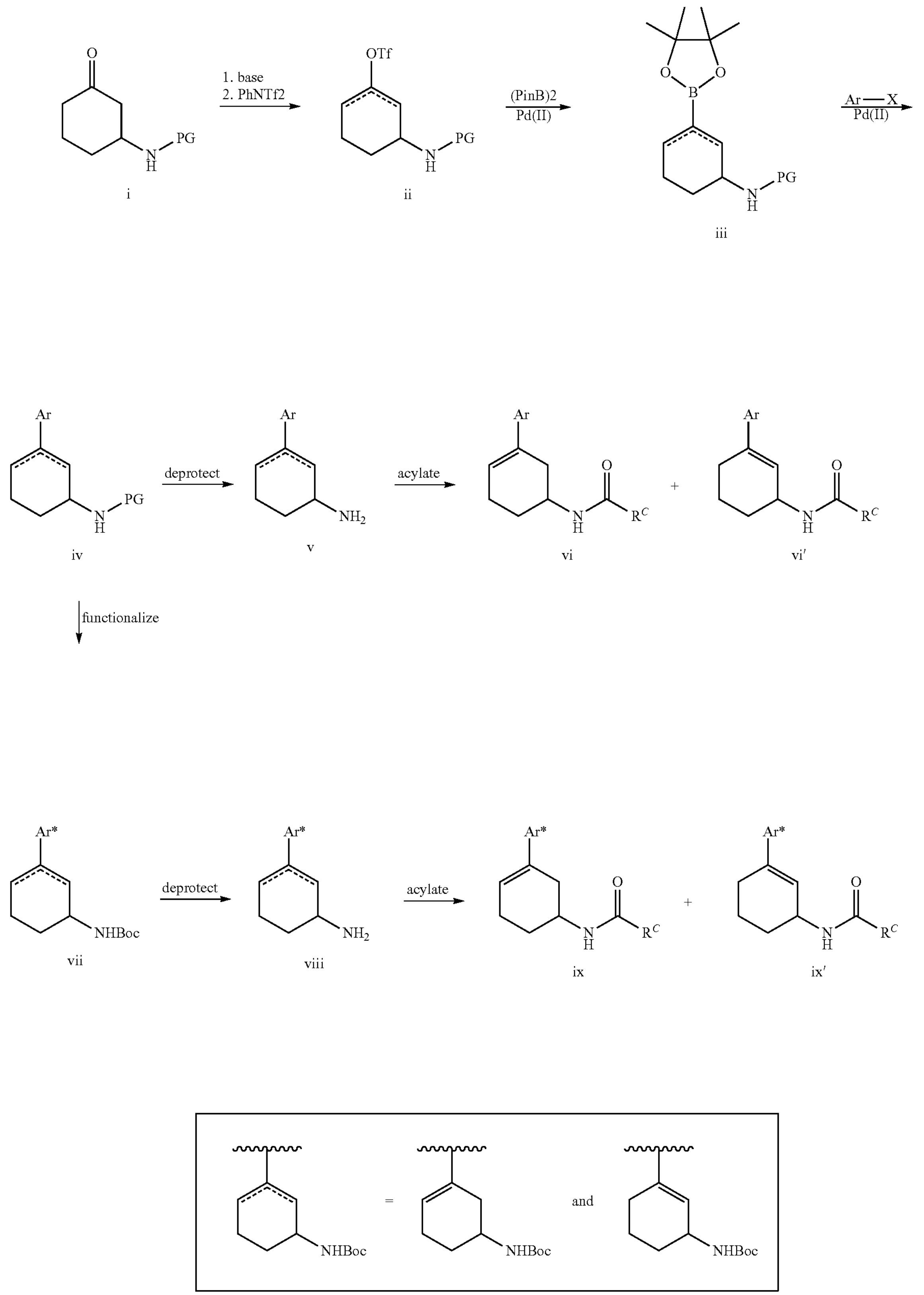
More detailed procedures are outlined below.

I Protected 3-(4,4,5,5-tetramethyl-1,3,2-dioxaborolan-2-yl)cyclohex-3-en-1-amine Amine protected 3-aminocyclohexan-1-one is reacted with 1,1,1-trifluoro-N-phenyl-N-(trifluoromethylsulfonyl) methanesulfonamide to provide the 5-amino protected cyclohex-1-en-1-yl triflate, which is then converted to amino protected 3-(4,4,5,5-tetramethyl-1,3,2-dioxaborolan-2-yl) cyclohex-3-en-1-amine by reaction with 4,4,5,5-tetra methyl-2-(4,4,5,5-tetra methyl-1,3,2-dioxaborolan-2-yl)-1,3,2-dioxaborolane, as shown in scheme 2.

Scheme 2: Protected 3-(4,4,5,5-tetramethyl-1,3,2-dioxaborolan-2-yl) cyclohex-3-en-1-amine

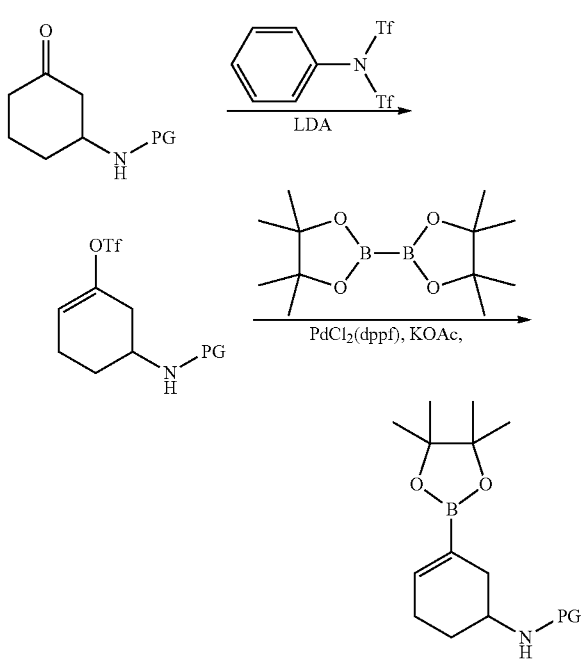

II Compounds of Formula (IA), wherein $R^{A1}$ is H or Cl; $R^{A2}$ is H or F and $R^B$ is H (ROUTE 1)

(IA)

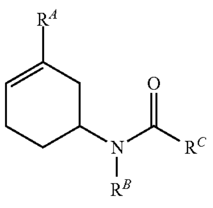

4-bromo-5-fluoro-2-nitrobenzoic acid ($R^{A2}$ is H) or 4-bromo-2,3-difluoro-6-nitrobenzoic acid ($R^{A2}$ is F) is converted to the indole by reaction with iso-propenyl magnesium bromide. The acid group is amidated and the 4-bromo indole then coupled with 3-(4,4,5,5-tetramethyl-1,3,2-dioxaborolan-2-yl)cyclohex-3-en-1-amine. $R^{A1}$ is optionally converted from H to Cl by reaction with a chlorinating agent, such as NCS. Any amine protecting group is removed, as appropriate, and the amine is reacted with $R^C$—COOH to provide the final compound of formula (IA), according to scheme 3.

Scheme 3: Compounds of formula (IA), ROUTE 1

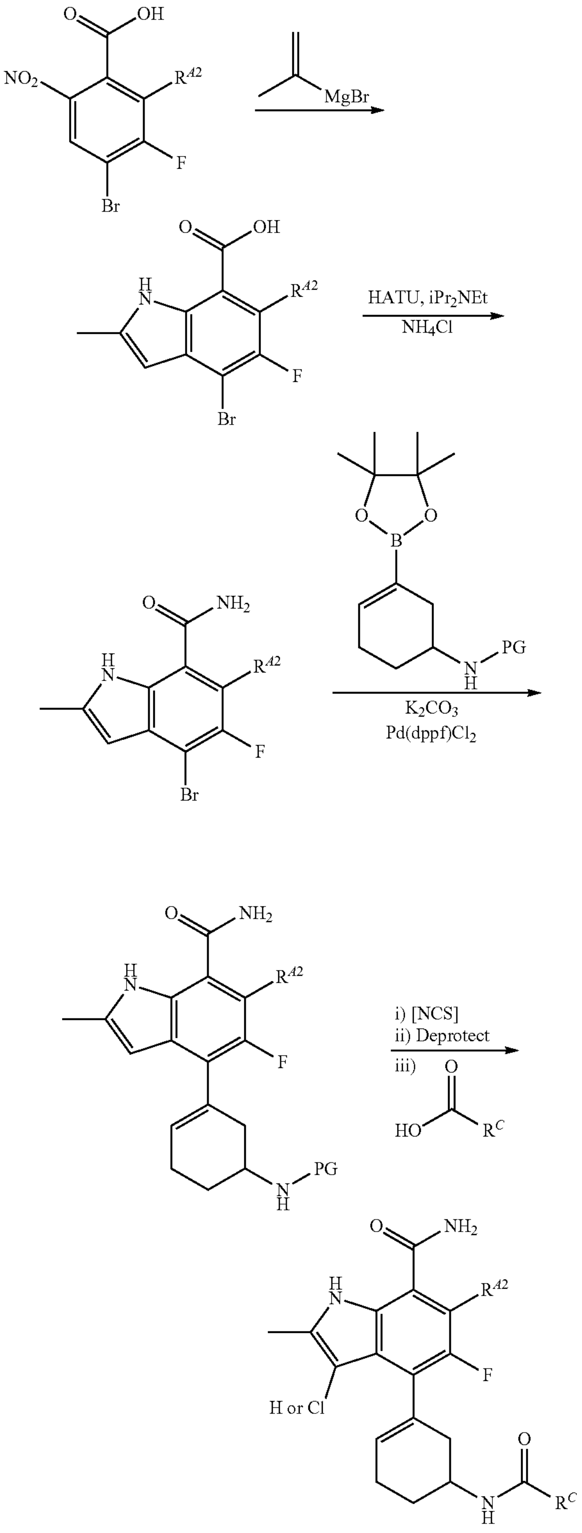

III Compounds of Formula (IA), wherein $R^{A1}$ is H or Cl; $R^{A2}$ is H or F and $R^B$ is H (ROUTE 2)

In an alternate synthesis, 1,4-dibromo-2-fluorobenzene ($R^{A2}$ is H) or 1,4-dibromo-2,3-difluorobenzene ($R^{A2}$ is F) is aminated in the 6 position and iodinated in the 5 position. Reaction with propyne converts the iodo to the propynyl derivative which is then cyclized to provide the indole. The 7-bromo is converted to the carboxy and then the amide. As with route 1, the 4-bromo indole then coupled with 3-(4,4,5,5-tetramethyl-1,3,2-dioxaborolan-2-yl)cyclohex-3-en-1-amine. $R^{A1}$ is optionally converted from H to Cl by reaction with an appropriate chlorinating agent, such as NCS, any protecting groups removed as appropriate, and the amine reacted with $R^C$—COOH to provide the final compound of formula (IA), according to scheme 4.

Scheme 4: Compounds of formula (IA), ROUTE 3

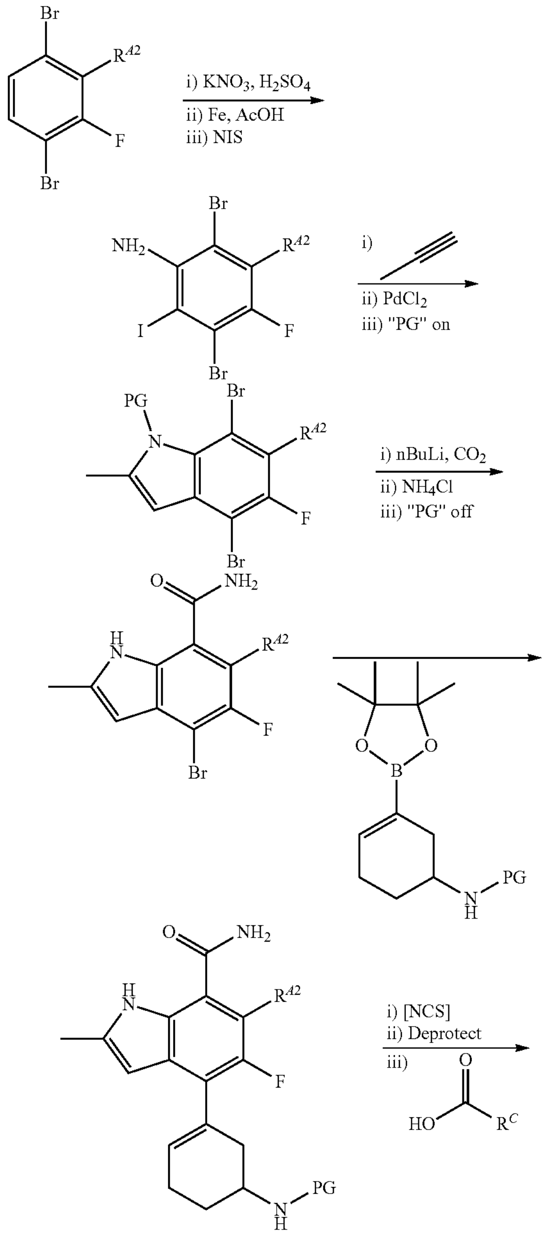

-continued

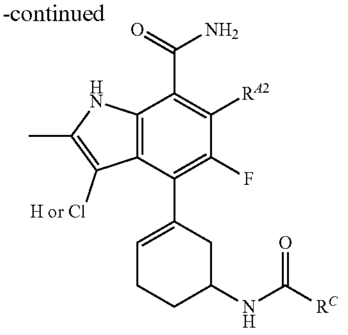

IV Compounds of Formula I-A-(S) or I-B-(S), wherein $R^{A1}$ is Me; $R^{A2}$ is H or F and $R^B$ is H Formula I-A-(S)

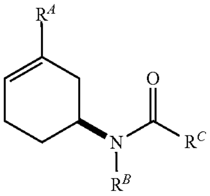

Formula I-B-(S)

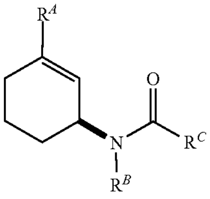

Amine protected (S)-3-aminocyclohexan-1-one is reacted with 1,1,1-trifluoro-N-phenyl-N-(trifluoromethylsulfonyl) methanesulfonamide in the presence of sodium bis(trimethylsilyl) amide (NAHMDS) to provide a mixture of the 3- and 5-amine protected cyclohexenyl triflate isomers. These are activated and coupled with 4-bromo-5-fluoro-2,3-dimethyl-1H-indole-7-carbonitrile ($R^{A2}$ is H) or 4-bromo-5,6-difluoro-2,3-dimethyl-1H-indole-7-carbonitrile ($R^{A2}$ is F). The nitrile group is then converted to the amide, and after removal of any protecting groups as required, the amine is reacted with $R^C$—COOH to provide a mixture of the final compounds, according to scheme 5. Chiral chromatography provides the individual isomers.

Scheme 5: Compounds of formula I-A-(S) or I-B-(S)

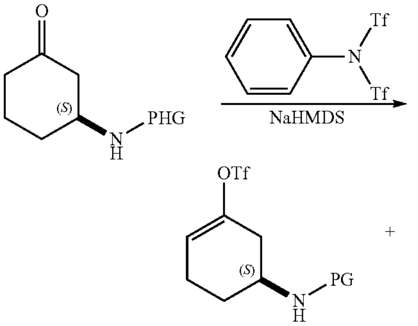

-continued
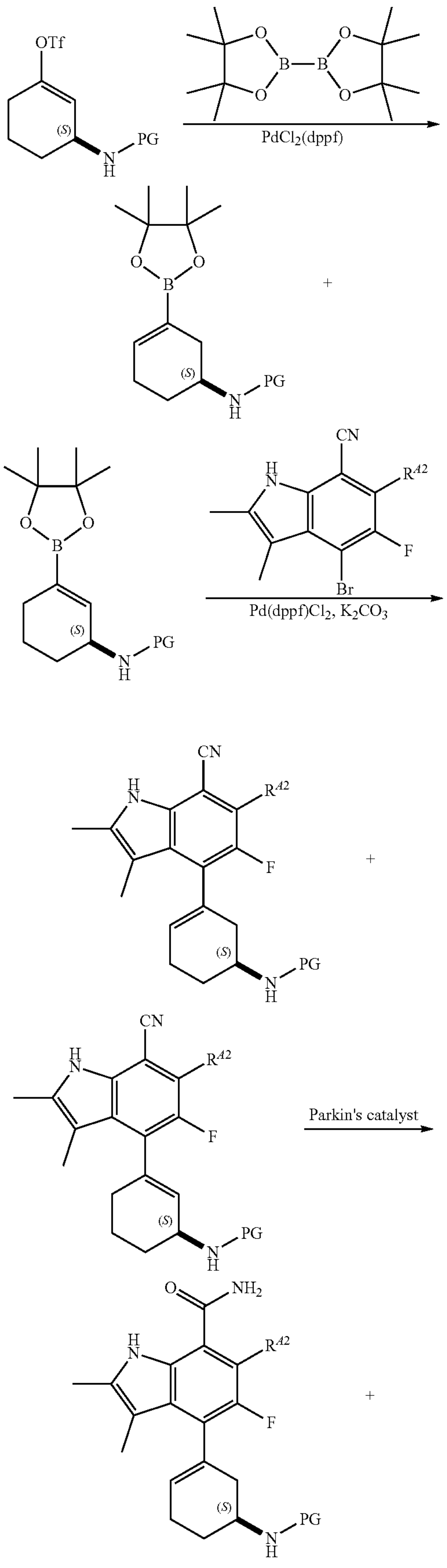
-continued
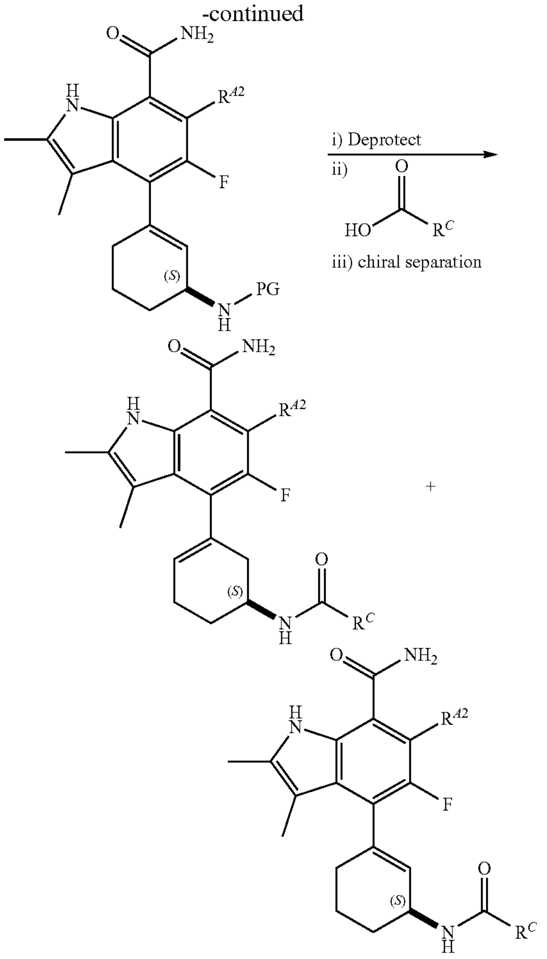
V Compounds of Formula I-A-(R) or I-B-(R), wherein $R^{A1}$ is Me; $R^{A2}$ is H or F and $R^B$ is H
Formula I-A-(R)
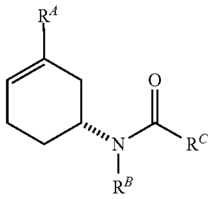
Formula I-B-(R)
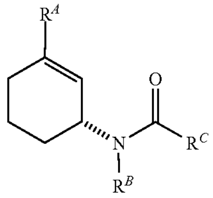
Compounds of formula I-A-(R) or I-B-(R), are prepared in a similar manner to compounds of formula I-A-(S) or I-B-(S), as described above and in scheme 5, starting with amine protected (R)-3-aminocyclohexan-1-one in place of amine protected (S)-3-aminocyclohexan-1-one.

Scheme 6: Compounds of formula I-A-(R) or I-B-(R)

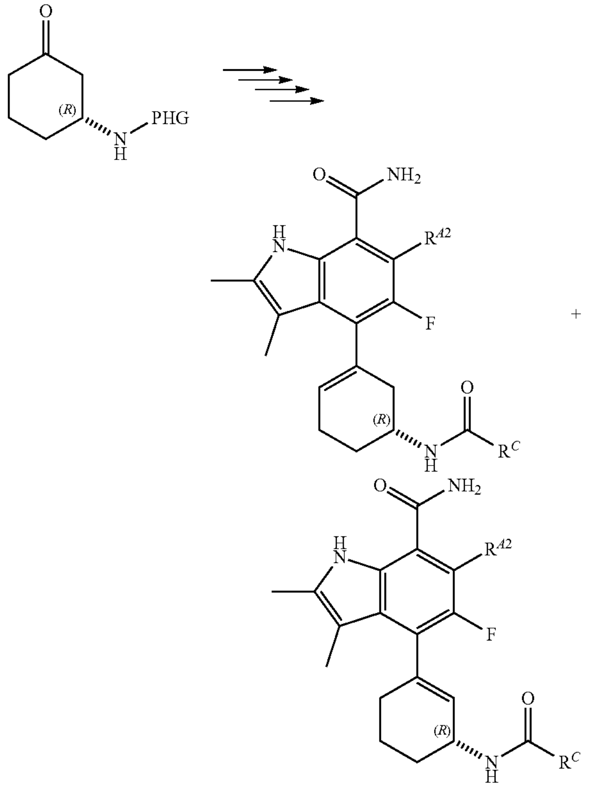

VI Compounds of Formula I-A-(S) or I-B-(S), wherein $R^{A1}$ is Me; $R^{A2}$ is H or F and $R^{B}$ is Me Formula 1-A-(S)

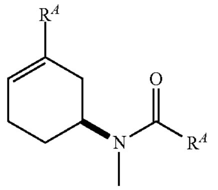

Compound 1-B-(S)

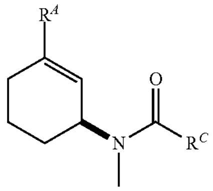

As described above, activated (S)-amine-protected cyclohexenes are coupled with protected 4-bromo-5-fluoro-2,3-dimethyl-1H-indole-7-carbonitrile ($R^{A2}$ is H) or 4-bromo-5, 6-difluoro-2,3-dimethyl-1H-indole-7-carbonitrile ($R^{A2}$ is F). After methylation, the indole is deprotected and the nitrile group converted to the amide. After removal of any protecting groups as required, the amine is reacted with $R^{C}$—COOH to provide a mixture of the final compounds, according to scheme 7. Chiral chromatography provides the individual isomers.

Scheme 7: Compounds of formula I-A-(S) or I-B-(S), wherein $R^{B}$ is Me

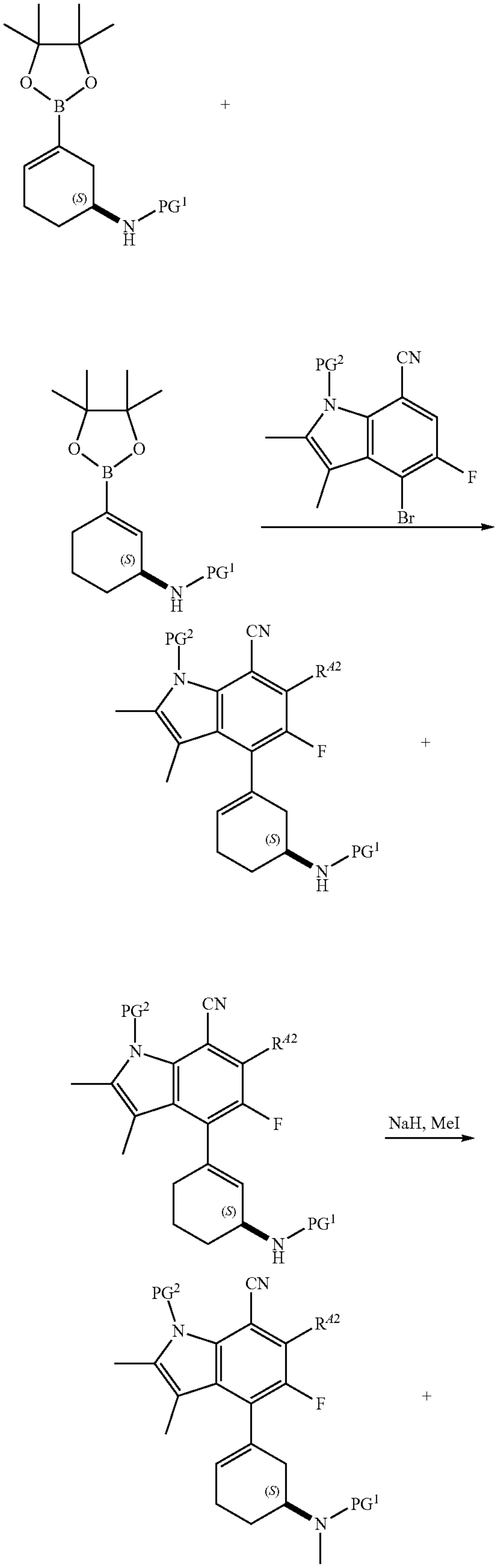

-continued

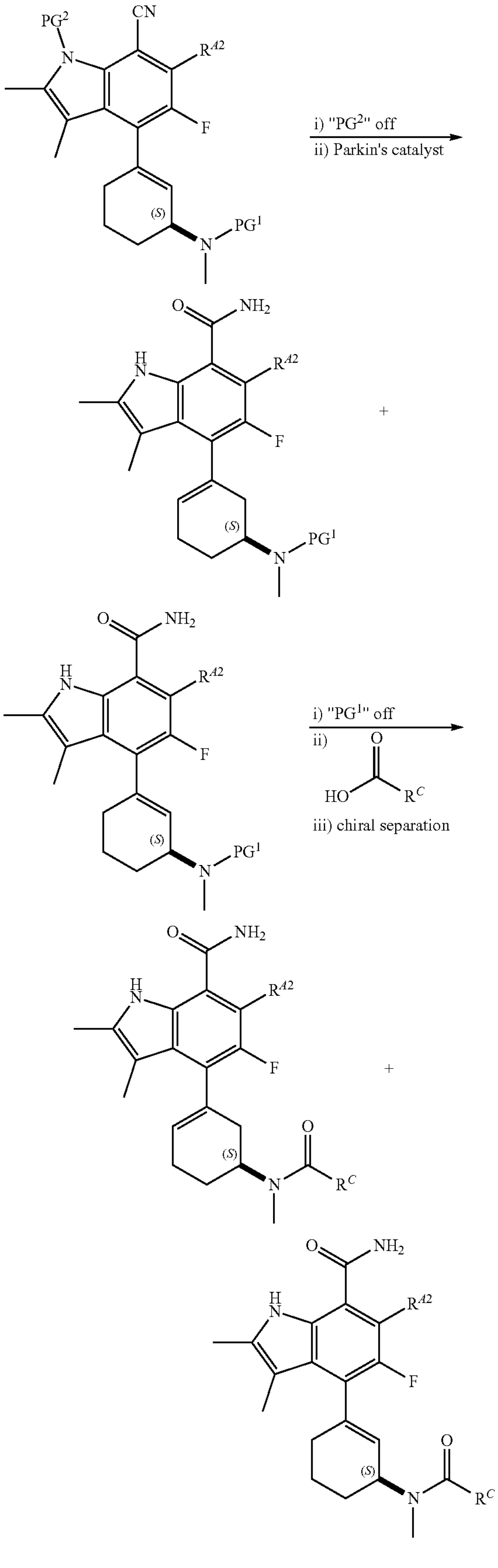

VII Compounds of Formula I-A-(R) or I-B-(R), wherein $R^{A1}$ is Me; $R^{A2}$ is H or F and $R^B$ is Me Formula 1-A-(R)

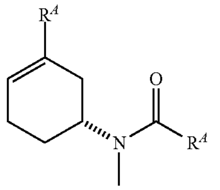

Compound 1-B-(R)

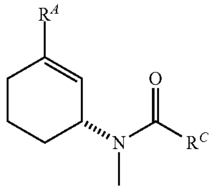

Compounds of formula I-A-(R) or I-B-(R), wherein $R^B$ is Me, are prepared in a similar manner to compounds of formula I-A-(S) or I-B-(S), wherein $R^B$ is Me, as described above and in scheme 7, starting with the (R) isomers in place of the (S).

Scheme 8: Compounds of formula I-A-(R) or I-B-(R), wherein $R^B$ is Me

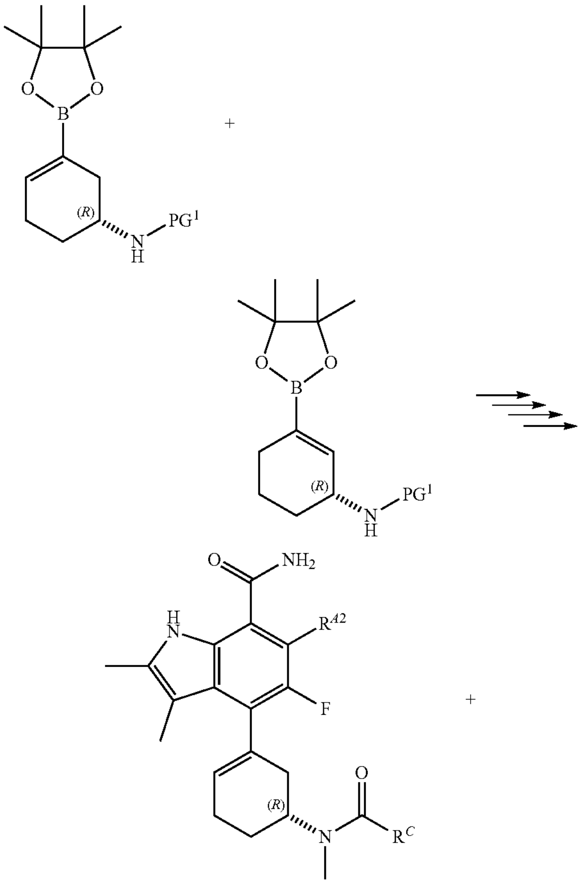

-continued

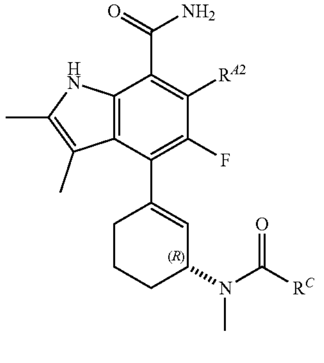

VIII Compounds of Formula I-C

Compounds of formula I-C are prepared according to scheme 9 below. 3-amino protected cyclohexan-1-one is treated with phenyl triflimide to provide 3-OTf cyclohexen amine, which is then activated and coupled with $R^A$ bromide. The cyclohexene is reduced to the cyclohexane, the amine protecting group removed and $R^C$ introduced by treatment with $R^C$ acid.

Scheme 9: Compounds of formula (IC)

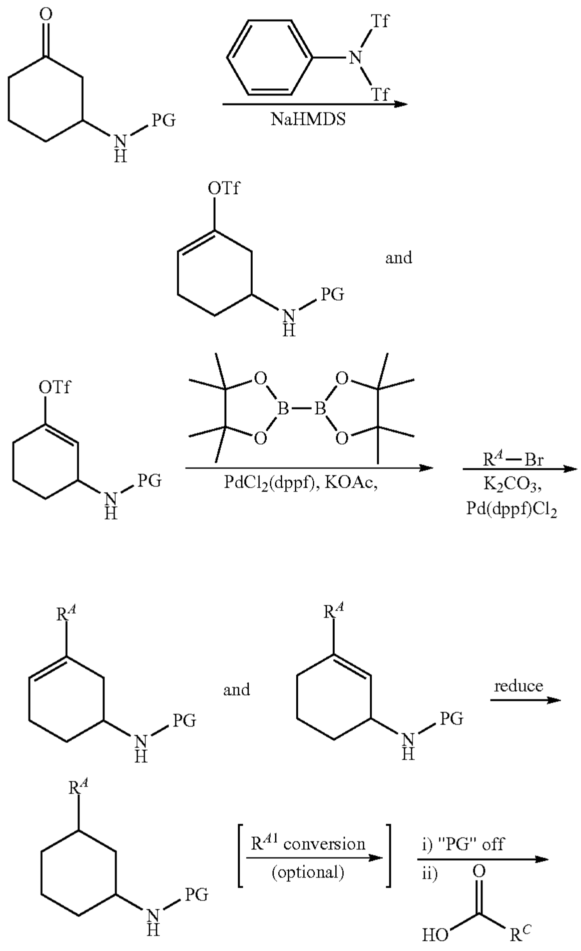

-continued

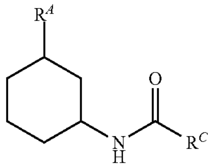

Introduction of an $R^{A1}$ group (e.g. halogen, CN) can be affected by treatment of the amine protected 3-$R^A$-cyclohexan-1-amine with the appropriate agent, to provide the 3-substituted indole, according to scheme 10.

Scheme 10: Introduction of $R^{A1}$ substituent

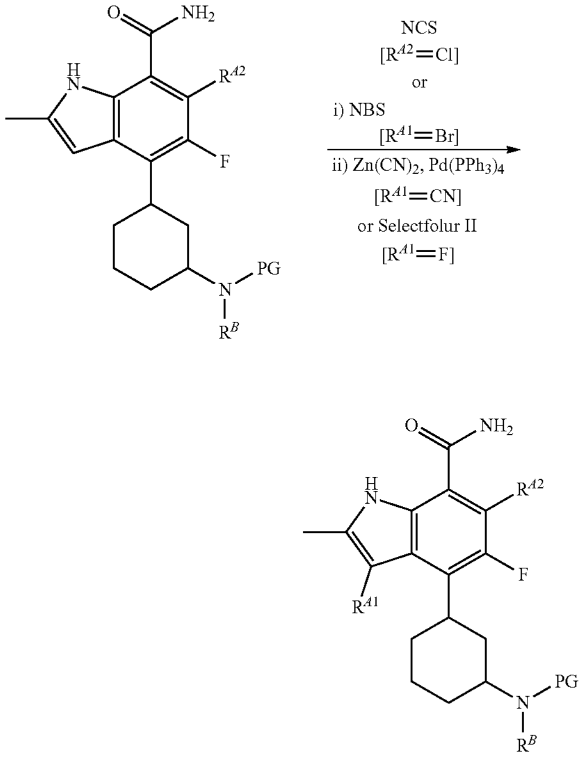

In an alternate route, shown in scheme 11, an activated amino-protected cyclohexene may be coupled with $R^A$ bromide, followed by reduction to the cyclohexane, amine deprotection and $R^C$ amide formation.

Scheme 11: Compounds of formula (IC), alternate synthetic route

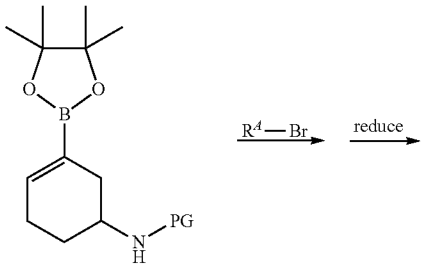

-continued
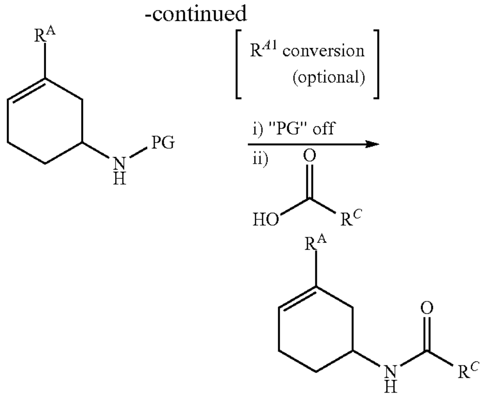
Compounds of formula I-C may be separated to individual isomers, by typical separation techniques, such as supercritical fluid chromatography (SFC), chiral HPLC and the like, according to scheme 12.
Scheme 12: Compounds of formula (IC): separation of isomers
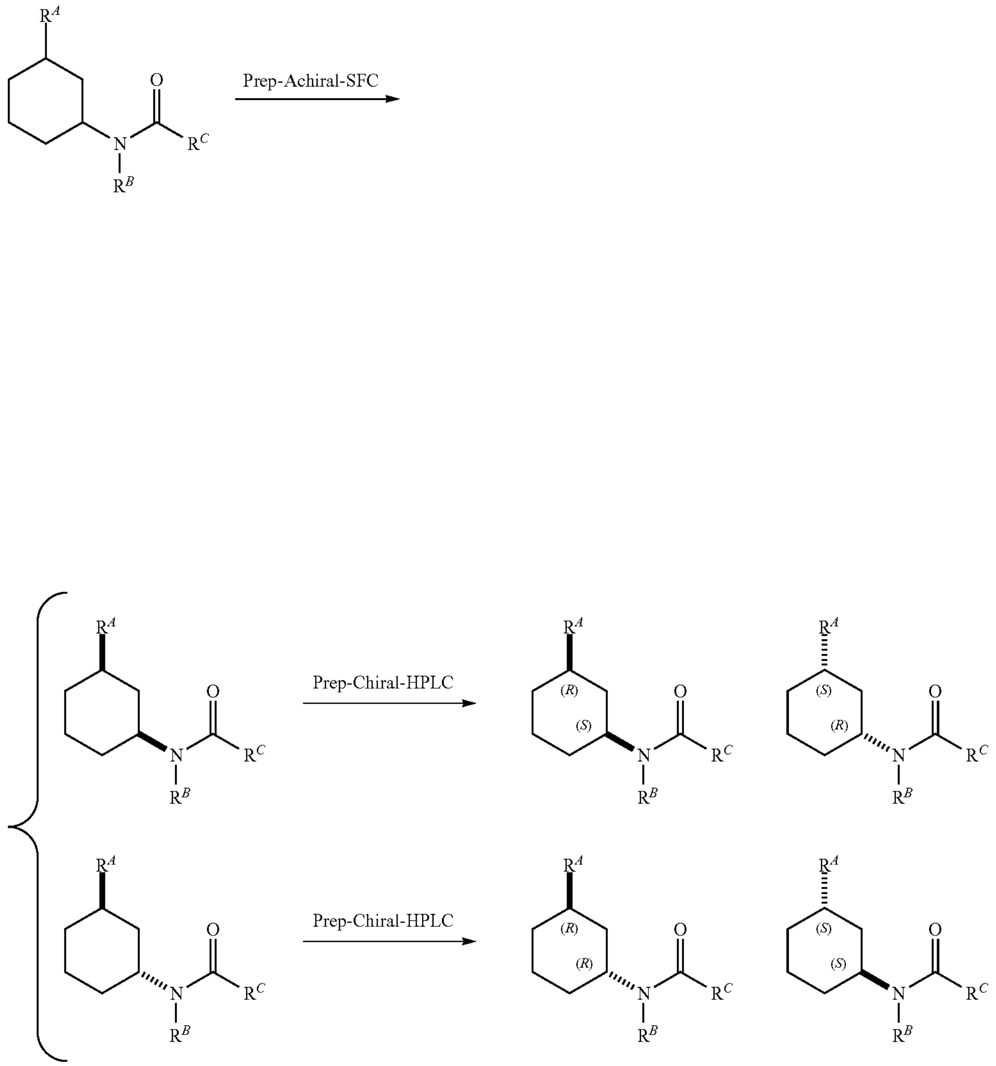

IX Compounds of Formula I-D

Compounds of formula I-D are prepared according to scheme 13 below. 3-amino protected cyclopentan-1-one is treated with phenyl triflimide to provide 3-OTf cyclopenten-1-amine, which is then activated and coupled with $R^A$ bromide. The cyclohexene is reduced to the cyclohexane, the amine protecting group removed and $R^C$ introduced by treatment with $R^C$ acid.

Scheme 13: Compound of formula (ID)

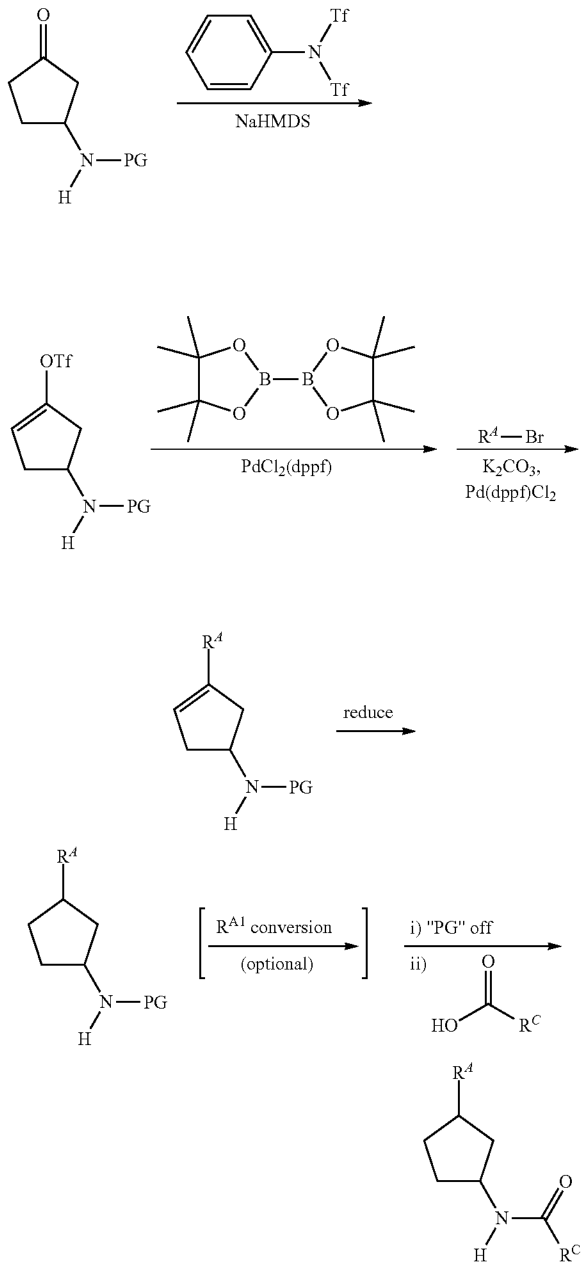

Introduction of an $R^{A1}$ group (e.g. halogen, CN) can be affected by treatment of the amine protected 3-$R^A$-cyclohexan-1-amine with the appropriate agent, to provide the 3-substituted indole, according to scheme 14.

Scheme 14: Introduction of $R^{A1}$ substituent

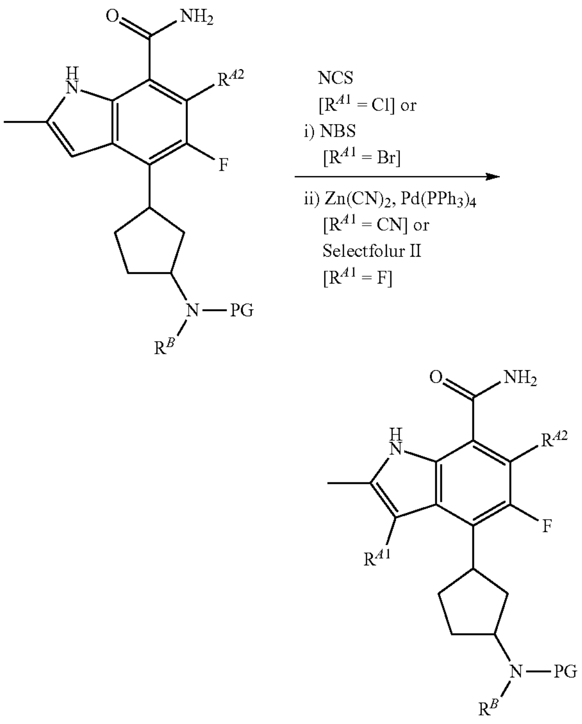

In an alternate route, shown in scheme 15, an activated amino-protected cyclopentene may be coupled with $R^A$ bromide, followed by reduction to the cyclopentane, amine deprotection and $R^C$ amide formation.

Scheme 15: Compounds of formula (ID), alternate synthetic route

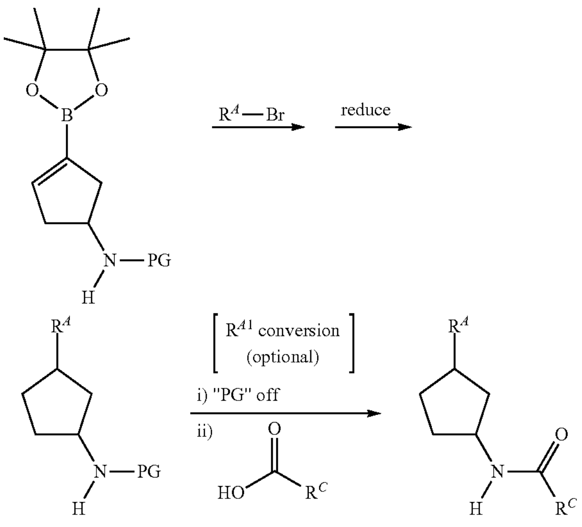

Introduction of the 7-carboxamide function on the indole ring, can be achieved by conversion of a nitrile group by treatment with, for example, Parkins catalyst ([PtH{$(PMe_2O)_2H$}($PMe_2OH$)]). Conversion of $R^B$ from H to methyl may be affected by treatment with a methylating agent, such as methyl iodide, see scheme 16.

Scheme 16: Formation of carboxamide and introduction of $R^B$ = Me
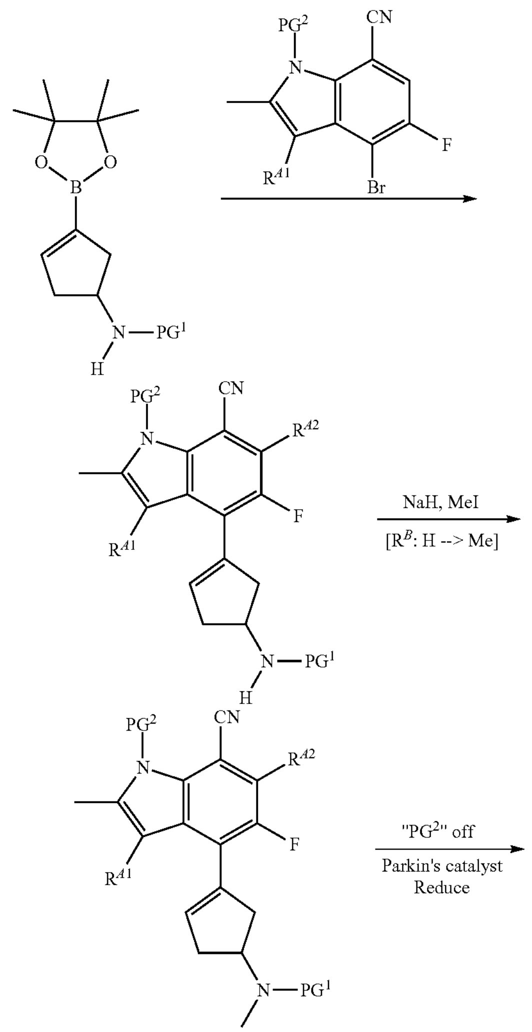
-continued
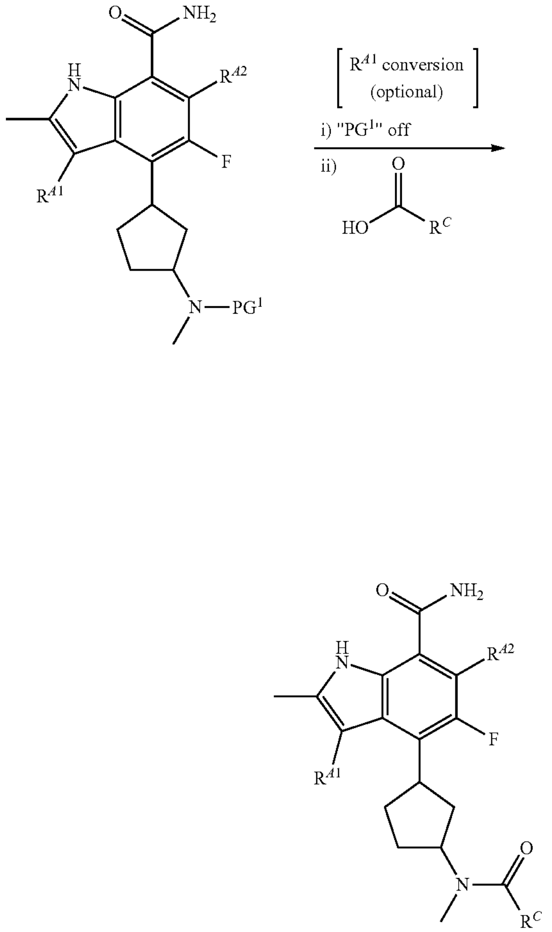
Compounds of formula I-D may be separated to individual isomers, by typical separation techniques, such as supercritical fluid chromatography (SFC), chiral HPLC and the like, according to scheme 17.
Scheme 17: Compounds of formula (IC): separation of isomers
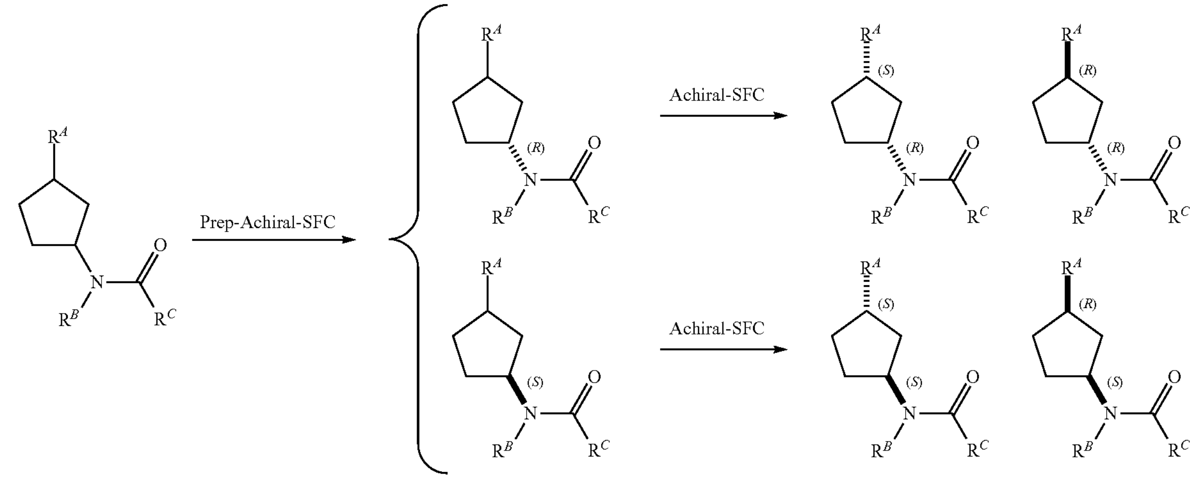

The reactions, processes and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

Unless otherwise indicated, conventional methods of mass spectroscopy (MS), liquid chromatography-mass spectroscopy (LCMS), NMR, HPLC, protein chemistry, biochemistry, recombinant DNA techniques, and pharmacology are employed. Compounds are prepared using standard organic chemistry techniques such as those described in, for example, March's Advanced Organic Chemistry, 7th Edition, John Wiley and Sons, Inc (2013). Alternate reaction conditions for the synthetic transformations described herein may be employed such as variation of solvent, reaction temperature, reaction time, as well as different chemical reagents and other reaction conditions. As necessary, the use of appropriate protecting groups may be required. The incorporation and cleavage of such groups may be carried out using standard methods described in Peter G. M. Wuts and Theodora W. Green, Protecting Groups in Organic Synthesis, 4th Edition, Wiley-Interscience. (2006). All starting materials and reagents are commercially available or readily prepared.

EXAMPLES

The following examples are provided for illustrative purposes only and not to limit the scope of the claims provided herein. While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1

Synthesis of racemic 4-(5-(but-2-ynamido)cyclohex-1-en-1-yl)-3-chloro-5-fluoro-2-methyl-1H-indole-7-carboxamide (Compound 1-A-(rac))

(S)-4-(5-(but-2-ynamido)cyclohex-1-en-1-yl)-3-chloro-5-fluoro-2-methyl-1H-indole-7-carboxamide (Compound 1-A-(5)) and

(R)-4-(5-(but-2-ynamido)cyclohex-1-en-1-yl)-3-chloro-5-fluoro-2-methyl-1H-indole-7-carboxamide (Compound 1-A-(R))

Compound 1-A-(rac)

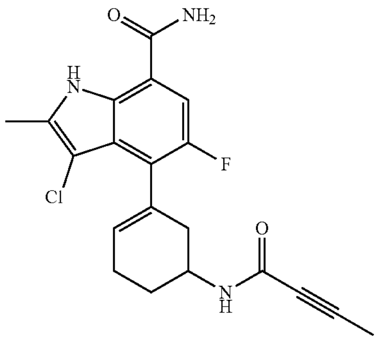

Compound 1-A-(S)

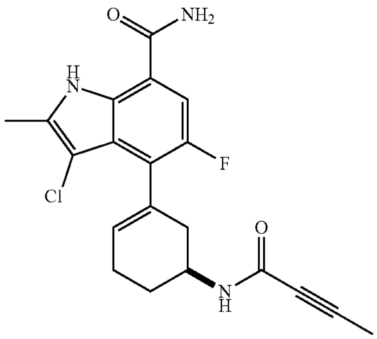

Compound 1-A-(R)

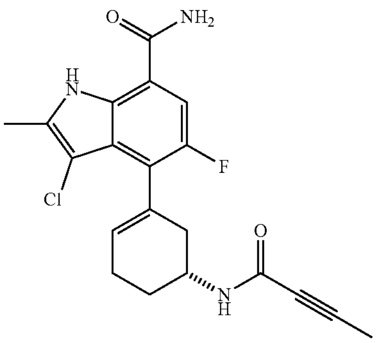

Step 1: 4-bromo-5-fluoro-2-methyl-1H-indole-7-carboxylic acid

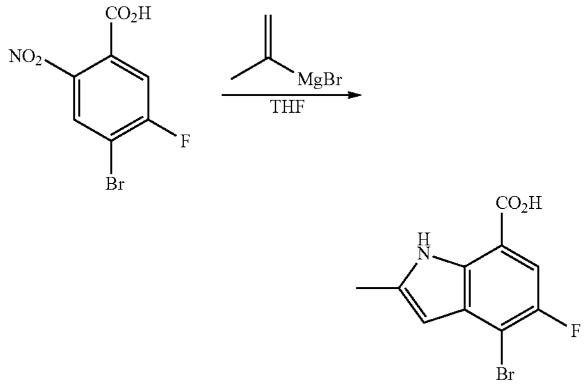

A 5 L, 4-necked flask equipped with a mechanical stirrer, a thermometer, an additional funnel, and a bubbler was charged with THF (1.1 L), followed by 4-bromo-5-fluoro-2-nitrobenzoic acid (100.0 g, 0.379 mole, 1.0 eq.). The resulting solution was flushed with $N_2$ for 5 min and cooled to below −70° C. in an EtOH-dry ice bath. Isopropenylmagnesium bromide solution (0.5 M in THF, 3.03 L, 1.52 mole, 4.0 eq.) was added dropwise, while ensuring the internal temperature was maintained below −65° C. during the addition. Thereafter, the reaction mixture was stirred at −70° C. for further 2 h. The reaction was quenched by addition of saturated aq. $NH_4Cl$ solution (200 mL), followed by aq. citric acid solution (1 L, 20 wt %). The cooling bath was removed, and the reaction was warmed to above 0° C. EtOAc (1 L) was added and the layers separated. The aqueous layer was extracted with EtOAc (200 mL×2) and the combined organic extracts concentrated under reduced pressure. The resulting yellow residue was re-dissolved in EtOAc (1.5 L), washed with saturated aq. $NH_4Cl$ solution (100 mL) and brine, dried over $MgSO_4$, filtered, and concentrated under reduced pressure. The crude product was triturated with DCM (300 mL) at room temperature (20° C.) for 16 h. The product was collected by vacuum filtration, rinsed with cold DCM (20 mL), and dried under IR lamp. 4-bromo-5-fluoro-2-methyl-1H-indole-7-carboxylic acid was obtained as a tan solid (38.0 g, 0.140 mole, 37% yield). $^1H$ NMR (400 MHz, DMSO-$d_6$) δ 13.36 (brs, 1H), 11.27 (s, 1H), 7.48 (d, J=9.8 Hz, 1H), 6.26 (dd, J=2.3, 1.1 Hz, 1H), 2.62-2.15 (m, 3H).

Step 2: 4-bromo-5-fluoro-2-methyl-1H-indole-7-carboxylic acid amide

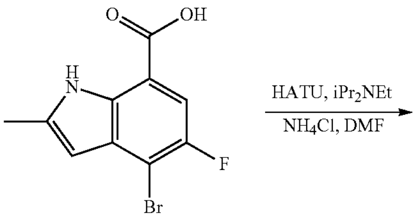

-continued

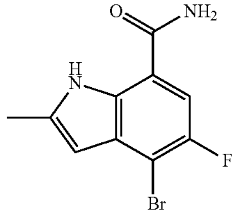

A solution of 4-bromo-5-fluoro-2-methyl-1H-indole-7-carboxylic acid (87.5 g, 0.322 mole, 1.0 eq.) in DMF (440 mL) was cooled to 0-5° C. in an ice-water bath. $NH_4Cl$ (34.4 g, 0.644 mole, 2.0 eq.) was added in one portion, followed by addition of $iPr_2NEt$ (124.8 g, 0.966 mole, 3.0 eq.). To the resulting solution was added solid HATU (146.8 g, 0.386 mole, 1.2 eq.) in portions over 10 min. The reaction was gently exothermic, and the internal temperature was maintained below 15° C. during the addition. Thereafter, the cooling bath was removed, and the reaction was stirred for an additional 2 h at room temperature. LC-MS analysis indicated completion of reaction. The brownish reaction solution was transferred to a 5 L flask and ice-cold water (ca. 3 L) was slowly added. The resulting tan precipitate was collected by vacuum filtration, washed with water (500 mL), and redissolved in EtOAc (1.5 L), which was further washed with brine, dried over $MgSO_4$, filtered, and concentrated under reduced pressure. The crude product was triturated with a mixture of DCM (200 mL) and EtOAc (20 mL) at room temperature for 1 h to afford 4-bromo-5-fluoro-2-methyl-1H-indole-7-carboxylic acid amide as a tan, powder after drying (73.2 g, 0.270 mole, 84% yield). $^1H$ NMR (400 MHz, DMSO-$d_6$) δ 11.29 (s, 1H), 8.13 (s, 1H), 7.61 (d, J=10.4 Hz, 1H), 7.59 (brs, 1H), 6.21 (dd, J=2.3, 1.1 Hz, 1H), 3.34 (s, 2H), 2.44 (d, J=0.9 Hz, 3H).

Step 3: 5-((tert-butoxycarbonyl)amino)cyclohex-1-en-1-yl trifluoromethanesulfonate

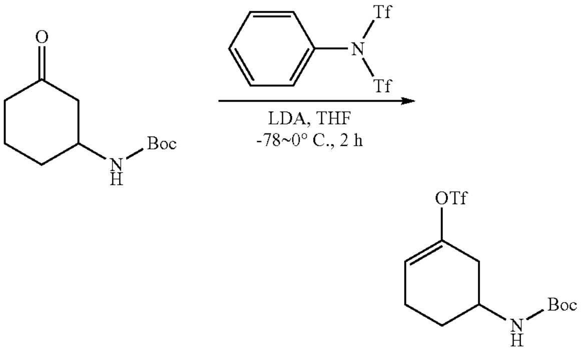

To a solution of tert-butyl (3-oxocyclohexyl)carbamate (20.00 g, 93.76 mmol) and 1,1,1-trifluoro-N-phenyl-N-(trifluoromethylsulfonyl)methanesulfonamide (43.55 g, 121.91 mmol) in THF (300 mL) was added LDA (2 M in THF, 103 mL, 206 mmol) at −78° C. under $N_2$. After addition the reaction mixture was stirred at 0° C. for 2 h, quenched with saturated aqueous ammonium chloride (500 mL) and extracted with ethyl acetate (300 mL×3). The combined organic layers were washed with water (200 mL) and brine (200 mL), dried over anhydrous sodium sulfate and concentrated under vacuum. The residue was purified by column chromatography on silica gel eluting with ethyl acetate in petroleum ether (0 to 10%) to give 5-((tert-butoxycarbonyl)amino)cyclohex-1-en-1-yl trifluoromethanesulfonate (30.0 g) as a yellow oil. $^{1}$H NMR (300 MHz, $CDCl_3$) δ 5.83-5.71 (m, 1H), 4.68-4.36 (m, 1H), 4.06-3.85 (m, 1H), 2.79-2.61 (m, 1H), 2.39-2.19 (m, 3H), 1.90-1.76 (m, 1H), 1.68-1.55 (m, 1H), 1.45 (s, 9H).

Step 4: tert-butyl (3-(4,4,5,5-tetramethyl-1,3,2-dioxaborolan-2-yl)cyclohex-3-en-1-yl)carbamate

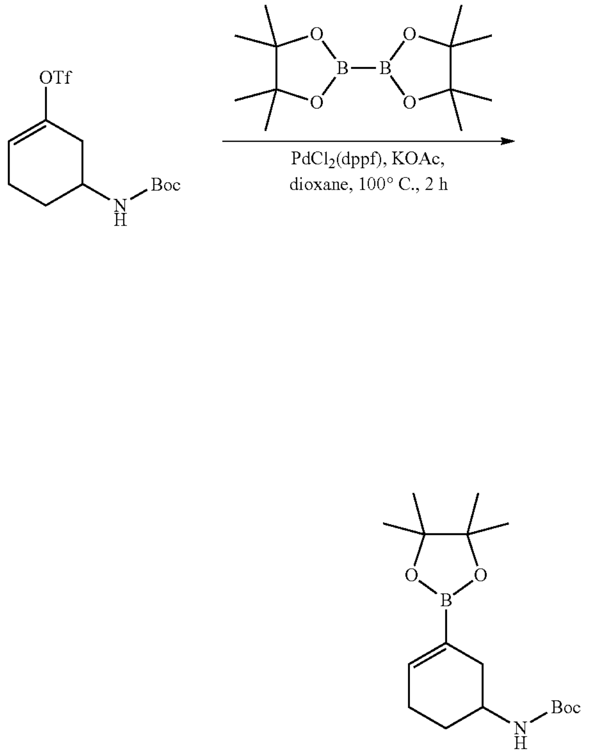

A mixture of 5-((tert-butoxycarbonyl)amino)cyclohex-1-en-1-yl trifluoromethanesulfonate (30.00 g, 86.87 mmol), 4,4,5,5-tetramethyl-2-(4,4,5,5-tetramethyl-1,3,2-dioxaborolan-2-yl)-1,3,2-dioxaborolane (22 g, 86.87 mmol), potassium acetate (25.58 g, 260.62 mmol) and Pd(dppf)$Cl_2$ (3.18 g, 4.34 mmol) in dioxane (300 mL) was degassed and backfilled with nitrogen five times. The reaction mixture was stirred under nitrogen at 100° C. for 2 h. The cooled reaction mixture was quenched with water (500 mL) and extracted with ethyl acetate (300 mL×3). The combined organic layers were washed with brine (300 mL), dried over anhydrous sodium sulfate and concentrated under vacuum. The resulting residue was purified by column chromatography on silica gel eluting with ethyl acetate in petroleum ether (0 to 15%) to give tert-butyl (3-(4,4,5,5-tetramethyl-1,3,2-dioxaborolan-2-yl)cyclohex-3-en-1-yl)carbamate (8.5 g) as a yellow oil. $^{1}$H NMR (300 MHz, $CDCl_3$) δ 6.61-6.49 (m, 1H), 4.64-4.40 (m, 1H), 3.85-3.63 (m, 1H), 2.60-2.43 (m, 1H), 2.32-2.17 (m, 2H), 2.00-1.80 (m, 2H), 1.72-1.60 (m, 1H), 1.44 (s, 9H), 1.25 (s, 12H). ESI-MS $[M+H-Boc]^+$ calcd for ($C_{17}H_{30}BNO_4$) 224.24 found: 224.15.

Step 5: tert-butyl (3-(7-carbamoyl-5-fluoro-2-methyl-1H-indol-4-yl)cyclohex-3-en-1-yl)carbamate

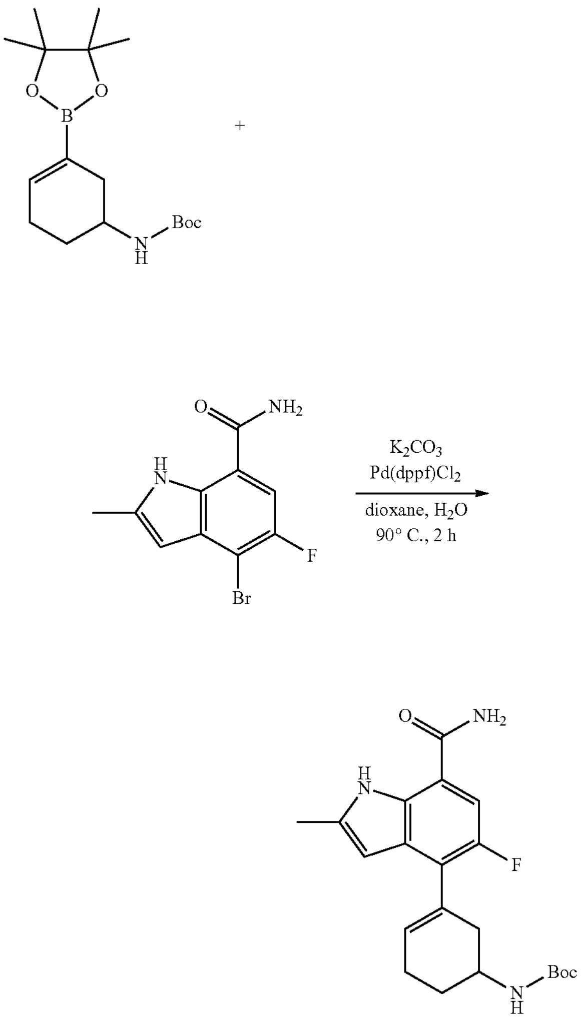 [SMILES: CC(C)(C)OC(=O)NC1CCC=C(B2OC(C)(C)C(C)(C)O2)C1 ; Cc1cc2c(Br)c(F)cc(C(N)=O)c2[nH]1 ; Cc1cc2c(C3=CCCC(NC(=O)OC(C)(C)C)C3)c(F)cc(C(N)=O)c2[nH]1]

A mixture of tert-butyl (3-(4,4,5,5-tetramethyl-1,3,2-dioxaborolan-2-yl)cyclohex-3-en-1-yl)carbamate (6.56 g, 20.29 mmol), 4-bromo-5-fluoro-2-methyl-1H-indole-7-carboxamide (5 g, 18.44 mmol), potassium carbonate (7.65 g, 55.33 mmol) and Pd(dppf)$Cl_2$ (675 mg, 0.92 mmol) in dioxane (80 mL) and water (20 mL) was degassed and backfilled with nitrogen five times. The reaction mixture was heated under nitrogen at 90° C. for 2 h. The cooled reaction mixture was diluted with water (200 mL) and extracted with ethyl acetate (150 mL×3). The combined organic layers were washed with brine (150 mL), dried over sodium sulfate and concentrated under vacuum. The residue was purified by column chromatography on silica gel eluting with ethyl acetate in petroleum ether (0 to 45%) to give tert-butyl (3-(7-carbamoyl-5-fluoro-2-methyl-1H-indol-4-yl)cyclohex-3-en-1-yl)carbamate (7.0 g) as a yellow solid. $^{1}$H NMR (400 MHz, DMSO-$d_6$) δ 10.91 (s, 1H), 8.01 (s, 1H), 7.51-7.36 (m, 2H), 6.96-6.84 (m, 1H), 6.14 (s, 1H), 5.84-5.77 (m, 1H), 3.76-3.56 (m, 1H), 2.44-2.24 (m, 7H), 1.93-1.81 (m, 1H), 1.65-1.45 (m, 1H), 1.40 (s, 9H). ESI-MS $[M-H]^-$ calcd for ($C_{21}H_{26}FN_3O_3$) 386.20 found: 386.15

Step 6: tert-butyl (3-(7-carbamoyl-3-chloro-5-fluoro-2-methyl-1H-indol-4-yl)cyclohex-3-en-1-yl) carbamate

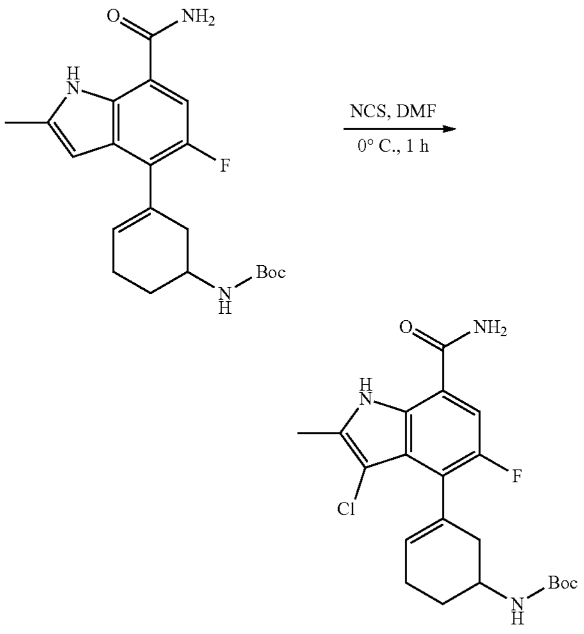

To a solution of tert-butyl (3-(7-carbamoyl-5-fluoro-2-methyl-1H-indol-4-yl)cyclohex-3-en-1-yl)carbamate (7.0 g, 18.07 mmol) in DMF (50 mL) was added N-chlorosuccinimide (2.65 g, 19.88 mmol,) at 0° C. The reaction mixture was stirred at 0° C. for 1 h. The reaction mixture was quenched with water (200 mL) and extracted with ethyl acetate (100 mL×3). The combined organic layers were washed with brine (150 mL), dried over anhydrous sodium sulfate and concentrated under vacuum. The residue was purified by column chromatography on silica gel eluting with ethyl acetate in petroleum ether (0 to 50%) to give tert-butyl (3-(7-carbamoyl-3-chloro-5-fluoro-2-methyl-1H-indol-4-yl)cyclohex-3-en-1-yl)carbamate (7.0 g) as a yellow solid. ESI-MS $[M+H\text{-}tBu]^+$ calcd for ($C_{21}H_{25}ClFN_3O_3$) 366.16, 368.15 found: 366.30, 368.30.

Step 7: 4-(5-aminocyclohex-1-en-1-yl)-3-chloro-5-fluoro-2-methyl-1H-indole-7-carboxamide hydrochloride

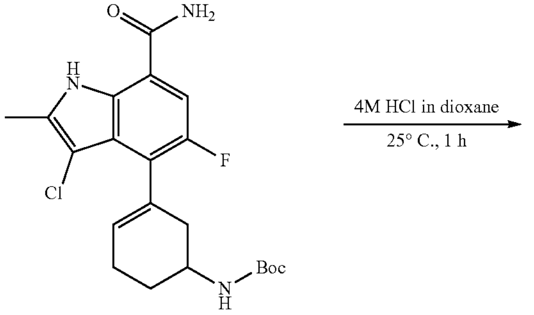

-continued

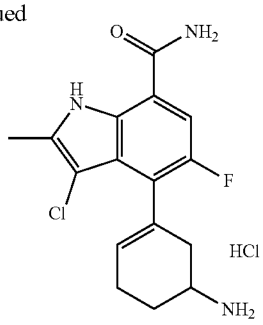

A mixture of tert-butyl (3-(7-carbamoyl-3-chloro-5-fluoro-2-methyl-1H-indol-4-yl)cyclohex-3-en-1-yl)carbamate (7 g, 16.59 mmol) and hydrogen chloride (4 M in dioxane, 70 mL) was stirred at 25° C. for 1 h. The reaction mixture was concentrated under vacuum to give 4-(5-aminocyclohex-1-en-1-yl)-3-chloro-5-fluoro-2-methyl-1H-indole-7-carboxamide hydrochloride (6.0 g, crude) as a yellow solid. ESI-MS $[M+H]^+$ calcd for ($C_{16}H_{17}ClFN_3O$) 322.10, 324.10 found: 322.35, 324.35.

Step 8: racemic 4-(5-(but-2-ynamido)cyclohex-1-en-1-yl)-3-chloro-5-fluoro-2-methyl-1H-indole-7-carboxamide (Compound 1-A-(rac))

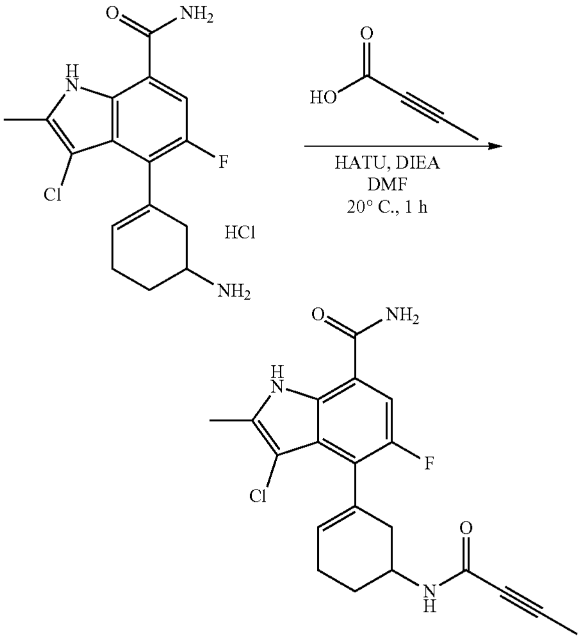

To a mixture of 4-(5-aminocyclohex-1-en-1-yl)-3-chloro-5-fluoro-2-methyl-1H-indole-7-carboxamide hydrochloride (6.0 g, 16.75 mmol) in DMF (60 mL) were added HATU (7.64 g, 20.1 mmol), but-2-ynoic acid (1.69 g, 20.1 mmol) and DIEA (10.82 g, 83.75 mmol). The reaction mixture was stirred at 20° C. for 1 h. The resulting mixture was diluted with water (200 mL) and extracted with ethyl acetate (100 mL×3). The combined organic layers were washed with water (100 mL×2) and brine (100 mL), dried over anhydrous sodium sulfate and concentrated under vacuum. The residue was purified by column chromatography on silica gel eluting with ethyl acetate in petroleum ether (0 to 50%) to give 4-(5-(but-2-ynamido) cyclohex-1-en-1-yl)-3-chloro-5-fluoro-2-methyl-1H-indole-7-carboxamide (3.5 g) as a white solid. $^1$H NMR (400 MHz, DMSO-$d_6$) δ 11.32 (s, 1H), 8.61-8.50 (m, 1H), 8.10 (s, 1H), 7.55-7.52 (m, 2H), 5.60 (s, 1H), 4.14-3.93 (m, 1H), 2.39 (s, 3H), 2.35-2.22 (m, 4H), 1.94 (s, 3H), 1.90-1.82 (m, 1H), 1.68-1.47 (m, 1H). ESI-MS $[M+H]^+$ calcd for ($C_{20}H_{19}ClFN_3O_2$) 388.11, 390.11, found: 388.05, 390.05.

Step 9: (S)-4-(5-(but-2-ynamido) cyclohex-1-en-1-yl)-3-chloro-5-fluoro-2-methyl-1H-indole-7-carboxamide and (R)-4-(5-(but-2-ynamido)cyclohex-1-en-1-yl)-3-chloro-5-fluoro-2-methyl-1H-indole-7-carboxamide (Compounds 1-A-(5) and 1-A-(R))

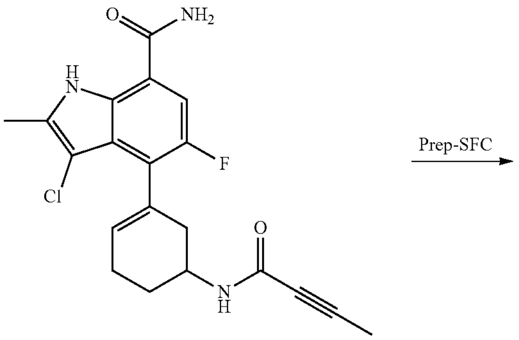

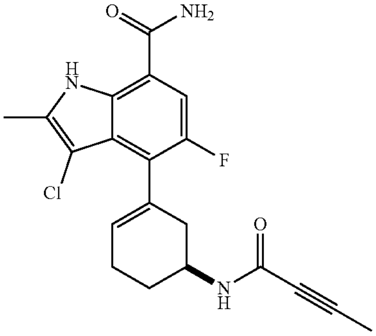

(S)

and

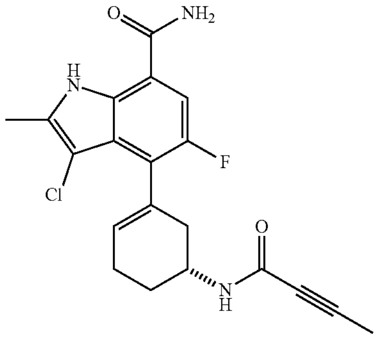

(R)

4-(5-(but-2-ynamido)cyclohex-1-en-1-yl)-3-chloro-5-fluoro-2-methyl-1H-indole-7-carboxamide (3.5 g, 9 mmol) was separated by Prep-SFC with the following conditions: Column: CHIRALPAK AD-H, 2×25 cm, 5 μm; Mobile Phase A: $CO_2$, Mobile Phase B: MeOH (0.1% 2 M $NH_3$-MeOH); Flow rate: 70 mL/min; Gradient: 30% B; Column Temperature: 35° C.;

Back Pressure: 100 bar; 220 nm;
Retention Time=3.69 min (R)-4-(5-(but-2-ynamido) cyclohex-1-en-1-yl)-3-chloro-5-fluoro-2-methyl-1H-indole-7-carboxamide or (S)-4-(5-(but-2-ynamido)cyclohex-1-en-1-yl)-3-chloro-5-fluoro-2-methyl-1H-indole-7-carboxamide (1.02 g, 40%) as a light yellow solid. $^1$H NMR (300 MHz, DMSO-$d_6$) δ 11.32 (s, 1H), 8.55 (s, 1H), 8.09 (s, 1H), 7.60-7.48 (m, 2H), 5.61 (s, 1H), 4.14-3.93 (m, 1H), 2.45-2.20 (m, 7H), 2.05-1.80 (m, 4H), 1.70-1.45 (m, 1H). ESI-MS $[M+H]^+$ calcd for ($C_{20}H_{19}ClFN_3O_2$) 388.11, 390.11, found: 388.10, 390.10.
Retention Time=4.13 min (S)-4-(5-(but-2-ynamido)cyclohex-1-en-1-yl)-3-chloro-5-fluoro-2-methyl-1H-indole-7-carboxamide or (R)-4-(5-(but-2-ynamido)cyclohex-1-en-1-yl)-3-chloro-5-fluoro-2-methyl-1H-indole-7-carboxamide (1.13 g, 41%) as an off-white solid. $^1$H NMR (300 MHz, DMSO-$d_6$) δ 11.31 (s, 1H), 8.55 (s, 1H), 8.09 (s, 1H), 7.61-7.47 (m, 2H), 5.61 (s, 1H), 4.14-3.93 (m, 1H), 2.45-2.20 (m, 7H), 2.05-1.80 (m, 4H), 1.70-1.45 (m, 1H). ESI-MS $[M+H]^+$ calcd for ($C_{20}H_{19}ClFN_3O_2$) 388.11, 390.11, found: 388.10, 390.10.

Example 2

Synthesis of Racemic 4-(5-(but-2-ynamido) cyclohex-1-en-1-yl)-3-chloro-5,6-difluoro-2-methyl-1H-indole-7-carboxamide (Compound 2-A-(rac))

(S)-4-(5-(but-2-ynamido) cyclohex-1-en-1-yl)-3-chloro-5,6-difluoro-2-methyl-1H-indole-7-carboxamide (Compound 2-A-(S)) and

(R)-4-(5-(but-2-ynamido) cyclohex-1-en-1-yl)-3-chloro-5,6-difluoro-2-methyl-1H-indole-7-carboxamide (Compound 2-A-(R))

Compound 2-A-(rac)

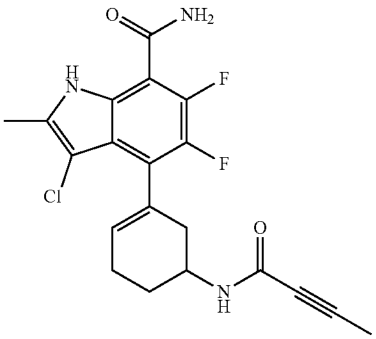

Compound 2-A-(S)

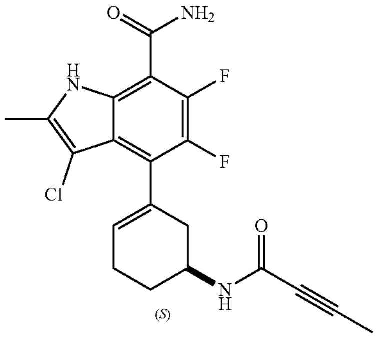

-continued

Compound 2-A-(R)

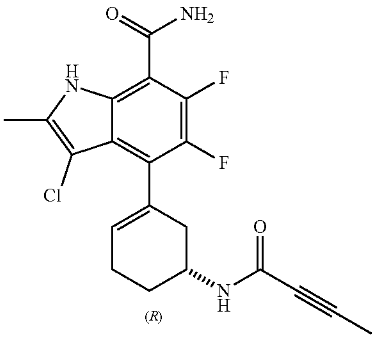

Step 1: 1,4-dibromo-2,3-difluoro-5-nitrobenzene

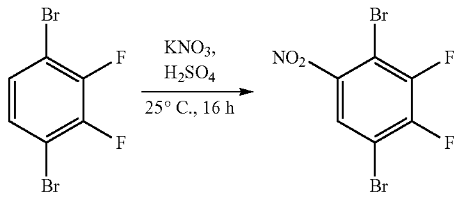 [SMILES: Fc1c(Br)ccc(Br)c1F ; O=[N+]([O-])c1cc(Br)c(F)c(F)c1Br]

To a solution of 1,4-dibromo-2,3-difluorobenzene (25.0 g, 91.95 mmol) in conc. sulfuric acid (200 mL) was added potassium nitrate (11.0 g, 108.8 mmol) at 0° C. The reaction mixture was stirred at 25° C. for 16 h. The reaction mixture was poured into ice-water (1 L) and stirred at 0° C. for 30 min. The resulting precipitate was filtered, the filter cake was washed with water and dried under reduced pressure to afford 1,4-dibromo-2,3-difluoro-5-nitrobenzene (27.0 g) as a yellow solid. $^1H$ NMR (300 MHz, DMSO-$d_6$) δ 8.47 (dd, J=6.0, 2.4 Hz 1H).

Step 2: 2,5-dibromo-3,4-difluoroaniline

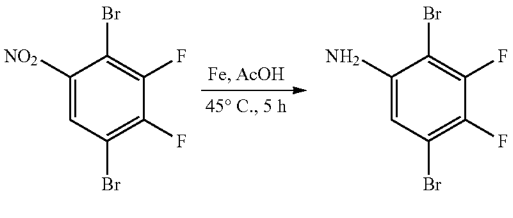 [SMILES: O=[N+]([O-])c1cc(Br)c(F)c(F)c1Br ; Nc1cc(Br)c(F)c(F)c1Br]

To a solution of 1,4-dibromo-2,3-difluoro-5-nitrobenzene (27.0 g, 85.21 mmol) in acetic acid (260 mL) was added iron powder (47.6 g, 852.0 mmol). The reaction mixture was stirred at 45° C. for 5 h. The cooled reaction mixture was filtered, and the filtrate poured into ice-water (500 mL) and re-filtered. The filter cake was washed with water (300 mL) and dried under reduced pressure to afford 2,5-dibromo-3,4-difluoroaniline (23.0 g, 94% yield) as a yellow solid. $^1H$ NMR (300 MHz, DMSO-$d_6$) δ 6.88 (dd, J=6.0, 2.4 Hz 1H), 5.74 (brs, 2H).

Step 3: 2,5-dibromo-3,4-difluoro-6-iodoaniline

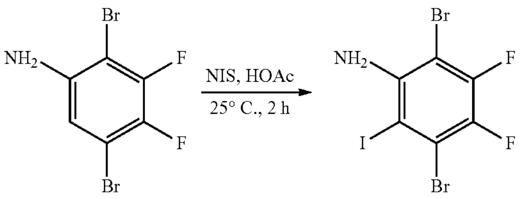 [SMILES: Nc1cc(Br)c(F)c(F)c1Br ; Nc1c(Br)c(F)c(F)c(Br)c1I]

To a solution of 2,5-dibromo-3,4-difluoroaniline (23.0 g, 80.17 mmol) in acetic acid (250 mL) was added N-iodo-succinimide (19.84 g, 88.18 mmol). The reaction mixture was stirred at 25° C. for 2 h, and then poured into ice-water (500 mL) and filtered. The filter cake was washed with water (100 mL) and dried under reduced pressure. The crude product was purified by column chromatography on silica gel eluting with ethyl acetate in petroleum ether (0 to 5%) to give 2,5-dibromo-3,4-difluoro-6-iodoaniline (30.0 g, 90%) as an off-white solid. $^1H$ NMR (300 MHz, DMSO-$d_6$) δ 5.63 (s, 2H). ESI-MS $[M-H]^-$ calcd for ($C_6H_2Br_2F_2IN$) 409.76, 411.75, 413.75 found: 409.75, 411.75, 413.70.

Step 4: 2,5-dibromo-3,4-difluoro-6-(prop-1-yn-1-yl) aniline

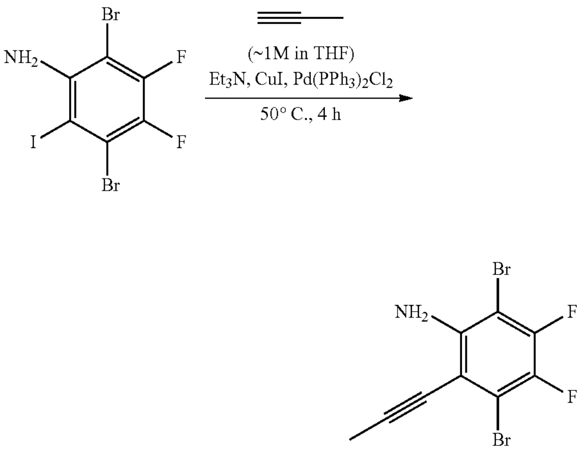

To a mixture of 2,5-dibromo-3,4-difluoro-6-iodoaniline (30.0 g, 72.68 mmol), copper(I) iodide (2.77 g, 14.54 mmol) and $Pd(PPh_3)_2Cl_2$ (5.12 g, 7.27 mmol) in triethylamine (365 mL) was added prop-1-yne (1 M in THF, 364 mL) under nitrogen. The reaction mixture was stirred in a sealed flask at 50° C. for 4 h. The cooled reaction mixture was quenched with water (300 ml) and extracted with ethyl acetate (300 ml×3). The combined organic layers were dried over anhydrous sodium sulfate, filtered and concentrated under vacuum. The residue was purified by column chromatography onto silica gel eluting with ethyl acetate in petroleum ether (0 to 10%) to give 2,5-dibromo-3,4-difluoro-6-(prop-1-yn-1-yl)aniline (20.0 g, 84%) as a yellow solid. $^1H$ NMR (300 MHz, DMSO-$d_6$) δ 5.79 (s, 2H), 2.18 (s, 3H). ESI-MS $[M-H]^-$ calcd for ($C_9H_5Br_2F_2N$) 321.88, 323.87, 325.87 found: 322.00, 324.00, 326.00

Step 5: 4,7-dibromo-5,6-difluoro-2-methyl-1H-indole

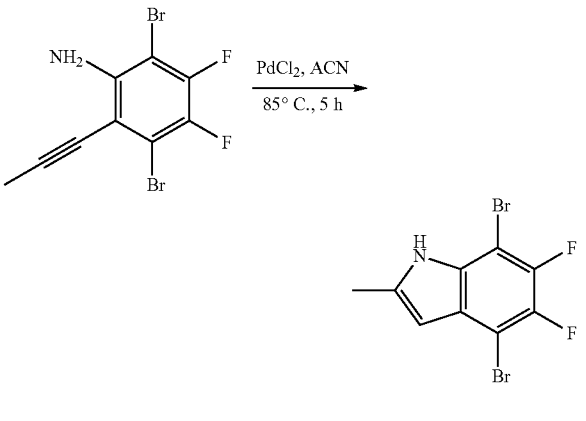

A mixture of 2,5-dibromo-3,4-difluoro-6-(prop-1-yn-1-yl)aniline (20.0 g, 61.55 mmol) and $PdCl_2$ (1.09 g, 6.15 mmol) in acetonitrile (400 mL) was degassed and backfilled with nitrogen three times and then stirred at 85° C. for 5 h. The cooled reaction mixture was concentrated under vacuum. The residue was purified by column chromatography on silica gel eluting with ethyl acetate in petroleum ether (0 to 10%) to afford 4,7-dibromo-5,6-difluoro-2-methyl-1H-indole (17.0 g, 85%) as a yellow solid. $^1H$ NMR (300 MHz, DMSO-$d_6$) δ 11.75 (s, 1H), 6.28 (s, 1H), 2.41 (s, 3H). ESI-MS $[M-H]^-$ calcd for ($C_9H_5Br_2F_2N$) 321.88, 323.87, 325.87 found: 321.80, 323.80, 325.80

Step 6: 4,7-dibromo-5,6-difluoro-2-methyl-1-((2-(trimethylsilyl)ethoxy)-methyl)-1H-indole

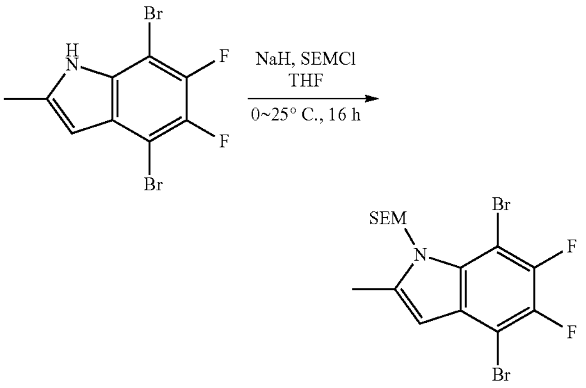

To a stirred solution of 4,7-dibromo-5,6-difluoro-2-methyl-1H-indole (10.0 g, 30.77 mmol) in THF (200 mL) was added sodium hydride (1.60 g, 40.01 mmol, 60%) at 0° C. After stirring at this temperature for 1 h, 2-(trimethylsilyl)ethoxymethyl chloride (7.70 g, 46.16 mmol) was added at 0° C. The reaction mixture was then stirred at 25° C. for 16 h, quenched with water (200 mL) and extracted with ethyl acetate (150 mL×3). The combined organic layers were washed with brine (100 mL), dried over anhydrous sodium sulfate and concentrated under vacuum. The residue was purified by column chromatography on silica gel eluting with ethyl acetate in petroleum ether (0 to 10%) to afford 4,7-dibromo-5,6-difluoro-2-methyl-1-((2-(trimethylsilyl)ethoxy)methyl)-1H-indole (12.3 g, 87%) as a yellow oil. $^1H$ NMR (300 MHz, DMSO-$d_6$) δ 6.42 (s, 1H), 5.78 (s, 2H), 3.55 (t, J=7.8 Hz, 2H), 2.47 (s, 3H), 0.83 (t, J=8.1 Hz, 2H), −0.08 (s, 9H).

Step 7: 4-bromo-5,6-difluoro-2-methyl-1-((2-(trimethylsilyl)ethoxy)methyl)-1H-indole-7-carboxylic acid

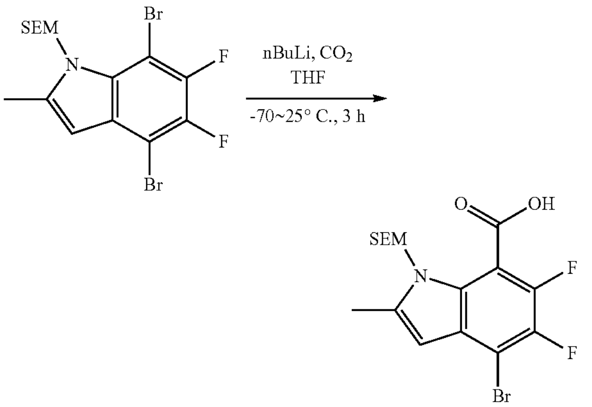

To a solution of 4,7-dibromo-5,6-difluoro-2-methyl-1-((2-(trimethylsilyl)ethoxy)methyl)-1H-indole (12.3 g, 27.03 mmol) in THF (130 mL) was added n-butyllithium (2.5 M in n-hexane, 13 mL, 32.5 mmol) under nitrogen at −70° C. After stirring at this temperature for 0.5 h and 0° C. 0.5 h, the reaction mixture was cooled to −70° C. and bubbled with carbon dioxide for 30 min. After stirring at 25° C. for 1.5 h, the reaction mixture was quenched with saturated aqueous ammonium chloride (100 mL) and extracted with dichloromethane (100 mL×3). The combined organic layers was washed with brine (100 mL), dried over anhydrous sodium sulfate and concentrated under vacuum to afford 4-bromo-5,6-difluoro-2-methyl-1-((2-(trimethylsilyl)ethoxy)methyl)-1H-indole-7-carboxylic acid (11.4 g, crude) as a yellow oil. ESI-MS $[M-H]^-$ calcd for ($C_{16}H_{20}BrF_2NO_3Si$) 418.04, 420.03 found: 417.95, 419.95.

Step 8: 4-bromo-5,6-difluoro-2-methyl-1-((2-(trimethylsilyl)ethoxy)methyl)-1H-indole-7-carboxamide

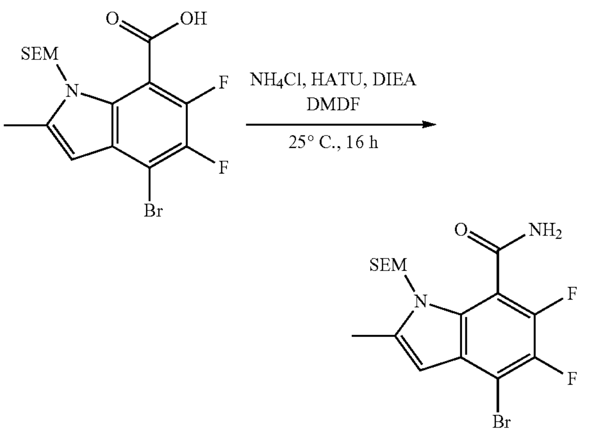

To a stirred mixture of 4-bromo-5,6-difluoro-2-methyl-1-(2-trimethylsilylethoxymethyl)indole-7-carboxylic acid (11.4 g, 27.12 mmol) and ammonium chloride (2.18 g, 40.68 mmol) in DMF (100 mL) were added HATU (12.38 g, 32.55 mmol) and DIPEA (17.53 g, 135.61 mmol) at 0° C. After stirring at 25° C. for 16 h, the reaction mixture was quenched with water (300 ml) and extracted with ethyl acetate (300 ml×3). The combined organic layers were washed with brine (200 ml×3), dried over anhydrous sodium sulfate and concentrated under vacuum. The residue was purified by column chromatography on silica gel eluting with ethyl acetate in petroleum ether (0 to 50%) to afford 4-bromo-5,6-difluoro-2-methyl-1-((2-(trimethylsilyl)ethoxy)methyl)-1H-indole-7-carboxamide (6.3 g, 55%) as a yellow solid. $^1$H NMR (300 MHz, DMSO-$d_6$) δ 8.34 (s, 1H), 8.10 (s, 1H), 6.40 (s, 1H), 5.50 (s, 2H), 3.42 (t, J=8.1 Hz, 2H), 2.46 (s, 3H), 0.81 (t, J=8.1 Hz, 2H), −0.06 (s, 9H). ESI-MS $[M+H]^+$ calcd for ($C_{16}H_{21}BrF_2N_2O_2Si$) 419.05, 421.05 found: 419.20, 421.20

Step 9: 4-bromo-5,6-difluoro-2-methyl-1H-indole-7-carboxamide

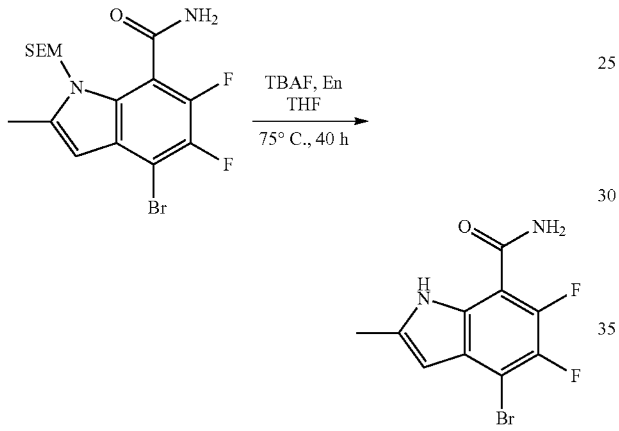

A mixture of 4-bromo-5,6-difluoro-2-methyl-1-((2-(trimethylsilyl)ethoxy)methyl)-1H-indole-7-carboxamide (6.3 g, 15.02 mmol), TBAF (1 M in THF, 150 mL, 150.2 mmol), and ethane-1,2-diamine (30 mL, 450.6 mmol) in THF (60 mL) was stirred at 75° C. for 40 h. The reaction mixture was cooled to 0° C. and acidified to pH4 with 2M hydrochloric acid. The resulting precipitate was collected by filtration, washed with water (100 mL) and dried under reduced pressure to afford 4-bromo-5,6-difluoro-2-methyl-1H-indole-7-carboxamide (3.5 g, 80%) as a yellow solid. $^1$H NMR (300 MHz, DMSO-$d_6$) δ 11.38 (s, 1H), 7.97 (s, 1H), 7.90 (s, 1H), 6.20 (s, 1H), 2.40 (s, 3H). ESI-MS $[M+H]^+$ calcd for ($C_{10}H_7BrF_2N_2O$) 288.97, 290.97 found: 288.95, 290.95.

Step 10: tert-butyl (3-(7-carbamoyl-5,6-difluoro-2-methyl-1H-indol-4-yl)cyclohex-3-en-1-yl)carbamate

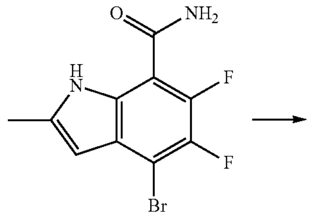

-continued

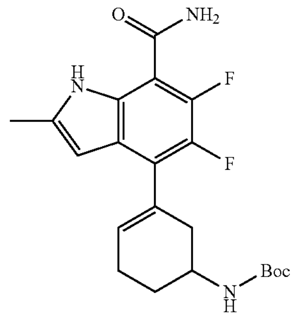

A mixture of 4-bromo-5,6-difluoro-2-methyl-1H-indole-7-carboxamide (1.5 g, 5.19 mmol), tert-butyl (3-(4,4,5,5-tetra methyl-1,3,2-dioxaborolan-2-yl)cyclohex-3-en-1-yl) carbamate (1.84 g, 5.71 mmol), potassium carbonate (2.9 g, 20.76 mmol,) and Pd(dppf)$Cl_2$ (378 mg, 0.519 mmol) in dioxane (16 mL) and water (4 mL) was degassed and backfilled with nitrogen for five times. The reaction mixture was heated at 90° C. for 2 h. The cooled reaction mixture was quenched with water (60 mL) and extracted with ethyl acetate (3×50 mL). The combined organic layers was washed with brine (50 mL), dried over $Na_2SO_4$ and concentrated under vacuum. The residue was purified by column chromatography on silica gel eluting with ethyl acetate in petroleum ether (0 to 30%) to give tert-butyl (3-(7-carbamoyl-5,6-difluoro-2-methyl-1H-indol-4-yl)cyclohex-3-en-1-yl)carbamate (1.6 g, 76%) as a yellow solid. ESI-MS $[M+H]^+$ calcd for ($C_{21}H_{25}F_2N_3O_3$) 406.19 found: 406.20.

Step 11: tert-butyl (3-(7-carbamoyl-3-chloro-5,6-difluoro-2-methyl-1H-indol-4-yl) cyclohex-3-en-1-yl) carbamate

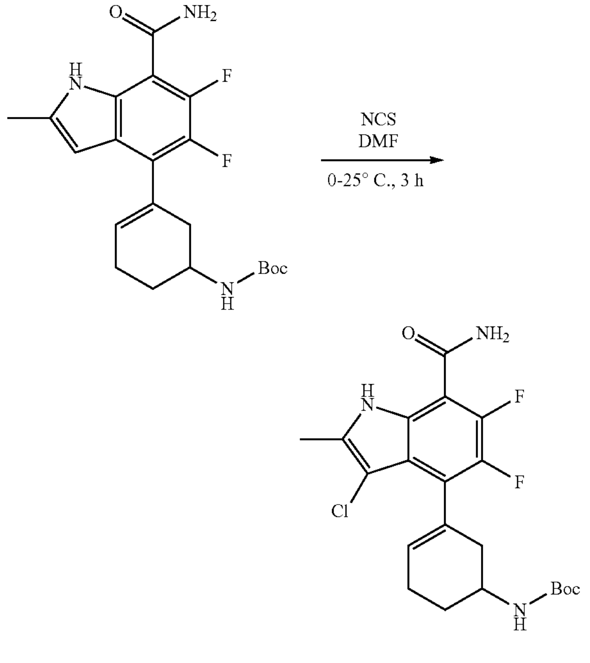

To a stirred solution of tert-butyl (3-(7-carbamoyl-5,6-difluoro-2-methyl-1H-indol-4-yl) cyclohex-3-en-1-yl)carbamate (300 mg, 0.74 mmol) in DMF (6 mL) was added NCS (99 mg, 0.74 mmol) at 0° C. The reaction mixture was stirred for 3 h at 25° C., quenched with water (30 mL) and extracted with ethyl acetate (3×30 mL). The combined organic layers were washed with brine (40 mL), dried over $Na_2SO_4$ and concentrated under vacuum. The residue was purified by column chromatography on silica gel eluting with ethyl acetate in petroleum ether (0 to 35%) to give tert-butyl (3-(7-carbamoyl-3-chloro-5,6-difluoro-2-methyl-1H-indol-4-yl) cyclohex-3-en-1-yl)carbamate. (270 mg, 83%) as a yellow solid. ESI-MS $[M+H-^{t}Bu]^+$ calcd for ($C_{21}H_{24}ClF_2N_3O_3$) 384.15, 386.15 found: 384.20, 386.20

Step 12: 4-(5-aminocyclohex-1-en-1-yl)-3-chloro-5,6-difluoro-2-methyl-1H-indole-7-carboxamide hydrochloride

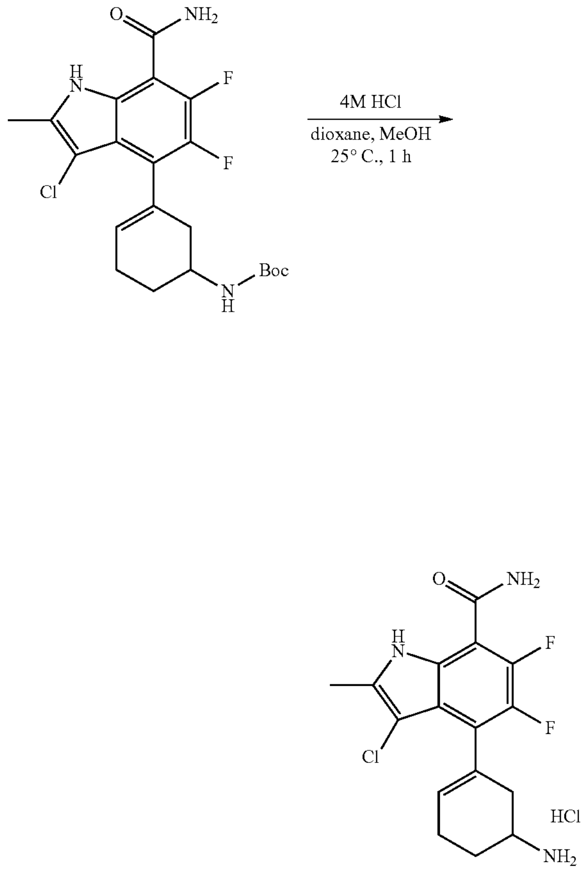

To a stirred solution of tert-butyl (3-(7-carbamoyl-3-chloro-5,6-difluoro-2-methyl-1H-indol-4-yl) cyclohex-3-en-1-yl)carbamate (230 mg, 0.52 mmol) in MeOH (1 mL) was added 4 M hydrogen chloride in dioxane (3 mL). The reaction mixture was stirred at 25° C. for 1 h, and then concentrated under vacuum to give 4-(5-aminocyclohex-1-en-1-yl)-3-chloro-5,6-difluoro-2-methyl-1H-indole-7-carboxamide hydrochloride (190 mg, crude) as a yellow solid. ESI-MS $[M+H]^+$ calcd for ($C_{16}H_{16}ClF_2N_3O$) 340.09, 342.09 found: 340.25, 342.25.

Step 13: racemic 4-(5-(but-2-ynamido) cyclohex-1-en-1-yl)-3-chloro-5,6-difluoro-2-methyl-1H-indole-7-carboxamide (Compound 2-A-(rac))

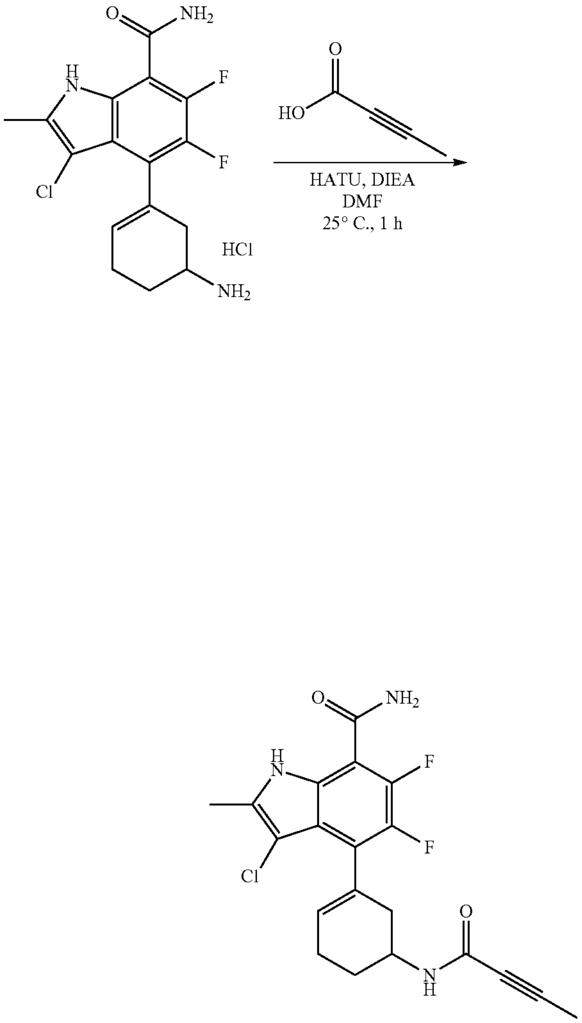

To a stirred solution of 4-(5-aminocyclohex-1-en-1-yl)-3-chloro-5,6-difluoro-2-methyl-1H-indole-7-carboxamide hydrochloride (160 mg, 0.43 mmol) in DMF (5 mL) were added 2-butynoic acid (36 mg, 0.43 mmol), HATU (210 mg, 0.55 mmol) and DIEA (275 mg, 2.13 mmol, 0.35 mL). The reaction mixture was stirred for 1 h at 25° C., quenched with water (30 mL) and extracted with ethyl acetate (3×30 mL). The combined organic layers were washed with brine (30 mL), dried over $Na_2SO_4$ and concentrated under vacuum. The residue was purified by Prep-HPLC with the following conditions: Column: XBridge Prep C18 OBD Column, 19×150 mm 5 um; Mobile Phase A: Water (10 mmol/L $NH_4HCO_3$+0.1% $NH_3 \cdot H_2O$), Mobile Phase B: Acetonitrile; Flow rate: 25 mL/min; Gradient: 28% B to 43% B in 10 min; 220 nm; RT1: 10.88 min to give 4-(5-(but-2-ynamido) cyclohex-1-en-1-yl)-3-chloro-5,6-difluoro-2-methyl-1H-indole-7-carboxamide (120 mg, 69%) as a white solid. ESI-MS $[M+H]^+$ calcd for ($C_{20}H_{18}ClF_2N_3O_2$) 406.11, 40811 found: 406.05, 408.05.

Step 14: (S)-4-(5-(but-2-ynamido) cyclohex-1-en-1-yl)-3-chloro-5,6-difluoro-2-methyl-1H-indole-7-carboxamide (Compound 2-A-(S)) and (R)-4-(5-(but-2-ynamido) cyclohex-1-en-1-yl)-3-chloro-5,6-difluoro-2-methyl-1H-indole-7-carboxamide (Compound 2-A-(R))

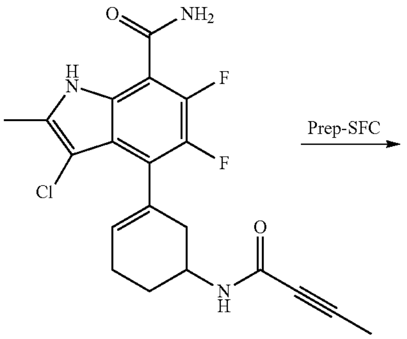

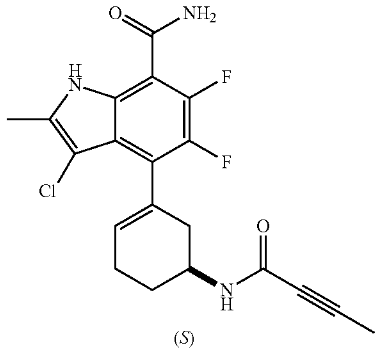

(S)

and

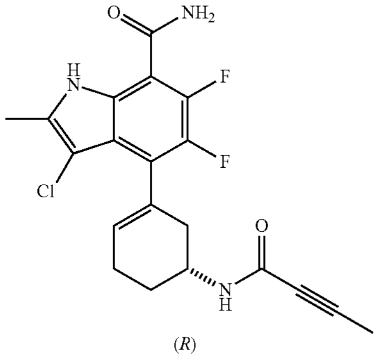

(R)

4-(5-(but-2-ynamido) cyclohex-1-en-1-yl)-3-chloro-5,6-difluoro-2-methyl-1H-indole-7-carboxamide (120 mg) was separated by Chiral-Prep-HPLC with the following conditions: Column: (R, R)-WHELK-O1-Kromasil, 2.12×25 cm, 5 um; Mobile Phase A: Hexane (0.5% 2 M NH3-MeOH)-HPLC, Mobile Phase B: EtOH-HPLC; Flow rate: 20 mL/min; Gradient: 30% B to 30% B in 24 min; 220/254 nm.

Retention Time=17.654 Min (S)-4-(5-(but-2-ynamido) cyclohex-1-en-1-yl)-3-chloro-5,6-difluoro-2-methyl-1H-indole-7-carboxamide or (R)-4-(5-(but-2-ynamido) cyclohex-1-en-1-yl)-3-chloro-5,6-difluoro-2-methyl-1H-indole-7-carboxamide (49.9 mg, 42% yield) as an off-white solid. 1H NMR (400 MHz, DMSO-d6) δ 11.39 (s, 1H), 8.65-8.50 (m, 1H), 7.97-7.81 (m, 2H), 5.66 (s, 1H), 4.03 (s, 1H), 2.40-2.18 (m, 7H), 1.94 (s, 3H), 1.91-1.80 (m, 1H), 1.66-1.46 (m, 1H). ESI-MS [M+H]+ calcd for (C20H18ClF2N3O2) 406.11, 408.11 found: 406.10, 408 10.

Retention Time=20.658 Min (R)-4-(5-(but-2-ynamido) cyclohex-1-en-1-yl)-3-chloro-5,6-difluoro-2-methyl-1H-indole-7-carboxamide or (S)-4-(5-(but-2-ynamido) cyclohex-1-en-1-yl)-3-chloro-5,6-difluoro-2-methyl-1H-indole-7-carboxamide (51.2 mg, 43%) as an off-white solid. 1H NMR (400 MHz, DMSO-d6) δ 11.40 (s, 1H), 8.55 (s, 1H), 7.97-7.82 (m, 2H), 5.66 (s, 1H), 4.04 (s, 1H), 2.34 (s, 3H), 2.33-2.10 (m, 4H), 1.94 (s, 3H), 1.91-1.80 (m, 1H), 1.64-1.50 (m, 1H). ESI-MS [M+H]+ calcd for (C20H18ClF2N3O2) 406.11, 408.11 found: 406.10, 408 10.

Example 3

Synthesis of (S)-4-(5-(but-2-ynamido)cyclohex-1-en-1-yl)-5-fluoro-2,3-dimethyl-1H-indole-7-carboxamide (Compound 3-A-(S))

and

(S)-4-(3-(but-2-ynamido)cyclohex-1-en-1-yl)-5-fluoro-2,3-dimethyl-1H-indole-7-carboxamide (Compound 3-B-(S))

(Compound 3-A-(S))

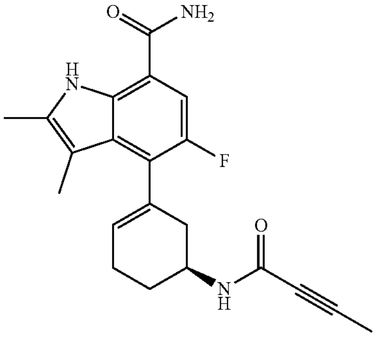

(Compound 3-B-(S))

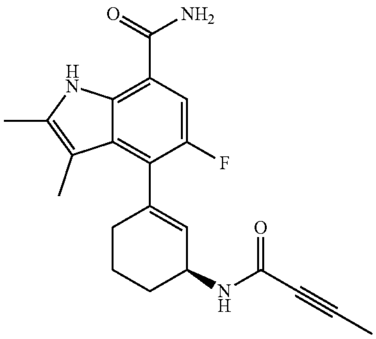

Step 1: (S)-5-((tert-butoxycarbonyl)amino)cyclohex-1-en-1-yl trifluoromethanesulfonate and (S)-3-((tert-butoxycarbonyl)amino)cyclohex-1-en-1-yl trifluoromethanesulfonate

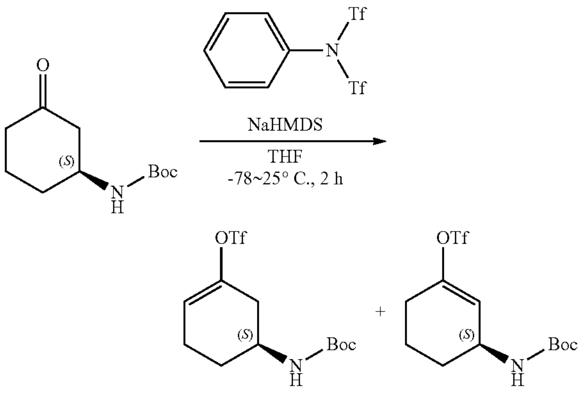

To a mixture of tert-butyl (S)-(3-oxocyclohexyl)carbamate (10.0 g, 46.89 mmol) and 1,1,1-trifluoro-N-phenyl-N-((trifluoromethyl)sulfonyl)methanesulfonamide (21.8 g, 60.95 mmol) in THF (150 mL) was added dropwise sodium bis(trimethylsilyl)amide (2 M in THF, 58.6 mL, 117.2 mmol) at −78° C. After addition, the reaction mixture was stirred at 25° C. for 2 h. The resulting mixture was quenched with water (300 mL) and extracted with ethyl acetate (150 mL×3). The combined organic layers were washed with brine (150 mL), dried over anhydrous sodium sulfate, filtered and concentrated under vacuum. The residue was purified by column chromatography on silica gel eluting with ethyl acetate in petroleum ether (5%) to give the mixture of (S)-5-((tert-butoxycarbonyl)amino)cyclohex-1-en-1-yl trifluoromethanesulfonate and (S)-3-((tert-butoxycarbonyl)amino)cyclo hex-1-en-1-yl trifluoromethanesulfonate (17.5 g, crude) as a yellow oil.

Step 2: tert-butyl (S)-(3-(4,4,5,5-tetramethyl-1,3,2-dioxaborolan-2-yl)cyclohex-3-en-1-yl)carbamate and tert-butyl (S)-(3-(4,4,5,5-tetramethyl-1,3,2-dioxaborolan-2-yl)cyclohex-2-en-1-yl)carbamate

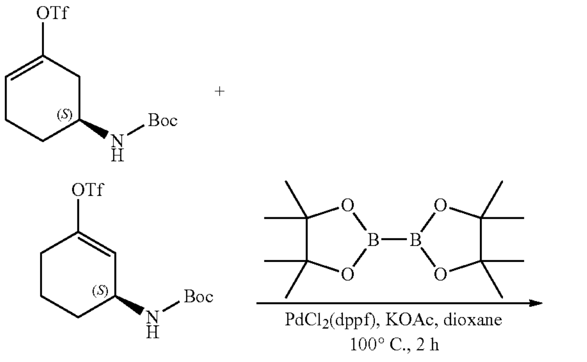

-continued

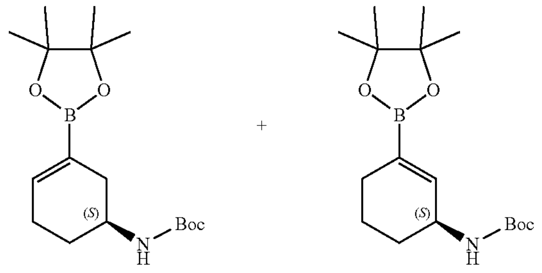

A mixture of (S)-5-((cert-butoxycarbonyl)amino)cyclohex-1-en-1-yl trifluoromethane-sulfonate and (S)-3-((cert-butoxycarbonyl)amino)cyclohex-1-en-1-yl trifluoromethanesulfonate (17.5 g, crude), 4,4,4',4',5,5,5',5'-octamethyl-2,2'-bi(1,3,2-dioxaborolane) (12.9 g, 50.68 mmol), Pd(dppf)$Cl_2$·DCM (4.14 g, 5.07 mmol) and potassium acetate (14.92 g, 152.03 mmol) in dioxane (250 mL) was degassed and backfilled with nitrogen for five times. The reaction mixture was heated at 100° C. for 2 h. The cooled reaction mixture was diluted with water (500 mL) and extracted with ethyl acetate (300 mL×3). The combined organic layers were washed with brine (300 mL), dried over anhydrous sodium sulfate, filtered and concentrated under vacuum. The residue was purified by column chromatography on silica gel eluting with ethyl acetate in petroleum ether (5%) to provide a mixture of tert-butyl (S)-(3-(4,4,5,5-tetramethyl-1,3,2-dioxaborolan-2-yl)cyclohex-3-en-1-yl)carbamate and tert-butyl (S)-(3-(4,4,5,5-tetramethyl-1,3,2-dioxaborolan-2-yl)cyclohex-2-en-1-yl)carbamate (15.0 g, crude) as a colorless oil.

Step 3: tert-butyl (S)-(3-(7-cyano-5-fluoro-2,3-dimethyl-1H-indol-4-yl)cyclohex-3-en-1-yl)carbamate and tert-butyl (S)-(3-(7-cyano-5-fluoro-2,3-dimethyl-1H-indol-4-yl)cyclohex-2-en-1-yl)carbamate

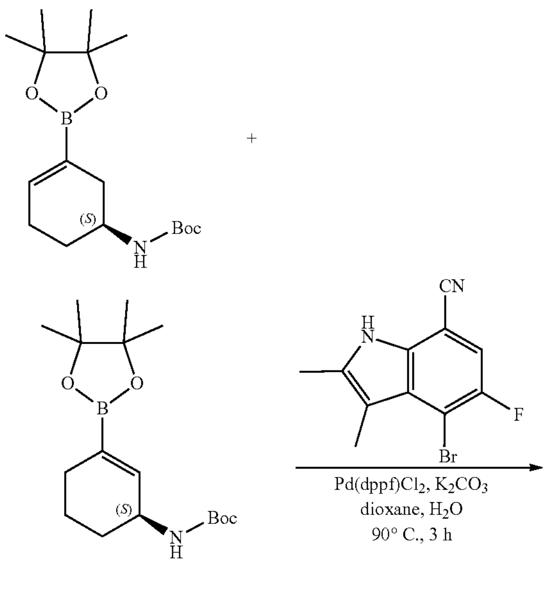

-continued

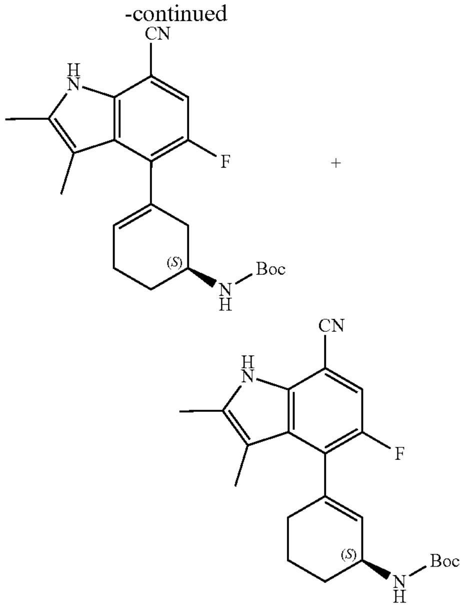

A mixture of tert-butyl (S)-(3-(4,4,5,5-tetramethyl-1,3,2-dioxaborolan-2-yl)cyclohex-3-en-1-yl)carbamate and tert-butyl (S)-(3-(4,4,5,5-tetra methyl-1,3,2-dioxaborolan-2-yl) cyclohex-2-en-1-yl)carbamate (3.1 g, 7.8 mmol), 4-bromo-5-fluoro-2,3-dimethyl-1H-indole-7-carbonitrile (2.5 g, 9.36 mmol), Pd(dppf)$Cl_2$·DCM (764 mg, 0.94 mmol) and potassium phosphate (3.88 g, 28.08 mmol) in 1,4-dioxane (30 mL) and water (8 mL) was degassed and backfilled with nitrogen five times and stirred at 90° C. for 3 h. The cooled reaction mixture was diluted with water (60 mL) and extracted with ethyl acetate (60 mL×3). The combined organic layers was washed with water (50 mL×2) and brine (60 mL), dried over anhydrous sodium sulfate and concentrated under vacuum to provide a the mixture of tert-butyl (S)-(3-(7-cyano-5-fluoro-2,3-dimethyl-1H-indol-4-yl)cyclohex-3-en-1-yl)carbamate and tert-butyl (S)-(3-(7-cyano-5-fluoro-2,3-dimethyl-1H-indol-4-yl)cyclohex-2-en-1-yl) carbamate (4.0 g, crude) as a brown oil.

ESI-MS $[M-H]^-$ calcd for ($C_{22}H_{26}FN_3O_2$) 382.20, found: 382.20

Step 4: tert-butyl (S)-(3-(7-carbamoyl-5-fluoro-2,3-dimethyl-1H-indol-4-yl)cyclohex-3-en-1-yl)carbamate and tert-butyl (S)-(3-(7-carbamoyl-5-fluoro-2,3-dimethyl-1H-indol-4-yl)cyclohex-2-en-1-yl) carbamate

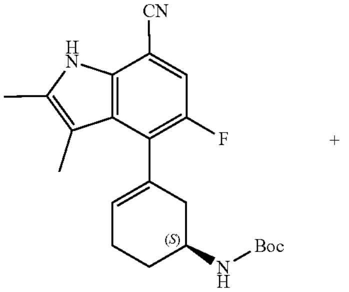

-continued

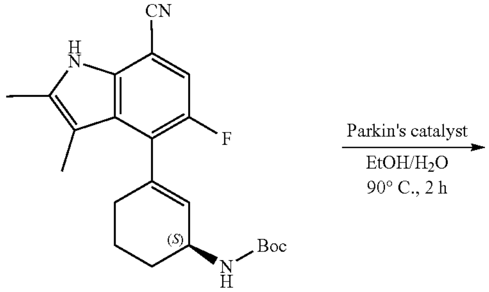

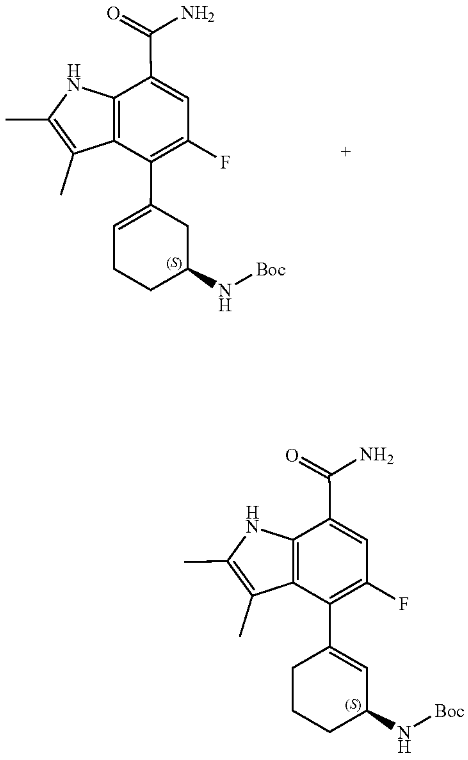

To a mixture of tert-butyl tert-butyl (S)-(3-(7-cyano-5-fluoro-2,3-dimethyl-1H-indol-4-yl)cyclohex-3-en-1-yl)carbamate and tert-butyl (S)-(3-(7-cyano-5-fluoro-2,3-dimethyl-1H-indol-4-yl)cyclohex-2-en-1-yl)carbamate (4.0 g, crude) in ethanol (40 mL) and water (10 mL) was added Parkin's catalyst (445 mg, 1.04 mmol). The reaction mixture was stirred at 90° C. for 2 h, allowed to cool, diluted with water (60 mL) and extracted with ethyl acetate (60 mL×3). The combined organic layers were washed water (50 mL×2) and brine (60 mL), dried over anhydrous sodium sulfate, filtered and concentrated under vacuum. The residue was purified by column chromatography on silica gel eluting with ethyl acetate in petroleum ether (45%) to give the mixture of tert-butyl (S)-(3-(7-carbamoyl fluoro-2,3-dimethyl-1H-indol-4-yl)cyclohex-3-en-1-yl)carbamate and tert-butyl (S)-(3-(7-carbamoyl-5-fluoro-2,3-dimethyl-1H-indol-4-yl)cyclohex-2-en-1-yl)carbamate (2.58 g) as a yellow solid.

ESI-MS $[M+H]^+$ calcd for ($C_{22}H_{28}FN_3O_3$) 402.21, found: 402.35

Step 5: (S)-4-(5-aminocyclohex-1-en-1-yl)-5-fluoro-2,3-dimethyl-1H-indole-7-carboxamide hydrochloride and (S)-4-(3-aminocyclohex-1-en-1-yl)-5-fluoro-2,3-dimethyl-1H-indole-7-carboxamide hydrochloride

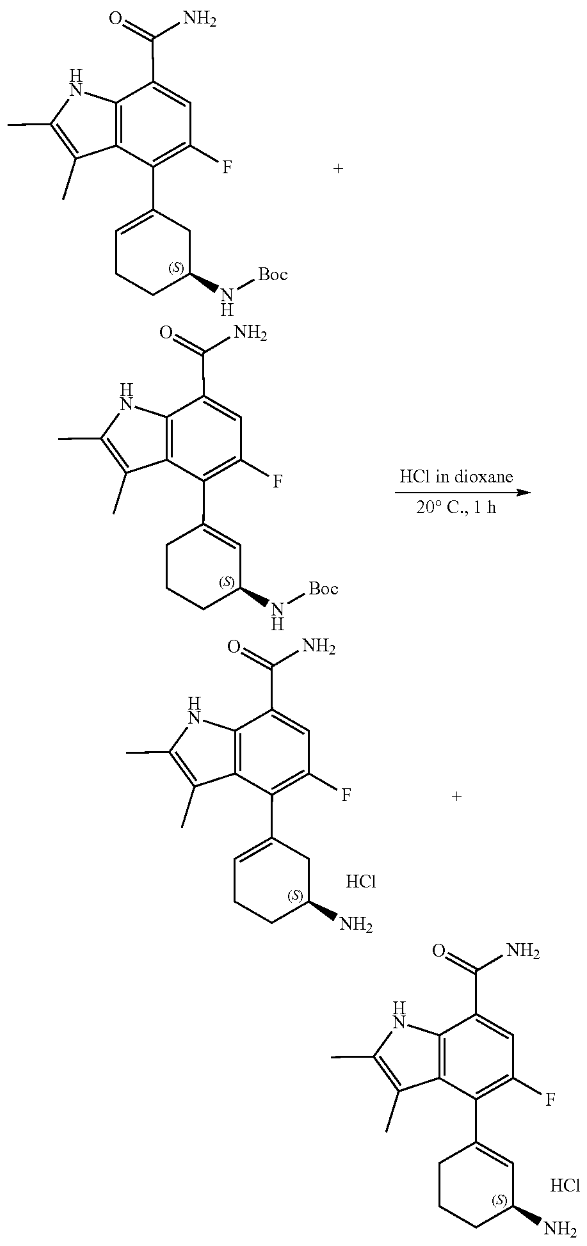

A mixture of tert-butyl (S)-(3-(7-carbamoyl-5-fluoro-2,3-dimethyl-1H-indol-4-yl)cyclohex-3-en-1-yl)carbamate and tert-butyl (S)-(3-(7-carbamoyl-5-fluoro-2,3-dimethyl-1H-indol-4-yl)cyclohex-2-en-1-yl)carbamate (2.58 g, 6.43 mmol) and hydrogen chloride (4.0 M in 1,4-dioxane, 20 mL) was stirred at 20° C. for 1 h. The resulting mixture was concentrated under vacuum to give mixture of (S)-4-(5-aminocyclohex-1-en-1-yl)-5-fluoro-2,3-dimethyl-1H-indole-7-carboxamide hydrochloride and (S)-4-(3-aminocyclohex-1-en-1-yl)-5-fluoro-2,3-dimethyl-1H-indole-7-carboxamide hydrochloride (2.15 g, crude) as a yellow solid. ESI-MS $[M+H]^+$ calcd for ($C_{17}H_{20}FN_3O$) 302.16, found: 302.15.

Step 6: (S)-4-(5-(but-2-ynamido)cyclohex-1-en-1-yl)-5-fluoro-2,3-dimethyl-1H-indole-7-carboxamide (Compound 3-A-(S)) and (S)-4-(3-(but-2-ynamido)cyclohex-1-en-1-yl)-5-fluoro-2,3-dimethyl-1H-indole-7-carboxamide (Compound 3-B-(S))

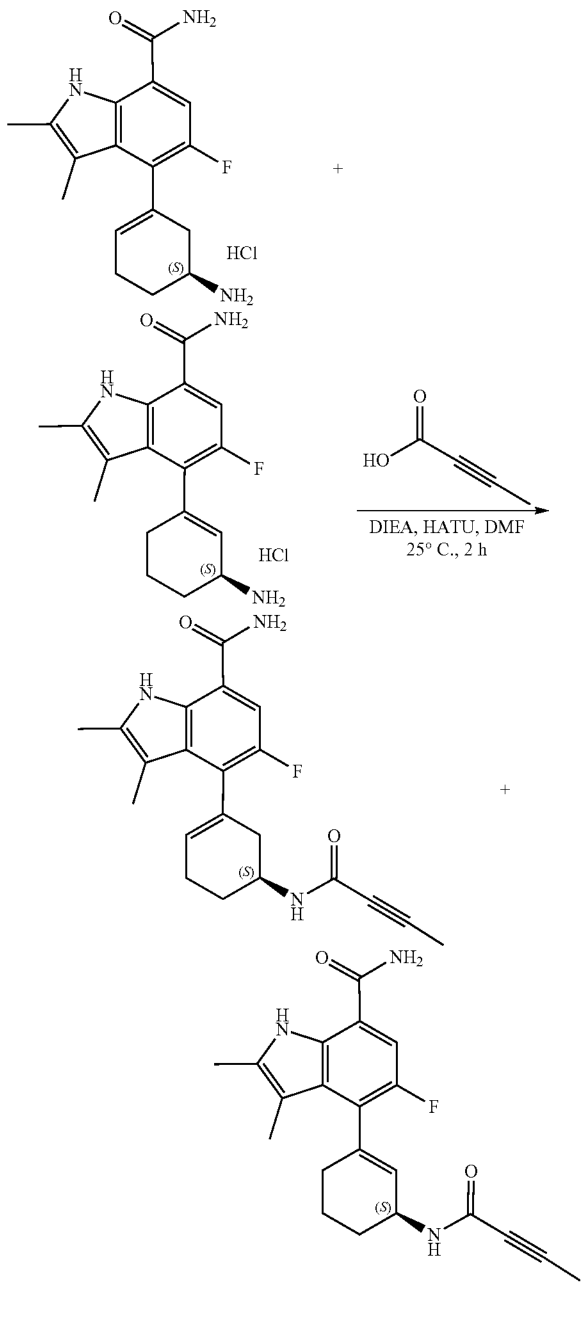

To a mixture of (S)-4-(5-aminocyclohex-1-en-1-yl)-5-fluoro-2,3-dimethyl-1H-indole-7-carboxamide hydrochloride and (S)-4-(3-aminocyclohex-1-en-1-yl)-5-fluoro-2,3-dimethyl-1H-indole-7-carboxamide hydrochloride (2.15 g, crude) in DMF (30 mL) were added O-(7-Azabenzotriazol- 1-yl)-N,N,N',N'-tetramethyluronium hexafluorophosphate (3.63 g, 9.55 mmol), but-2-ynoic acid (642 mg, 7.64 mmol) and N,N-diisopropylethylamine (4.11 g, 31.82 mmol). The reaction mixture was stirred at 25° C. for 2 h. The resulting mixture was diluted with water (60 mL) and extracted with ethyl acetate (50 mL×2). The combined organic layers were washed with water (40 mL×3) and brine (50 mL), dried over anhydrous sodium sulfate, filtered and concentrated under vacuum. The residue was purified by column chromatography on silica gel eluting with ethyl acetate in petroleum ether (60%) to give 1.7 g of the mixed isomers.

The mixture (1.7 g) was separated by Prep-SFC with the following conditions: Column: GreenSep Basic, 3×15 cm, 5 μm; Mobile Phase A: $CO_2$, Mobile Phase B: IPA (0.5% 2 M $NH_3$-MeOH); Flow rate: 80 mL/min; Gradient: 40% B; Column Temperature: 35° C.; Back Pressure: 100 bar; 220 nm.

Retention Time=5.3 min Compound 3-B-(S)

(S)-4-(3-(but-2-ynamido)cyclohex-1-en-1-yl)-5-fluoro-2,3-dimethyl-1H-indole-7-carboxamide (345 mg) as a white solid; $^1$H NMR (400 MHz, DMSO-$d_6$) δ 10.71 (s, 1H), 8.56 (d, J=7.6 Hz, 1H), 8.00 (s, 1H), 7.54-7.27 (m, 2H), 5.56 (s, 1H), 3.98 (s, 1H), 2.46-2.15 (m, 7H), 2.15-1.99 m, 3H), 1.92 (s, 3H), 1.91-1.82 (m, 1H), 1.63-1.48 (m, 1H). ESI-MS $[M+H]^+$ calcd for ($C_{21}H_{22}FN_3O_2$) 368.17, found: 368.35.

Retention Time=6.32 min Compound 3-A-(S)

(S)-4-(5-(but-2-ynamido)cyclohex-1-en-1-yl)-5-fluoro-2,3-dimethyl-1H-indole-7-carboxamide (825.2 mg) as a white solid. $^1$H NMR (400 MHz, DMSO-$d_6$) δ 10.72 (s, 1H), 8.75 (d, J=7.6 Hz, 1H), 8.00 (s, 1H), 7.54-7.27 (m, 2H), 5.56 (s, 1H), 4.55-4.33 (m, 1H), 2.46-2.15 (m, 7H), 2.15-1.99 m, 3H), 1.92 (s, 3H), 1.91-1.82 (m, 1H), 1.80-1.48 (m, 1H). ESI-MS $[M+H]^+$ calcd for ($C_{21}H_{22}FN_3O_2$) 368.17, found: 368.35.

Example 4

Synthesis of (S)-5-fluoro-2,3-dimethyl-4-(5-(N-methylbut-2-ynamido)cyclohex-1-en-1-yl)-1H-indole-7-carboxamide (Compound 4-A-(S))

and (S)-5-fluoro-2,3-dimethyl-4-(3-(N-methylbut-2-ynamido)cyclohex-1-en-1-yl)-1H-indole-7-carboxamide (Compound 4-B-(S))

Compound 4-A-(S)

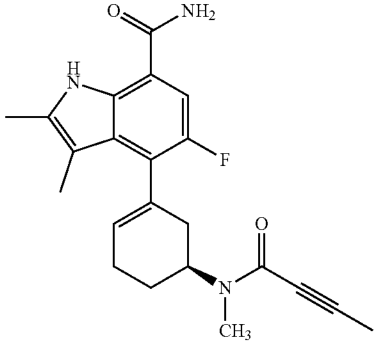

-continued

Compound 4-B-(S)

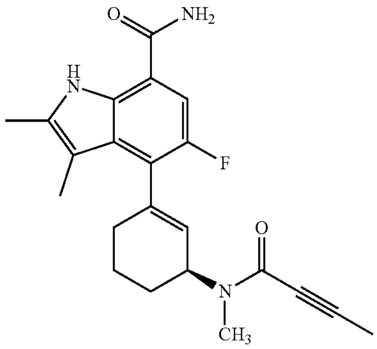

Step 1: 4-bromo-5-fluoro-2,3-dimethyl-1-((2-(trimethylsilyl)ethoxy)methyl)-1H-indole-7-carbonitrile

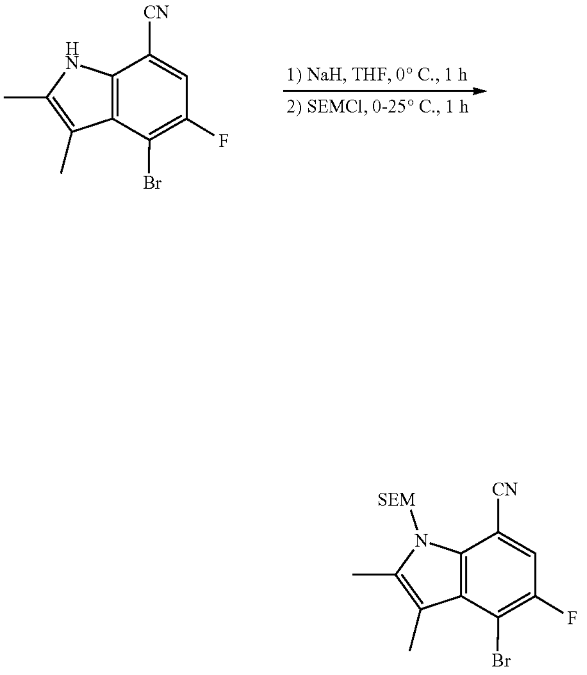

To a solution of 4-bromo-5-fluoro-2,3-dimethyl-1H-indole-7-carbonitrile (1.00 g, 3.74 mmol) in THF (10 mL) was added sodium hydride (225 mg, 5.63 mmol, 60%) at 0° C. under nitrogen atmosphere. After stirring for 1 hour at 0° C., 2-(chloromethoxy)ethyl-trimethylsilane (1.25 g, 7.49 mmol) was added at 0° C. The reaction mixture was further stirred for 1 hour at 25° C. The reaction mixture was quenched with saturated aqueous ammonium chloride (50 mL) and extracted with ethyl acetate (30 mL×3). The combined organic layers were washed with water (30 mL×2) and brine (30 mL), dried over anhydrous sodium sulfate and concentrated under vacuum to give 4-bromo-5-fluoro-2,3-dimethyl-1-((2-(trimethylsilyl)ethoxy)methyl)-1H-indole-7-carbonitrile (1.50 g, crude) as a brown oil. $^1$H NMR (400 MHz, DMSO-$d_6$) δ 7.69 (d, J=9.0 Hz, 1H), 5.69 (s, 2H), 3.53 (t, J=7.8 Hz, 2H), 2.42 (s, 3H), 2.37 (s, 3H), 0.82 (t, J=7.8 Hz, 2H), −0.10 (s, 9H).

Step 2: tert-butyl (S)-(3-(7-cyano-5-fluoro-2,3-dimethyl-1-((2-(trimethylsilyl)-ethoxy)methyl)-1H-indol-4-yl)cyclohex-3-en-1-yl)carbamate and tert-butyl (S)-(3-(7-cyano-5-fluoro-2,3-dimethyl-1-((2-(trimethylsilyl)ethoxy)methyl)-1H-indol-4-yl)cyclohex-2-en-1-yl)carbamate

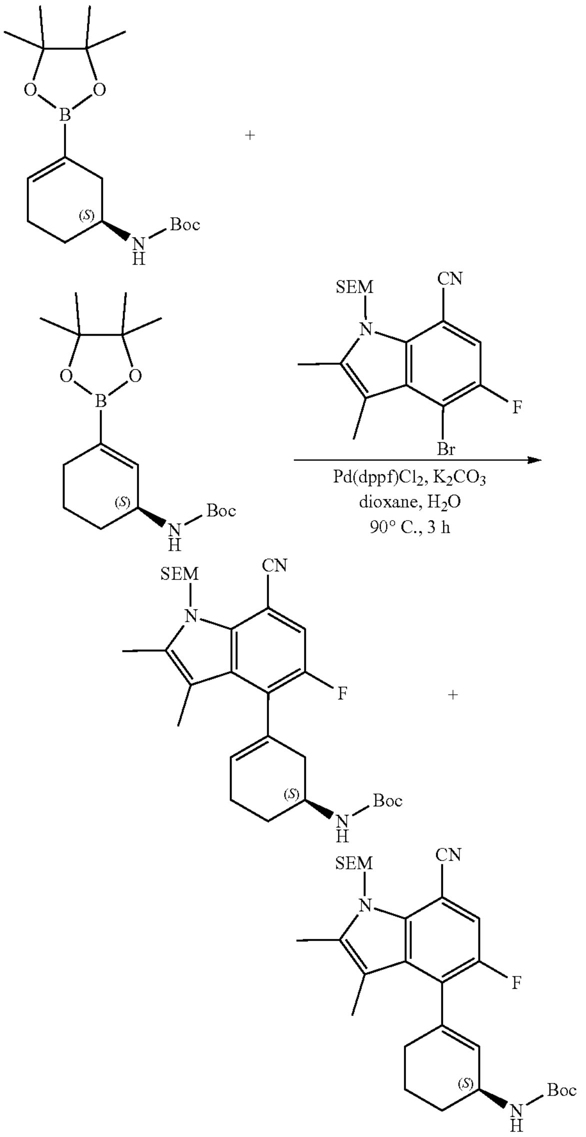

To a mixture of 4-bromo-5-fluoro-2,3-dimethyl-1-((2-(trimethylsilyl)ethoxy)methyl)-1H-indole-7-carbonitrile (1.50 g, 3.77 mmol) and a mixture of tert-butyl (S)-(3-(4,4,5,5-tetramethyl-1,3,2-dioxaborolan-2-yl)cyclohex-3-en-1-yl)carbamate and tert-butyl (S)-(3-(4,4,5,5-tetramethyl-1,3,2-dioxaborolan-2-yl)cyclohex-2-en-1-yl)carbamate (see example 3, step 2; 1.46 g, 4.53 mmol) in THF (8 mL) and water (2 mL) were added $Pd(dppf)Cl_2$ (276 mg, 0.38 mmol) and potassium phosphate (2.40 g, 11.32 mmol). The reaction mixture was degassed and backfilled with nitrogen for three times and stirred for 2 hours at 60° C. The cooled reaction mixture was diluted with water (50 mL) and extracted with ethyl acetate (40 mL×3). The combined organic layers were washed with water (50 mL×2) and brine (50 mL), dried over anhydrous sodium sulfate, filtered and concentrated under vacuum. The residue was purified by column chromatography on silica gel eluting with ethyl acetate in petroleum ether (0 to 10%) to give tert-butyl (S)-(3-(7-cyano-5-fluoro-2,3-dimethyl-1-((2-(trimethylsilyl)-ethoxy)methyl)-1H-indol-4-yl)cyclohex-3-en-1-yl)carbamate and tert-butyl (S)-(3-(7-cyano-5-fluoro-2,3-dimethyl-1-((2-(trimethylsilyl)ethoxy)methyl)-1H-indol-4-yl)cyclohex-2-en-1-yl)carbamate (1.40 g, 72%) as a light yellow oil. ESI-MS $[M-H]^-$ calcd for $(C_{28}H_{40}FN_3O_3Si)$ 512.28, found: 512.20.

Step 3: tert-butyl (S)-(3-(7-cyano-5-fluoro-2,3-dimethyl-1-((2-(trimethylsilyl)ethoxy)methyl)-1H-indol-4-yl)cyclohex-3-en-1-yl)(methyl)carbamate and tert-butyl (S)-(3-(7-cyano-5-fluoro-2,3-dimethyl-1-((2-(trimethylsilyl)ethoxy)methyl)-1H-indol-4-yl)cyclohex-2-en-1-yl)(methyl)carbamate

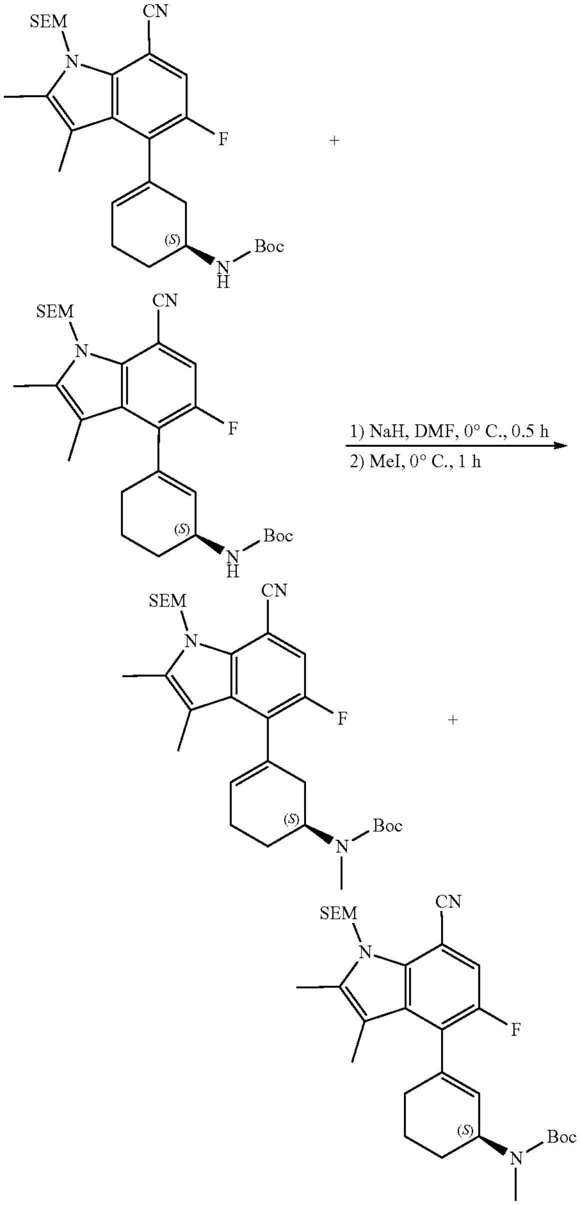

To a solution of tert-butyl (S)-(3-(7-cyano-5-fluoro-2,3-dimethyl-1-((2-(trimethylsilyl)ethoxy)methyl)-1H-indol-4-yl)cyclohex-3-en-1-yl)carbamate (1.30 g, 2.53 mmol) in DMF (15 mL) was added sodium hydride (202 mg, 5.06 mmol, 60%) at 0° C. under nitrogen atmosphere. After stirring for 30 minutes, iodomethane (1.08 g, 7.59 mmol) was added at 0° C. The reaction mixture was further stirred for 1 hour at 0° C. The mixture was quenched with saturated aqueous ammonium chloride (60 mL) and extracted with ethyl acetate (50 mL×3). The combined organic layers were washed with water (50 mL×3) and brine (50 mL), dried over anhydrous sodium sulfate, filtered and concentrated under vacuum. The residue was purified by column chromatography on silica gel eluting with ethyl acetate in petroleum ether (0 to 15%) to give a mixture of tert-butyl (S)-(3-(7-cyano-5-fluoro-2,3-dimethyl-1-((2-(trimethylsilyl)ethoxy)methyl)-1H-indol-4-yl)cyclohex-3-en-1-yl)(methyl)carbamate and tert-butyl (S)-(3-(7-cyano-5-fluoro-2,3-dimethyl-1-((2-(trimethylsilyl)ethoxy)methyl)-1H-indol-4-yl)cyclohex-2-en-1-yl)(methyl)carbamate (1.10 g, 82%) as a light yellow oil. ESI-MS $[M+H]^+$ calcd for $(C_{29}H_{42}FN_3O_3Si)$ 528.30, found: 528.30.

Step 4: tert-butyl (S)-(3-(7-cyano-5-fluoro-2,3-dimethyl-1H-indol-4-yl)cyclohex-3-en-1-yl)(methyl)carbamate and tert-butyl (S)-(3-(7-cyano-5-fluoro-2,3-dimethyl-1H-indol-4-yl)cyclohex-2-en-1-yl)(methyl)carbamate

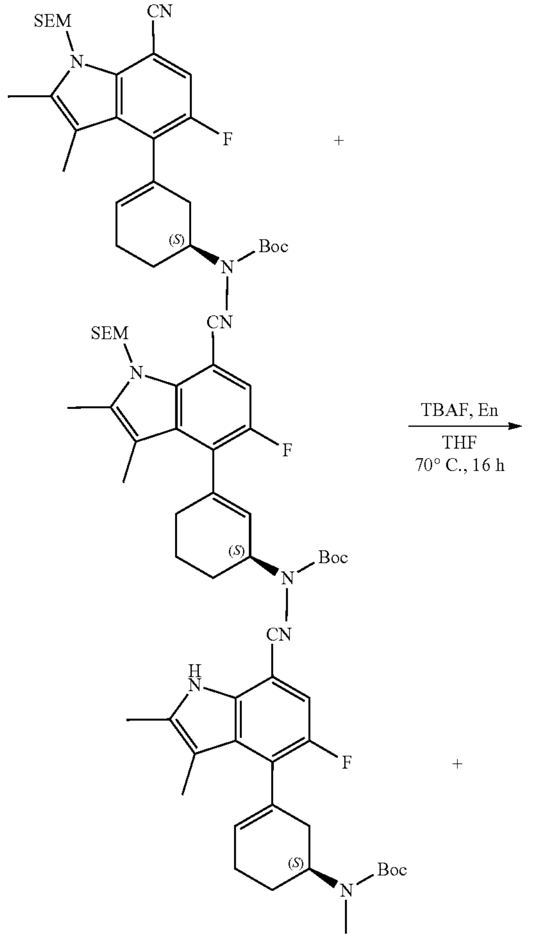

-continued

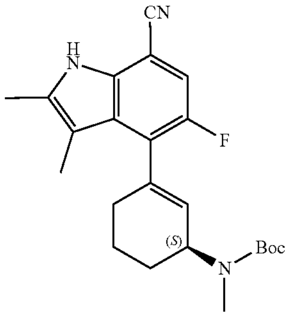

To a solution of the mixture from step 3 above (1.10 g, 2.08 mmol) in THF (10 mL) were added TBAF (5.45 g, 20.84 mmol) and diethylamine (3.05 g, 41.69 mmol) at 25° C. After stirring for 16 hours at 70° C., the cooled mixture was diluted with water (70 mL) and extracted with ethyl acetate (50 mL×3). The combined organic layers were washed with water (50 mL×2) and brine (50 mL), dried over anhydrous sodium sulfate, filtered and concentrated under vacuum. The residue was purified by column chromatography on silica gel eluting with ethyl acetate in petroleum ether (0 to 25%) to give a mixture of tert-butyl (S)-(3-(7-cyano-5-fluoro-2,3-dimethyl-1H-indol-4-yl)cyclohex-3-en-1-yl)(methyl)carbamate and tert-butyl (S)-(3-(7-cyano-5-fluoro-2,3-dimethyl-1H-indol-4-yl)cyclohex-2-en-1-yl)(methyl)carbamate (340 mg, 41%) as a brown solid. ESI-MS $[M+H]^+$ calcd for $(C_{23}H_{28}FN_3O_3)$ 398.22, found: 398.35.

Step 5: tert-butyl (S)-(3-(7-carbamoyl-5-fluoro-2,3-dimethyl-1H-indol-4-yl)cyclohex-3-en-1-yl)(methyl)carbamate and tert-butyl (S)-(3-(7-carbamoyl-5-fluoro-2,3-dimethyl-1H-indol-4-yl)cyclohex-2-en-1-yl)(methyl)carbamate

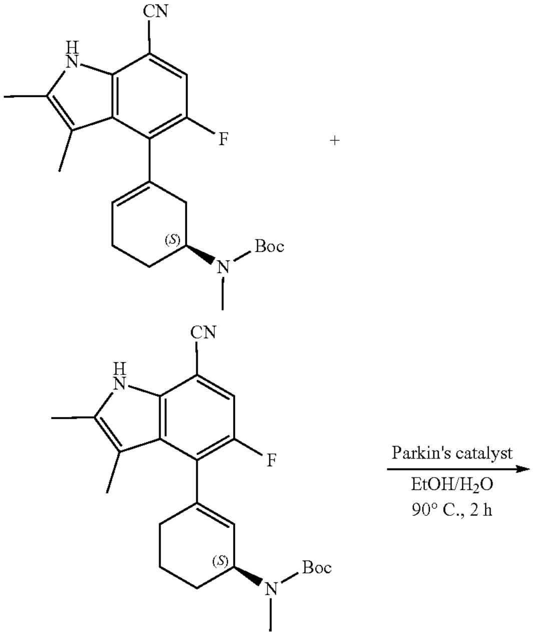

-continued

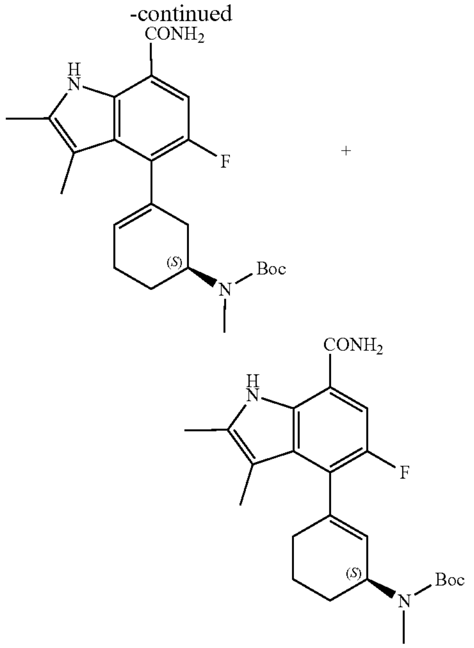

To a mixture of tert-butyl (S)-(3-(7-cyano-5-fluoro-2,3-dimethyl-1H-indol-4-yl)cyclohex-3-en-1-yl)(methyl)carbamate and tert-butyl (S)-(3-(7-cyano-5-fluoro-2,3-dimethyl-1H-indol-4-yl)cyclohex-2-en-1-yl)(methyl)carbamate (340 mg, 0.86 mmol) in ethanol (5 mL) and water (5 mL) was added Parkin's catalyst (18 mg, 0.04 mmol). The reaction mixture was stirred for 2 h at 90° C. The cooled reaction mixture was diluted with water (30 mL) and extracted with ethyl acetate (30 mL×3). The combined organic layers were washed with water (50 mL×2) and brine (50 mL), dried over anhydrous sodium sulfate, filtered and concentrated under vacuum. The residue was purified by column chromatography on silica gel eluting with ethyl acetate in petroleum ether (0 to 60%) to give a mixture of tert-butyl (S)-(3-(7-carbamoyl-5-fluoro-2,3-dimethyl-1H-indol-4-yl)cyclohex-3-en-1-yl)(methyl)carbamate and tert-butyl (S)-(3-(7-carbamoyl-5-fluoro-2,3-dimethyl-1H-indol-4-yl)cyclohex-2-en-1-yl)(methyl)carbamate (270 mg, 76%) as a yellow solid. ESI-MS $[M+H]^+$ calcd for ($C_{23}H_{30}FN_3O_3$) 416.23, found: 416.25.

Step 6: (S)-5-fluoro-2,3-dimethyl-4-(5-(methylamino)cyclohex-1-en-1-yl)-1H-indole-7-carboxamide hydrochloride and (S)-5-fluoro-2,3-dimethyl-4-(3-(methylamino)cyclohex-1-en-1-yl)-1H-indole-7-carboxamide

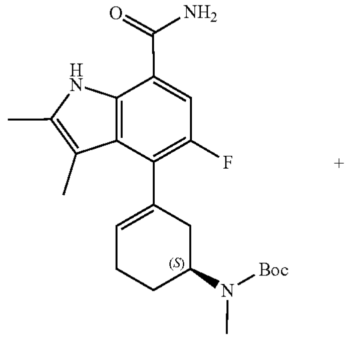

-continued

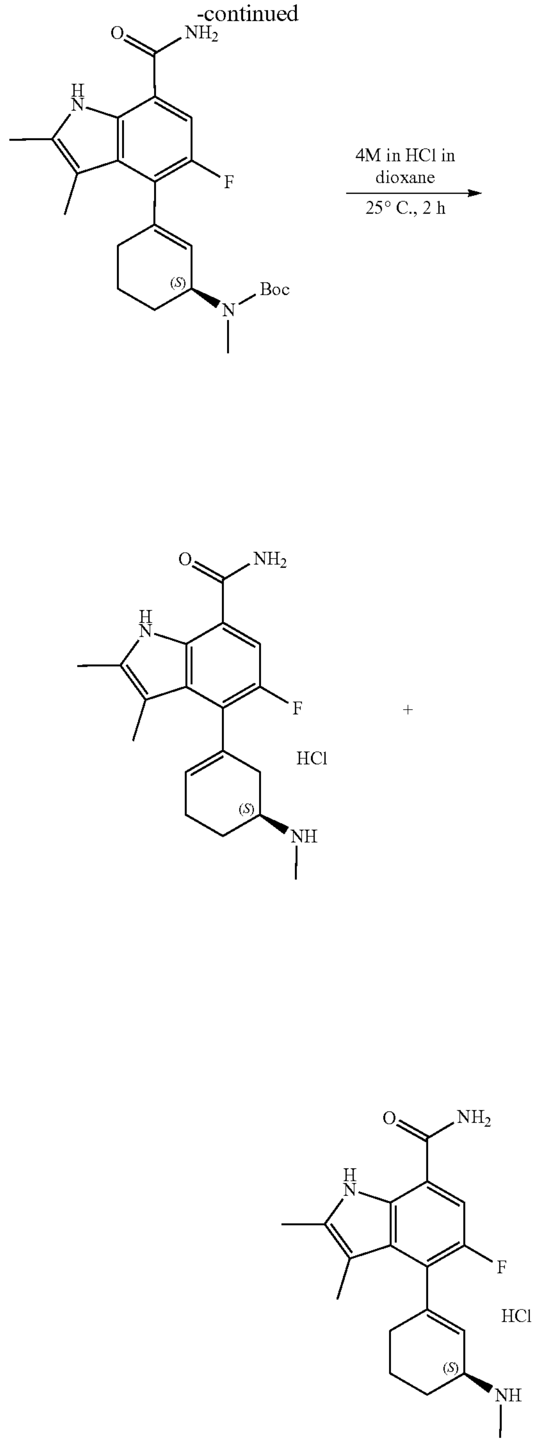

A mixture of the compounds from step 5 above (270 mg, 0.65 mmol) and hydrogen chloride (4M in 1,4-dioxane, 5 mL) was stirred at 25° C. for 2 h. The reaction mixture was concentrated under vacuum to (S)-5-fluoro-2,3-dimethyl-4-(5-(methylamino)cyclohex-1-en-1-yl)-1H-indole-7-carboxamide hydrochloride and (S)-5-fluoro-2,3-dimethyl-4-(3-(methylamino)cyclohex-1-en-1-yl)-1H-indole-7-carboxamide (240 mg, crude) as a yellow solid.

ESI-MS $[M+H]^+$ calcd for ($C_{18}H_{22}FN_3O$) 316.17, found: 316.15.

Step 7: (S)-5-fluoro-2,3-dimethyl-4-(5-(N-methylbut-2-ynamido)cyclohex-1-en-1-yl)-1H-indole-7-carboxamide (Compound 4-A-(S)) and (S)-5-fluoro-2,3-dimethyl-4-(3-(N-methylbut-2-ynamido)cyclohex-1-en-1-yl)-1H-indole-7-carboxamide (Compound 4-B-(S))

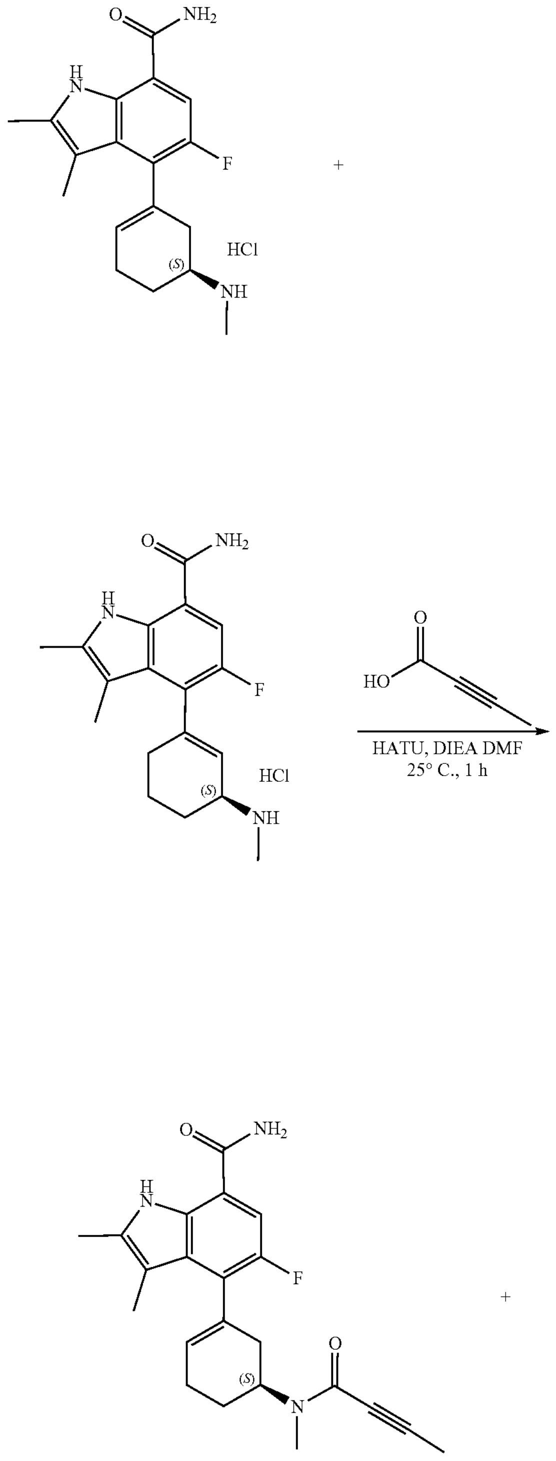

4-A-(S)

-continued

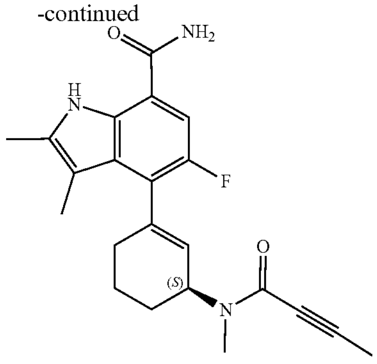

4-B-(S)

To a mixture of the compounds from step 6 above (240 mg, 0.68 mmol) in DMF (5 mL) were added O-(7-Azabenzotriazol-1-yl)-N,N,N',N'-tetramethyluronium hexafluorophosphate (391 mg, 1.02 mmol), but-2-ynoic acid (69 mg, 0.82 mmol) and N,N-diisopropylethylamine (441 mg, 3.41 mmol). The reaction mixture was stirred at 25° C. for 1 h. The resulting mixture was diluted with water (30 mL) and extracted with ethyl acetate (20 mL×3). The combined organic layers were washed with water (20 mL×3) and brine (30 mL), dried over anhydrous sodium sulfate, filtered and concentrated under vacuum. The residue was purified by Prep-HPLC with the following conditions: Column: XBridge Shield RP18 OBD Column, 30×150 mm, 5 um; Mobile Phase A: Water (10 mmol/L $NH_4HCO_3$+0.1% $NH_3 \cdot H_2O$), Mobile Phase B: Acetonitrile; Flow rate: 60 mL/min; Gradient: 34% B to 54% B in 7 min, 254 nm; RT: 6.95 min to give the mixture.

The mixture was further separated by Prep-SFC with the following conditions: Column: CHIRAL ART Cellulose-SB, 2×25 cm, 5 um; Mobile Phase A: Hexane (0.1% FA), Mobile Phase B: EtOH; Flow rate: 20 mL/min; Gradient: 10% B to 10% B in 25 min; 254 nm.

Retention Time=34.34 min Compound 4-B-(S)

(S)-5-fluoro-2,3-dimethyl-4-(3-(N-methylbut-2-ynamido)cyclohex-1-en-1-yl)-1H-indole-7-carboxamide (19.6 mg, 7%) as a white solid. $^1H$ NMR (400 MHz, DMSO-$d_6$) δ 10.72 (d, J=7.2 Hz, 1H), 8.00 (s, 1H), 7.53-7.31 (m, 2H), 5.62 (d, J=4.0 Hz, 1H), 4.79-4.46 (m, 1H), 3.10-3.05 (m, 1H), 2.79 (s, 2H), 2.69-2.55 (m, 0.6H), 2.45-2.30 (m, 5.4H), 2.24-2.10 (m, 3.5H), 2.08-1.96 (m, 3.5H), 1.95-1.68 (m, 2H). ESI-MS $[M+H]^+$ calcd for ($C_{22}H_{24}FN_3O_2$) 382.19, found: 382.10

Retention Time=40.95 min Compound 4-A-(S)

(S)-5-fluoro-2,3-dimethyl-4-(5-(N-methylbut-2-ynamido)cyclohex-1-en-1-yl)-1H-indole-7-carboxamide (54.8 mg, 21%) as a white solid. $^1H$ NMR (400 MHz, DMSO-$d_6$) δ 10.75 (d, J=8.8 Hz, 1H), 8.01 (s, 1H), 7.53-7.31 (m, 2H), 5.52-5.30 (m, 1H), 5.21-5.02 (m, 1H), 3.10-3.05 (m, 1H), 2.81-2.70 (m, 2H), 2.45-2.23 (m, 4H), 2.29-2.19 (m, 1H), 2.19-2.10 (m, 3H), 2.09-2.01 (m, 3H), 1.97-1.63 (m, 4H). ESI-MS $[M+H]^+$ calcd for ($C_{22}H_{24}FN_3O_2$) 382.19, found: 382.10

Example 5

Synthesis of 4-(3-(but-2-ynamido)cyclohex-1-en-1-yl)-3-chloro-5-fluoro-2-methyl-1H-indole-7-carboxamide (Compound 5-B-(rac))

(S)-4-(3-(but-2-ynamido)cyclohex-1-en-1-yl)-3-chloro-5-fluoro-2-methyl-1H-indole-7-carboxamide (Compound 5-B-(S))

and (R)-4-(3-(but-2-ynamido)cyclohex-1-en-1-yl)-3-chloro-5-fluoro-2-methyl-1H-indole-7-carboxamide (Compound 5-B—(R))

Compound 5-B-(rac)

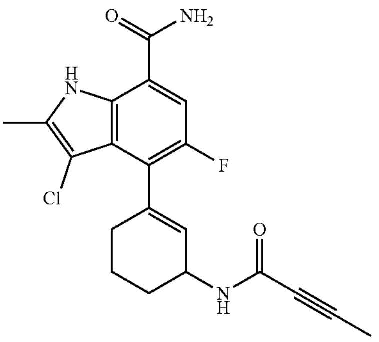

Compound 5-B-(S)

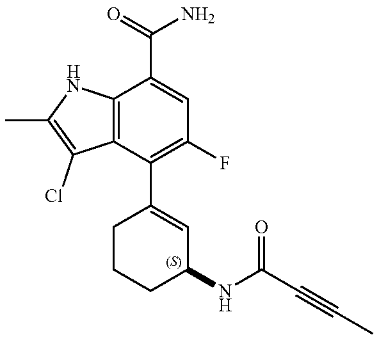

Compound 5-B-(R)

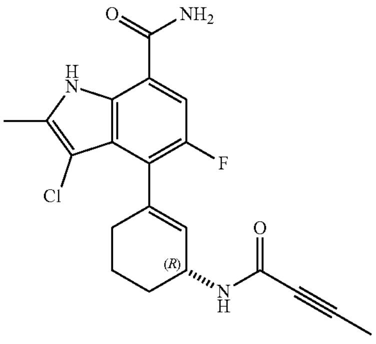

Step 1: tert-butyl (3-(7-carbamoyl-5-fluoro-2-methyl-1H-indol-4-yl)cyclohex-3-en-1-yl)carbamate and tert-butyl (3-(7-carbamoyl-5-fluoro-2-methyl-1H-indol-4-yl)cyclohex-2-en-1-yl)carbamate

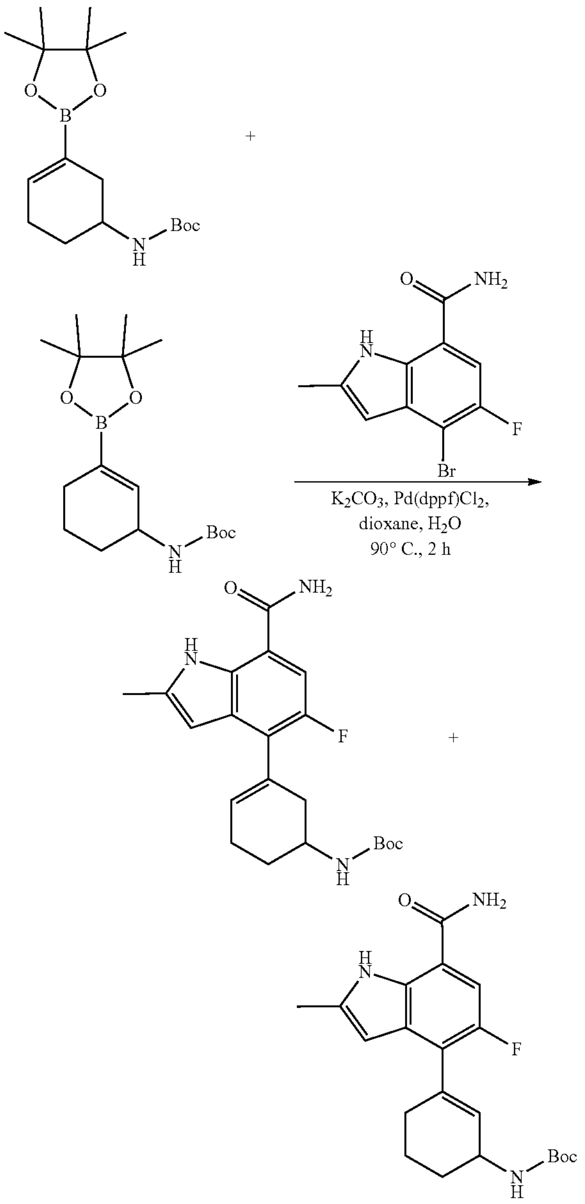

A mixture of tert-butyl (3-(4,4,5,5-tetramethyl-1,3,2-dioxaborolan-2-yl)cyclohex-3-en-1-yl)carbamate and tert-butyl (3-(4,4,5,5-tetramethyl-1,3,2-dioxaborolan-2-yl)cyclohex-2-en-1-yl)carbamate from Example 3, Step 2 above (1.00 g, 3.09 mmol), 4-bromo-5-fluoro-2-methyl-1H-indole-7-carboxamide (704 mg, 2.58 mmol), potassium carbonate (1.07 g, 7.73 mmol) and Pd(dppf)$Cl_2$ (189 mg, 0.26 mmol) in dioxane (20 mL) and water (5 mL) was degassed and backfilled with nitrogen for five times. The reaction mixture was heated under nitrogen at 90° C. for 2 h. The cooled reaction mixture was diluted with water (80 mL), and extracted with ethyl acetate (60 mL×3). The combined organic layers was washed with brine (60 mL), dried over sodium sulfate and concentrated under vacuum. The residue was purified by column chromatography on silica gel eluting with ethyl acetate in petroleum ether (0 to 15%) to give the mixture of tert-butyl (3-(7-carbamoyl-5-fluoro-2-methyl-1H-indol-4-yl)cyclohex-3-en-1-yl)carbamate and tert-butyl (3-(7-carbamoyl-5-fluoro-2-methyl-1H-indol-4-yl)cyclohex-2-en-1-yl)carbamate (700 mg, 70%) as a yellow solid. $^1$H NMR (400 MHz, DMSO-$d_6$) δ 10.91 (s, 1H), 8.01 (s, 1H), 7.51-7.36 (m, 2H), 6.96-6.84 (m, 1H), 6.14 (s, 1H), 5.84-5.77 (m, 1H), 3.76-3.56 (m, 1H), 2.44-2.24 (m, 7H), 1.93-1.81 (m, 1H), 1.65-1.45 (m, 1H), 1.40 (s, 9H). ESI-MS $[M-H]^-$ calcd for ($C_{21}H_{26}FN_3O_3$) 386.20 found: 386.15

Step 2: tert-butyl (3-(7-carbamoyl-3-chloro-5-fluoro-2-methyl-1H-indol-4-yl)cyclohex-3-en-1-yl) carbamate and tert-butyl (3-(7-carbamoyl-3-chloro-5-fluoro-2-methyl-1H-indol-4-yl)cyclohex-2-en-1-yl)carbamate

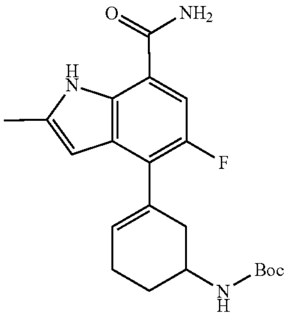

+

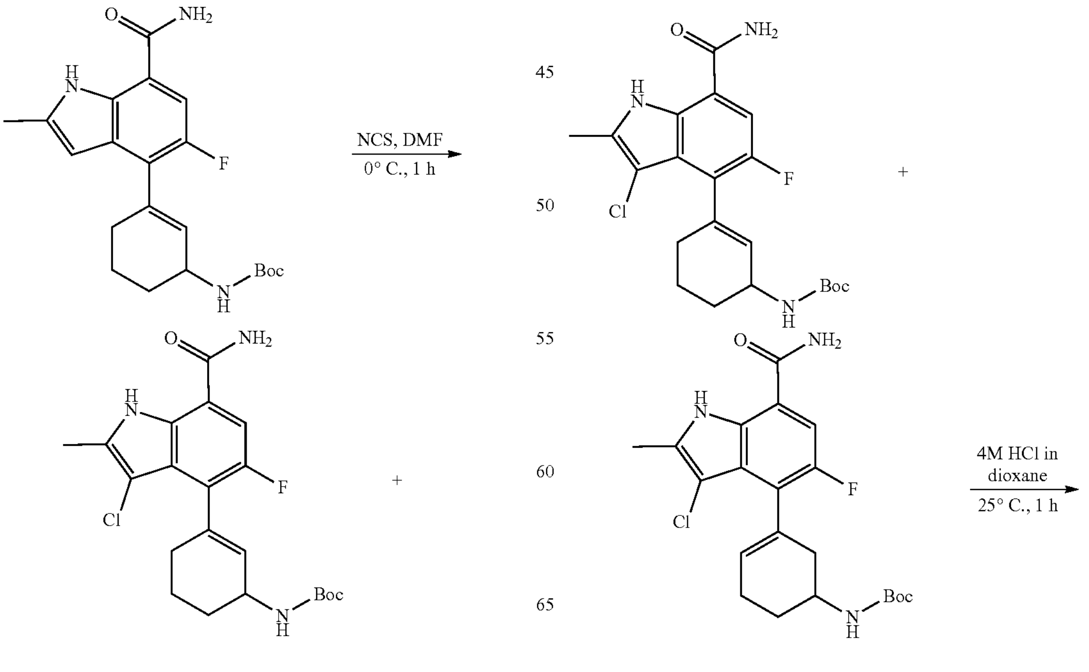

-continued

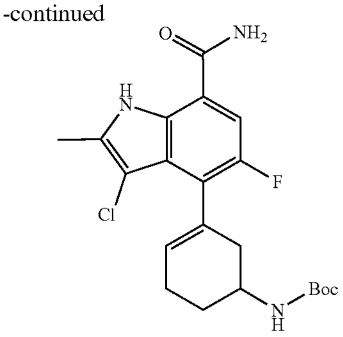

To a solution of tert-butyl (3-(7-carbamoyl-5-fluoro-2-methyl-1H-indol-4-yl)cyclohex-3-en-1-yl)carbamate and tert-butyl (3-(7-carbamoyl-5-fluoro-2-methyl-1H-indol-4-yl)cyclohex-2-en-1-yl)carbamate (350 mg, 0.90 mmol) in DMF (10 mL) was added N-chlorosuccinimide (133 mg, 0.99 mmol,) at 0° C. The reaction mixture was stirred at 0° C. for 1 h. After completed, the reaction mixture was quenched with water (30 ml) and extracted with ethyl acetate (20 ml×3). The combined organic layers were washed with brine (30 ml), dried over anhydrous sodium sulfate and concentrated under vacuum. The residue was purified by column chromatography on silica gel eluting with ethyl acetate in petroleum ether (0 to 60%) to give the mixture of tert-butyl (3-(7-carbamoyl-3-chloro-5-fluoro-2-methyl-1H-indol-4-yl)cyclohex-3-en-1-yl)carbamate and tert-butyl (3-(7-carbamoyl-3-chloro-5-fluoro-2-methyl-1H-indol-4-yl)cyclohex-2-en-1-yl)carbamate (280 mg, 73%) as a yellow solid. ESI-MS $[M+H-tBu]^+$ calcd for ($C_{21}H_{25}ClFN_3O_3$) 366.16, 368.15 found: 366.00, 368.00.

Step 3: 4-(5-aminocyclohex-1-en-1-yl)-3-chloro-5-fluoro-2-methyl-1H-indole-7-carboxamide hydrochloride and 4-(3-aminocyclohex-1-en-1-yl)-3-chloro-5-fluoro-2-methyl-1H-indole-7-carboxamide hydrochloride -continued

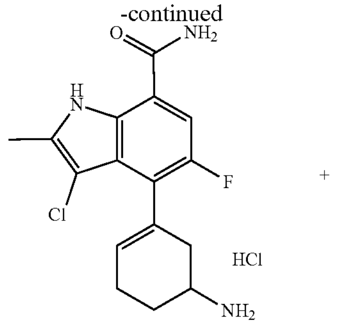

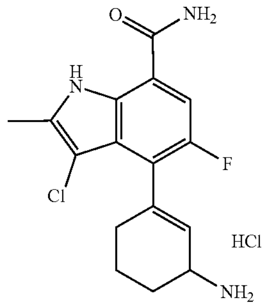

A mixture of tert-butyl (3-(7-carbamoyl-3-chloro-5-fluoro-2-methyl-1H-indol-4-yl)cyclohex-3-en-1-yl)carbamate and tert-butyl (3-(7-carbamoyl-3-chloro-5-fluoro-2-methyl-1H-indol-4-yl)cyclohex-2-en-1-yl)carbamate (280 mg, 0.66 mmol) and hydrogen chloride (4 M in dioxane, 6 mL) was stirred at 25° C. for 1 h. After completed, the reaction mixture was concentrated under vacuum to give the mixture of 4-(5-aminocyclohex-1-en-1-yl)-3-chloro-5-fluoro-2-methyl-1H-indole-7-carboxamide hydrochloride and 4-(3-aminocyclohex-1-en-1-yl)-3-chloro-5-fluoro-2-methyl-1H-indole-7-carboxamide hydrochloride (200 mg, crude) as a yellow solid. ESI-MS $[M+H]^+$ calcd for $(C_{16}H_{17}ClFN_3O)$ 322.10, 324.10 found: 322.10, 324.10

Step 4: Preparation of 4-(5-(but-2-ynamido)cyclohex-1-en-1-yl)-3-chloro-5-fluoro-2-methyl-1H-indole-7-carboxamide and 4-(3-(but-2-ynamido)cyclohex-1-en-1-yl)-3-chloro-5-fluoro-2-methyl-1H-indole-7-carboxamide

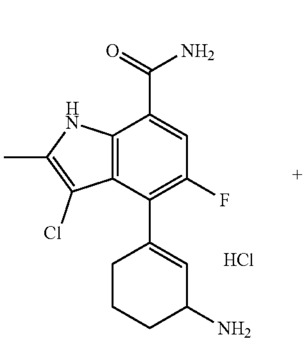

-continued

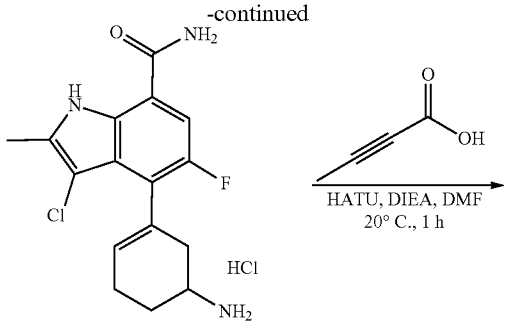

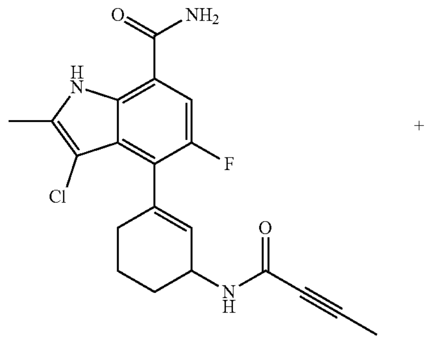

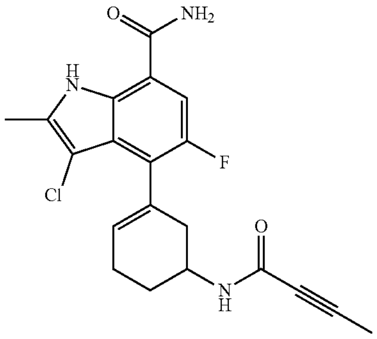

To a mixture of 4-(5-aminocyclohex-1-en-1-yl)-3-chloro-5-fluoro-2-methyl-1H-indole-7-carboxamide hydrochloride and 4-(3-aminocyclohex-1-en-1-yl)-3-chloro-5-fluoro-2-methyl-1H-indole-7-carboxamide hydrochloride (200 mg, 0.56 mmol) in DMF (6 mL) were added O-(7-Azabenzotriazol-1-yl)-N,N,N',N'-tetraMethyluroniuM hexafluorophosphate (255 mg, 0.67 mmol), but-2-ynoic acid (56 mg, 0.67 mmol) and N,N-diisopropylethylamine (361 mg, 2.80 mmol). The reaction mixture was stirred at 20° C. for 1 h. The resulting mixture was diluted with water (30 mL) and extracted with ethyl acetate (30 mL×2). The combined organic layers was washed with water (30 mL×2) and brine (30 mL), dried over anhydrous sodium sulfate and concentrated under vacuum.

The residue was purified by Prep-HPLC with the following conditions: Column: XBridge Prep OBD C18 Column 19×250 mm 5 um; Mobile Phase A: Water (10 MMOL/L $NH_4HCO_3$+0.1% $NH_3 \cdot H_2O$), Mobile Phase B: Acetonitrile; Flow rate: 25 mL/min; Gradient: 33% B to 47% B in 10 min; 220 nm.

4-(5-(but-2-ynamido)cyclohex-1-en-1-yl)-3-chloro-5-fluoro-2-methyl-1H-indole-7-carboxamide Retention time=9.03 min as a white solid (85 mg, 39%). $^1$H NMR (400 MHz, DMSO-$d_6$) δ 11.32 (s, 1H), 8.61-8.50 (m, 1H), 8.10 (s, 1H), 7.55-7.52 (m, 2H), 5.60 (s, 1H), 4.14-3.93 (m, 1H), 2.39 (s, 3H), 2.35-2.22 (m, 4H), 1.94 (s, 3H), 1.90-1.82 (m, 1H), 1.68-1.47 (m, 1H). ESI-MS $[M+H]^+$ calcd for ($C_{20}H_{19}ClFN_3O_2$) 388.11, 390.11, found: 388.10, 390.10.

4-(3-(but-2-ynamido)cyclohex-1-en-1-yl)-3-chloro-5-fluoro-2-methyl-1H-indole-7-carboxamide Retention time=9.65 min as an off-white solid (10.2 mg, 5%). $^1$H NMR (400 MHz, DMSO-$d_6$) δ 11.32 (s, 1H), 8.79-8.57 (m, 1H), 8.09 (s, 1H), 7.59-7.49 (m, 2H), 5.44 (s, 1H), 4.52-4.39 (m, 1H), 2.38 (s, 3H), 2.31-2.21 (m, 1H), 2.19-2.09 (m, 1H), 1.95 (s, 3H), 1.92-1.52 (m, 4H). ESI-MS $[M+H]^+$ calcd for ($C_{20}H_{19}ClFN_2O_2$) 388.11, 390.11, found: 388.10, 390.10.

Step 5: Preparation of Assumed (S)-4-(3-(but-2-ynamido)cyclohex-1-en-1-yl)-3-chloro-5-fluoro-2-methyl-1H-indole-7-carboxamide and Assumed (R)-4-(3-(but-2-ynamido)cyclohex-1-en-1-yl)-3-chloro-5-fluoro-2-methyl-1H-indole-7-carboxamide

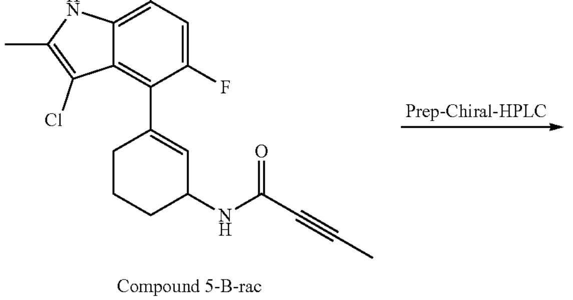

Compound 5-B-rac

-continued

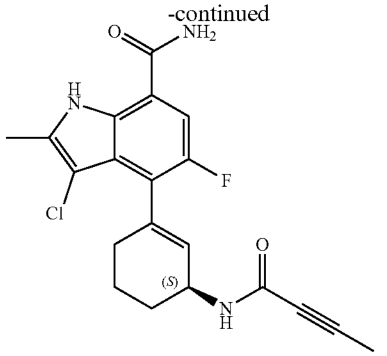

+

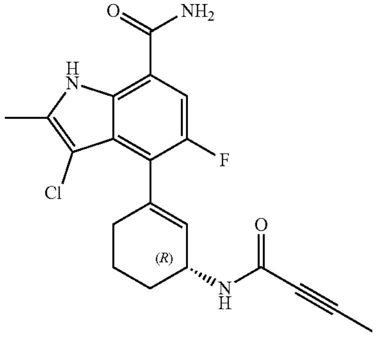

4-(3-(but-2-ynamido)cyclohex-1-en-1-yl)-3-chloro-5-fluoro-2-methyl-1H-indole-7-carboxamide (Compound 5-B-rac, 160 mg) was separated by Prep-Chiral-HPLC with the following conditions: Column: (R,R)-WHELK-O1-Kromasil, 2.12×25 cm, 5 um; Mobile Phase A: MTBE (0.5% 2 M $NH_3$-MeOH)-HPLC, Mobile Phase B: EtOH-HPLC; Flow rate: 20 mL/min; Gradient: 10% B to 10% B in 12 min; 220/254 nm.

(S)-4-(3-(but-2-ynamido)cyclohex-1-en-1-yl)-3-chloro-5-fluoro-2-methyl-1H-indole-7-carboxamide or (R)-4-(3-(but-2-ynamido)cyclohex-1-en-1-yl)-3-chloro-5-fluoro-2-methyl-1H-indole-7-carboxamide Retention time=7.31 min (51.1 mg, 32%) as a white solid. $^1$H NMR (300 MHz, DMSO-$d_6$) δ 11.32 (s, 1H), 8.87-8.52 (m, 1H), 8.09 (s, 1H), 7.82-7.35 (m, 2H), 5.61 (s, 1H), 4.03 (s, 1H), 2.45-2.08 (m, 5H), 2.08-1.45 (m, 7H). ESI-MS $[M-H]^-$ calcd for ($C_{20}H_{19}ClFN_3O_2$) 386.10, 388.11 found: 386.10, 388.10

(R)-4-(3-(but-2-ynamido)cyclohex-1-en-1-yl)-3-chloro-5-fluoro-2-methyl-1H-indole-7-carboxamide or (S)-4-(3-(but-2-ynamido)cyclohex-1-en-1-yl)-3-chloro-5-fluoro-2-methyl-1H-indole-7-carboxamide Retention time=8.818 min (52.1 mg, 33%) as a white solid. $^1$H NMR (300 MHz, DMSO-$d_6$) δ 11.31 (s, 1H), 8.87-8.52 (m, 1H), 8.09 (s, 1H), 7.82-7.35 (m, 2H), 5.61 (s, 1H), 4.03 (s, 1H), 2.45-2.08 (m, 5H), 2.08-1.45 (m, 7H). ESI-MS $[M+H]^+$ calcd for ($C_{20}H_{19}ClFN_3O_2$) 386.10, 388.11 found: 386.10, 388.10

Example 6

Synthesis of

Racemic 4-(3-(but-2-ynamido)cyclohexyl)-3-chloro-5-fluoro-2-methyl-1H-indole-7-carboxamide (compound 6-(rac)

4-((cis)-3-(but-2-ynamido)cyclohexyl)-3-chloro-5-fluoro-2-methyl-1H-indole-7-carboxamide (compound 6-(cis)

4-((trans)-3-(but-2-ynamido)cyclohexyl)-3-chloro-5-fluoro-2-methyl-1H-indole-7-carboxamide (compound 6-(trans)

4-((1R,3S)-3-(but-2-ynamido)cyclohexyl)-3-chloro-5-fluoro-2-methyl-1H-indole-7-carboxamide (compound 6-(1R,3S)

4-((1S,3R)-3-(but-2-ynamido)cyclohexyl)-3-chloro-5-fluoro-2-methyl-1H-indole-7-carboxamide (compound 6-(1S,3R)

4-((1R,3R)-3-(but-2-ynamido)cyclohexyl)-3-chloro-5-fluoro-2-methyl-1H-indole-7-carboxamide (compound 6-(1R,3R)

and 4-((1S,3S)-3-(but-2-ynamido)cyclohexyl)-3-chloro-5-fluoro-2-methyl-1H-indole-7-carboxamide (compound 6-(1S,3S)

Compound 6-(rac)

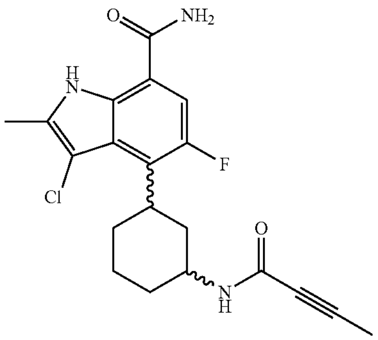

Compound 6-(cis)

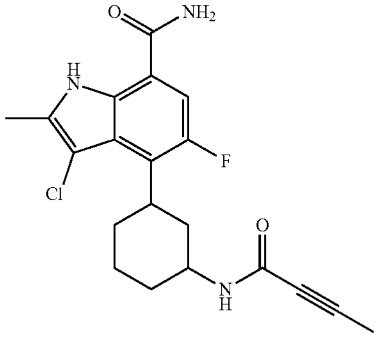

-continued

Compound 6-(trans)

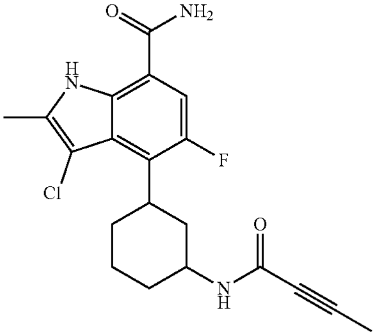

6-(1R,3S)

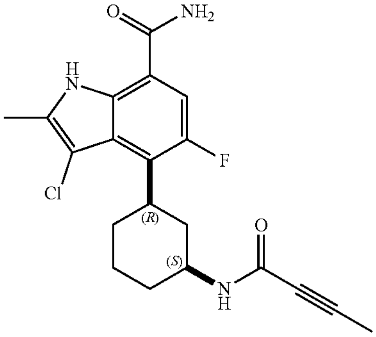

6-(1S,3R)

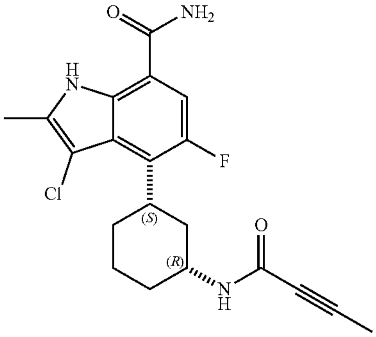

6-(1R,3R)

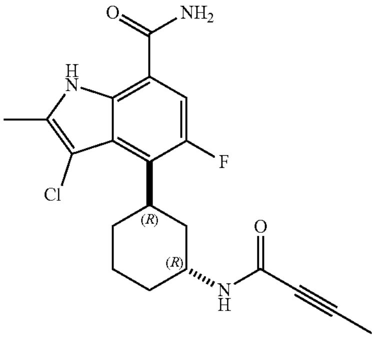

-continued 6-(1S,3S)

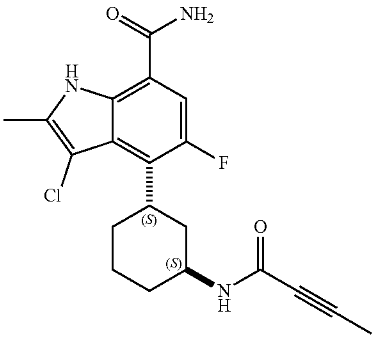

Step 1: Mixture of 5-((tert-butoxycarbonyl)amino)cyclohex-1-en-1-yl trifluoromethanesulfonate and 3-((tert-butoxycarbonyl)amino)cyclohex-1-en-1-yl trifluoromethanesulfonate

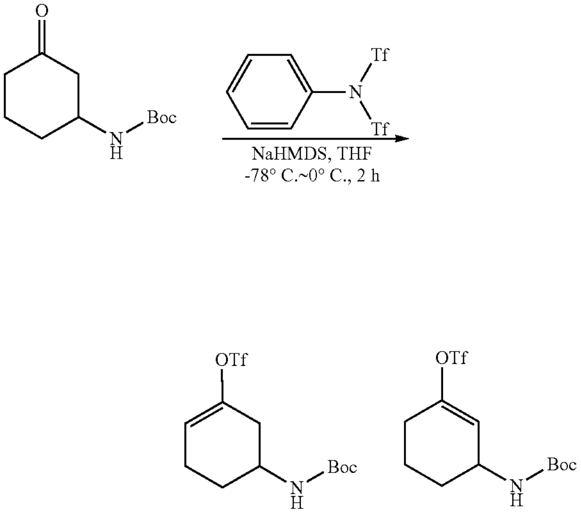

To a solution of tert-butyl (3-oxocyclohexyl)carbamate (5.00 g, 23.44 mmol) and 1,1,1-trifluoro-N-phenyl-N-(trifluoromethylsulfonyl)methanesulfonamide (10.89 g, 30.48 mmol) in THF (75 mL) was added NaHMDS (2M in THF, 26 mL, 52 mmol) at −78° C. under $N_2$. After addition, the reaction mixture was stirred at 0° C. for 2 h. The reaction mixture was quenched with saturated aqueous ammonium chloride (150 mL) and extracted with ethyl acetate (100 mL×3). The combined extracts were washed with water (100 mL) and brine (100 mL), dried over anhydrous sodium sulfate and concentrated under vacuum. The residue was purified by column chromatography on silica gel eluting with ethyl acetate in petroleum ether (0 to 10%) to give the mixture of 5-((tert-butoxycarbonyl)amino)cyclohex-1-en-1-yl trifluoromethanesulfonate and 3-((tert-butoxycarbonyl)amino)cyclohex-1-en-1-yl trifluoromethanesulfonate (7.0 g, crude) as a yellow oil. $^1H$ NMR (300 MHz, Chloroform-d) δ 5.83-5.71 (m, 1H), 4.68-4.36 (m, 1H), 4.06-3.85 (m, 1H), 2.79-2.61 (m, 1H), 2.39-2.19 (m, 3H), 1.90-1.76 (m, 1H), 1.68-1.55 (m, 1H), 1.45 (s, 9H).

Step 2: Mixture of tert-butyl (3-(4,4,5,5-tetramethyl-1,3,2-dioxaborolan-2-yl)cyclohex-3-en-1-yl)carbamate and tert-butyl (3-(4,4,5,5-tetramethyl-1,3,2-dioxaborolan-2-yl)cyclohex-2-en-1-yl)carbamate

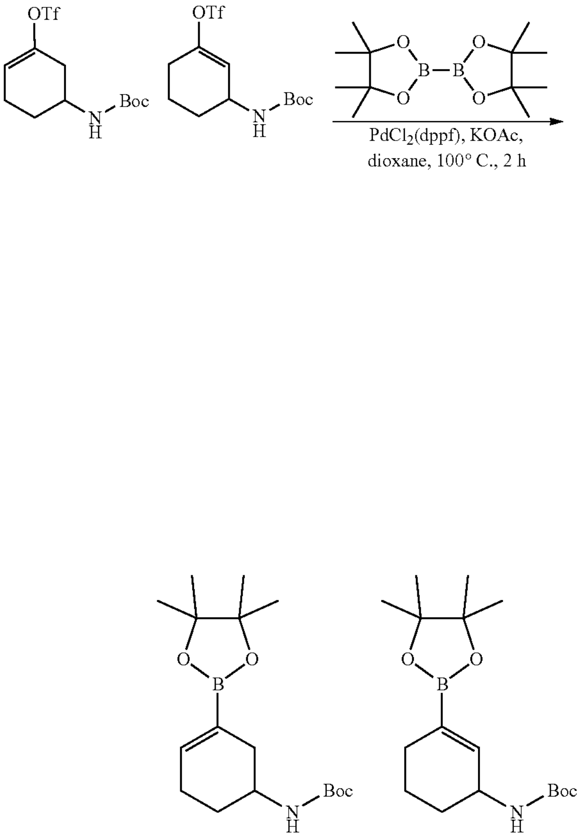

A mixture of 5-((tert-butoxycarbonyl)amino)cyclohex-1-en-1-yl trifluoromethanesulfonate and 3-((tert-butoxycarbonyl)amino)cyclohex-1-en-1-yl trifluoromethanesulfonate (6.00 g, 17.37 mmol), 4,4,5,5-tetramethyl-2-(4,4,5,5-tetramethyl-1,3,2-dioxaborolan-2-yl)-1,3,2-dioxaborolane (4.41 g, 17.4 mmol), potassium acetate (5.12 g, 52.1 mmol) and Pd(dppf)Cl2 (635 mg, 0.87 mmol) in dioxane (90 mL) was degassed and backfilled with nitrogen for five times. The reaction mixture was stirred under nitrogen at 100° C. for 2 h. The cooled reaction mixture was quenched with water (200 mL) and extracted with ethyl acetate (150 mL×3). The combined extracts were washed with brine (150 mL), dried over anhydrous sodium sulfate and concentrated under vacuum. The residue was purified by column chromatography on silica gel eluting with ethyl acetate in petroleum ether (0 to 15%) to give the mixture of tert-butyl (3-(4,4,5,5-tetramethyl-1,3,2-dioxaborolan-2-yl)cyclohex-3-en-1-yl)carbamate and tert-butyl (3-(4,4,5,5-tetramethyl-1,3,2-dioxaborolan-2-yl)cyclohex-2-en-1-yl)carbamate (3.26 g, 58%) as a yellow oil. $^1H$ NMR (300 MHz, Chloroform-d) δ 6.62-6.49 (m, 1H), 4.64-4.40 (m, 1H), 3.85-3.63 (m, 1H), 2.60-2.43 (m, 1H), 2.32-2.17 (m, 2H), 2.00-1.80 (m, 2H), 1.72-1.60 (m, 1H), 1.44 (s, 9H), 1.25 (s, 12H). ESI-MS [M+H-Boc]+ calcd for (C17H30BNO4) 224.24 found: 224.15.

Step 3: Mixture of tert-butyl (3-(7-carbamoyl-5-fluoro-2-methyl-1H-indol-4-yl)cyclohex-3-en-1-yl) carbamate and tert-butyl (3-(7-carbamoyl-5-fluoro-2-methyl-1H-indol-4-yl)cyclohex-2-en-1-yl) carbamate

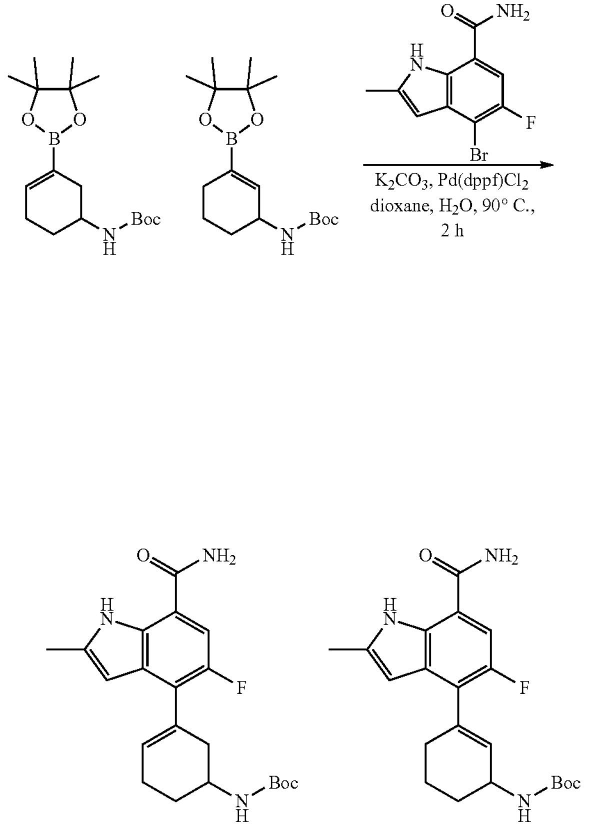

A mixture of tert-butyl (3-(4,4,5,5-tetramethyl-1,3,2-dioxaborolan-2-yl)cyclohex-3-en-1-yl)carbamate and tert-butyl (3-(4,4,5,5-tetramethyl-1,3,2-dioxaborolan-2-yl)cyclohex-2-en-1-yl)carbamate (1.00 g, 3.09 mmol), 4-bromo-5-fluoro-2-methyl-1H-indole-7-carboxamide (704 mg, 2.58 mmol), potassium carbonate (1.07 g, 7.73 mmol) and Pd(dppf)Cl2 (189 mg, 0.26 mmol) in dioxane (20 mL) and water (5.0 mL) was degassed and backfilled with nitrogen for five times. The reaction mixture was heated under nitrogen at 90° C. for 2 h. The cooled reaction mixture was diluted with water (80 mL), and extracted with ethyl acetate (60 mL×3). The combined extracts were washed with brine (60 mL), dried over sodium sulfate and concentrated under vacuum. The residue was purified by column chromatography on silica gel eluting with ethyl acetate in petroleum ether (0 to 15%) to give the mixture of tert-butyl (3-(7-carbamoyl-5-fluoro-2-methyl-1H-indol-4-yl)cyclohex-3-en-1-yl)carbamate and tert-butyl (3-(7-carbamoyl-5-fluoro-2-methyl-1H-indol-4-yl)cyclohex-2-en-1-yl)carbamate (700 mg, 70%) as a yellow solid. $^1$H NMR (400 MHz, DMSO-d6) δ 10.91 (s, 1H), 8.01 (s, 1H), 7.51-7.36 (m, 2H), 6.96-6.84 (m, 1H), 6.14 (s, 1H), 5.84-5.77 (m, 1H), 3.76-3.56 (m, 1H), 2.44-2.24 (m, 7H), 1.93-1.81 (m, 1H), 1.65-1.45 (m, 1H), 1.40 (s, 9H). ESI-MS [M−H]− calcd for (C21H26FN3O3) 386.20 found: 386.15

Step 4: tert-butyl (3-(7-carbamoyl-5-fluoro-2-methyl-1H-indol-4-yl)cyclohexyl)carbamate

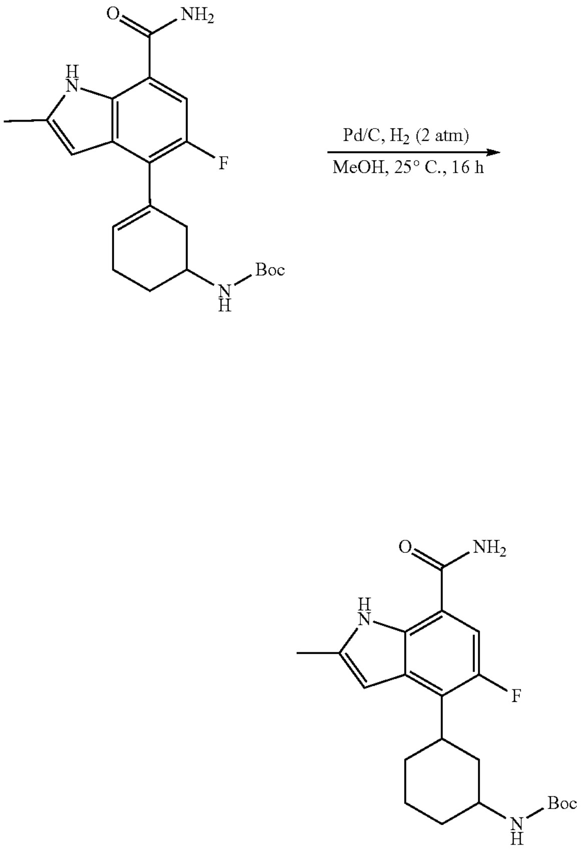

A mixture of tert-butyl (3-(7-carbamoyl-5-fluoro-2-methyl-1H-indol-4-yl)cyclohex-3-en-1-yl)carbamate (350 mg, 0.90 mmol) and Pd/C (10%, 200 mg) in methanol (25 mL) was stirred under hydrogen (2 atm) at 25° C. for 16 h. After completion, the reaction mixture was filtered. The filtrate was concentrated uncer vacuum to give tert-butyl (3-(7-carbamoyl-5-fluoro-2-methyl-1H-indol-4-yl)cyclohexyl)carbamate (270 mg, 77%) as a yellow solid. ESI-MS [M+H]+ calcd for (C21H28FN3O3) 390.21 found: 390.15.

Step 5: tert-butyl (3-(7-carbamoyl-3-chloro-5-fluoro-2-methyl-1H-indol-4-yl)cyclohexyl)carbamate

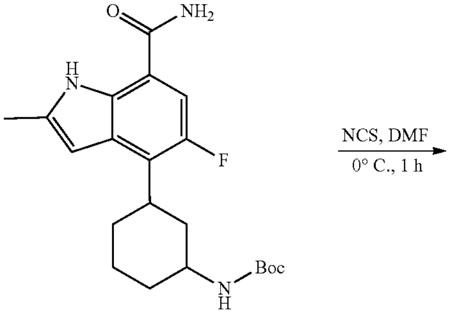

-continued

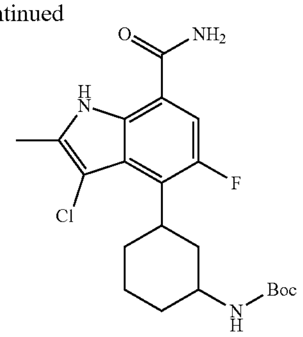

To a mixture of tert-butyl (3-(7-carbamoyl-5-fluoro-2-methyl-1H-indol-4-yl)cyclohexyl)carbamate (270 mg, 0.70 mmol) in DMF (7.0 mL) was added N-chlorosuccinimide (94 mg, 0.70 mmol,) at 0° C. The reaction mixture was stirred at 0° C. for 1 h. After completion, the reaction mixture was quenched with water (30 mL) and extracted with ethyl acetate (20 mL×3). The combined extracts were washed with brine (30 mL), dried over anhydrous sodium sulfate and concentrated under vacuum. The residue was purified by column chromatography on silica gel eluting with ethyl acetate in petroleum ether (0 to 60%) to give tert-butyl (3-(7-carbamoyl-3-chloro-5-fluoro-2-methyl-1H-indol-4-yl)cyclohexyl)carbamate (220 mg, 73%) as a yellow solid. ESI-MS [M−H]− calcd for (C21H27ClFN3O3) 422.17, 424.17 found: 422.10, 424.10.

Step 6: 4-(3-aminocyclohexyl)-3-chloro-5-fluoro-2-methyl-1H-indole-7-carboxamide hydrochloride

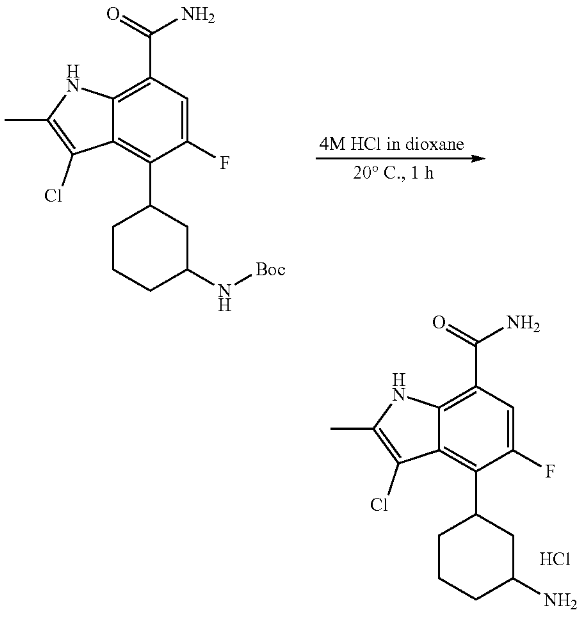

A mixture of tert-butyl (3-(7-carbamoyl-3-chloro-5-fluoro-2-methyl-1H-indol-4-yl)cyclohexyl)carbamate (220 mg, 0.52 mmol) and hydrogen chloride (4 M in dioxane, 7 mL) was stirred at 20° C. for 1 h. After completion, the reaction mixture was concentrated under vacuum to give 4-(3-aminocyclohexyl)-3-chloro-5-fluoro-2-methyl-1H-indole-7-carboxamide hydrochloride (200 mg, crude) as a yellow solid. ESI-MS [M+H]+ calcd for (C16H19ClFN3O3) 324.12, 326.12 found: 324.10, 326.10

Step 7: 4-(3-(but-2-ynamido)cyclohexyl)-3-chloro-5-fluoro-2-methyl-1H-indole-7-carboxamide

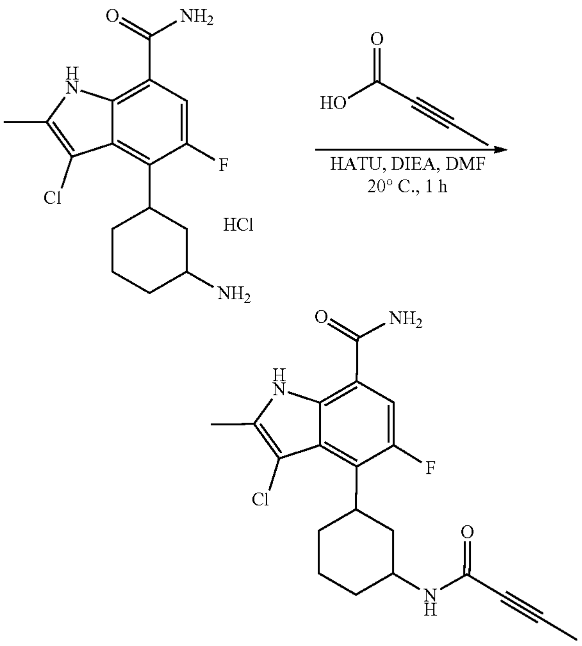

To a mixture of 4-(3-aminocyclohexyl)-3-chloro-5-fluoro-2-methyl-1H-indole-7-carboxamide hydrochloride (200 mg, 0.56 mmol) in DMF (6.0 mL) were added O-(7-Azabenzotriazol-1-yl)-N,N,N',N'-tetraMethyluronium hexafluorophosphate (254 mg, 0.67 mmol), but-2-ynoic acid (56 mg, 0.67 mmol) and N,N-diisopropylethylamine (358 mg, 2.78 mmol). The reaction mixture was stirred at 20° C. for 1 h. The resulting mixture was diluted with water (30 mL) and extracted with ethyl acetate (30 mL×2). The combined extracts were washed with water (30 mL×2) and brine (30 mL), dried over anhydrous sodium sulfate, filtered and concentrated under vacuum.

Step 8: 4-(cis-3-(but-2-ynamido)cyclohexyl)-3-chloro-5-fluoro-2-methyl-1H-indole-7-carboxamide and 4-(trans-3-(but-2-ynamido)cyclohexyl)-3-chloro-5-fluoro-2-methyl-1H-indole-7-carboxamide

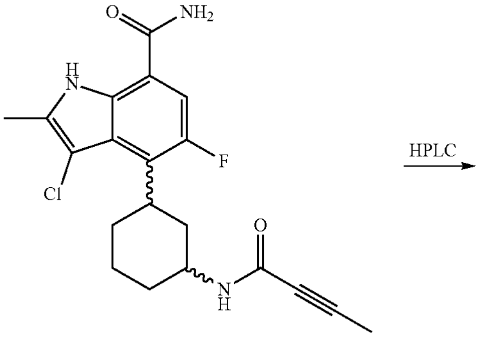

-continued

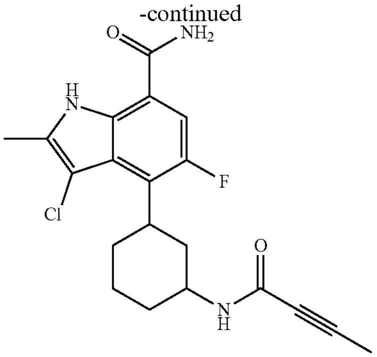

Compound 6-cis

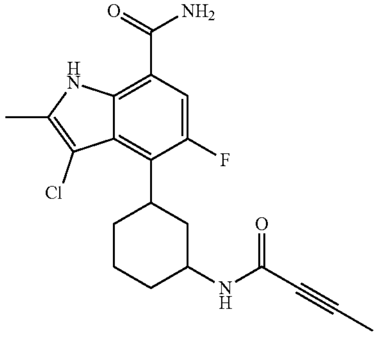

Compound 6-trans 4-(3-(but-2-ynamido)cyclohexyl)-3-chloro-5-fluoro-2-methyl-1H-indole-7-carboxamide was purified by HPLC under the following conditions: Column: XBridge Prep OBD C18 Column 30×250 mm, 5 um; Mobile Phase A: Water (10 MMOL/L NH4HCO3+0.1% NH3·H2O), Mobile Phase B: Acetonitrile; Flow rate: 25 mL/min; Gradient: 35% B to 45% B in 7 min; 220 nm. 4-(cis-3-(but-2-ynamido)cyclohexyl)-3-chloro-5-fluoro-2-methyl-1H-indole-7-carboxamide.

Compound 6-(cis)

Retention Time=5.68 min (100 mg, 46%) as a white solid. $^1$H NMR (400 MHz, DMSO-d6) δ 11.28 (s, 1H), 8.53 (d, J=6.0 Hz, 1H), 8.05 (s, 1H), 7.57-7.42 (m, 2H), 4.19 (t, J=9.2 Hz, 1H), 4.05-3.96 (m, 1H), 2.39 (s, 3H), 2.07-1.82 (m, 7H), 1.78-1.65 (m, 2H), 1.63-1.50 (m, 2H). ESI-MS [M+H]+ calcd for (C20H21ClFN3O2) 390.13, 392.13, found: 390.10, 392.10.

Compound 6-(trans)

Retention Time=6.80 min (23.6 mg, 10%) as a white solid. $^1$H NMR (400 MHz, DMSO-d6) δ 11.33 (s, 1H), 8.52 (d, J=7.6 Hz, 1H), 8.07 (s, 1H), 7.56-7.47 (m, 2H), 4.09-3.97 (m, 1H), 3.76-3.64 (m, 1H), 2.39 (s, 3H), 1.93 (s, 3H), 1.89-1.64 (m, 6H), 1.51-1.34 (m, 1H), 1.32-1.17 (m, 1H). ESI-MS [M+H]+ calcd for (C20H21ClFN2O2) 390.13, 392.13, found: 390.10, 392.10.

Step 9A: Separation of Cis Isomers

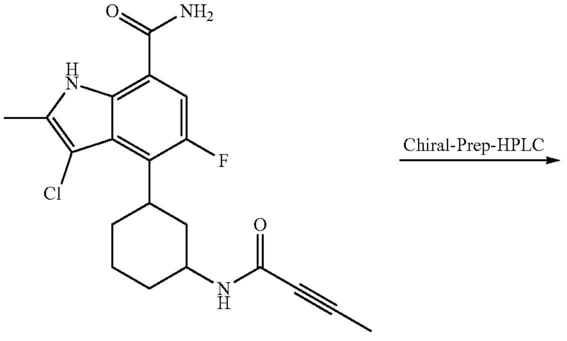

6-(cis)

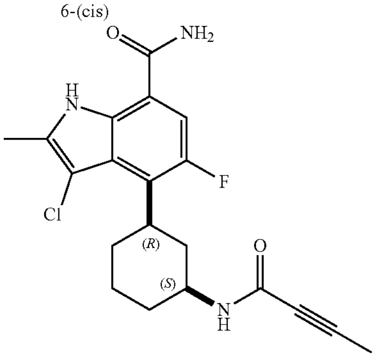

6-(1R,3S)

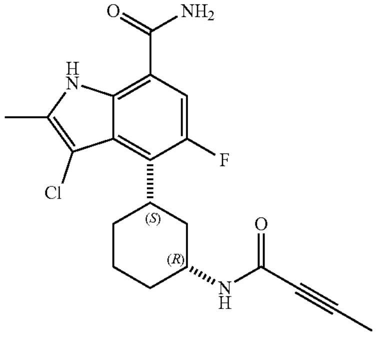

6-(1S,3R)

4-(cis-3-(but-2-ynamido)cyclohexyl)-3-chloro-5-fluoro-2-methyl-1H-indole-7-carboxamide (90 mg) was separated by Prep-Chiral-HPLC under the following conditions: Column: CHIRALPAK IG, 20×250 mm, 5 um; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 18 min; 220/254 nm.

4-((1R,3S)-3-(but-2-ynamido)cyclohexyl)-3-chloro-5-fluoro-2-methyl-1H-indole-7-carboxamide or 4-((1S,3R)-3-(but-2-ynamido)cyclohexyl)-3-chloro-5-fluoro-2-methyl-1H-indole-7-carboxamide Retention Time=8.691 min (34.5 mg, 38%) as a white solid. $^1$H NMR (300 MHz, DMSO-$d_6$) δ 11.28 (s, 1H), 8.54 (d, J=6.0 Hz, 1H), 8.06 (s, 1H), 7.60-7.40 (m, 2H), 4.30-4.10 (m, 1H), 4.00 (s, 1H), 2.39 (s, 3H), 2.10-1.80 (m, 7H), 1.78-1.48 (m, 4H). ESI-MS $[M+H]^+$ calcd for ($C_{20}H_{19}ClFN_3O_2$) 390.13, 392.13 found: 390.10, 392.10.

4-((1S,3R)-3-(but-2-ynamido)cyclohexyl)-3-chloro-5-fluoro-2-methyl-1H-indole-7-carboxamide or 4-((1R,3S)-3-(but-2-ynamido)cyclohexyl)-3-chloro-5-fluoro-2-methyl-1H-indole-7-carboxamide Retention Time=16.192 min (34.1 mg, 38%) as a white solid. $^1$H NMR (300 MHz, DMSO-$d_6$) δ 11.29 (s, 1H), 8.54 (d, J=5.7 Hz, 1H), 8.06 (s, 1H), 7.60-7.40 (m, 2H), 4.30-4.10 (m, 1H), 4.01 (s, 1H), 2.39 (s, 3H), 2.10-1.80 (m, 7H), 1.78-1.48 (m, 4H). ESI-MS [M+H]$^+$ calcd for ($C_{20}H_{21}ClFN_3O_2$) 390.13, 392.13 found: 390.10, 392.10

Step 9B: Separation of Trans Isomers

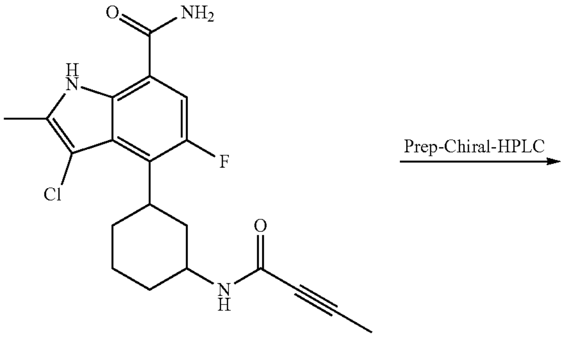

6-(trans)

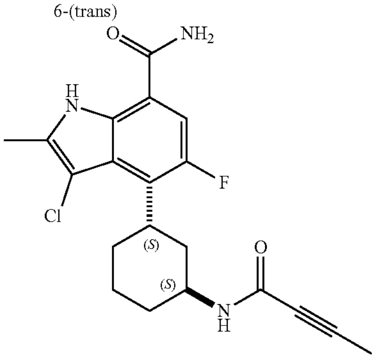

6-(1S,3S)

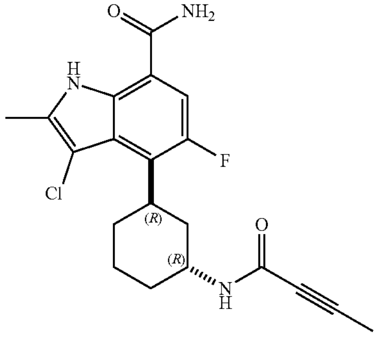

6-(1R,3R)

4-(trans-3-(but-2-ynamido)cyclohexyl]-3-chloro-5-fluoro-2-methyl-1H-indole-7-carboxamide (250 mg) was separated by Chiral-Prep-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 15 min; 254/220 nm.

4-[(1S,3S)-3-(but-2-ynoylamino)cyclohexyl]-3-chloro-5-fluoro-2-methyl-1H-indole-7-carboxamide or 4-[(1R,3R)-3-(but-2-ynoylamino) cyclohexyl]-3-chloro-5-fluoro-2-methyl-1H-indole-7-carboxamide Retention Time=7.327 min (101.3 mg, 41%) as a light yellow solid. $^1$H NMR (400 MHz, DMSO-$d_6$) δ 11.32 (s, 1H), 8.51 (d, J=8.0 Hz, 1H), 8.07 (s, 1H), 7.56-7.45 (m, 2H), 4.10-3.95 (m, 1H), 3.78-3.65 (m, 1H), 2.39 (s, 3H), 2.01-1.71 (m, 8H), 1.54-1.16 (m, 3H). ESI-MS [M+H]$^+$ calcd for ($C_{20}H_{19}ClFN_3O_2$) 390.13, 392.13 found: 390.15, 392.15.

4-[(1R,3R)-3-(but-2-ynoylamino)cyclohexyl]-3-chloro-5-fluoro-2-methyl-1H-indole-7-carboxamide or 4-[(1S,3S)-3-(but-2-ynoylamino)cyclohexyl]-3-chloro-5-fluoro-2-methyl-1H-indole-7-carboxamide Retention Time=12.317 min (100.9 mg, 40%) as a light yellow solid. $^1$H NMR (400 MHz, DMSO-$d_6$) δ 11.33 (s, 1H), 8.51 (d, J=8.0 Hz, 1H), 8.07 (s, 1H), 7.55-7.45 (m, 2H), 4.11-3.95 (m, 1H), 3.78-3.67 (m, 1H), 2.39 (s, 3H), 2.01-1.71 (m, 8H), 1.50-1.18 (m, 3H). ESI-MS [M+H]$^+$ calcd for ($C_{20}H_{21}ClFN_3O_2$) 390.13, 392.13 found: 390.15, 392.15.

Example 7

Synthesis of 4-((1R,3S)-3-(but-2-ynamido)cyclohexyl)-3-cyano-5,6-difluoro-2-methyl-1H-indole-7-carboxamide (Compound 7-(1R,3S))

4-((1S,3R)-3-(but-2-ynamido)cyclohexyl)-3-cyano-5,6-difluoro-2-methyl-1H-indole-7-carboxamide (Compound 7-(1S,3R))

4-((1R,3R)-3-(but-2-ynamido)cyclohexyl)-3-cyano-5,6-difluoro-2-methyl-1H-indole-7-carboxamide (Compound 7-(1R,3R))

and 4-((1S,3S)-3-(but-2-ynamido)cyclohexyl)-3-cyano-5,6-difluoro-2-methyl-1H-indole-7-carboxamide (Compound 7-(1S,3S))

7-(1R,3S)

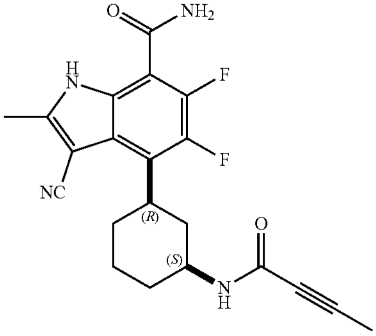

-continued 7-(1S,3R)

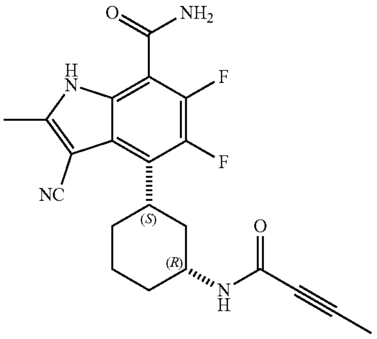

7-(1R,3R)

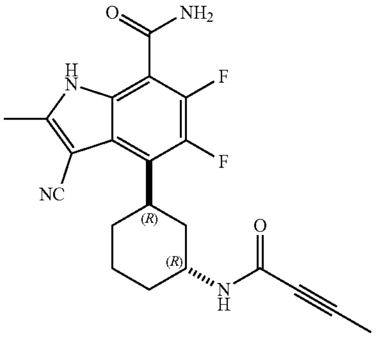

7-(1S,3S)

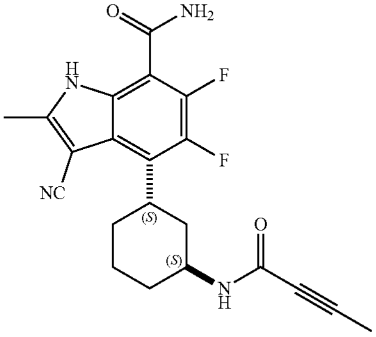

Step 1: tert-butyl (3-(3-bromo-7-carbamoyl-5,6-difluoro-2-methyl-1H-indol-4-yl)cyclohexyl)carbamate

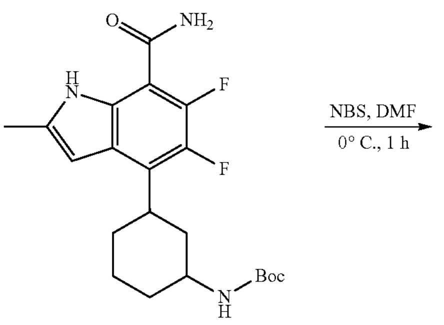

-continued

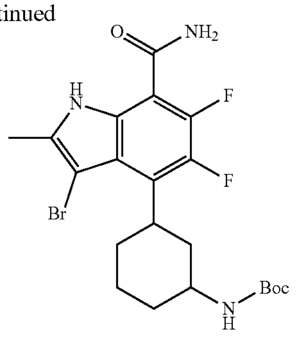

To a stirred solution of tert-butyl (3-(7-carbamoyl-5,6-difluoro-2-methyl-1H-indol-4-yl)cyclohexyl)carbamate (500 mg, 1.23 mmol) in DMF (10 mL) was added NBS (218 mg, 1.23 mmol) at 0° C. The reaction mixture was stirred at 0° C. for 1 h. The reaction mixture was quenched with water (30 mL) and extracted with ethyl acetate (3×30 mL). The combined organic layers were washed with brine (30 mL), dried over $Na_2SO_4$ and concentrated under vacuum. The residue was purified by column chromatography on silica gel eluting with ethyl acetate in petroleum ether (0 to 33%) to give tert-butyl (3-(3-bromo-7-carbamoyl-5,6-difluoro-2-methyl-1H-indol-4-yl)cyclohexyl)carbamate (500 mg, 83%) as a yellow solid. ESI-MS $[M+H-Boc]^+$ calcd for ($C_{21}H_{26}BrF_2N_3O_3$) 386.11, 388.11 found: 386.00, 388.00.

Step 2: tert-butyl (3-(7-carbamoyl-3-cyano-5,6-difluoro-2-methyl-1H-indol-4-yl)cyclohexyl)carbamate

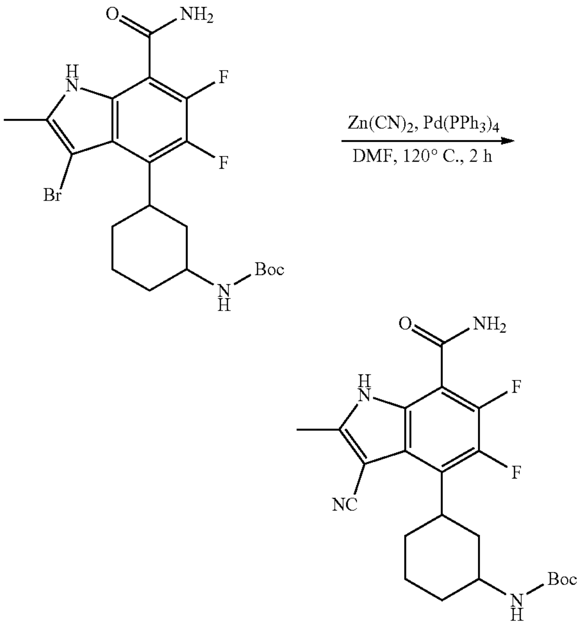

A mixture of tert-butyl (3-(3-bromo-7-carbamoyl-5,6-difluoro-2-methyl-1H-indol-4-yl)cyclohexyl)carbamate (500 mg, 1.03 mmol), $Zn(CN)_2$ (499 mg, 1.03 mmol) and $Pd(PPh_3)_4$ (119 mg, 0.10 mmol) in DMF (15 mL) was degassed and backfilled with nitrogen for five times. The reaction mixture was heated at 120° C. for 2 h. The cooled reaction mixture was quenched with water (60 mL) and extracted with ethyl acetate (3×50 mL). The combined organic layers were washed with brine (50 mL), dried over $Na_2SO_4$ and concentrated under vacuum. The residue was purified by column chromatography on silica gel eluting with ethyl acetate in petroleum ether (0 to 35%) to give tert-butyl (3-(7-carbamoyl-3-cyano-5,6-difluoro-2-methyl-1H-indol-4-yl)cyclohexyl)carbamate (200 mg, 44%) as a yellow solid. ESI-MS $[M+H-Boc]^+$ calcd for ($C_{22}H_{26}F_2N_4O_3$) 333.20 found: 333.35

Step 3: 4-(3-aminocyclohexyl)-3-cyano-5,6-difluoro-2-methyl-1H-indole-7-carboxamide hydrochloride

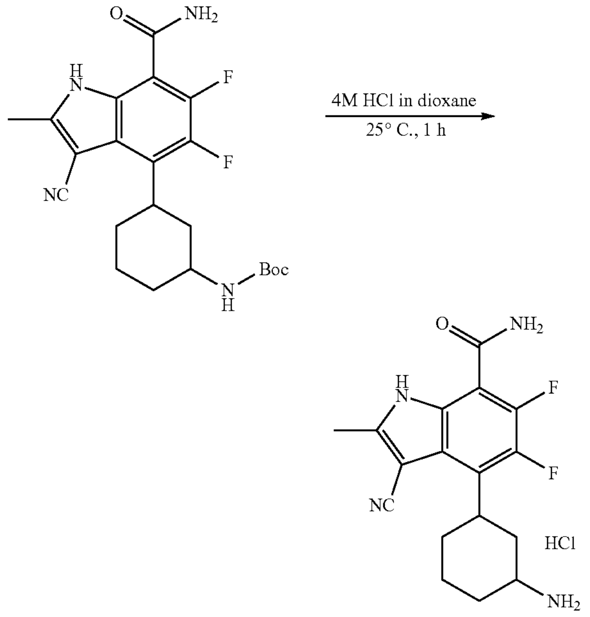

A mixture of tert-butyl (3-(7-carbamoyl-3-cyano-5,6-difluoro-2-methyl-1H-indol-4-yl)cyclohexyl)carbamate (200 mg, 0.462 mmol) and hydrogen chloride (4 M in dioxane, 5 mL) was stirred at 25° C. for 1 h. The resulting mixture was concentrated under vacuum to give 4-(3-aminocyclohexyl)-3-cyano-5,6-difluoro-2-methyl-1H-indole-7-carboxamide hydrochloride (170 mg, crude) as a yellow solid. ESI-MS $[M+H]^+$ calcd for ($C_{17}H_{18}F_2N_4O$) 333.14 found: 333.15.

Step 4: 4-(3-(but-2-ynamido)cyclohexyl)-3-cyano-5,6-difluoro-2-methyl-1H-indole-7-carboxamide

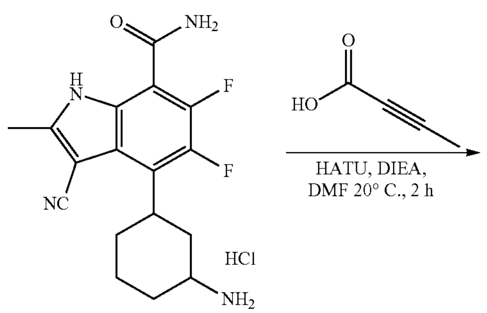

-continued

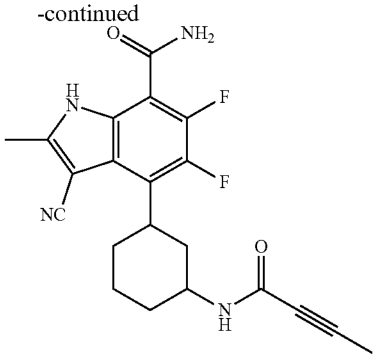

To a solution of 4-(3-aminocyclohexyl)-3-cyano-5,6-difluoro-2-methyl-1H-indole-7-carboxamide hydrochloride (150 mg, 0.406 mmol) in DMF (5 mL) were added 2-butynoic acid (34 mg, 0.406 mmol), HATU (185 mg, 0.488 mmol) and DIEA (263 mg, 2.03 mmol). The reaction mixture was stirred at 20° C. for 2 h. The reaction mixture was quenched with water (40 mL) and extracted with ethyl acetate (3×30 mL). The combined organic layers was washed with brine (30 mL), dried over $Na_2SO_4$ and concentrated under vacuum. The residue was purified by Prep-HPLC with the following conditions: Column: YMC-Actus Triart C18, 30 mm×150 mm, 5 um; Mobile Phase A: Water (50 mmol/L $NH_4HCO_3$), Mobile Phase B: Acetonitrile; Flow rate: 60 mL/min; Gradient: 33% B to 53% B in 9 min, 254 nm; RT: 7.27 min to give 4-(3-(but-2-ynamido) cyclohexyl)-3-cyano-5,6-difluoro-2-methyl-1H-indole-7-carboxamide (130 mg, 80%) as a white solid. ESI-MS $[M+H]^+$ calcd for ($C_{21}H_{20}F_2N_4O_2$) 399.16 found: 399.20.

Step 5: Separation of Cis and Trans Isomers

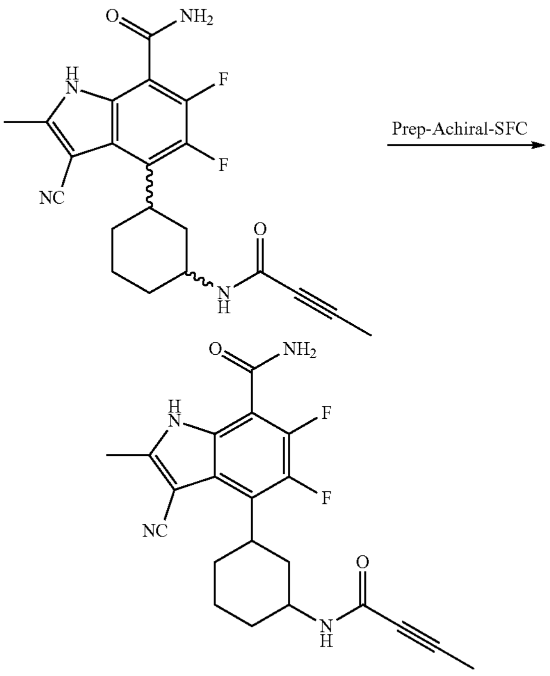

Compound 7-cis

-continued

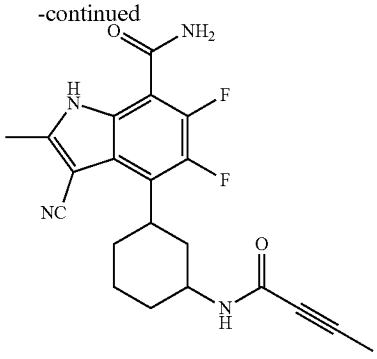

Compound 7-trans 4-(3-(but-2-ynamido)cyclohexyl)-3-cyano-5,6-difluoro-2-methyl-1H-indole-7-carboxamide (130 mg) was separated by Prep-Achiral-SFC with the following conditions: Column: Viridis BEH 2-Ethylpyridine Prep OBD, 3×15 cm, 5 μm; Mobile Phase A: $CO_2$, Mobile Phase B: MeOH (0.5% 2 M $NH_3$-MeOH)-HPLC; Flow rate: 60 mL/min; Gradient: 12% B; Column Temperature: 35° C.; Back Pressure: 100 bar; 254 nm.

cis-4-(3-(but-2-ynamido)cyclohexyl)-3-cyano-5,6-difluoro-2-methyl-1H-indole-7-carboxamide (compound 7-(cis))

Retention Time=6.53 min (70 mg, 54%) as a white solid.

trans-4-(3-(but-2-ynamido)cyclohexyl)-3-cyano-5,6-difluoro-2-methyl-1H-indole-7-carboxamide (compound 7-(trans))

Retention Time=10.55 min (40 mg, 31%) as a white solid.

Step 6A: Separation of Cis Isomers

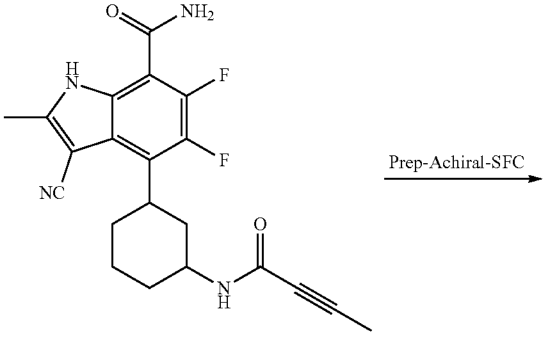

7-(cis)

-continued

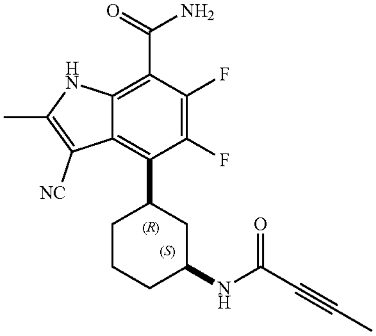

7-(1R,3S)

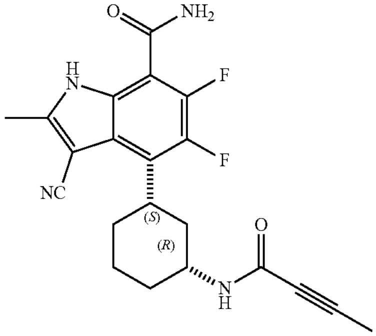

7-(1S,3R)

cis-4-(3-(but-2-ynamido)cyclohexyl)-3-cyano-5,6-difluoro-2-methyl-1H-indole-7-carboxamide (70 mg) was separated by Prep-Chiral-HPLC under the following conditions: Column: CHIRALPAK IG, 2×25 cm, 5 μm; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 23 min; 220/254 nm.

4-((1R,3S)-3-(but-2-ynamido)cyclohexyl)-3-cyano-5,6-difluoro-2-methyl-1H-indole-7-carboxamide (compound 7-(1R,3S)) or 4-((1S,3R)-3-(but-2-ynamido)cyclohexyl)-3-cyano-5,6-difluoro-2-methyl-1H-indole-7-carboxamide Retention Time=8.68 min (28.9 mg, 41%) as a white solid. $^1H$ NMR (400 MHz, DMSO-$d_6$) δ 12.11 (s, 1H), 8.33 (brs, 1H), 8.14-7.76 (m, 2H), 4.03 (s, 1H), 3.77 (s, 1H), 2.55 (s, 3H), 2.28-1.90 (m, 5H), 1.89-1.70 (m, 4H), 1.69-1.47 (m, 2H). ESI-MS $[M+H]^+$ calcd for ($C_{21}H_{20}F_2N_4O_2$) 399.16 found: 399.15.

4-((1S,3R)-3-(but-2-ynamido)cyclohexyl)-3-cyano-5,6-difluoro-2-methyl-1H-indole-7-carboxamide (compound 7-(1S,3R)) or 4-((1R,3S)-3-(but-2-ynamido)cyclohexyl)-3-cyano-5,6-difluoro-2-methyl-1H-indole-7-carboxamide Retention Time=19.003 min (29.4 mg, 42%) as a white solid. $^1H$ NMR (400 MHz, DMSO-$d_6$) δ 12.11 (s, 1H), 8.33 (brs, 1H), 8.09-7.76 (m, 2H), 4.03 (s, 1H), 3.77 (s, 1H), 2.55 (s, 3H), 2.29-1.92 (m, 5H), 1.90-1.68 (m, 4H), 1.69-1.51 (m, 2H). ESI-MS $[M+H]^+$ calcd for ($C_{21}H_{20}F_2N_4O_2$) 399.16 found: 399.15.

Step 6B: Separation of Trans Isomers

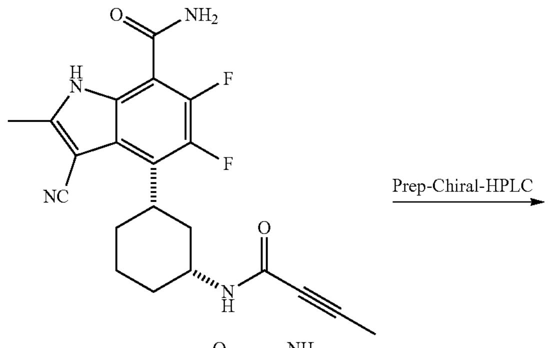

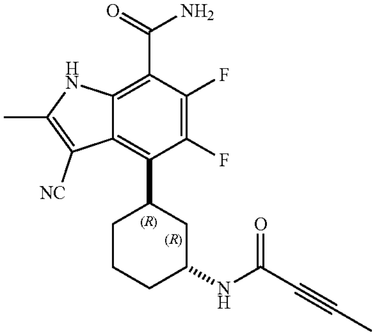

7-(1R,3R)

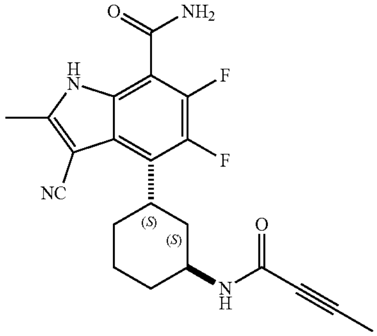

7-(1S,3S)

trans-4-(3-(but-2-ynamido)cyclohexyl)-3-cyano-5,6-difluoro-2-methyl-1H-indole-7-carboxamide (40 mg) was separated by Prep-Chiral-HPLC under the following conditions: Column: CHIRALPAK IG, 2×25 cm, 5 μm; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 23 min; 220/254 nm.

4-((1R,3R)-3-(but-2-ynamido)cyclohexyl)-3-cyano-5,6-difluoro-2-methyl-1H-indole-7-carboxamide (compound 7-(1R,3R)) or 4-((1S,3S)-3-(but-2-ynamido)cyclohexyl)-3-cyano-5,6-difluoro-2-methyl-1H-indole-7-carboxamide Retention Time=7.036 min (15 mg, 37%) as a white solid. $^1H$ NMR (300 MHz, DMSO-$d_6$) δ 12.13 (s, 1H), 8.55 (d, J=7.2 Hz, 1H), 8.13-7.75 (m, 2H), 3.84-3.50 (m, 2H), 2.55 (s, 3H), 2.09-1.59 (m, 9H), 1.56-1.38 (m, 1H), 1.37-1.26 (m, 1H). ESI-MS $[M+H]^+$ calcd for ($C_{21}H_{20}F_2N_4O_2$) 399.16 found: 399.15.

4-((1S,3S)-3-(but-2-ynamido)cyclohexyl)-3-cyano-5,6-difluoro-2-methyl-1H-indole-7-carboxamide (compound 7-(1S,3S)) or 4-((1R,3R)-3-(but-2-ynamido)cyclohexyl)-3-cyano-5,6-difluoro-2-methyl-1H-indole-7-carboxamide Retention Time=14.867 min (14 mg) as a white solid. $^1H$ NMR (300 MHz, DMSO-$d_6$) δ 12.13 (s, 1H), 8.55 (d, J=7.2 Hz, 1H), 8.07-7.75 (m, 2H), 3.79-3.48 (m, 2H), 2.55 (s, 3H), 2.09-1.61 (m, 9H), 1.52-1.20 (m, 2H). ESI-MS $[M+H]^+$ calcd for ($C_{21}H_{20}F_2N_4O_2$) 399.16 found: 399.10.

Example 8

Synthesis of 4-((1R,3S)-3-(but-2-ynamido)cyclohexyl)-3,5,6-trifluoro-2-methyl-1H-indole-7-carboxamide 4-((1S,3R)-3-(but-2-ynamido)cyclohexyl)-3,5,6-trifluoro-2-methyl-1H-indole-7-carboxamide 4-((1R,3R)-3-(but-2-ynamido)cyclohexyl)-3,5,6-trifluoro-2-methyl-1H-indole-7-carboxamide and 4-((1S,3S)-3-(but-2-ynamido)cyclohexyl)-3,5,6-trifluoro-2-methyl-1H-indole-7-carboxamide 8-(1R,3S)

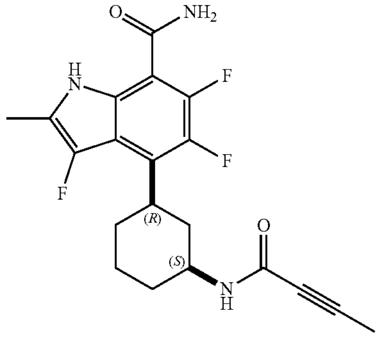

8-(1S,3R)

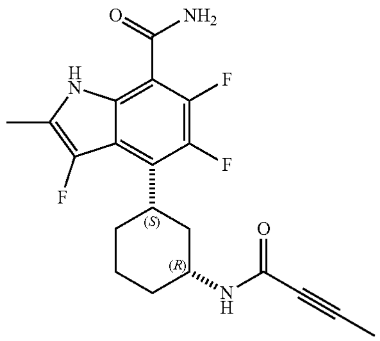

-continued 8-(1R,3R)

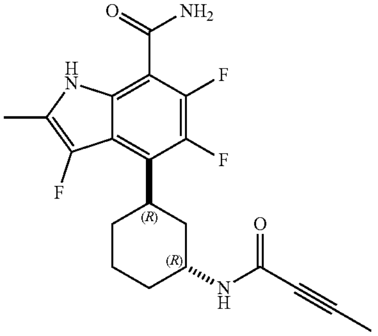

8-(1S,3S)

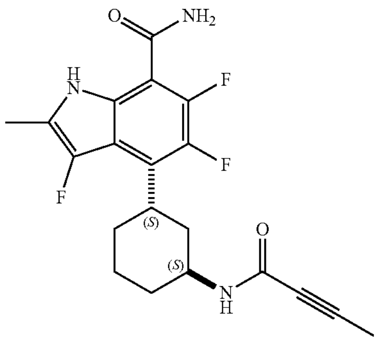

Step 1: tert-butyl (3-(7-carbamoyl-3,5,6-trifluoro-2-methyl-1H-indol-4-yl)cyclohexyl)carbamate

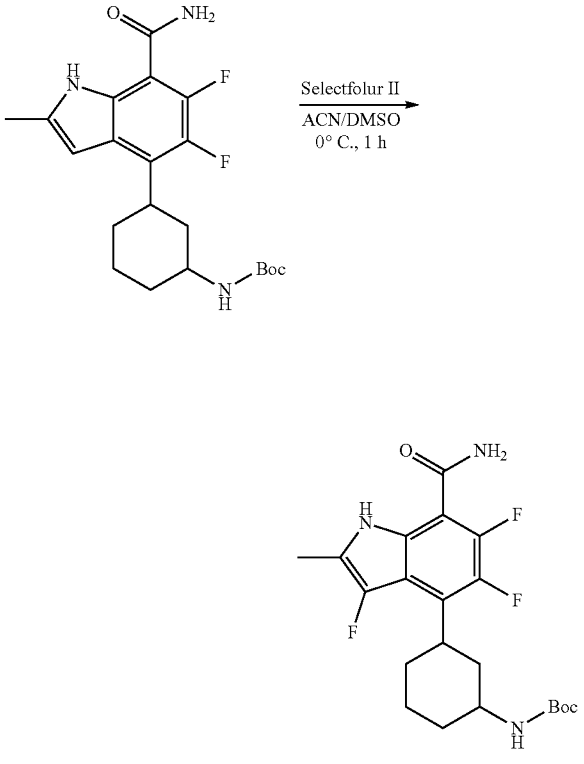

To a stirred solution of tert-butyl (3-(7-carbamoyl-5,6-difluoro-2-methyl-1H-indol-4-yl)cyclohexyl)carbamate (1.8 g, 4.42 mmol) in acetonitrile (20 mL) and DMSO (5 mL) was added Selectfluor II (1.27 g, 3.98 mmol) at 0° C. The reaction mixture was stirred for 1 h at 0° C. The reaction mixture was quenched with water (60 mL) and extracted with ethyl acetate (3×50 mL). The combined organic layers were washed with brine (50 mL), dried over $Na_2SO_4$ and concentrated under vacuum. The residue was purified by Prep-HPLC with the following conditions: Column: YMC-Actus Triart C18, 30 mm×150 mm, 5 um; Mobile Phase A: Water (10 mmol/L $NH_4HCO_3$+0.1% $NH_3 \cdot H_2O$), Mobile Phase B: Acetonitrile; Flow rate: 60 mL/min; Gradient: 54% B to 74% B in 7 min, 254 nm; RT: 6.53 min to give tert-butyl (3-(7-carbamoyl-3,5,6-trifluoro-2-methyl-1H-indol-4-yl)cyclohexyl)carbamate (510 mg, 27%) as a yellow solid. $^1H$ NMR (400 MHz, DMSO-$d_6$) δ 10.86 (d, J=12.4 Hz, 1H), 7.94-7.71 (m, 2H), 7.06-6.79 (m, 1H), 3.80 (s, 1H), 3.65-3.50 (m, 1H), 2.36-2.25 (m, 3H), 1.98-1.65 (m, 6H), 1.60-1.47 (m, 2H), 1.42-1.32 (m, 9H). ESI-MS $[M+H-Boc]^+$ calcd for ($C_{21}H_{26}F_3N_3O_3$) 326.19 found: 326.10.

Step 2: 4-(3-aminocyclohexyl)-3,5,6-trifluoro-2-methyl-1H-indole-7-carboxamide hydrochloride

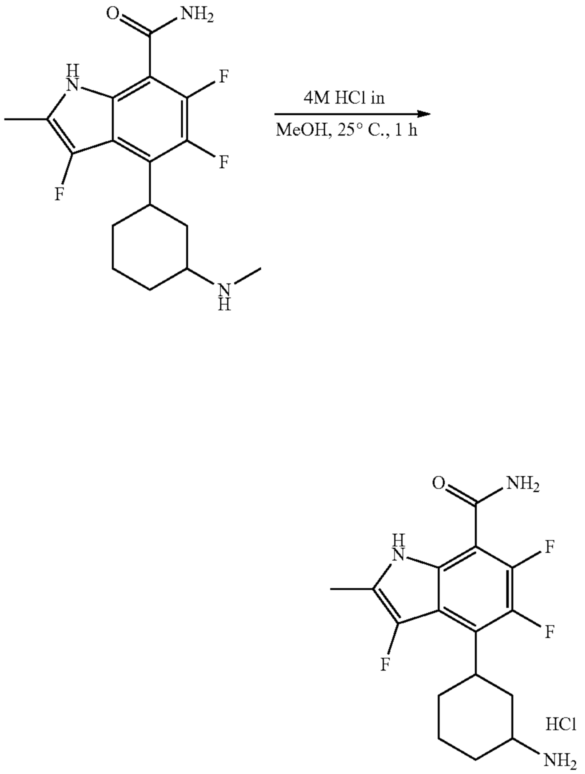

To a stirred solution of tert-butyl (3-(7-carbamoyl-3,5,6-trifluoro-2-methyl-1H-indol-4-yl)cyclohexyl)carbamate (510 mg, 1.20 mmol) in MeOH (1 mL) was added 4 M hydrogen chloride in dioxane (6 mL). The reaction mixture was stirred for 1 h at 25° C. The resulting mixture was concentrated under vacuum to give 4-(3-aminocyclohexyl)-3,5,6-trifluoro-2-methyl-1H-indole-7-carboxamide hydrochloride (420 mg, crude) as a yellow solid. ESI-MS $[M+H]^+$ calcd for ($C_{16}H_{18}F_3N_3O$) 326.14 found: 326.10.

Step 3: 4-(3-(but-2-ynamido)cyclohexyl)-3,5,6-trifluoro-2-methyl-1H-indole-7-carboxamide

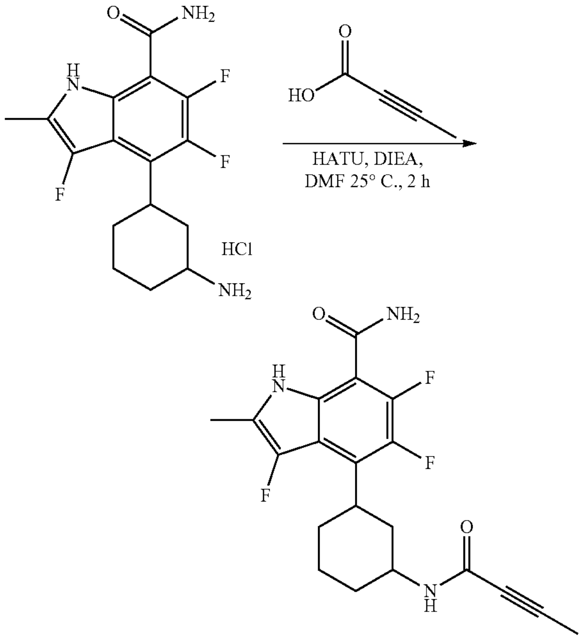

To a stirred solution of 4-(3-aminocyclohexyl)-3,5,6-trifluoro-2-methyl-1H-indole-7-carboxamide (420 mg, 1.16 mmol) in DMF (8 mL) were added 2-Butynoic acid (107 mg, 1.28 mmol), DIEA (750 mg, 5.80 mmol) and HATU (574 mg, 1.51 mmol). The reaction mixture was stirred at 25° C. for 1 h. The reaction mixture was quenched with water (50 mL) and extracted with ethyl acetate (3×40 mL). The combined organic layers was washed with brine (40 mL), dried over $Na_2SO_4$ and concentrated under vacuum. The residue was purified by Prep-HPLC with the following conditions: Column: XBridge Prep OBD C18 Column, 30×150 mm, 5 um; Mobile Phase A: Water (50 mmol/L $NH_4HCO_3$), Mobile Phase B: Acetonitrile; Flow rate: 60 mL/min; Gradient: 40% B to 60% B in 9 min, 254 nm; RT: 7.8 min to give 4-(3-(but-2-ynamido)cyclohexyl)-3,5,6-trifluoro-2-methyl-1H-indole-7-carboxamide (300 mg, 66%) as a white solid. ESI-MS $[M+H]^+$ calcd for ($C_{20}H_{20}F_3N_3O_2$) 392.15 found: 392.35.

Step 4: Separation of Cis and Trans Isomers

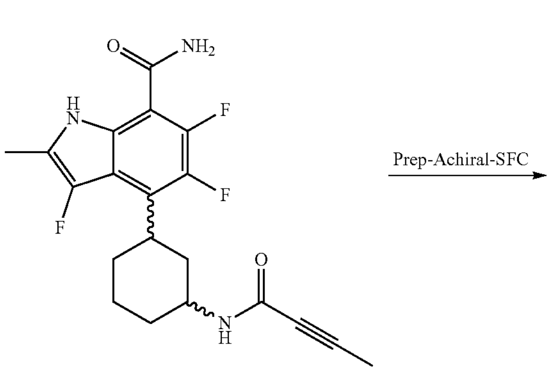

-continued

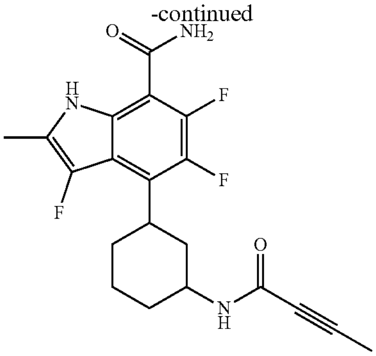

Compound 8-cis

+

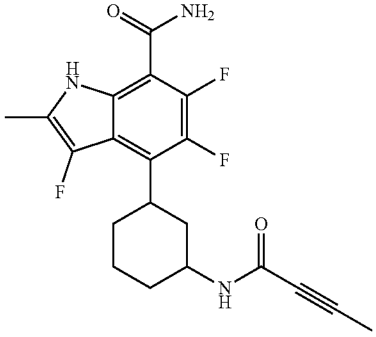

Compound 8-trans 4-(3-(but-2-ynamido)cyclohexyl)-3,5,6-trifluoro-2-methyl-1H-indole-7-carboxamide (300 mg) was separated by Prep-Achiral-HPLC with the following conditions: Column: DAICEL DCpak P4VP, 2×25 cm, 5 μm; Mobile Phase A: $CO_2$, Mobile Phase B: Acetonitrile/MeOH=4:1 (0.1% 2 M $NH_3$-MeOH); Flow rate: 50 mL/min; Gradient: 35% B; Column Temperature: 35° C.; Back Pressure: 100 bar; 254 nm.

cis-4-(3-(but-2-ynamido)cyclohexyl)-3,5,6-trifluoro-2-methyl-1H-indole-7-carboxamide (Compound 8-(cis))

Retention Time=3.97 min (120 mg, 40%) as an off-white solid trans-4-(3-(but-2-ynamido)cyclohexyl)-3,5,6-trifluoro-2-methyl-1H-indole-7-carboxamide (Compound 8-(trans))

Retention Time=5.0 min (120 mg, 40%) as an off-white solid.

ESI-MS $[M+H]^+$ calcd for ($C_{20}H_{20}F_3N_3O_2$) 392.15 found: 392.15.

Step 5A: Separation of Cis Isomers

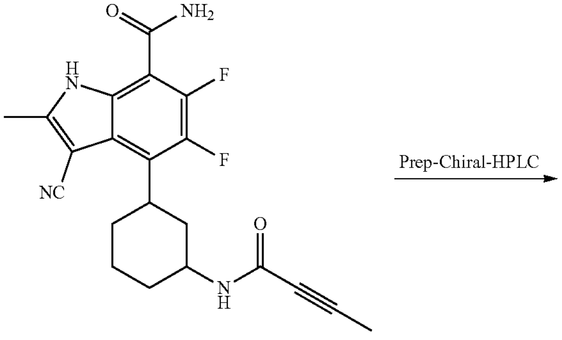

8-(cis)

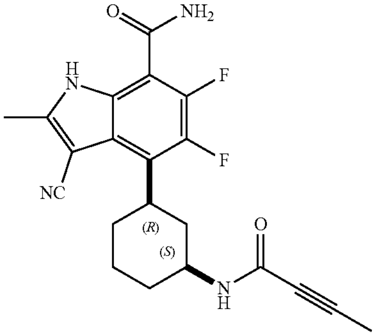

8-(1R,3S)

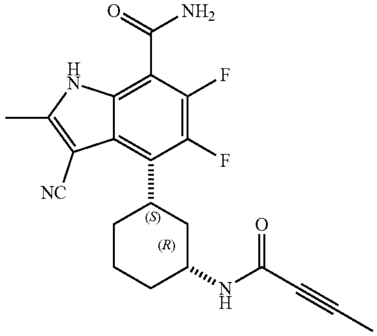

8-(1S,3R)

cis-4-(3-(but-2-ynamido)cyclohexyl)-3,5,6-trifluoro-2-methyl-1H-indole-7-carboxamide (120 mg) was separated by Prep-Chiral-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 16 min; 254/220 nm.

4-((1R,3S)-3-(but-2-ynamido)cyclohexyl)-3,5,6-trifluoro-2-methyl-1H-indole-7-carboxamide (Compound 8-(1R,3S)) or 4-((1S,3R)-3-(but-2-ynamido)cyclohexyl)-3,5,6-trifluoro-2-methyl-1H-indole-7-carboxamide Retention Time=5.332 min (46.7 mg, 39%) as an off-white solid. $^1$H NMR (400 MHz, DMSO-$d_6$) δ 10.79 (s, 1H), 8.70 (d, J=6.8 Hz, 1H), 7.93-7.73 (m, 2H), 4.17-4.03 (m, 1H), 3.67-3.56 (m, 1H), 2.31 (s, 3H), 1.98 (s, 3H), 1.96-1.76 (m, 4H), 1.75-1.65 (m, 2H), 1.62-1.48 (m, 2H). ESI-MS $[M+H]^+$ calcd for ($C_{20}H_{20}F_3N_3O_2$) 392.15 found: 392.35.

4-((1S,3R)-3-(but-2-ynamido)cyclohexyl)-3,5,6-trifluoro-2-methyl-1H-indole-7-carboxamide (Compound 8-(1S,3R)) or 4-((1R,3S)-3-(but-2-ynamido)cyclohexyl)-3,5,6-trifluoro-2-methyl-1H-indole-7-carboxamide Retention Time=13.386 min (48.5 mg, 40%) as an off-white solid. $^1$H NMR (400 MHz, DMSO-$d_6$) δ 10.87 (s, 1H), 8.70 (d, J=6.8 Hz, 1H), 7.97-7.70 (m, 2H), 4.17-4.02 (m, 1H), 3.61-3.56 (m, 1H), 2.32 (s, 3H), 1.98 (s, 3H), 1.97-1.75 (m, 4H), 1.74-1.65 (m, 2H), 1.63-1.48 (m, 2H). ESI-MS $[M+H]^+$ calcd for ($C_{20}H_{20}F_3N_3O_2$) 392.15 found: 392.15.

Step 5B: Separation of Trans Isomers

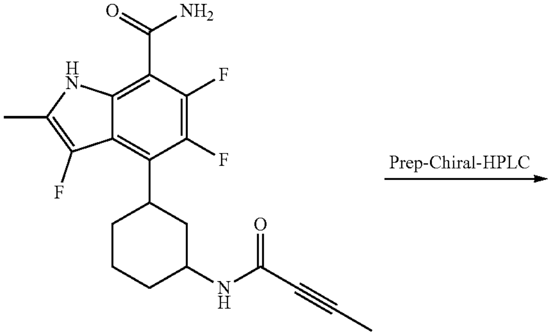

1-084B 8-trans

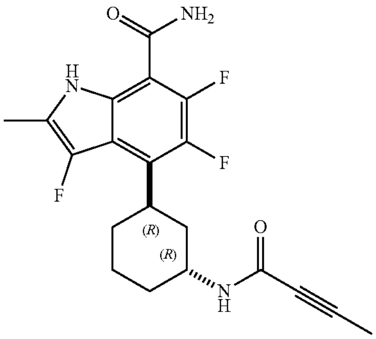

1-084B-0A 8-(1R,3R)

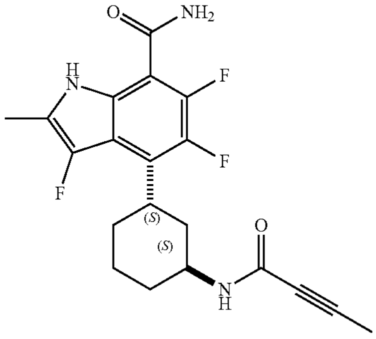

1-084B-0B 8-(1S,3S)

trans-4-(3-(but-2-ynamido)cyclohexyl)-3,5,6-trifluoro-2-methyl-1H-indole-7-carboxamide (120 mg) was separated by Prep-Chiral-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 20 mL/min; Gradient: 50% B to 50% B in 15 min; 254/220 nm.

4-((1R,3R)-3-(but-2-ynamido)cyclohexyl)-3,5,6-trifluoro-2-methyl-1H-indole-7-carboxamide (Compound 8-(1R,3R)) or 4-((1S,3S)-3-(but-2-ynamido)cyclohexyl)-3,5,6-trifluoro-2-methyl-1H-indole-7-carboxamide Retention Time=6.029 min (46.7 mg, 39%) as an off-white solid. $^1$H NMR (400 MHz, DMSO-$d_6$) δ 10.89 (s, 1H), 8.53 (d, J=8.0 Hz, 1H), 7.95-7.73 (m, 2H), 3.69 (s, 1H), 3.31-3.25 (m, 1H), 2.31 (m, 3H), 1.92 (s, 3H), 1.89-1.65 (m, 6H), 1.46-1.42 (m, 1H), 1.39-1.32 (m, 1H). ESI-MS $[M+H]^+$ calcd for ($C_{20}H_{20}F_3N_3O_2$) 392.15 found: 392.15.

4-((1S,3S)-3-(but-2-ynamido)cyclohexyl)-3,5,6-trifluoro-2-methyl-1H-indole-7-carboxamide (Compound 8-(1S,3S)) or 4-((1R,3R)-3-(but-2-ynamido)cyclohexyl)-3,5,6-trifluoro-2-methyl-1H-indole-7-carboxamide Retention Time=9.994 min (46.6 mg, 39%) as an off-white solid. $^1$H NMR (400 MHz, DMSO-$d_6$) δ 10.89 (s, 1H), 8.53 (d, J=8.0 Hz, 1H), 7.93-7.75 (m, 2H), 3.69 (s, 1H), 3.31-3.26 (m, 1H), 2.32 (m, 3H), 1.92 (s, 3H), 1.89-1.66 (m, 6H), 1.50-1.35 (m, 1H), 1.34-1.26 (m, 1H). ESI-MS $[M+H]^+$ calcd for ($C_{20}H_{20}F_3N_3O_2$) 392.15 found: 392.20.

Example 9

Synthesis of 4-((1S,3S)-3-(but-2-ynamido)cyclohexyl)-5,6-difluoro-2,3-dimethyl-1H-indole-7-carboxamide 4-((1R,3S)-3-(but-2-ynamido)cyclohexyl)-5,6-difluoro-2,3-dimethyl-1H-indole-7-carboxamide 4-((1S,3R)-3-(but-2-ynamido)cyclohexyl)-5,6-difluoro-2,3-dimethyl-1H-indole-7-carboxamide and 4-((1R,3R)-3-(but-2-ynamido)cyclohexyl)-5,6-difluoro-2,3-dimethyl-1H-indole-7-carboxamide 9-(1S,3S)

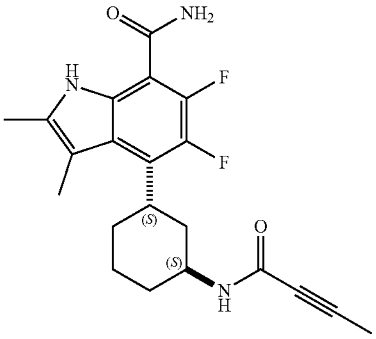

-continued 9-(1R,3S)

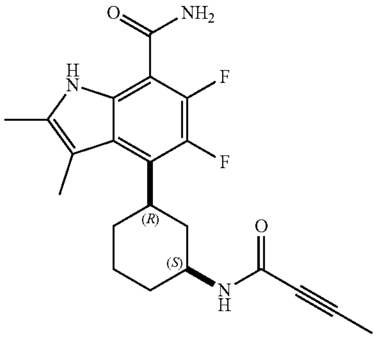

9-(1S,3R)

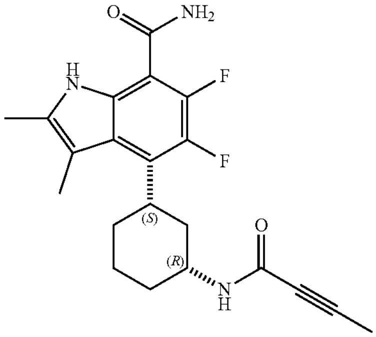

9-(1R,3R)

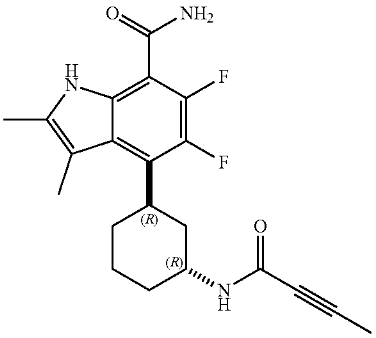

Step 1: tert-butyl (3-(7-carbamoyl-5,6-difluoro-2,3-dimethyl-1H-indol-4-yl)cyclohex-2-en-1-yl)carbamate

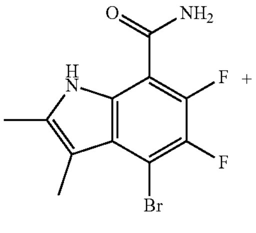

-continued

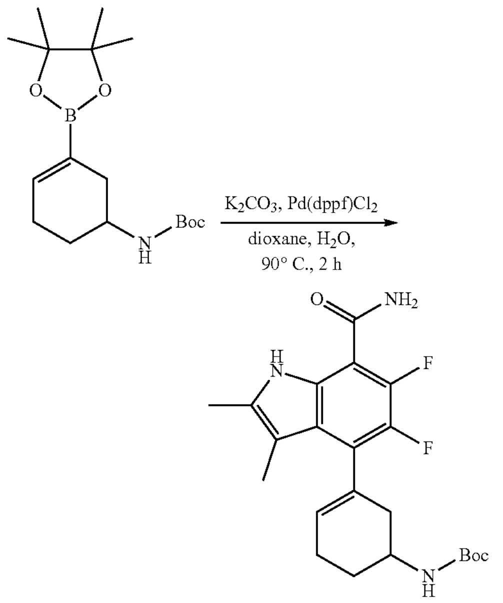

A mixture of 4-bromo-5,6-difluoro-2,3-dimethyl-1H-indole-7-carboxamide (450 mg, 1.48 mmol), tert-butyl (3-(4,4,5,5-tetra methyl-1,3,2-dioxaborolan-2-yl)cyclohex-3-en-1-yl)carbamate (528 mg, 1.63 mmol), potassium carbonate (616 mg, 4.45 mmol) and $Pd(dppf)Cl_2·CH_2Cl_2$ (121 mg, 0.148 mmol) in dioxane (12 mL) and water (3 mL) was degassed and backfilled with nitrogen for five times. The reaction mixture was heated at 90° C. for 2 h. The cooled reaction mixture was quenched with water (60 mL) and extracted with ethyl acetate (3×50 mL). The combined organic layers was washed with brine (50 mL), dried over $Na_2SO_4$ and concentrated under vacuum. The residue was purified by column chromatography on silica gel eluting with ethyl acetate in petroleum ether (0 to 34%) to give tert-butyl (3-(7-carbamoyl-5,6-difluoro-2,3-dimethyl-1H-indol-4-yl)cyclohex-2-en-1-yl)carbamate (560 mg, 89%) as a yellow solid. $^1H$ NMR (300 MHz, DMSO-$d_6$) δ 10.76 (s, 1H), 7.91-7.59 (m, 2H), 7.14-6.81 (m, 1H), 5.70-5.44 (m, 1H), 4.25-3.51 (m, 1H), 2.44-2.00 (m, 9H), 1.99-1.46 (m, 3H), 1.38 (s, 9H). ESI-MS $[M+H]^+$ calcd for ($C_{22}H_{27}F_2N_3O_3$) 420.20 found: 420.35.

Step 2: tert-butyl (3-(7-carbamoyl-5,6-difluoro-2,3-dimethyl-1H-indol-4-yl)cyclohexyl)carbamate

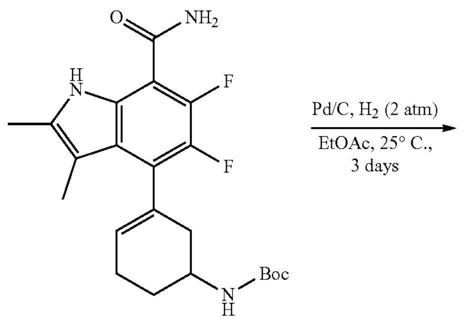

-continued

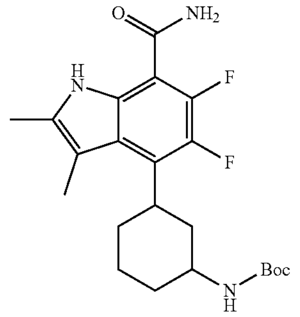

To a solution of tert-butyl (3-(7-carbamoyl-5,6-difluoro-2,3-dimethyl-1H-indol-4-yl)cyclohex-2-en-1-yl)carbamate (500 mg, 1.19 mmol) in ethyl acetate (30 mL) was added Pd/C (1 g, 10%). The reaction mixture was stirred under hydrogen (2 atm) at 25° C. for 3 days. The reaction mixture was filtered. The filtrate was concentrated under vacuum. The residue was purified by column chromatography on silica gel eluting with ethyl acetate in petroleum ether (53%) to give tert-butyl (3-(7-carbamoyl-5,6-difluoro-2,3-dimethyl-1H-indol-4-yl)cyclohexyl)carbamate (490 mg, 97%) as a white solid. ESI-MS $[M+H]^+$ calcd for ($C_{22}H_{29}F_2N_3O_3$) 422.22 found: 422.20.

Step 3: 4-(3-aminocyclohexyl)-5,6-difluoro-2,3-dimethyl-1H-indole-7-carboxamide hydrochloride

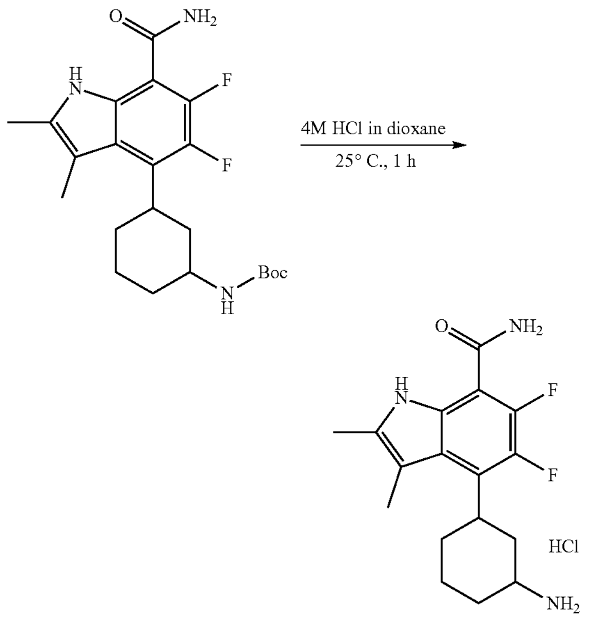

A mixture of tert-butyl (3-(7-carbamoyl-5,6-difluoro-2,3-dimethyl-1H-indol-4-yl)cyclohexyl)carbamate (490 mg, 1.16 mmol) and hydrogen chloride (4 M in dioxane, 6 mL) was stirred at 25° C. for 1 h. The resulting mixture was concentrated under vacuum to give 4-(3-aminocyclohexyl)-5,6-difluoro-2,3-dimethyl-1H-indole-7-carboxamide hydrochloride (400 mg, crude) as a yellow solid. ESI-MS $[M+H]^+$ calcd for ($C_{17}H_{21}F_2N_3O$) 322.17 found: 322.15.

Step 4: 4-(3-(but-2-ynamido)cyclohexyl)-5,6-difluoro-2,3-dimethyl-1H-indole-7-carboxamide

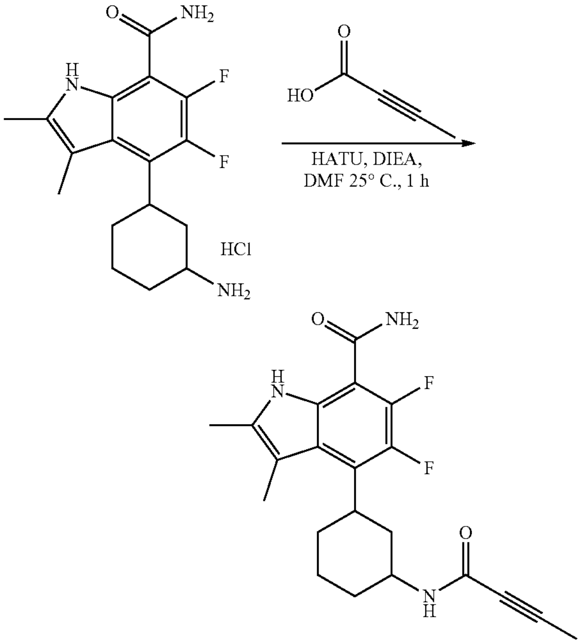

A mixture of 4-(3-aminocyclohexyl)-5,6-difluoro-2,3-dimethyl-1H-indole-7-carboxamide hydrochloride (400 mg, 1.16 mmol) and 2-butynoic acid (117 mg, 1.40 mmol) in DMF (10 mL) were added HATU (663 mg, 1.75 mmol), and DIEA (902 mg, 6.98 mmol). The reaction mixture was stirred at 25° C. for 1 h. The reaction mixture was quenched with water (40 mL) and extracted with ethyl acetate (2×30 mL). The combined organic layers were washed with water (2×30 mL) and brine (30 mL), dried over anhydrous sodium sulfate, filtered and concentrated under vacuum. The residue was purified by column chromatography on silica gel eluting with methanol in dichloromethane (0 to 15%) to give 4-(3-(but-2-ynamido)cyclohexyl)-5,6-difluoro-2,3-dimethyl-1H-indole-7-carboxamide (200 mg, 44%) as a yellow solid. ESI-MS $[M+H]^+$ calcd for ($C_{21}H_{23}F_2N_3O_2$) 388.18 found: 388.15.

Step 5: Separation of Cis and Trans Isomers

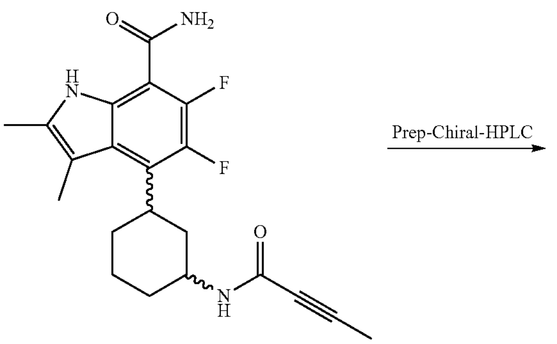

-continued

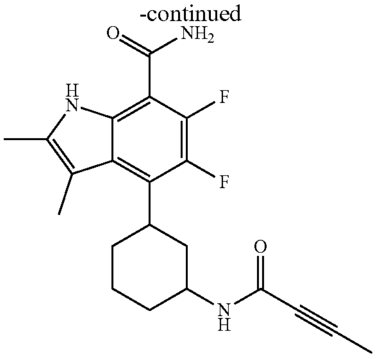

Compound 9-cis

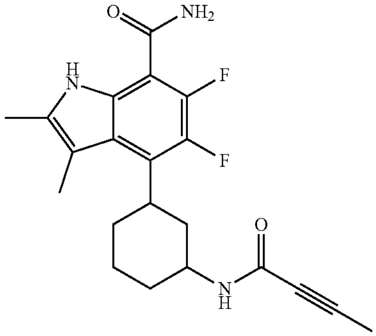

Compound 9-trans 4-(3-(but-2-ynamido)cyclohexyl)-5,6-difluoro-2,3-dimethyl-1H-indole-7-carboxamide (200 mg) was separated by Prep-Chiral-HPLC with the following conditions: Column: CHIRALPAK IG, 2×25 cm, 5 um; Mobile Phase A: Hexane/DCM=3:1 (0.5% 2 M $NH_3$-MeOH)-HPLC, Mobile Phase B: EtOH-HPLC; Flow rate: 20 mL/min; Gradient: 20% B to 20% B in 26 min; 220/254 nm.

4-((3S)-3-(but-2-ynamido)cyclohexyl)-5,6-difluoro-2,3-dimethyl-1H-indole-7-carboxamide Retention Time=10.291 min (100 mg, 50%) as a white solid.

4-((3R)-3-(but-2-ynamido)cyclohexyl)-5,6-difluoro-2,3-dimethyl-1H-indole-7-carboxamide Retention Time=13.464 min (80 mg, 40%) as a white solid.

Step 6A: Separation of Cis Isomers

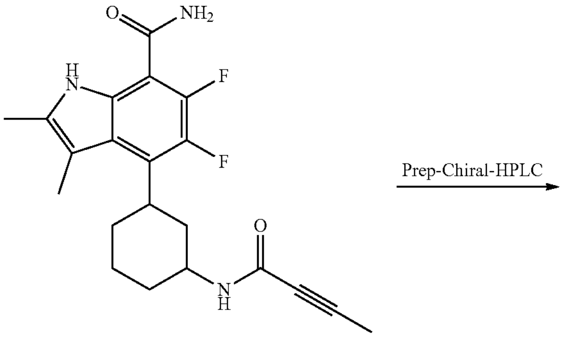

Compound 9-cis

-continued

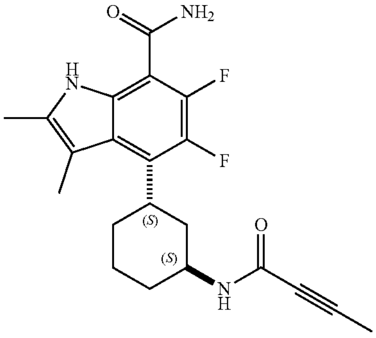

9-(1S,3S)

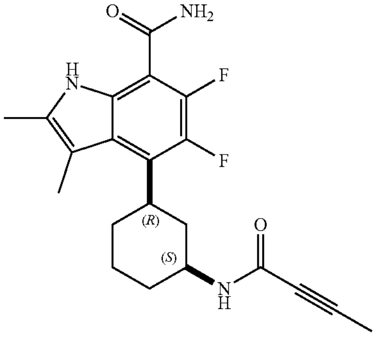

9-(1R,3S)

Cis-4-3-(but-2-ynoylamino)cyclohexyl-5,6-difluoro-2,3-dimethyl-1H-indole-7-carboxamide (100 mg) was separated by Prep-Chiral-HPLC with the following conditions: Column: CHIRALPAK IG, 2×25 cm, 5 um; Mobile Phase A: Hexane/DCM=3:1 (0.5% 2 M $NH_3$-MeOH)-HPLC, Mobile Phase B: EtOH-HPLC; Flow rate: 20 mL/min; Gradient: 20% B to 20% B in 26 min; 220/254 nm.

4-((1S,3S)-3-(but-2-ynamido)cyclohexyl)-5,6-difluoro-2,3-dimethyl-1H-indole-7-carboxamide (Compound 9-(1S,3S)) or 4-((1R,3S)-3-(but-2-ynamido)cyclohexyl)-5,6-difluoro-2,3-dimethyl-1H-indole-7-carboxamide Retention Time=10.291 min (16.2 mg, 16%) as a white solid. $^1$H NMR (300 MHz, DMSO-$d_6$) δ 10.72 (s, 1H), 8.51 (d, J=8.1 Hz, 1H), 7.78 (s, 1H), 7.76 (s, 1H), 3.83-3.62 (m, 1H), 3.59-3.41 (m, 1H), 2.39-2.18 (m, 6H), 1.98-1.63 (m, 9H), 1.58-1.36 (m, 1H), 1.35-1.02 (m, 1H). ESI-MS $[M+H]^+$ calcd for $(C_{21}H_{23}F_2N_3O_2)$ 388.18 found: 388.15.

4-((1R,3S)-3-(but-2-ynamido)cyclohexyl)-5,6-difluoro-2,3-dimethyl-1H-indole-7-carboxamide (Compound 9-(1R,3S)) or 4-((1S,3S)-3-(but-2-ynamido)cyclohexyl)-5,6-difluoro-2,3-dimethyl-1H-indole-7-carboxamide Retention Time=13.464 min (41.4 mg, 41%) as a white solid. $^1$H NMR (400 MHz, DMSO-$d_6$) δ 10.69 (s, 1H), 8.65 (d, J=6.0 Hz, 1H), 7.77 (s, 1H), 7.65 (s, 1H), 4.04 (s, 1H), 3.70 (t, J=12.0 Hz, 1H), 2.31 (s, 6H), 2.05-1.53 (m, 11H). ESI-MS $[M+H]^+$ calcd for $(C_{21}H_{23}F_2N_3O_2)$ 388.18 found: 388.15.

Step 6B: Separation of Trans Isomers

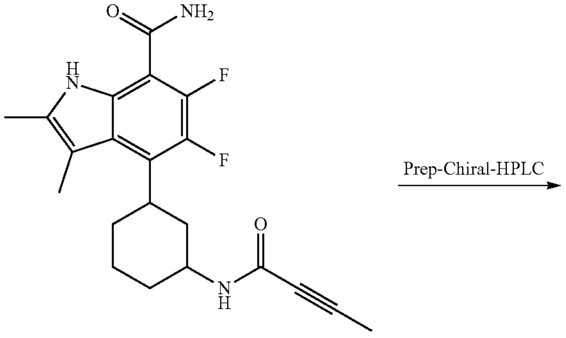

Compound 9-trans

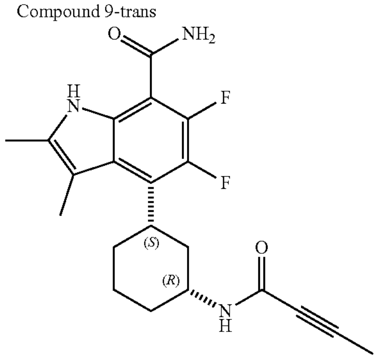

9-(1S,3R)

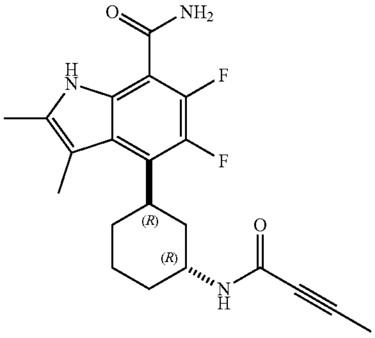

9-(1R,3R)

Trans-4-(3-(but-2-ynamido)cyclohexyl)-5,6-difluoro-2,3-dimethyl-1H-indole-7-carboxamide (80 mg) was separated by Prep-Chiral-HPLC with the following conditions: Column: CHIRALPAK IG, 2×25 cm, 5 um; Mobile Phase A: Hexane/DCM=3:1 (0.5% 2 M $NH_3$-MeOH)-HPLC, Mobile Phase B: EtOH-HPLC; Flow rate: 20 mL/min; Gradient: 20% B to 20% B in 16 min; 220/254 nm.

4-((1S,3R)-3-(but-2-ynamido)cyclohexyl)-5,6-difluoro-2,3-dimethyl-1H-indole-7-carboxamide (Compound 9-(1S,3R)) or 4-((1R,3R)-3-(but-2-ynamido)cyclohexyl)-5,6-difluoro-2,3-dimethyl-1H-indole-7-carboxamide Retention Time=: 8.78 min (28 mg, 34%) as a white solid. $^1$H NMR (400 MHz, DMSO-$d_6$) δ 10.69 (s, 1H), 8.65 (d, J=6.0 Hz, 1H), 7.77 (s, 1H), 7.65 (s, 1H), 4.03 (s, 1H), 3.70 (t, J=12.0 Hz, 1H), 2.31 (s, 6H), 2.03-1.54 (m, 11H). ESI-MS $[M+H]^+$ calcd for $(C_{21}H_{23}F_2N_3O_2)$ 388.18 found: 388.10.

4-((1R,3R)-3-(but-2-ynamido)cyclohexyl)-5,6-difluoro-2,3-dimethyl-1H-indole-7-carboxamide (Compound 9-(1R,3R)) or 4-((1S,3R)-3-(but-2-ynamido)cyclohexyl)-5,6-difluoro-2,3-dimethyl-1H-indole-7-carboxamide Retention Time=14.032 min (15.9 mg, 19%) as a white solid. $^{1}H$ NMR (400 MHz, DMSO-$d_6$) δ 10.74 (s, 1H), 8.52 (d, J=8.0 Hz, 1H), 7.79 (s, 1H), 7.68 (s, 1H), 3.80-3.64 (m, 1H), 3.59-3.46 (m, 1H), 2.42-2.16 (m, 6H), 1.97-1.63 (m, 9H), 1.53-1.36 (m, 1H), 1.33-1.16 (m, 1H). ESI-MS $[M+H]^+$ calcd for ($C_{21}H_{23}F_2N_3O_2$) 388.18 found: 388.35.

Example 10

Synthesis of 4-((1S,3S)-3-(but-2-ynamido)cyclohexyl)-5-fluoro-2,3-dimethyl-1H-indole-7-carboxamide and 4-((1R,3S)-3-(but-2-ynamido)cyclohexyl)-5-fluoro-2,3-dimethyl-1H-indole-7-carboxamide

10--(1S,3S)

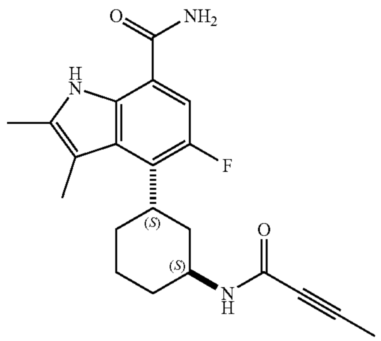

10--(1R,3S)

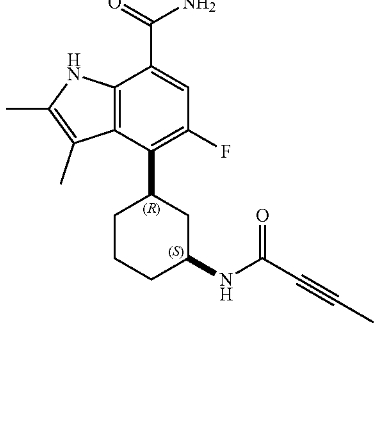

Step 1: tert-butyl ((1S)-3-(7-carbamoyl-5-fluoro-2,3-dimethyl-1H-indol-4-yl)cyclohexyl) carbamate

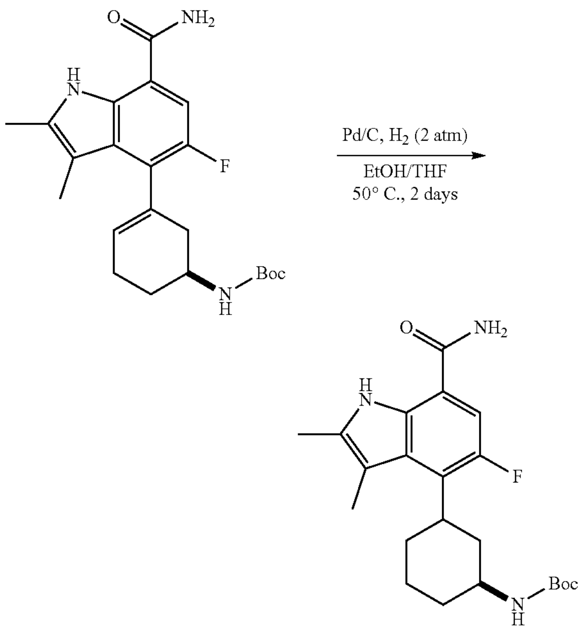

A mixture of tert-butyl (S)-(3-(7-carbamoyl-5-fluoro-2,3-dimethyl-1H-indol-4-yl)cyclohex-3-en-1-yl)carbamate (700 mg, 1.74 mmol) and 10% palladium on carbon (700 mg) in ethanol (10 mL) and tetrahydrofuran (10 mL) was stirred under hydrogen (2 atm) for 2 days at 50° C. The cooled reaction mixture was filtered. The filtrate was concentrated under vacuum. The residue was purified by column chromatography on silica gel eluting with ethyl acetate in petroleum ether (40%) to give tert-butyl ((1S)-3-(7-carbamoyl fluoro-2,3-dimethyl-1H-indol-4-yl)cyclohexyl)carbamate (650 mg, 92%) as a yellow solid. ESI-MS $[M+H]^+$ calcd for ($C_{22}H_{30}FN_3O_3$) 404.23 found: 404.30.

Step 2: 4-((3S)-3-aminocyclohexyl)-5-fluoro-2,3-dimethyl-1H-indole-7-carboxamide 2,2,2-trifluoroacetate

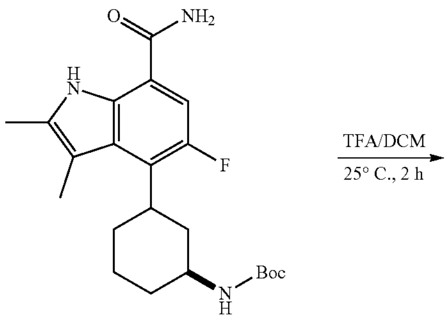

-continued

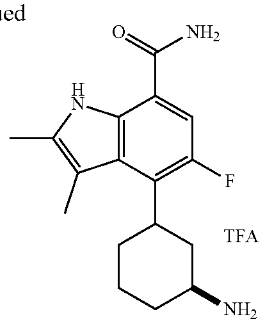

To a solution of tert-butyl ((1S)-3-(7-carbamoyl-5-fluoro-2,3-dimethyl-1H-indol-4-yl)cyclohexyl)carbamate (250 mg, 0.61 mmol) in dichloromethane (10 mL) was added trifluoroacetic acid (2 mL). The reaction mixture was stirred for 2 h at 25° C. The resulting mixture was concentrated under vacuum to give 4-((3S)-3-aminocyclohexyl)-5-fluoro-2,3-dimethyl-1H-indole-7-carboxamide 2,2,2-trifluoroacetate (300 mg, crude) as a brown solid. ESI-MS $[M+H]^+$ calcd for $(C_{17}H_{22}FN_3O)$ 304.18 found: 304.45.

Step 3: 4-((3S)-3-(but-2-ynamido)cyclohexyl)-5-fluoro-2,3-dimethyl-1H-indole-7-carboxamide

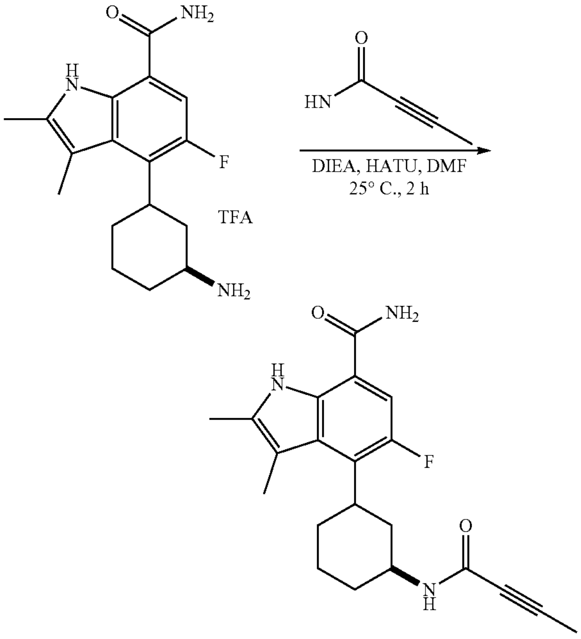

To a mixture of 4-((3S)-3-aminocyclohexyl)-5-fluoro-2,3-dimethyl-1H-indole-7-carboxamide 2,2,2-trifluoroacetate (300 mg, crude) in DMF (10 mL) were added O-(7-Azabenzotriazol-1-yl)-N,N,N',N'-tetramethyluronium hexafluorophosphate (412 mg, 1.08 mmol), but-2-ynoic acid (72.5 mg, 0.86 mmol) and N,N-diisopropylethylamine (464 mg, 3.59 mmol). The reaction mixture was stirred at 25° C. for 2 h. The resulting mixture was diluted with water (50 mL) and extracted with ethyl acetate (50 mL×2). The combined organic layers were washed with water (50 mL×2) and brine (50 mL), dried over anhydrous sodium sulfate, filtered and concentrated under vacuum. The residue was purified by Prep-HPLC with the following conditions: Column: XBridge Prep OBD C18 Column, 30×150 mm, 5 um; Mobile Phase A: Water (20 mmol/L $NH_4HCO_3$), Mobile Phase B: Acetonitrile; Flow rate: 60 mL/min; Gradient: 30% B to 50% B in 7 min, 254 nm; RT: 5.28 min to give 4-((3S)-3-(but-2-ynamido)cyclohexyl)-5-fluoro-2,3-dimethyl-1H-indole-7-carboxamide (140 mg, 61% over two steps) as a white solid. ESI-MS $[M+H]^+$ calcd for $(C_{21}H_{24}FN_3O_2)$ 370.19 found: 370.15.

Step 5: Separation of Isomers

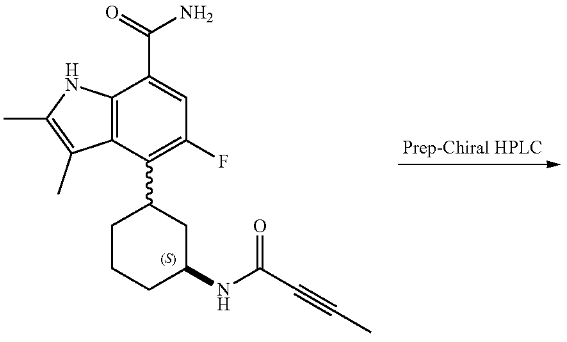

10-(3S)10-(1S,3S)

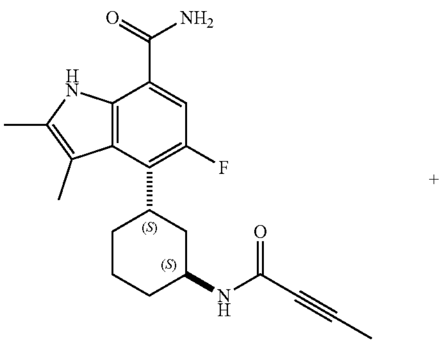

+

10-(1R,3S)

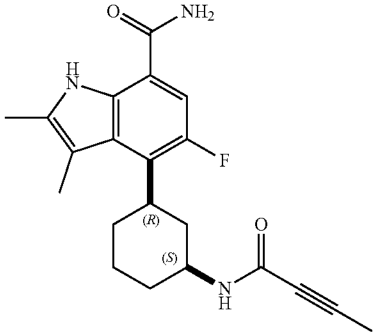

4-((3S)-3-(but-2-ynamido)cyclohexyl)-5-fluoro-2,3-dimethyl-1H-indole-7-carboxamide (140 mg) was separated by Prep-Chiral-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 20 mL/min; Gradient: 40% B to 40% B in 20 min; 254 nm.

4-((1S,3S)-3-(but-2-ynamido)cyclohexyl)-5-fluoro-2,3-dimethyl-1H-indole-7-carboxamide or 4-((1R,3S)-3-(but-2-ynamido)cyclohexyl)-5-fluoro-2,3-dimethyl-1H-indole-7-carboxamide Retention time=10.599 min (25.2 mg, 18%) as a white solid. $^{1}H$ NMR (300 MHz, DMSO-$d_6$) δ 10.68 (s, 1H), 8.49 (d, J=7.5 Hz, 1H), 7.96 (s, 1H), 7.53-7.28 (m, 2H), 3.86-3.64 (m, 1H), 3.60-3.42 (m, 1H), 2.44-2.22 (m, 6H), 1.93 (s, 3H), 1.89-1.68 (m, 6H), 1.56-1.37 (m, 1H), 1.35-1.15 (m, 1H). ESI-MS $[M+H]^+$ calcd for ($C_{21}H_{24}FN_3O_2$) 370.19 found: 370.15.

4-((1R,3S)-3-(but-2-ynamido)cyclohexyl)-5-fluoro-2,3-dimethyl-1H-indole-7-carboxamide or 4-((1S,3S)-3-(but-2-ynamido)cyclohexyl)-5-fluoro-2,3-dimethyl-1H-indole-7-carboxamide Retention time=18.172 min (47.4 mg, 33%) as a white solid. $^{1}H$ NMR (300 MHz, DMSO-$d_6$) δ 10.65 (s, 1H), 8.63 (d, J=6.0 Hz, 1H), 7.95 (s, 1H), 7.48-7.25 (m, 2H), 4.09-3.96 (m, 1H), 3.86-3.60 (m, 1H), 2.40-2.27 (m, 6H), 2.08-1.81 (m, 7H), 1.80-1.47 (m, 4H). ESI-MS $[M+H]^+$ calcd for ($C_{21}H_{24}FN_3O_2$) 370.19 found: 370.15.

Example 11

Synthesis of 4-((1R,3S)-3-(but-2-ynamido)cyclohexyl)-3-chloro-5,6-difluoro-2-methyl-1H-indole-7-carboxamide 4-((1S,3R)-3-(but-2-ynamido)cyclohexyl)-3-chloro-5,6-difluoro-2-methyl-1H-indole-7-carboxamide 4-((1R,3R)-3-(but-2-ynamido)cyclohexyl)-3-chloro-5,6-difluoro-2-methyl-1H-indole-7-carboxamide and 4-((1S,3S)-3-(but-2-ynamido)cyclohexyl)-3-chloro-5,6-difluoro-2-methyl-1H-indole-7-carboxamide 11-(1R,3S)

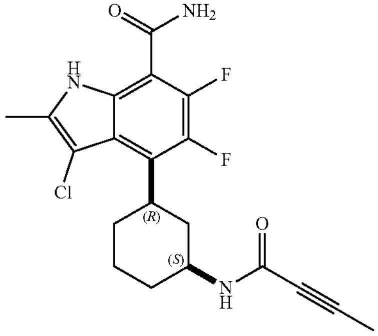

-continued 11-(1S,3R)

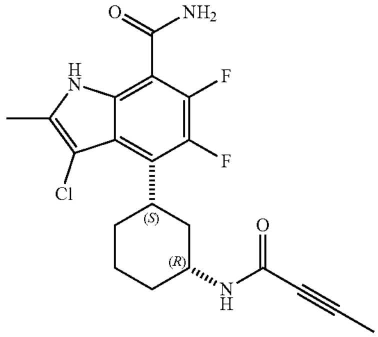

11-(1R,3R)

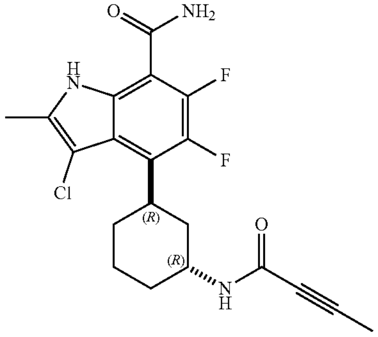

11-(1S,3S)

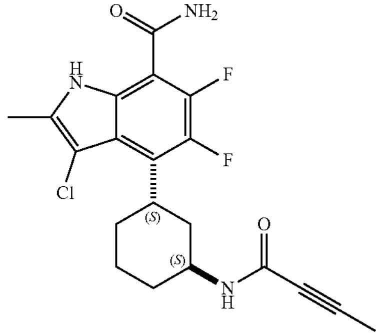

Step 1: tert-butyl (3-(7-carbamoyl-5,6-difluoro-2-methyl-1H-indol-4-yl)cyclohex-3-en-1-yl)carbamate

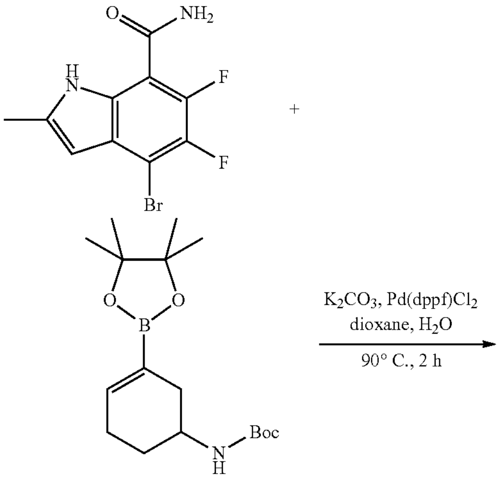

-continued

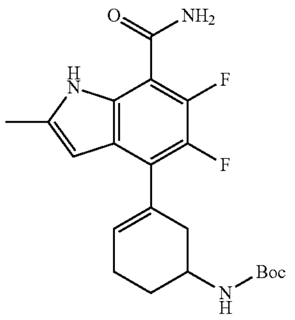

A mixture of 4-bromo-5,6-difluoro-2-methyl-1H-indole-7-carboxamide (1.5 g, 5.19 mmol), tert-butyl (3-(4,4,5,5-tetra methyl-1,3,2-dioxaborolan-2-yl)cyclohex-3-en-1-yl) carbamate (1.84 g, 5.71 mmol), potassium carbonate (2.9 g, 20.76 mmol,) and Pd(dppf)$Cl_2$ (378 mg, 0.519 mmol) in dioxane (16 mL) and water (4 mL) was degassed and backfilled with nitrogen for five times. The reaction mixture was heated at 90° C. for 2 h. The cooled reaction mixture was quenched with water (60 mL) and extracted with ethyl acetate (3×50 mL). The combined organic layers was washed with brine (50 mL), dried over $Na_2SO_4$ and concentrated under vacuum. The residue was purified by column chromatography on silica gel eluting with ethyl acetate in petroleum ether (0 to 30%) to give tert-butyl (3-(7-carbamoyl-5,6-difluoro methyl-1H-indol-4-yl)cyclohex-3-en-1-yl)carbamate (1.6 g, 76%) as a yellow solid. ESI-MS $[M+H]^+$ calcd for ($C_{21}H_{25}F_2N_3O_3$) 406.19 found: 406.20.

Step 2: tert-butyl (3-(7-carbamoyl-5,6-difluoro-2-methyl-1H-indol-4-yl)cyclohexyl)carbamate

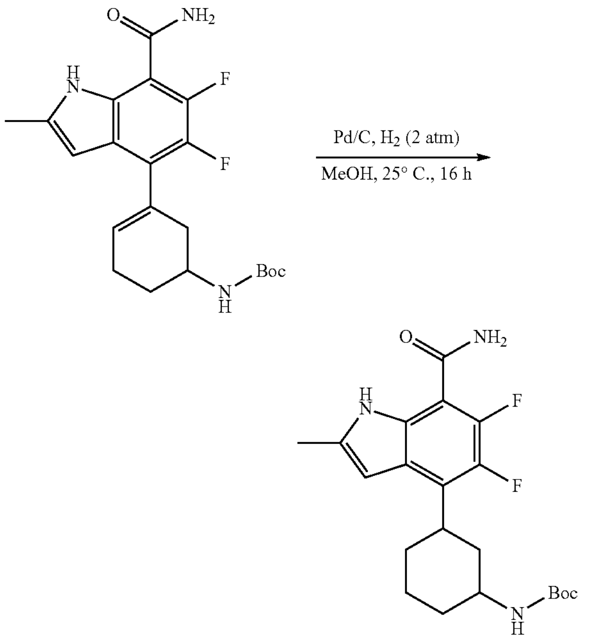

To a stirred solution of tert-butyl (3-(7-carbamoyl-5,6-difluoro-2-methyl-1H-indol-4-yl)cyclohex-3-en-1-yl)carbamate (1.6 g, 3.95 mmol) in methanol (100 mL) was added Pd/C (1.6 g, 10%). The reaction mixture was stirred under hydrogen (2 atm) at 25° C. for 16 h. The reaction mixture was filtered. The filtrate was concentrated under vacuum. The residue was purified by column chromatography on silica gel eluting with ethyl acetate in petroleum ether (0 to 35%) to give tert-butyl (3-(7-carbamoyl-5,6-difluoro-2-methyl-1H-indol-4-yl)cyclohexyl)carbamate (1.5 g, 93%) as a yellow solid. ESI-MS $[M+H]^+$ calcd for ($C_{21}H_{27}F_2N_3O_3$) 408.20 found: 408.20.

Step 3: tert-butyl (3-(7-carbamoyl-3-chloro-5,6-difluoro-2-methyl-1H-indol-4-yl)cyclohexyl)carbamate

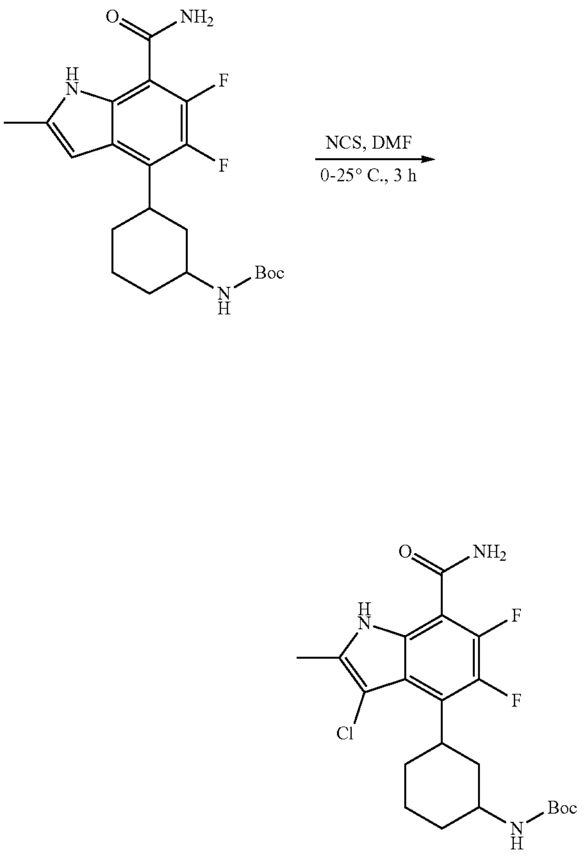

To a stirred solution of tert-butyl (3-(7-carbamoyl-5,6-difluoro-2-methyl-1H-indol-4-yl)cyclohexyl)carbamate (450 mg, 1.10 mmol) in DMF (8 mL) was added NCS (147 mg, 1.10 mmol) at 0° C. The reaction mixture was stirred for 3 h at 25° C. The reaction mixture was quenched with water (50 mL) and extracted with ethyl acetate (3×30 mL). The combined organic layers were washed with brine (50 mL), dried over $Na_2SO_4$ and concentrated under vacuum. The residue was purified by column chromatography on silica gel eluting with ethyl acetate in petroleum ether (0 to 34%) to give tert-butyl (3-(7-carbamoyl-3-chloro-5,6-difluoro-2-methyl-1H-indol-4-yl)cyclohexyl)carbamate (400 mg, 82%) as a yellow solid. ESI-MS $[M+H-tBu]^+$ calcd for ($C_{21}H_{26}ClF_2N_3O_3$) 386.16, 388.16 found: 386.10, 388.10.

Step 4: 4-(3-aminocyclohexyl)-3-chloro-5,6-difluoro-2-methyl-1H-indole-7-carboxamide hydrochloride

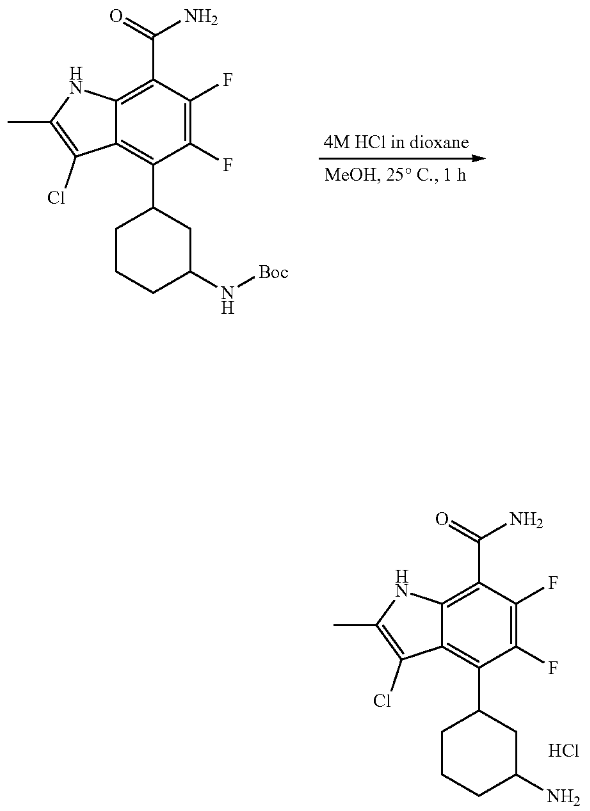

To a stirred solution of tert-butyl (3-(7-carbamoyl-3-chloro-5,6-difluoro-2-methyl-1H-indol-4-yl)cyclohexyl) carbamate (400 mg, 0.9 mmol) in methanol (2 mL) was added 4 M hydrogen chloride in dioxane (5 mL). The reaction mixture was stirred at 25° C. for 1 h. The resulting mixture was concentrated under vacuum to give 4-(3-aminocyclohexyl)-3-chloro-5,6-difluoro-2-methyl-1H-indole-7-carboxamide hydrochloride (340 mg, crude) as a yellow solid. ESI-MS $[M+H]^+$ calcd for $(C_{16}H_{18}ClF_2N_3O)$ 342.11, 344.11 found: 342.15, 344.15.

Step 5: 4-(3-(but-2-ynamido)cyclohexyl)-3-chloro-5,6-difluoro-2-methyl-1H-indole-7-carboxamide

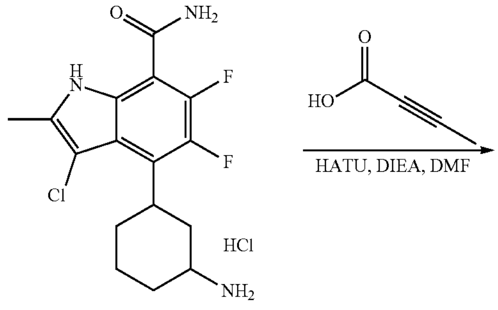

-continued

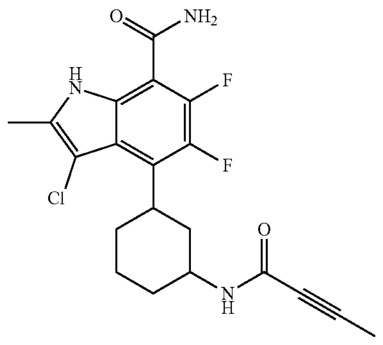

To a stirred solution of 4-(3-aminocyclohexyl)-3-chloro-5,6-difluoro-2-methyl-1H-indole-7-carboxamide hydrochloride (300 mg, 0.88 mmol) in DMF (6 mL) were added 2-Butynoic acid (74 mg, 0.88 mmol), HATU (401 mg, 1.06 mmol) and DIEA (581 mg, 4.4 mmol, 0.8 mL). The reaction mixture was stirred at 25° C. for 1 h. The reaction mixture was quenched with water (40 mL) and extracted with ethyl acetate (3x30 mL). The combined organic layers were washed with brine (40 mL), dried over $Na_2SO_4$ and concentrated under vacuum. The residue was purified by column chromatography on silica gel eluting with methanol in dichloromethane (0 to 34%) to give 4-(3-(but-2-ynamido)cyclohexyl)-3-chloro-5,6-difluoro-2-methyl-1H-indole-7-carboxamide (300 mg, 84%) as a yellow solid. ESI-MS $[M+H]^+$ calcd for $(C_{20}H_{20}ClF_2N_3O_2)$ 408.12, 410.12 found: 408.35, 410.35.

Step 6: Separation of Cis and Trans Isomers

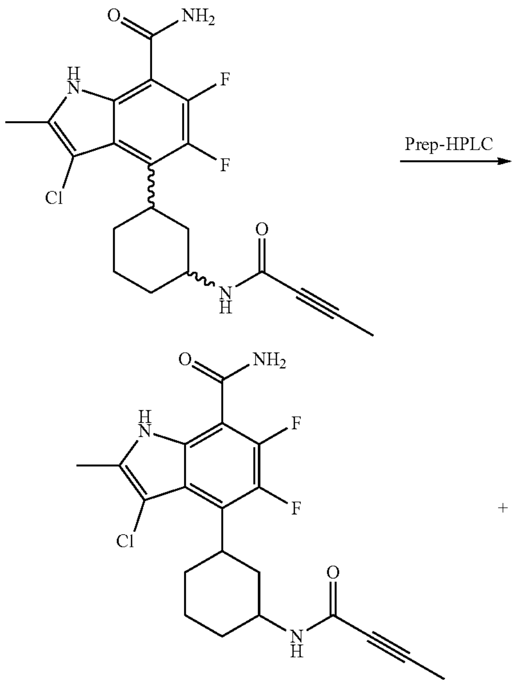

\+

11-cis

-continued

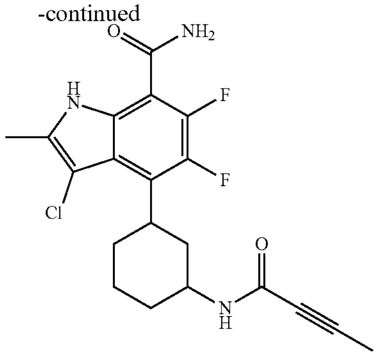

11-trans 4-(3-(but-2-ynamido)cyclohexyl)-3-chloro-5,6-difluoro-2-methyl-1H-indole-7-carboxamide (300 mg) was separated by Prep-HPLC with the following conditions: Column: XBridge Prep C18 OBD Column, 19×150 mm 5 um; Mobile Phase A: Water (10 mmol/L $NH_4HCO_3$+0.1% $NH_3 \cdot H_2O$), Mobile Phase B: Acetonitrile; Flow rate: 25 mL/min; Gradient: 38% B to 58% B in 7 min; 220 nm.

cis-4-(3-(but-2-ynamido)cyclohexyl)-3-chloro-5,6-difluoro-2-methyl-1H-indole-7-carboxamide (Compound 10-cis)

Retention time=4.95 min (150 mg, 50%)

trans-4-(3-(but-2-ynamido)cyclohexyl)-3-chloro-5,6-difluoro-2-methyl-1H-indole-7-carboxamide (Compound 10-tans)

Retention time=5.58 min (130 mg, 43%) as a white solid. ESI-MS $[M+H]^+$ calcd for ($C_{20}H_{20}ClF_2N_3O_2$) 408.12, 410.12 found: 408.10, 410.10.

Step 7A: Separation of Cis Isomers

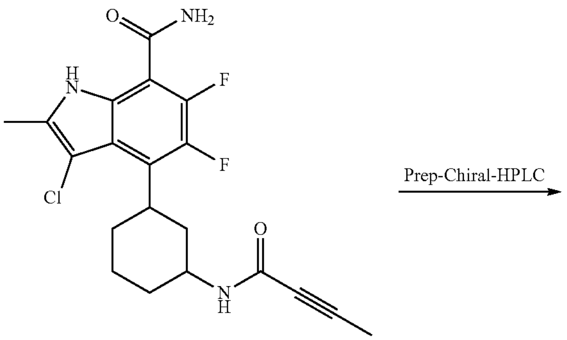

11-cis

-continued

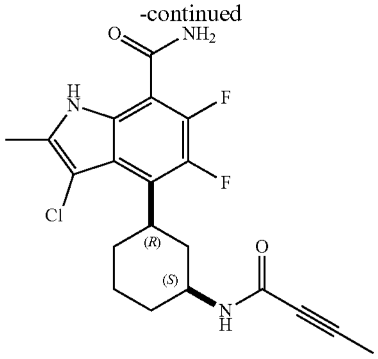

11-(1R,3S)

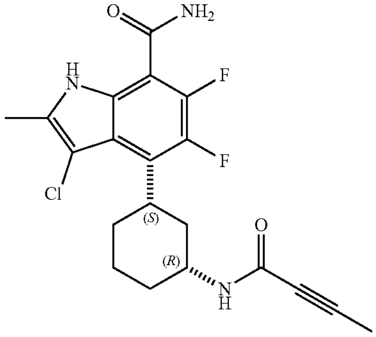

11-(1S,3R)

cis-4-(3-(but-2-ynamido)cyclohexyl)-3-chloro-5,6-difluoro-2-methyl-1H-indole-7-carboxamide (150 mg) was separated by Chiral-Prep-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 18 mL/min; Gradient: 50% B to 50% B in 19 min; 220/254 nm.

4-((1R,3S)-3-(but-2-ynamido)cyclohexyl)-3-chloro-5,6-difluoro-2-methyl-1H-indole-7-carboxamide (Compound 11-(1R,3S)) or 4-((1S,3R)-3-(but-2-ynamido)cyclohexyl)-3-chloro-5,6-difluoro-2-methyl-1H-indole-7-carboxamide Retention time=6.88 min (57.6 mg, 38%) as a white solid. $^1H$ NMR (400 MHz, DMSO-$d_6$) δ 11.33 (s, 1H), 8.55 (d, J=6.0 Hz, 1H), 7.98-7.74 (m, 2H), 4.20 (t, J=12.4 Hz, 1H), 4.01 (s, 1H), 2.35 (s, 3H), 2.06 (d, J=13.0 Hz, 1H), 1.97 (s, 3H), 1.95-1.49 (m, 7H). ESI-MS $[M+H]^+$ calcd for ($C_{20}H_{20}ClF_2N_3O_2$) 408.12, 410.12 found: 408.30, 410.30.

4-((1S,3R)-3-(but-2-ynamido)cyclohexyl)-3-chloro-5,6-difluoro-2-methyl-1H-indole-7-carboxamide (Compound 11-(1S,3R)) or 4-((1R,3S)-3-(but-2-ynamido)cyclohexyl)-3-chloro-5,6-difluoro-2-methyl-1H-indole-7-carboxamide Retention time=16.692 min (57.9 mg, 39%) as a white solid. $^1H$ NMR (400 MHz, DMSO-$d_6$) δ 11.33 (s, 1H), 8.55 (d, J=6.0 Hz, 1H), 7.97-7.75 (m, 2H), 4.18 (t, J=12.6 Hz, 1H), 4.01 (s, 1H), 2.35 (s, 3H), 2.06 (d, J=13.0 Hz, 1H), 1.97 (s, 3H), 1.95-1.52 (m, 7H). ESI-MS $[M+H]^+$ calcd for ($C_{20}H_{20}ClF_2N_3O_2$) 408.12, 410.12 found: 408.30, 410.30.

Step 7B: Separation of Trans Isomers

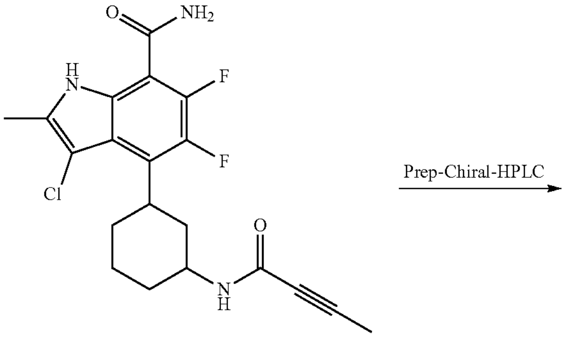

11-trans

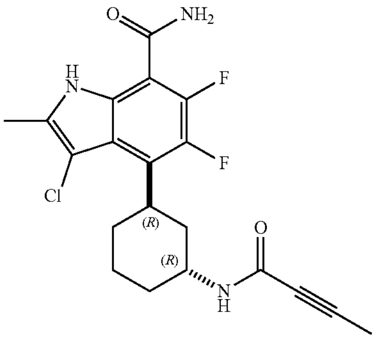

11-(1R,3R)

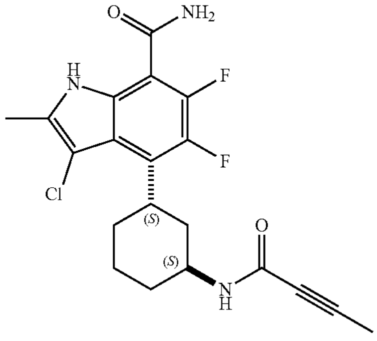

11-(1S,3S)

trans-4-(3-(but-2-ynamido)cyclohexyl)-3-chloro-5,6-difluoro-2-methyl-1H-indole-7-carboxamide (130 mg) was separated by Chiral-Prep-HPLC with the following conditions: Column: CHIRALPAK IG, 2×25 cm, 5 um; Mobile Phase A: Hexane (0.5% 2 M $NH_3$-MeOH)-HPLC, Mobile Phase B: EtOH-HPLC; Flow rate: 18 mL/min; Gradient: 50% B to 50% B in 15 min; 220/254 nm.

4-[(1R,3R)-3-(but-2-ynoylamino)cyclohexyl]-3-chloro-5,6-difluoro-2-methyl-1H-indole-7-carboxamide (compound 11-(1R,3R)) or 4-[(1S,3S)-3-(but-2-ynoylamino)cyclohexyl]-3-chloro-5,6-difluoro-2-methyl-1H-indole-7-carboxamide Retention time=7.396 min (47.9 mg, 37%) as an off-white solid. $^1$H NMR (300 MHz, DMSO-$d_6$) δ 11.39 (s, 1H), 8.52 (d, J=8.0 Hz, 1H), 7.99-7.71 (m, 2H), 4.04 (t, J=7.5 Hz, 1H), 3.70 (s, 1H), 2.35 (s, 3H), 1.93 (s, 3H), 1.90-1.60 (m, 6H), 1.53-1.15 (m, 2H). ESI-MS $[M+H]^+$ calcd for ($C_{20}H_{20}ClF_2N_3O_2$) 408.12, 410.12 found: 408.10, 410.10.

4-[(1S,3S)-3-(but-2-ynoylamino)cyclohexyl]-3-chloro-5,6-difluoro-2-methyl-1H-indole-7-carboxamide (compound 11-(1S,3S)) or 4-[(1R,3R)-3-(but-2-ynoylamino)cyclohexyl]-3-chloro-5,6-difluoro-2-methyl-1H-indole-7-carboxamide Retention time=12.384 min (46.5 mg, 36%) as an off-white solid. $^1$H NMR (300 MHz, DMSO-$d_6$) δ 11.39 (s, 1H), 8.52 (d, J=8.0 Hz, 1H), 7.91-7.84 (m, 2H), 4.04 (t, J=7.5 Hz, 1H), 3.70 (s, 1H), 2.35 (s, 3H), 1.93 (s, 3H), 1.90-1.60 (m, 6H), 1.53-1.15 (m, 2H). ESI-MS $[M+H]^+$ calcd for ($C_{20}H_{20}Cl_2N_3O_2$) 408.12, 410.12 found: 408.15, 410.15.

Example 12

Synthesis of 4-((1R,3S)-3-(but-2-ynamido)cyclopentyl)-5-fluoro-2,3-dimethyl-1H-indole-7-carboxamide and 4-((1S,3S)-3-(but-2-ynamido)cyclopentyl)-5-fluoro-2,3-dimethyl-1H-indole-7-carboxamide Compound 12-(1R,3S)

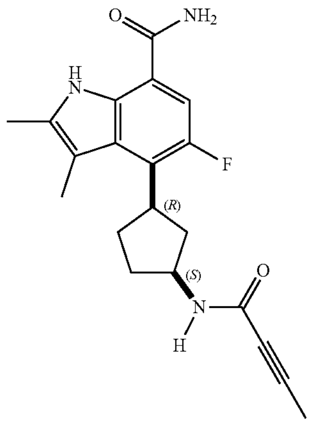

Compound 12-(1S,3S)

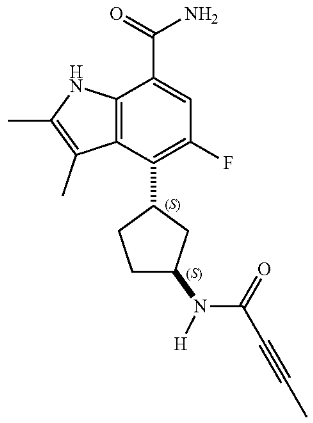

Step 1: (S)-4-((tert-butoxycarbonyl)amino)cyclopent-1-en-1-yl trifluoromethane sulfonate

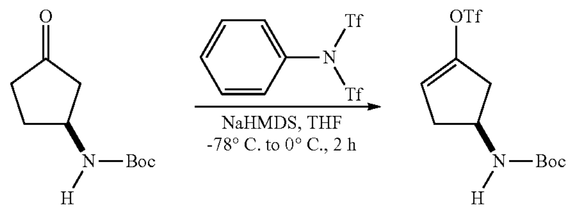

To a stirred mixture of tert-butyl (S)-(3-oxocyclopentyl) carbamate (1 g, 5.02 mmol) and 1,1,1-trifluoro-N-phenyl-N-((trifluoromethyl)sulfonyl)methanesulfonamide (2.33 g, 6.52 mmol) in THF (20 mL) was added sodium bis(trimethylsilyl)amide (2M in tetrahydrofuran, 7.53 mL) at −78° C. under nitrogen atmosphere. The reaction mixture was stirred for 0.5 h at −78° C. and for 2 h at 0° C. The reaction mixture was quenched with saturated aqueous ammonium chloride (60 mL) and extracted with ethyl acetate (50 mL×3). The combined organic layers was washed water (50 mL×2) and brine (50 mL), dried over anhydrous sodium sulfate and concentrated under vacuum to give (S)-4-((tert-butoxycarbonyl)amino)cyclopent-1-en-1-yl trifluoromethanesulfonate (1.60 g, crude) as a brown oil. ESI-MS $[M-H]^-$ calcd for ($C_{11}H_{16}F_3NO_5S$) 330.07 found: 330.20.

Step 2: tert-butyl (S)-(3-(4,4,5,5-tetramethyl-1,3,2-dioxaborolan-2-yl)cyclopent-3-en-1-yl)carbamate

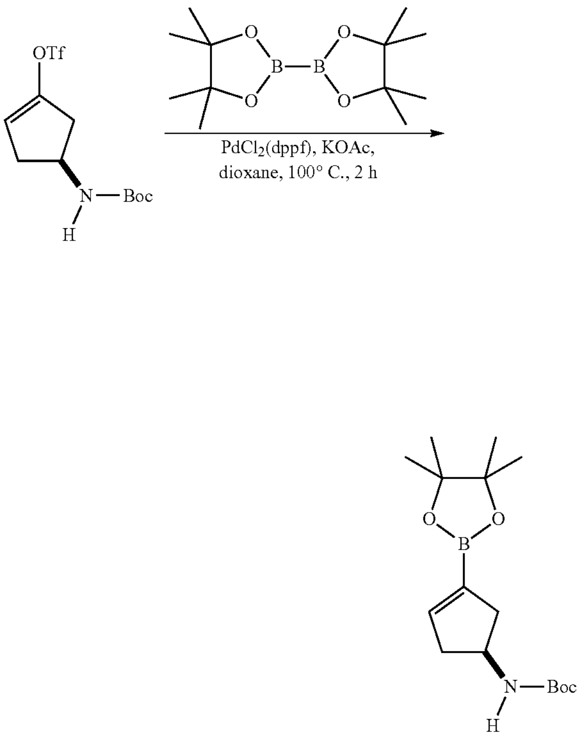

A mixture of (S)-4-((tert-butoxycarbonyl)amino)cyclopent-1-en-1-yl trifluoromethanesulfonate (1.60 g, crude), 4,4,4',4',5,5,5',5'-octamethyl-2,2'-bi(1,3,2-dioxaborolane) (1.59 g, 6.28 mmol), potassium acetate (1.42 g, 14.49 mmol) and $Pd(dppf)Cl_2$ (353 mg, 0.483 mmol) in 1,4-dioxane (20 mL) was degased and backfilled with nitrogen for several times. The reaction mixture was stirred under nitrogen at 100° C. for 2 h. The reaction mixture was diluted with water (100 mL) and extracted with ethyl acetate (3×60 mL). The combined organic layers were washed with brine (60 mL), dried over sodium sulfate and concentrated under vacuum. The residue was purified by column chromatography on silica gel eluting with ethyl acetate in petroleum ether (0 to 20%) to give tert-butyl (S)-(3-(4,4,5,5-tetra methyl-1,3,2-dioxaborolan-2-yl)cyclopent-3-en-1-yl)carbamate (550 mg, crude) as a brown oil.

Step 3: tert-butyl (S)-(3-(7-cyano-5-fluoro-2,3-dimethyl-1H-indol-4-yl)cyclopent-3-en-1-yl)carbamate

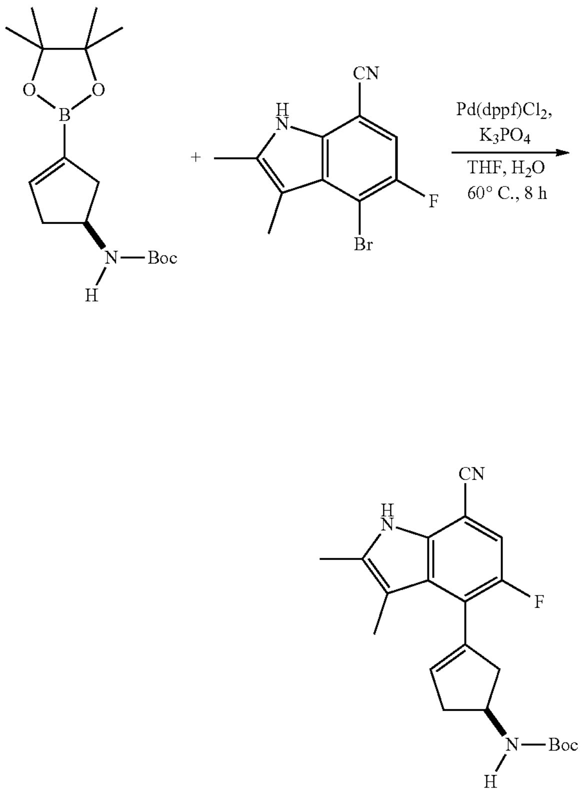

A mixture of 4-bromo-5-fluoro-2,3-dimethyl-1H-indole-7-carbonitrile (300 mg, 1.12 mmol), $Pd(dppf)Cl_2$ (82.18 mg, 0.112 mmol), tert-butyl (S)-(3-(4,4,5,5-tetramethyl-1,3,2-dioxaborolan-2-yl)cyclopent-3-en-1-yl)carbamate (451.5 mg, crude) and potassium phosphate (715 mg, 3.37 mmol) in tetrahydrofuran (12 mL) and water (3 mL) was degassed and backfilled with nitrogen for five times. The reaction mixture was stirred under nitrogen at 60° C. for 8 h. The cooled mixture was diluted with water (50 mL) and extracted with ethyl acetate (3×40 mL). The combined organic layers was washed with brine (50 mL), dried over sodium sulfate and concentrated under vacuum to give tert-butyl (S)-(3-(7-cyano-5-fluoro-2,3-dimethyl-1H-indol-4-yl)cyclopent-3-en-1-yl)carbamate (550 mg, crude) as a brown oil. ESI-MS $[M-H]^-$ calcd for ($C_{21}H_{24}FN_3O_2$) 368.19 found: 368.15.

Step 4: tert-butyl (S)-(3-(7-carbamoyl-5-fluoro-2,3-dimethyl-1H-indol-4-yl)cyclopent-3-en-1-yl) carbamate

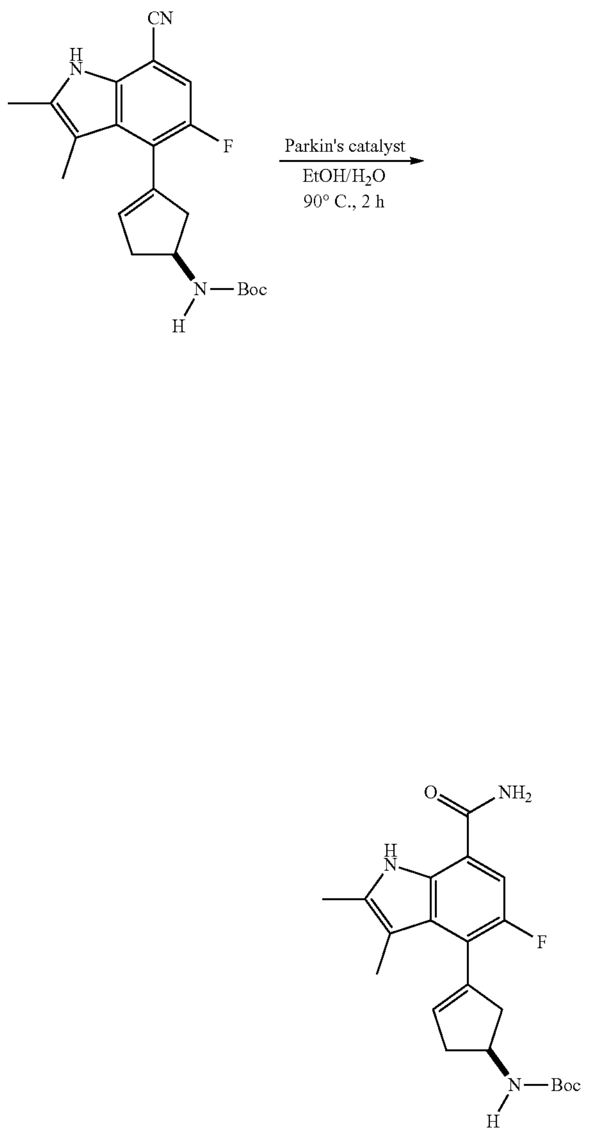

To a mixture of tert-butyl (S)-(3-(7-cyano-5-fluoro-2,3-dimethyl-1H-indol-4-yl)cyclopent-3-en-1-yl)carbamate (550 mg, crude) in ethanol (10 mL) and water (10 mL) was added parkin's catalyst (63 mg, 0.148 mmol). The reaction mixture was stirred for 2 hours at 90° C. The cooled mixture was diluted with water (60 mL) and extracted with ethyl acetate (3×50 mL). The combined organic layers was washed with brine (50 mL), dried over sodium sulfate and concentrated under vacuum to give tert-butyl (S)-(3-(7-carbamoyl-5-fluoro-2,3-dimethyl-1H-indol-4-yl)cyclopent-3-en-1-yl)carbamate (110 mg, 25% over two steps) as a yellow solid. $^1H$ NMR (400 MHz, DMSO-$d_6$) δ 10.74 (s, 1H), 8.01 (s, 1H), 7.57-7.35 (m, 2H), 7.23-7.05 (m, 1H), 5.69-5.51 (m, 1H), 4.84-4.55 (m, 1H), 2.73-2.52 (m, 2H), 2.43-2.35 (m, 1H), 2.34 (s, 3H), 2.07 (s, 3H), 1.87-1.74 (m, 1H), 1.41 (s, 9H). ESI-MS $[M+H]^+$ calcd for ($C_{21}H_{26}FN_3O_3$) 388.20 found: 388.15.

Step 5: tert-butyl ((1S)-3-(7-carbamoyl-5-fluoro-2,3-dimethyl-1H-indol-4-yl)cyclopentyl) carbamate

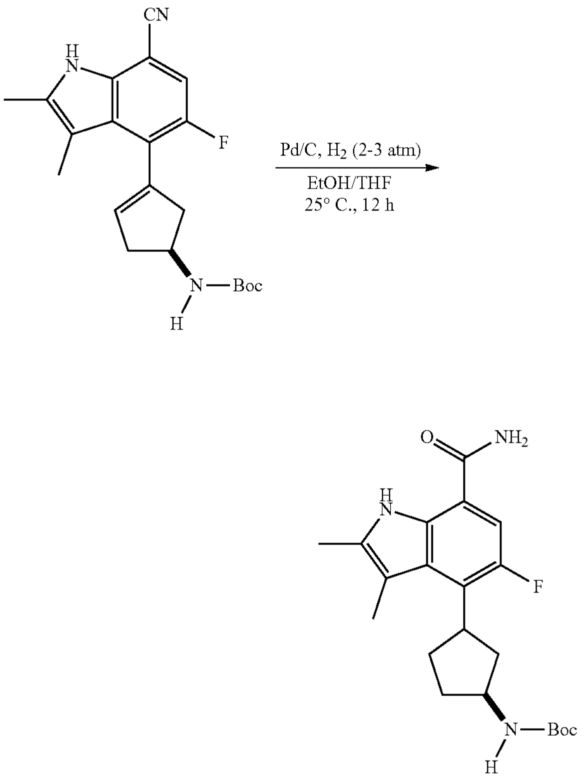

A mixture of tert-butyl (S)-(3-(7-carbamoyl-5-fluoro-2,3-dimethyl-1H-indol-4-yl)cyclopent-3-en-1-yl)carbamate (110 mg, 0.28 mmol) and 10% palladium on carbon (100 mg) in ethanol (5 mL) and tetrahydrofuran (5 mL) was stirred under hydrogen (2-3 atm) for 12 h at 25° C. The reaction mixture was filtered. The filtrate was concentrated under vacuum to give tert-butyl ((1S)-3-(7-carbamoyl-5-fluoro-2,3-dimethyl-1H-indol-4-yl)cyclopentyl)carbamate (100 mg, 91%) as a yellow solid. ESI-MS $[M+H]^+$ calcd for ($C_{21}H_{28}FN_3O_3$) 390.21 found: 390.40.

Step 6: 4-((3S)-3-aminocyclopentyl)-5-fluoro-2,3-dimethyl-1H-indole-7-carboxamide 2,2,2-trifluoroacetate

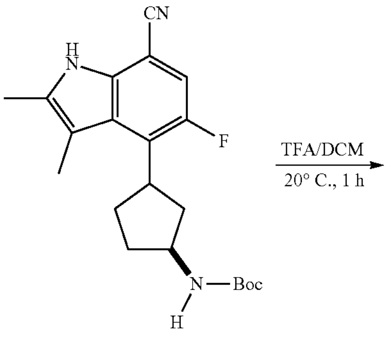

-continued

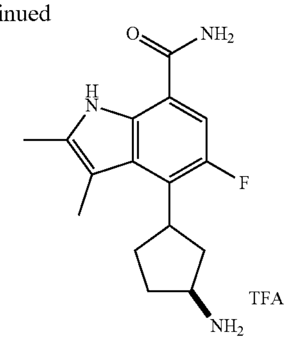

To a solution of tert-butyl ((1S)-3-(7-carbamoyl-5-fluoro-2,3-dimethyl-1H-indol-4-yl)cyclopentyl)carbamate (100 mg, 0.26 mmol) in dichloromethane (10 mL) was added trifluoroacetic acid (2 mL). The reaction mixture was stirred for 1 hour at 25° C. The resulting mixture was concentrated under vacuum to give 4-((3S)-3-aminocyclopentyl)-5-fluoro-2,3-dimethyl-1H-indole-7-carboxamide 2,2,2-trifluoroacetate (130 mg, crude) as a brown solid. ESI-MS $[M+H]^+$ calcd for ($C_{16}H_{20}FN_3O$) 290.16, found: 290.15.

Step 7: 4-((3S)-3-(but-2-ynamido)cyclopentyl)-5-fluoro-2,3-dimethyl-1H-indole-7-carboxamide

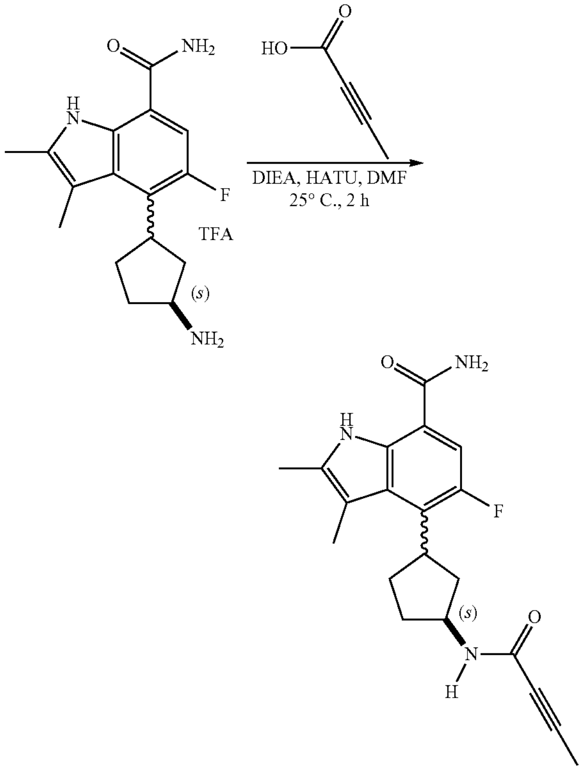

To a mixture of 4-((3S)-3-aminocyclopentyl)-5-fluoro-2,3-dimethyl-1H-indole-7-carboxamide 2,2,2-trifluoroacetate (130 mg, crude) in DMF (10 mL) were added O-(7-Azabenzotriazol-1-yl)-N,N,N',N'-tetraMethyluroniuM hexafluorophosphate (185 mg, 0.483 mmol), but-2-ynoic acid (32.5 mg, 0.386 mmol) and N,N-diisopropylethylamine (208 mg, 1.61 mmol). The reaction mixture was stirred at 25° C. for 2 h. The resulting mixture was diluted with water (50 mL) and extracted with ethyl acetate (30 mL×2). The combined organic layers were washed with water (30 mL×2) and brine (30 mL), dried over anhydrous sodium sulfate, filtered and concentrated under vacuum. The crude product was purified by Prep-HPLC under the following conditions: Column: Column: YMC-Actus Triart C18, 30 mm×150 mm, 5 um; Mobile Phase A: water (10 mmol/L $NH_4HCO_3$+0.1% $NH_3·H_2O$), Mobile Phase B: Acetonitrile; Flow rate: 60 mL/min; Gradient: 36% B to 56% B in 7 min, 254 nm, which eluted at RT: 6.50 min to give 4-((3S)-3-(but-2-ynamido)cyclopentyl)-5-fluoro-2,3-dimethyl-1H-indole-7-carboxamide (50 mg).

Step 8: Separation of Isomers

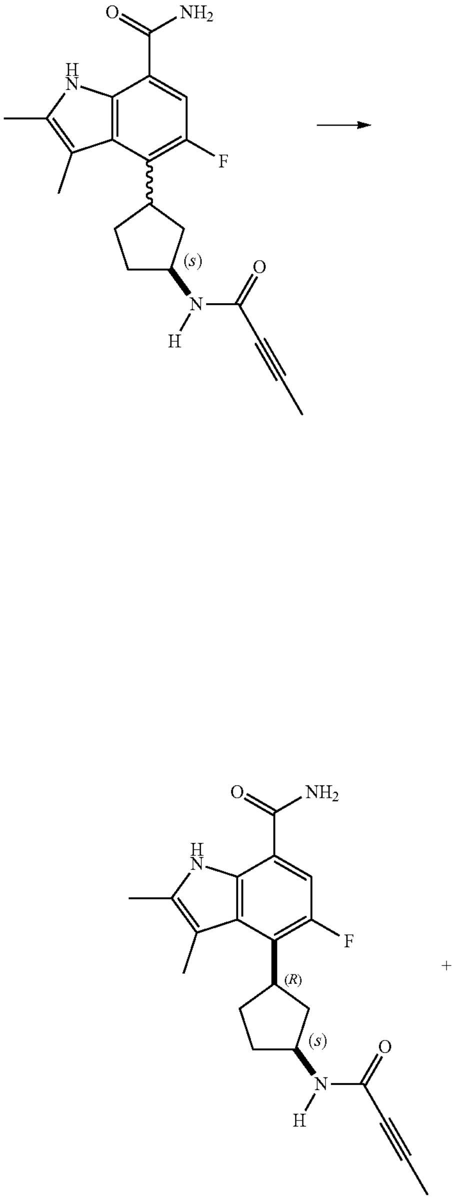

12-(1R,3S)

-continued

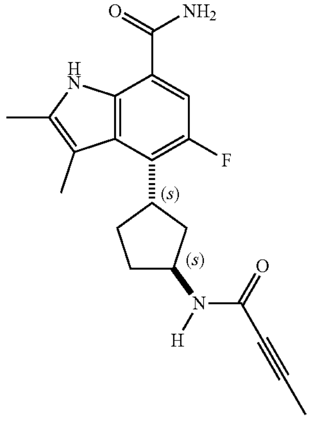

12-(1S,3S)

4-((3S)-3-(but-2-ynamido)cyclopentyl)-5-fluoro-2,3-dimethyl-1H-indole-7-carboxamide (50 mg), which was further separated by Prep-Achiral-SFC under the following conditions: Column: DAICEL DCpak P4VP, 2×25 cm, 5 μm; Mobile Phase A: $CO_2$, Mobile Phase B: MeOH (0.5% 2 M $NH_3$-MeOH)-HPLC; Flow rate: 50 mL/min; Gradient: 40% B; Column Temperature: 35° C.; Back Pressure: 100 bar; 254 nm.

4-((1R,3S)-3-(but-2-ynamido)cyclopentyl)-5-fluoro-2,3-dimethyl-1H-indole-7-carboxamide or 4-((1S,3S)-3-(but-2-ynamido)cyclopentyl)-5-fluoro-2,3-dimethyl-1H-indole-7-carboxamide Retention time=3.88 min(15.8 mg, 31%) as a white solid. $^1H$ NMR (300 MHz, DMSO-d6) δ 10.66 (s, 1H), 8.68 (d, J=7.3 Hz, 1H), 7.96 (s, 1H), 7.49-7.27 (m, 2H), 4.35-4.08 (m, 1H), 4.03-3.81 (m, 1H), 2.38-2.23 (m, 6H), 2.21-2.08 (m, 1H), 2.06-1.80 (m, 7H), 1.79-1.61 (m, 1H). ESI-MS $[M+H]^+$ calcd for $(C_{20}H_{22}FN_3O_2)$ 356.17 found: 356.10.

4-((1S,3S)-3-(but-2-ynamido)cyclopentyl)-5-fluoro-2,3-dimethyl-1H-indole-7-carboxamide or 4-((1R,3S)-3-(but-2-ynamido)cyclopentyl)-5-fluoro-2,3-dimethyl-1H-indole-7-carboxamide Retention time=4.93 min (6.4 mg, 12%) as a white solid. $^1H$ NMR (300 MHz, DMSO-$d_6$) δ 10.66 (s, 1H), 8.67 (d, J=7.3 Hz, 1H), 7.97 (s, 1H), 7.53-7.23 (m, 2H), 4.41-4.28 (m, 1H), 4.16-4.04 (m, 1H), 2.42-2.24 (m, 6H), 2.18-2.02 (m, 3H), 1.96 (s, 3H), 1.92-1.77 (m, 2H), 1.71-1.53 (m, 1H). ESI-MS $[M+H]^+$ calcd for $(C_{20}H_{22}FN_3O_2)$ 356.17 found: 356.10.

Example 13

Synthesis of 4-((1S,3R)-3-(but-2-ynamido)cyclopentyl)-5-fluoro-2,3-dimethyl-1H-indole-7-carboxamide and 4-((1R,3R)-3-(but-2-ynamido)cyclopentyl)-5-fluoro-2,3-dimethyl-1H-indole-7-carboxamide 13-(1S,3R)

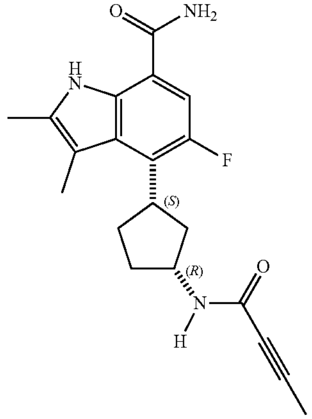

13-(1R,3R)

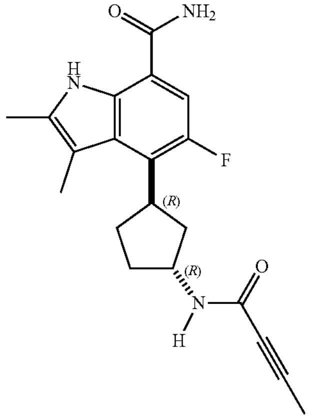

Step 1: (R)-4-((tert-butoxycarbonyl)amino)cyclopent-1-en-1-yl trifluoromethane sulfonate

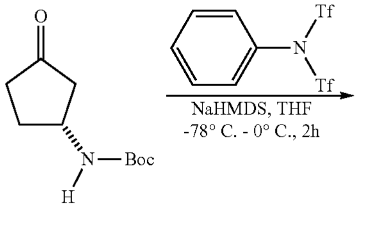

-continued

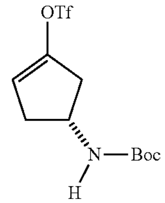

To a stirred mixture of tert-butyl (R)-(3-oxocyclopentyl) carbamate (1.0 g, 5.02 mmol) and 1,1,1-trifluoro-N-phenyl-N-((trifluoromethyl)sulfonyl)methanesulfonamide (2.33 g, 6.52 mmol) in THF (15 mL) was added sodium bis(trimethylsilyl)amide (2 M in tetrahydrofuran, 7.53 mL) at −78° C. under nitrogen atmosphere. The reaction mixture was stirred for 0.5 h at −78° C. and for 2 h at 0° C. The reaction mixture was quenched with saturated aqueous ammonium chloride (60 mL) and extracted with ethyl acetate (50 mL×3). The combined organic layers was washed water (50 mL×2) and brine (50 mL), dried over anhydrous sodium sulfate and concentrated under vacuum to give (R)-4-((tert-butoxycarbonyl)amino)cyclopent-1-en-1-yl trifluoromethanesulfonate (1.50 g, crude) as a brown oil. ESI-MS $[M-H]^-$ calcd for ($C_{11}H_{16}F_3NO_5S$) 330.07 found: 330.15.

Step 2: tert-butyl (R)-(3-(4,4,5,5-tetramethyl-1,3,2-dioxaborolan-2-yl)cyclopent-3-en-1-yl)carbamate

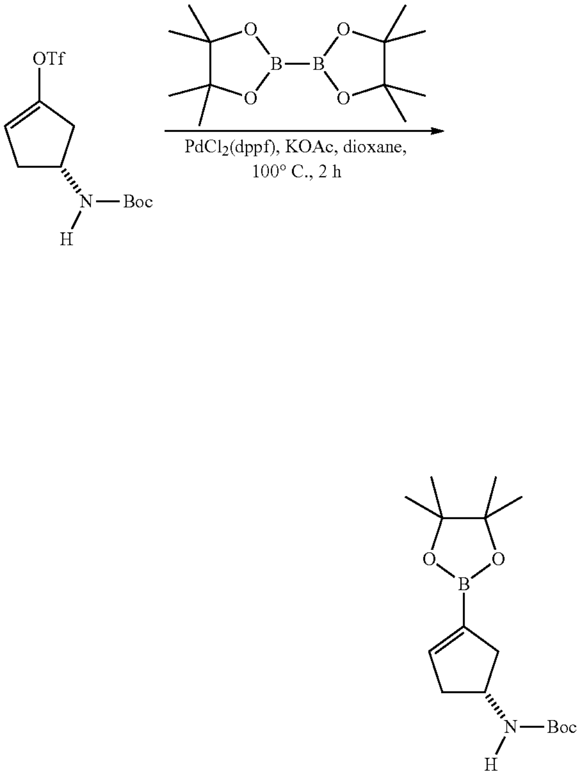

A mixture of (R)-4-((tert-butoxycarbonyl)amino)cyclopent-1-en-1-yl trifluoromethanesulfonate (1.50 g, crude), 4,4,4',4',5,5,5',5'-octamethyl-2,2'-bi(1,3,2-dioxaborolane) (1.38 g, 5.43 mmol), potassium acetate (1.33 g, 13.58 mmol) and Pd(dppf)$Cl_2$ (331 mg, 0.452 mmol) in 1,4-dioxane (20 mL) was degassed and backfilled with nitrogen for several times. The reaction mixture was stirred under nitrogen at 100° C. for 2 h. The reaction mixture was diluted with water (100 mL) and extracted with ethyl acetate (3×80 mL). The combined organic layers was washed with brine (100 mL), dried over sodium sulfate and concentrated under vacuum. The residue was purified by column chromatography on silica gel eluting with ethyl acetate in petroleum ether (0 to 20%) to give tert-butyl (R)-(3-(4,4,5,5-tetra methyl-1,3,2-dioxaborolan-2-yl)cyclopent-3-en-1-yl)carbamate (650 mg, crude) as a brown oil. $^1H$ NMR (300 MHz, DMSO-$d_6$) δ 7.08-6.86 (m, 1H), 6.28-6.14 (m, 1H), 4.68-4.38 (m, 1H), 2.32-2.06 (m, 2H), 1.60-1.41 (m, 2H), 1.38 (s, 9H), 1.24-1.20 (m, 12H).

Step 3: tert-butyl (R)-(3-(7-cyano-5-fluoro-2,3-dimethyl-1H-indol-4-yl)cyclopent-3-en-1-yl)carbamate

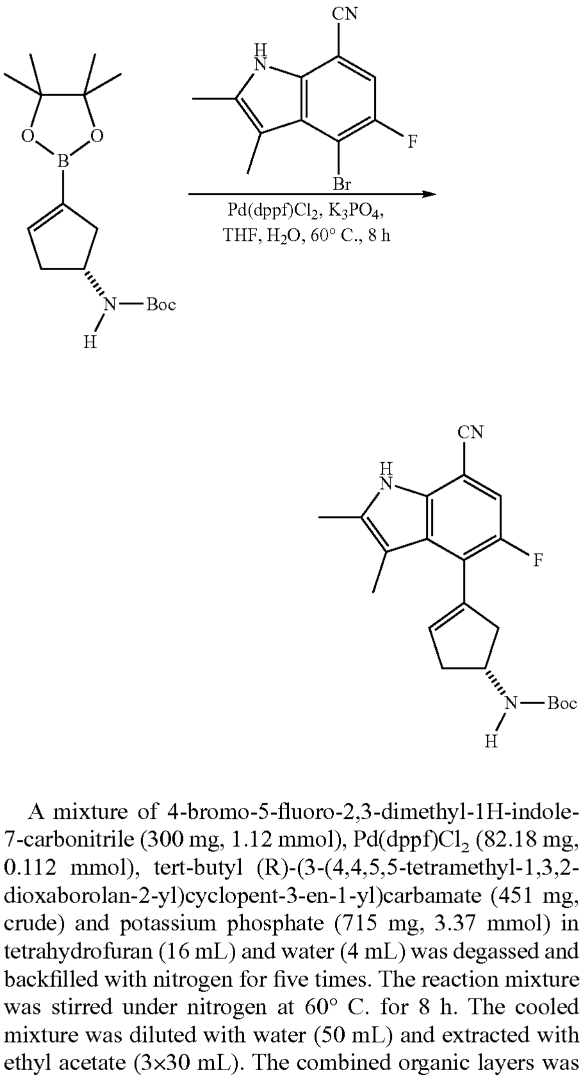

A mixture of 4-bromo-5-fluoro-2,3-dimethyl-1H-indole-7-carbonitrile (300 mg, 1.12 mmol), Pd(dppf)$Cl_2$ (82.18 mg, 0.112 mmol), tert-butyl (R)-(3-(4,4,5,5-tetramethyl-1,3,2-dioxaborolan-2-yl)cyclopent-3-en-1-yl)carbamate (451 mg, crude) and potassium phosphate (715 mg, 3.37 mmol) in tetrahydrofuran (16 mL) and water (4 mL) was degassed and backfilled with nitrogen for five times. The reaction mixture was stirred under nitrogen at 60° C. for 8 h. The cooled mixture was diluted with water (50 mL) and extracted with ethyl acetate (3×30 mL). The combined organic layers was washed with brine (50 mL), dried over sodium sulfate and concentrated under vacuum to give tert-butyl (R)-(3-(7-cyano-5-fluoro-2,3-dimethyl-1H-indol-4-yl)cyclopent-3-en-1-yl)carbamate (600 mg, crude) as a brown oil. ESI-MS $[M-H]^-$ calcd for ($C_{21}H_{24}FN_3O_2$) 368.19 found: 368.25.

Step 4: tert-butyl (R)-(3-(7-carbamoyl-5-fluoro-2,3-dimethyl-1H-indol-4-yl)cyclopent-3-en-1-yl)carbamate

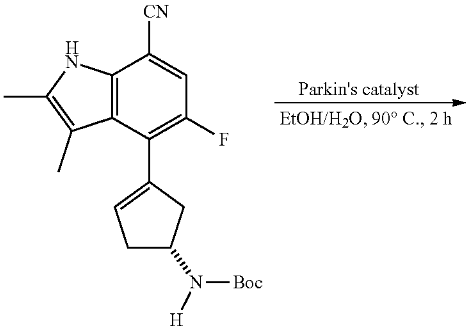

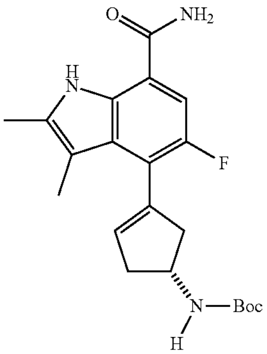

A mixture of tert-butyl (R)-(3-(7-cyano-5-fluoro-2,3-dimethyl-1H-indol-4-yl)cyclopent-3-en-1-yl)carbamate (600 mg, crude) in ethanol (15 mL) and water (15 mL) was added Parkin's catalyst (69 mg, 0.162 mmol). The reaction mixture was stirred for 2 h at 90° C. The cooled mixture was diluted with water (80 mL) and extracted with ethyl acetate (3×50 mL). The combined organic layers was washed with brine (50 mL), dried over sodium sulfate and concentrated under vacuum to give tert-butyl (R)-(3-(7-carbamoyl-5-fluoro-2,3-dimethyl-1H-indol-4-yl)cyclopent-3-en-1-yl)carbamate (280 mg, 64% over two steps) as a yellow solid. $^1$H NMR (300 MHz, DMSO-$d_6$) δ 10.74 (s, 1H), 8.01 (s, 1H), 7.62-7.34 (m, 2H), 7.25-7.01 (m, 1H), 5.72-5.48 (m, 1H), 4.85-4.49 (m, 1H), 2.80-2.53 (m, 2H), 2.43-2.21 (m, 4H), 2.07 (s, 3H), 1.90-1.74 (m, 1H), 1.40 (s, 9H). ESI-MS $[M+H]^+$ calcd for ($C_{21}H_{26}FN_3O_3$) 388.20 found: 388.35.

Step 5: tert-butyl ((1R)-3-(7-carbamoyl-5-fluoro-2,3-dimethyl-1H-indol-4-yl)cyclopentyl)carbamate

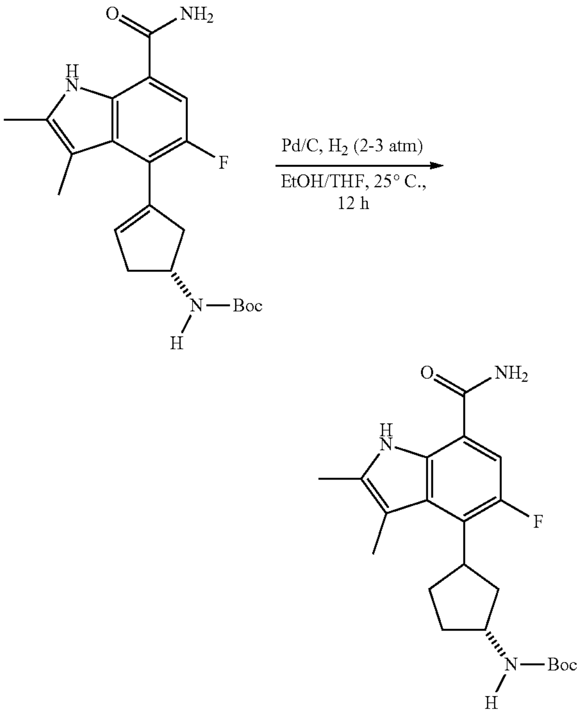

A mixture of tert-butyl (R)-(3-(7-carbamoyl-5-fluoro-2,3-dimethyl-1H-indol-4-yl)cyclopent-3-en-1-yl)carbamate (280 mg, 0.722 mmol) and 10% palladium on carbon (300 mg) in ethanol (10 mL) and tetrahydrofuran (10 mL) was stirred under hydrogen (2-3 atm) for 12 h at 25° C. The reaction mixture was filtered. The filtrate was concentrated under vacuum to give tert-butyl ((1R)-3-(7-carbamoyl-5-fluoro-2,3-dimethyl-1H-indol-4-yl)cyclopentyl)carbamate (270 mg, 96%) as a yellow solid. ESI-MS $[M+H]^+$ calcd for ($C_{21}H_{28}FN_3O_3$) 390.21 found: 390.40.

Step 6: 4-((3R)-3-aminocyclopentyl)-5-fluoro-2,3-dimethyl-1H-indole-7-carboxamide 2,2,2-trifluoroacetate

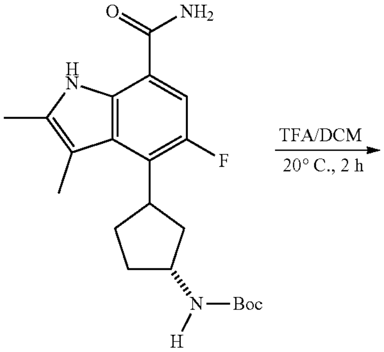

-continued

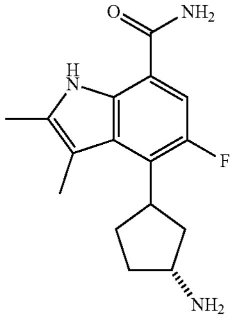

To a solution of tert-butyl ((1R)-3-(7-carbamoyl-5-fluoro-2,3-dimethyl-1H-indol-4-yl)cyclopentyl)carbamate (270 mg, 0.693 mmol) in dichloromethane (10 mL) was added trifluoroacetic acid (2 mL). The reaction mixture was stirred for 2 h at 25° C. The resulting mixture was concentrated under vacuum to give 4-((3R)-3-aminocyclopentyl)-5-fluoro-2,3-dimethyl-1H-indole-7-carboxamide 2,2,2-trifluoroacetate (350 mg, crude) as a brown solid. ESI-MS $[M+H]^+$ calcd for $(C_{16}H_{20}FN_3O)$ 290.16, found: 290.10.

Step 7: 4-((3R)-3-(but-2-ynamido)cyclopentyl)-5-fluoro-2,3-dimethyl-1H-indole-7-carboxamide

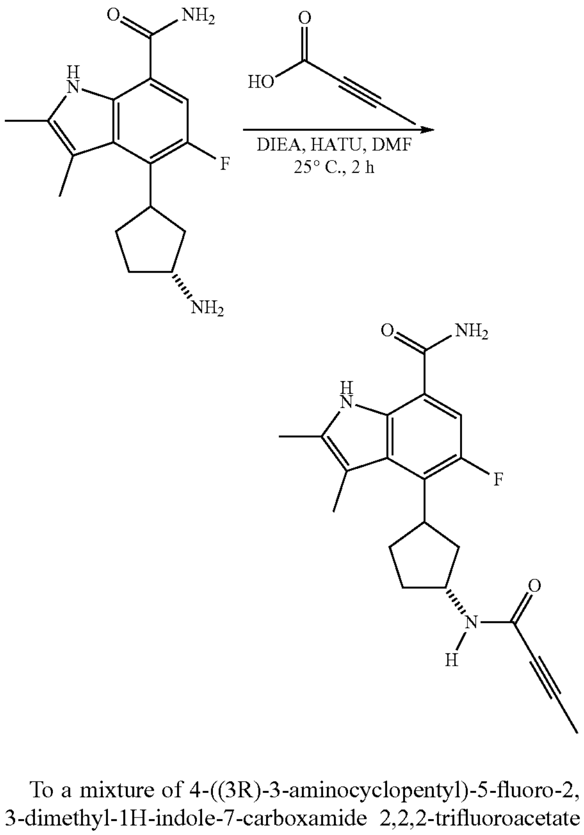

To a mixture of 4-((3R)-3-aminocyclopentyl)-5-fluoro-2,3-dimethyl-1H-indole-7-carboxamide 2,2,2-trifluoroacetate (350 mg, crude) in DMF (10 mL) was added O-(7-Azabenzotriazol-1-yl)-N,N,N',N'-tetramethyluronium hexafluorophosphate (497 mg, 1.30 mmol), but-2-ynoic acid (87.5 mg, 1.04 mmol) and N,N-diisopropylethylamine (560 mg, 4.34 mmol). The reaction mixture was stirred at 20° C. for 2 h. The resulting mixture was diluted with water (50 mL) and extracted with ethyl acetate (50 mL×2). The combined organic layers were washed with water (50 mL×2) and brine (50 mL), dried over anhydrous sodium sulfate, filtered and concentrated under vacuum.

The residue was purified by Prep-HPLC with the following conditions: Column: Xselect CSH OBD Column 30×150 mm, 5 um, Mobile Phase A: water (10 mmol/L $NH_4HCO_3$+0.1% $NH_3·H_2O$), Mobile Phase B: ACN; Flow rate: 60 mL/min; Gradient: 25 B to 51 B in 7 min; 220 nm; RT1: 6.37 min to give 4-((3R)-3-(but-2-ynamido)cyclopentyl)-5-fluoro-2,3-dimethyl-1H-indole-7-carboxamide (140 mg, 57% over two steps) as a white solid. ESI-MS $[M+H]^+$ calcd for $(C_{20}H_{22}FN_3O_2)$ 356.17, found: 356.10.

Step 8: Separation of Isomers

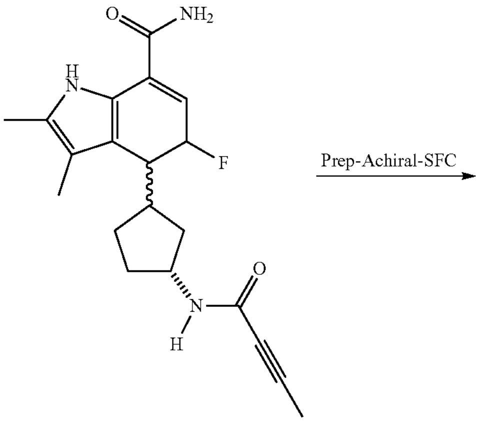

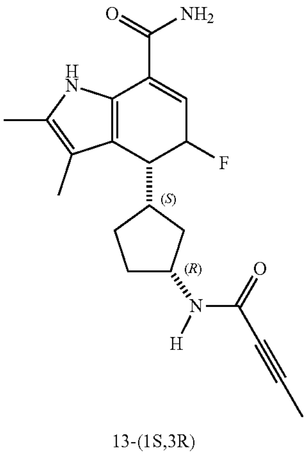

+

13-(1S,3R)

-continued

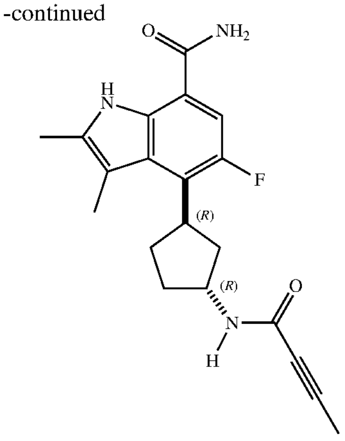

13-(1S,3R)

4-((3R)-3-(but-2-ynamido)cyclopentyl)-5-fluoro-2,3-dimethyl-1H-indole-7-carboxamide (140 mg) was separated by Prep-Achiral-SFC with the following conditions: Column: DAICEL DCpak P4VP, 2×25 cm, 5 μm; Mobile Phase A: $CO_2$, Mobile Phase B: MeOH (0.5% 2 M $NH_3$-MeOH)-HPLC; Flow rate: 50 mL/min; Gradient: 38% B; Column Temperature: 35° C.; Back Pressure: 100 bar; 254 nm.

4-((1S,3R)-3-(but-2-ynamido)cyclopentyl)-5-fluoro-2,3-dimethyl-1H-indole-7-carboxamide or 4-((1R,3R)-3-(but-2-ynamido)cyclopentyl)-5-fluoro-2,3-dimethyl-1H-indole-7-carboxamide (Compound 13-(1R,3R))

Retention time=4.35 min (56.7 mg, 40%) as a white solid. $^1$H NMR (300 MHz, DMSO-$d_6$) δ 10.66 (s, 1H), 8.68 (d, J=7.4 Hz, 1H), 7.97 (s, 1H), 7.48-7.28 (m, 2H), 4.26-4.04 (m, 1H), 4.01-3.82 (m, 1H), 2.39-2.25 (m, 6H), 2.22-2.06 (m, 1H), 2.05-1.81 (m, 7H), 1.80-1.66 (m, 1H). ESI-MS $[M+H]^+$ calcd for ($C_{20}H_{22}FN_3O_2$) 356.17 found: 356.10.

4-((1R,3R)-3-(but-2-ynamido)cyclopentyl)-5-fluoro-2,3-dimethyl-1H-indole-7-carboxamide (Compound 13-(1R,3R)) or 4-((1S,3R)-3-(but-2-ynamido)cyclopentyl)-5-fluoro-2,3-dimethyl-1H-indole-7-carboxamide Retention time=5.57 min (37.0 mg, 26%) as a white solid. $^1$H NMR (300 MHz, DMSO-$d_6$) δ 10.66 (s, 1H), 8.67 (d, J=7.3 Hz, 1H), 7.97 (s, 1H), 7.49-7.25 (m, 2H), 4.41-4.27 (m, 1H), 4.19-4.01 (m, 1H), 2.41-2.28 (m, 6H), 2.22-2.01 (m, 3H), 1.96 (s, 3H), 1.92-1.74 (m, 2H), 1.71-1.51 (m, 1H). ESI-MS $[M+H]^+$ calcd for ($C_{20}H_{22}FN_3O_2$) 356.17 found: 356.15.

Example 14

BTK $IC_{50}$

Solutions of compounds (test or control) in DMSO were prepared at the desired concentrations, and serially diluted to 11 concentrations by 3-fold dilution in 384pp-plate using TECAN EVO200. 20 nL of stock were transferred to 384 plate using Echo550. DMSO was used as vehicle control.

Two separate solutions were prepared—an ATP solution containing $MgCl_2$ (10 mM), Brij-35 (0.01%), DTT (2 mM), BSA (0.05%), EGTA (1 mM), HEPE (pH7.5) (50 mM), FLPeptide (6 uM) and ATP (4 mM); and a BTK solution containing $MgCl_2$ (10 mM), Brij-35 (0.01%), DTT (2 mM), BSA (0.05%), EGTA (1 mM), HEPE (pH7.5) (50 mM) and BTK (2.67 nM). (BTK was obtained from Carna; FLPeptide2 was obtained from PerkinElmer and Ibrutinib was obtained from Selleck.) 5 uL of ATP solution were added to each well, followed by addition of 15 uL of BTK solution to initiate the reaction. (Note the final volume of each well was 20 uL containing $MgCl_2$ (10 mM), Brij-35 (0.01%), DTT (2 mM), BSA (0.05%), EGTA (1 mM), HEPE (pH7.5) (50 mM), FLPeptide (1.5 uM), ATP (1 mM) and BTK (2 nM). The plates were incubated at room temperature for 90 minutes and then stopping buffer added (75 uL, containing 0.5 M EDTA) to terminate the reaction. Samples from each well were analyzed using EZ reader.

The % remaining activity was calculated using read conversion ratio (CR) according to the equation:

$$\text{Remaining Activity (\%)} = 100 \times \frac{CR_{Compound}}{CR_{Vehicle}}$$

XLFit (equation 201) was used to calculate $IC_{50}$'s by floating both bottom and top.

BTK $IC_{50}$ values are provided in Table 5, for the compounds described in Examples 1-13, wherein:

"A" denotes an $IC_{50}$<1 nM;

"B" denotes an $IC_{50}$ 1-10 nM; and

"C" denotes an $IC_{50}$>10 nM.

TABLE 5

BTK $IC_{50}$ (nM)

| Cmpd No | BTK $IC_{50}$ (nM) |
|---|---|
| 1A(rac) | B |
| 1A(S) | A |
| 1A(R) | B |
| 2A(S) | A |
| 2A(R) | B |
| 3A(S) | A |
| 3B(S) | B |
| 4A(S) | B |
| 4B(S) | B |
| 5B(rac) | B |
| 5B(S) | B |
| 5B(R) | B |
| 6-(cis) | B |
| 6-(trans) | B |
| 6-(1R,3S) | B |
| 6-(1S,3R) | — |
| 6-(1R,3R) | C |
| 6-(1S,3S) | B |
| 7-(1R,3S) | B |
| 7-(1S,3R) | — |
| 7-(1R,3R) | B |
| 7-(1S,3S) | C |
| 8-(1R,3S) | B |
| 8-(1S,3R) | C |
| 8-(1R,3R) | B |
| 8-(1S,3S) | C |
| 9-(1S,3S) | B |
| 9-(1R,3S) | C |
| 9-(1S,3R) | B |
| 9-(1R,3R) | C |
| 10-(1S,3S) | B |
| 10-(1R,3S) | — |
| 11-(1R,3S) | B |
| 11-(1S,3R) | — |
| 11-(1R,3R) | B |
| 11-(1S,3S) | C |
| 12-(1R,3S) | B |

TABLE 5-continued

| BTK $IC_{50}$ (nM) | |
|---|---|
| Cmpd No | BTK $IC_{50}$ (nM) |
| 12-(1S,3S) | C |
| 13-(1S,3R) | C |
| 13-(1R,3R) | B |

Example 15

Assay to Determine BTK Activity in RAMOS B Cells

On the day before assay, Ramos B cells were plated in plating medium (RPMI1640 medium containing 1% FBS and 1× pencillin-streptomycin). On the day of the assay, 2× dye solution was prepared following the manual of the FLIRP Calcium 6 Assay Kit: Dilute the dye with assay buffer (20 mM HEPES in 1×HBSS, pH7.4); Add probenecid to the final concentration of 5 mM; vortex vigorously for 1-2 minutes. Cells were collected by centrifuging, and the pellet was resuspended in plating medium. After counting, cells were resuspended at a density of $3\times10^6$/ml in plating medium. Equal volume of 2× dye solution was added to the cell suspension. Cells were then plated at 20 µl/well into a 384-well poly-D-lysine coated plate. Plate was centrifuged at 1000 rpm for 3 minutes and then incubated at 37° C. for 2 hours followed by an additional 15-minute incubation at 25° C. Compounds were prepared at 3× concentration in dilution buffer (20 mM HEPES and 0.1% BSA in 1×HBSS, pH 7.4). Serially diluted compound was transferred from source plate to a 384-well compound plate by using an Echo 550 (Labcyte). 20 µl/well compound dilution buffer was added to the compound plate and mixed on plate shaker for 2 mins. 4×EC80 of Anti-IgM (Jackson ImmunoResearch) was prepared in dilution buffer and 20 µl/well was added to a new 384-well compound plate. After 60 mins of incubation at 25° C. in the dark; cell plate, compound plate containing $4\times EC_{80}$ of anti-IgM and FLIPR tips were placed into FLIPR (Molecular Devices). 10 ul/well of $4\times EC_{80}$ anti-IgM was transferred to the cell plate by FLIPR. Plates were read for 160 sec with 1 sec interval. $IC_{50}$ values with respect to Ramos activity for the compounds described in Examples 1-13 are less than 10 nM.

Example 16

Assay to Determine BTK Inactivation Rate

This example employed a BTK active site probe-based assay using a biotinylated covalent inhibitor in human and mouse blood or mouse brain lysate.

Experimental Procedures

Human and Whole Blood Compound Treatment and Lysis

Human whole blood was obtained from StemExpress (Stockton, CA) and kept at ambient temperature until the time of the experiment, which was approximately 24 hours after it had been collected.

1. A 1× lysis buffer was prepared by using 10× lysis buffer (Cell Signaling Technology, #9083S, Danvers, MA), molecular biology grade water, 100× Halt Protease and Phosphatase Inhibitor Cocktail, (ThermoFisher, #78440, Waltham, MA), and BTK active site probe (final: 0.4 µM). This was prepared fresh each experimental day.
2. Lysis buffer was added in the volume of 30 µL to all wells in a V-bottom plate (Greiner Bio-One, #651261, Monroe, NC) in preparation for timepoint collections.
3. Compounds were reconstituted to stocks of 10 mM in 100% DMSO and were diluted in 2-fold serial dilutions to generate an 8-point curve in DMSO, with the last point being DMSO only.
4. A working 10× dilution series was created using 1 µL of the prepared DMSO titration into 299 µL 1×PBS in order to keep the DMSO constant (0.03% DMSO final).
5. The whole blood was added in the volume of 225 µL per well in a new 96 w v-bottom plate.
6. For compound treatment, 25 µL of the 10× dilution series in PBS was added to the 225 µL whole blood, followed by briefly pipetting up and down, twice.
7. The plates were then covered with plastic lids and incubated at 37° C. for 5, 10, 15, 30, 60 minutes.
8. At each timepoint, 30 µL of compound- or DMSO (vehicle)-treated blood is pulled from each column and added to preloaded collection plates that contained 30 µL of lysis buffer supplemented with BTK active site probe. Samples were then mixed briefly by pipetting up and down, twice.
9. The plates with collected and lysed samples were shaken and covered with sealing film on a rotator for 60 minutes at room temperature. These samples were used fresh for detection via ELISA, and remaining sample was frozen at −80° C. if a repeat was necessary.

Determining Amount of Unoccupied BTK Using ELISA

1. All streptavidin pre-coated plates (R&D Systems, #CP004, Minneapolis, MN) were brought to room temperature while samples are lysing.
2. Assay Buffer 1, 1×PBS+0.05% Tween 20+1% BSA was prepared, filtered, and stored at 4° C. when not in use.
3. Using this Assay Buffer 1, assay buffer+1× protease/phosphatase inhibitor cocktail (PICS) was prepared in the amount needed for all samples.
4. Assay Buffer+PICS in the volume of 90 µL/well was added to the ELISA plate for blood samples.
5. Assay Buffer+PICs in the volume of 50 µL/well was added to the ELISA plate for brain samples.
6. Lysed blood sample (10 µL) was added to the ELISA plate.
7. Lysed brain sample (50 µL) was added to the ELISA plate.
8. Samples were loaded into the ELISA plate for a total of 100 µL/well, in duplicate, and remained in the plate, sealed, overnight at 4° C.
9. The following day, the plate was washed three times with 1× Wash Buffer (1×PBS+0.05% Tween 20) at 250 µL/well using a plate washer.
10. The plate was inverted to expel all fluid each time and blotted on clean paper towels to remove remaining liquid.
11. Assay Buffer 2 was prepared (1×PBS+0.05% Tween 20+0.5% BSA) and kept at 4° C. when not in use.
12. The primary antibody α-BTK (clone D3H5, Cell Signaling Technology #8547S Danvers, MA) was diluted 1:500 in Assay Buffer 2.
13. Diluted a-BTK antibody was added at 100 µL/well.
14. The plate was covered with adhesive film and incubated for 90 minutes at room temperature.
15. The plate was washed three times with 1× Wash Buffer at 250 µL/well using a plate washer.

16. The plate was inverted to expel all fluid each time and blotted on clean paper towels to remove remaining liquid.
17. The detection antibody (Jackson Immuno Research, #711-005-152) was diluted 1:2,500 with Assay Buffer 2.
18. The diluted antibody was added at 100 μL/well.
19. The plate was covered with adhesive film and incubated for one hour at room temperature.
20. The plate was washed three times with 1× Wash Buffer, at 250 μL/well using a plate washer.
21. The plate was inverted to expel all fluid each time and blotted on clean paper towels to remove remaining liquid.
22. Pre-warmed TMB substrate (ThermoFisher, #34029) was added to the plate at 100
23. The plate was incubated at room temperature in the dark for 3-5 minutes.
24. The reaction was stopped by adding 50 μL/well 2N sulfuric acid (H2SO4) (R&D Systems, #DY994).
25. The plate was read in a Pherastar plate reader (BMG, Germany) at the wavelengths 450 nm and 570 nm (correction wavelength).

Data Analysis

Using GraphPad Prism, raw absorbance data was plotted as time (x-axis, minutes) against concentration (y-axis, nM) and fitted to a One Phase Decay model (Y=(Y0−Plateau)*exp(−K*X)+Plateau). The best-fit values of each concentration were calculated by this model and reported in the results tabular summary provided by GraphPad as K (rate constant for inhibition, $k_{obs}$).

Again in Prism, rate constants ($k_{obs}$) for each concentration of Compouind were then re-plotted against the Compound concentrations and fitted to a hyperbolic equation (Michaelis-Menten model). Using this model, the best-fit values for $V_{max}$ ($k_{inact}$) and Km ($K_i$) were taken and used to determine a second order rate constant of the inactivation in whole blood by the formula $(k_{inact}/K_i)$*10,000, which was then represented as the calculated BTK inactivation rate constant $(k_{inact}/K_i)10^{-4}$ $nM^{-1}$ $min^{-1}$ (and averaged in cases of repeat measurements).

Calculated BTK inactivation rate constants are provided in Table 6 for the compounds noted, wherein:

"A" denotes $K_{inact}/K_i$<5 nM;

"B" denotes $K_{inact}/K_i$ 5-10 nM; and

"C" denotes $K_{inact}/K_i$>10 nM.

TABLE 6

| BTK $IC_{50}$ (nM) | |
|---|---|
| Cmpd No | BTK hWB (Kinact/Ki) |
| 1A(S) | A |
| 1A(R) | A |
| 2A(S) | C |
| 2A(R) | A |
| 3A(S) | C |
| 3B(S) | C |
| 5B(S) | A |
| 6-(cis) | A |
| 6-(1R,3S) | A |
| 6-(1S,3S) | B |
| 7-(1R,3S) | A |
| 7-(1R,3R) | B |
| 10-(1S,3S) | A |
| 11-(1R,3S) | A |

TABLE 6-continued

| BTK $IC_{50}$ (nM) | |
|---|---|
| Cmpd No | BTK hWB (Kinact/Ki) |
| 11-(1R,3R) | A |
| 12-(1R,3S) | A |
| 13-(1R,3R) | A |

Example 17

Assay to Determine Inhibition of BTK in B Cells

In order to study the effects of inhibition of BTK in B cells, upregulation of Cluster of Differentiation 69 (CD69), a lymphocyte activation marker, was measured after overnight stimulation of human whole blood (hWB).

10 mM stocks of test articles (TAs) were diluted to 2 mM in DMSO followed by 8 subsequent 1:4 serial dilutions in DMSO. Serially diluted compounds were then further diluted stepwise (1:10 and 1:5) in assay medium (RPMI+1% HI-FBS) to generate 4× working concentrations used for generating 9-point dose-response curves (DRCs).

NaHep hWB collected the previous day was diluted 1:1 (v/v) in assay medium and 70 μL of diluted hWB was as added to each well of a flat-bottom 96-well plate while excluding perimeter wells. For each plate, 25 μL of assay medium containing vehicle was added to triplicate wells designated for the non-stimulation (Bkg) and stimulation (Veh) control conditions to achieve 0.5% (v/v) final DMSO. Next, 25 μL of 4× working concentrations of TAs was added to triplicate wells at final concentrations ranging from 0.153 to 10,000 nM at 0.5% DMSO (v/v). After pre-treatment for 1 h, 5 μL of 20× anti IgD-dextran was added resulting in a final concentration of 1 ng/mL for stimulation of B cells (and an equal volume of media was added to non-stimulation control wells). After mixing, plates were moved to a humidified, 5% $CO_2$, 37° C. incubator overnight (~18 h). Surface staining for fluorescence-activated cell sorting (FACS) was accomplished by adding a master mix of antibodies (1 μL/well of BV421 anti-CD19, FITC anti-CD45, PE anti-CD69, PerCP/Cy5.5 anti-CD3) plus 0.5 μL/well of eFluor 506 fixable viability dye. After mixing, samples were transferred to a deep-well 96-well plate for RBC lysis and fixation using a combined buffer at 1×. Plates were centrifuged for 5 min at 300× g, supernatants were aspirated, and pelleted cells were resuspended in 600 μL of FACS buffer prior to acquisition on an Attune NxT flow cytometer. For FACS analysis, viable CD45+ WBCs cells were gated for further interrogation of CD19+ B cells, and the percentage of CD69+ events within this population was reported for each concentration of compound.

Calculation of % inhibition for was determined by substituting raw values into the following equation:

$$\left(1-\left(\frac{TA-Bkg}{Veh-Bkg}\right)\right)*100.$$

In this equation, 0% inhibition is the level of response by TA that is equivalent to Veh whereas 100% inhibition is defined as the level of response by TA equivalent to Bkg as defined separately for each assay. Inhibitory DRCs were generated from triplicate values at each concentration of TA using a nonlinear, 4-parameter, variable slope curve-fitting function using GraphPad Prism software.

By this experiment, ex vivo pre-treatment of hWB with the TAs listed in Table 7 below each provided inhibition of B cell activation as measured by CD69 upregulation with an average $IC_{50}$ of less than 35 nM.

TABLE 7

| CD69 inhibition in hWB $IC_{50}$ (nM) Cmpd No |
|---|
| 1A(rac) |
| 1A(S) |
| 1A(R) |
| 2A(S) |
| 2A(R) |
| 3A(S) |
| 3B(S) |
| 4A(S) |
| 6-(1R,3S) |

All of the U.S. patents, U.S. patent application publications, U.S. patent applications, foreign patents, foreign patent applications and non-patent publications referred to in this specification and/or listed in the Application Data Sheet are incorporated herein by reference, in their entirety. To this end, this application claims the benefit of priority to U.S. Provisional Application No. 63/136,594, filed Jan. 12, 2021, which application is hereby incorporated by reference in its entirety.

The invention claimed is:

1. A compound having the structure of Formula 1-C-(1S, 3R) or Formula 1-C-(1R,3R):

I-C-(1S, 3SR)

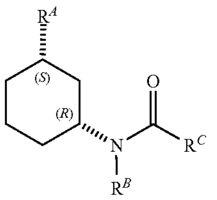

I-C-(1R, 3R)

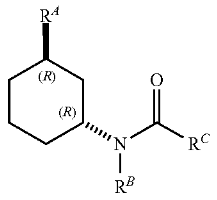

or a pharmaceutically acceptable salt, solvate, hydrate, tautomer, racemate or isotope thereof, wherein:

$R^B$ is H or Me;

$R^C$ is —CH—$CH_2$ or —C≡C—$CH_3$;

$R^A$ is

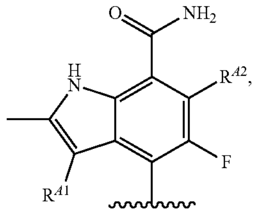

wherein $R^{A1}$ is —F or —Cl; and $R^{A2}$ is H or F.

2. A compound of claim 1, having the structure of Formula 1-C-(1S,3R):

Formula 1-C-(1S,3R)

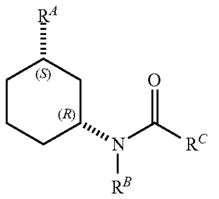

or a pharmaceutically acceptable salt, solvate, hydrate, tautomer, racemate or isotope thereof.

3. A compound of claim 1, having the structure of Formula 1-C-(1R,3R):

Formula 1-C-(1R,3R)

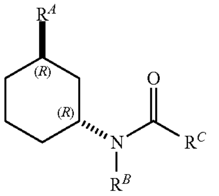

or a pharmaceutically acceptable salt, solvate, hydrate, tautomer, racemate or isotope thereof.

4. A compound of claim 1, wherein $R^B$ is H.

5. A compound of claim 1, wherein $R^B$ is Me.

6. A compound of claim 1, wherein $R^C$ is —CH=$CH_2$.

7. A compound of claim 1, wherein $R^C$ is —C≡C—$CH_3$.

8. A compound of claim 1, wherein $R^{A1}$ is —F.

9. A compound of claim 1, wherein $R^{A1}$ is —Cl.

10. A compound of claim 1, wherein $R^{A2}$ is —H.

11. A compound of claim 1, wherein $R^{A2}$ is —F.

12. A compound of claim 1, wherein $R^{A1}$ is —Cl;

$R^{A2}$ is —H; and $R^C$ is —C≡C—$CH_3$.

13. A compound of claim 1, wherein $R^{A1}$ is —Cl;

$R^{A2}$ is —H or —F;

$R^B$ is —H or -Me; and $R^C$ is —C≡C—$CH_3$.

14. A pharmaceutically acceptable salt of a compound of claim 1.

15. A pharmaceutical composition comprising the compound of claim 1, or a pharmaceutically acceptable salt, solvate, hydrate, tautomer, racemate, or isotope thereof, and at least one pharmaceutically acceptable excipient.

16. The compound of claim 1 having the structure:

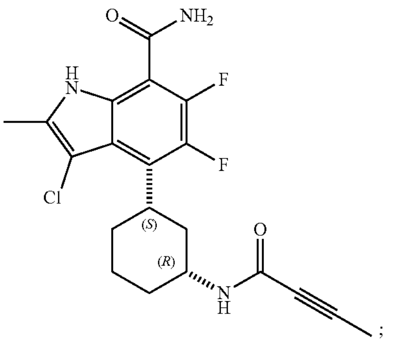

or a pharmaceutically acceptable salt or solvate thereof.

17. The compound of claim 1 having the structure:

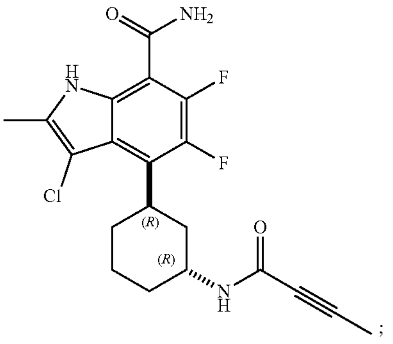

or a pharmaceutically acceptable salt or solvate thereof.

18. The compound of claim 1 having the structure:

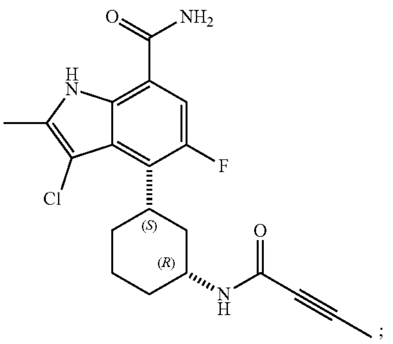

or a pharmaceutically acceptable salt or solvate thereof.

19. The compound of claim 1 having the structure:

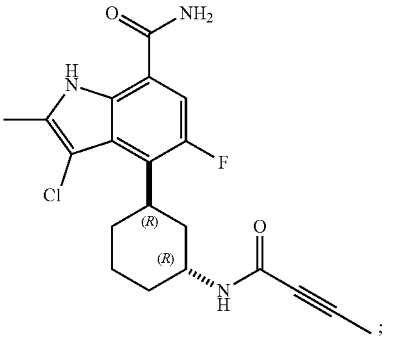

or a pharmaceutically acceptable salt or solvate thereof.

20. The compound of claim 1 having the structure:

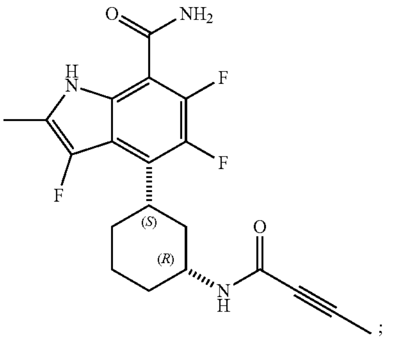

or a pharmaceutically acceptable salt or solvate thereof.

21. The compound of claim 1 having the structure:

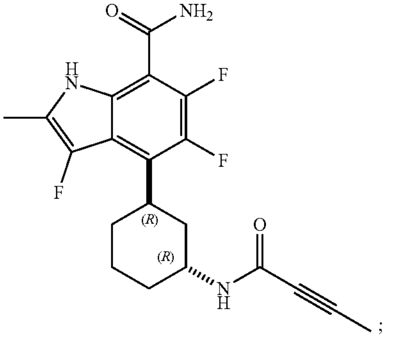

or a pharmaceutically acceptable salt or solvate thereof.

* * * * *